(12) United States Patent
Kim et al.

(10) Patent No.: US 9,388,126 B2
(45) Date of Patent: Jul. 12, 2016

(54) SIGMA RECEPTOR LIGANDS AND METHODS OF MODULATING CELLULAR PROTEIN HOMEOSTASIS USING SAME

(71) Applicant: Drexel University, Philadelphia, PA (US)

(72) Inventors: Felix J. Kim, Philadelphia, PA (US); Joseph M. Salvino, Chester Springs, PA (US)

(73) Assignee: Drexel University, Philadelphia, PA (US)

( * ) Notice: Subject to any disclaimer, the term of this patent is extended or adjusted under 35 U.S.C. 154(b) by 0 days.

(21) Appl. No.: 14/415,061

(22) PCT Filed: Jul. 18, 2013

(86) PCT No.: PCT/US2013/051110
§ 371 (c)(1),
(2) Date: Jan. 15, 2015

(87) PCT Pub. No.: WO2014/015157
PCT Pub. Date: Jan. 23, 2014

(65) Prior Publication Data
US 2015/0166472 A1   Jun. 18, 2015

Related U.S. Application Data

(60) Provisional application No. 61/673,565, filed on Jul. 19, 2012.

(51) Int. Cl.
*C07C 277/00*   (2006.01)
*A61K 45/06*   (2006.01)
(Continued)

(52) U.S. Cl.
CPC ............. *C07C 279/18* (2013.01); *A61K 31/138* (2013.01); *A61K 31/155* (2013.01);
(Continued)

(58) Field of Classification Search
CPC . A61K 31/138; A61K 31/155; A61K 31/366; A61K 31/4035; A61K 31/4706; A61K 31/496; A61K 31/69; A61K 45/06; C07D 209/48; C07D 311/16; C07C 279/18

USPC ............................................................ 514/64
See application file for complete search history.

(56) References Cited

U.S. PATENT DOCUMENTS 3,723,463 A   3/1973   Bernstein et al.
3,855,242 A   12/1974   Chapman et al.
(Continued)

FOREIGN PATENT DOCUMENTS

EP   241395 A2   10/1987
WO   9520950 A1   8/1995
(Continued)

OTHER PUBLICATIONS

Smith; J. Am. Chem. Soc., 1929, 51, 476-479.*
(Continued)

*Primary Examiner* — Janet L Andres
*Assistant Examiner* — Daniel Carcanague
(74) *Attorney, Agent, or Firm* — Saul Ewing LLP; Kathryn Doyle; Domingos J. Silva

(57) ABSTRACT

The present invention includes compounds useful in preventing, treating or ameliorating Sigma-related disorders or diseases. The compounds of the invention can modulate cellular protein homeostasis, which includes: translation initiation, folding, processing, transport, and degradation (including ubiquitin selective autophagy) of proteins. The present invention also includes methods of preventing, treating or ameliorating a Sigma-related disorder or disease in a subject in need thereof, the method comprising administering to the subject an effective amount of a Sigma-modulating compound. The present invention also includes methods of preventing, treating or ameliorating a Sigma-related disorder or disease in a subject in need thereof, the method comprising administering to the subject an effective amount of a Sigma-modulating compound, further comprising administering an effective amount of a compound that inhibits the ubiquitin proteasome system (UPS) and/or autophagic survival pathways.

31 Claims, 76 Drawing Sheets

(51) Int. Cl.

| | |
|---|---|
| C07C 279/18 | (2006.01) |
| A61K 31/138 | (2006.01) |
| A61K 31/496 | (2006.01) |
| A61K 31/155 | (2006.01) |
| A61K 31/366 | (2006.01) |
| A61K 31/4035 | (2006.01) |
| A61K 31/4706 | (2006.01) |
| A61K 31/69 | (2006.01) |
| C07D 209/48 | (2006.01) |
| C07D 311/16 | (2006.01) |

(52) U.S. Cl.
CPC .......... *A61K31/366* (2013.01); *A61K 31/4035* (2013.01); *A61K 31/4706* (2013.01); *A61K 31/496* (2013.01); *A61K 31/69* (2013.01); *A61K 45/06* (2013.01); *C07D 209/48* (2013.01); *C07D 311/16* (2013.01)

(56) References Cited

U.S. PATENT DOCUMENTS

| | | | |
|---|---|---|---|
| 4,680,300 | A | 7/1987 | Nelson et al. |
| 4,921,856 | A | 5/1990 | Schickaneder et al. |
| 4,921,939 | A | 5/1990 | Nofre et al. |
| 4,946,842 | A | 8/1990 | Coates et al. |
| 4,968,683 | A | 11/1990 | Moersdorf et al. |
| 5,006,523 | A | 4/1991 | Atwal |
| 5,116,838 | A | 5/1992 | Ishikawa et al. |
| 5,385,946 | A | 1/1995 | Keana et al. |
| 5,482,948 | A | 1/1996 | Soyka et al. |
| 5,741,796 | A | 4/1998 | Hartman et al. |
| 5,837,718 | A | 11/1998 | Timmerman et al. |
| 6,001,836 | A | 12/1999 | Poindexter et al. |
| 6,060,484 | A | 5/2000 | Fritz et al. |
| 6,143,791 | A | 11/2000 | Goldin et al. |
| 6,147,098 | A | 11/2000 | Mogensen et al. |
| 6,288,123 | B1 | 9/2001 | Goldin et al. |
| 6,875,759 | B1 | 4/2005 | Lipkowski et al. |
| 6,881,753 | B2 | 4/2005 | Lloyd et al. |
| 7,001,904 | B1 | 2/2006 | Poyser et al. |
| 7,138,530 | B2 | 11/2006 | Subasinghe et al. |
| 7,199,129 | B2 | 4/2007 | Jackson et al. |
| 7,304,086 | B2 | 12/2007 | Schilling et al. |
| 7,351,743 | B1 | 4/2008 | Goldin et al. |
| 7,371,871 | B2 | 5/2008 | Schilling et al. |
| 7,439,256 | B2 | 10/2008 | Castelhano et al. |
| 7,582,656 | B2 | 9/2009 | Roche et al. |
| 7,728,005 | B2 | 6/2010 | Okuzumi et al. |
| 7,732,162 | B2 | 6/2010 | Hoffman et al. |
| 7,790,719 | B2 | 9/2010 | Vos et al. |
| 7,863,465 | B2 | 1/2011 | Balkovec et al. |
| 7,872,005 | B2 | 1/2011 | Sun et al. |
| 7,956,219 | B2 | 6/2011 | Ede et al. |
| 8,168,787 | B2 | 5/2012 | Falchi et al. |
| 8,227,498 | B2 | 7/2012 | Buchholz et al. |
| 8,324,258 | B2 | 12/2012 | Glick et al. |
| 8,338,120 | B2 | 12/2012 | Schilling et al. |
| 8,409,837 | B2 | 4/2013 | Schilling et al. |
| 8,497,307 | B2 | 7/2013 | Glick et al. |
| 8,648,111 | B2 | 2/2014 | Kim et al. |
| 9,133,110 | B2 | 9/2015 | Kim et al. |
| 2005/0192314 | A1 | 9/2005 | Mehta et al. |
| 2007/0191366 | A1 | 8/2007 | Hoffmann et al. |
| 2008/0125424 | A1 | 5/2008 | DePrez et al. |
| 2008/0255143 | A1 | 10/2008 | Heerding et al. |
| 2014/0154182 | A1 | 6/2014 | Klein et al. |

FOREIGN PATENT DOCUMENTS

| | | | |
|---|---|---|---|
| WO | 9844797 | A1 | 10/1998 |
| WO | 0009115 | A1 | 2/2000 |
| WO | 0009116 | A1 | 2/2000 |
| WO | 02094265 | A1 | 11/2002 |
| WO | 03068738 | A1 | 8/2003 |
| WO | 2008034891 | A2 | 3/2008 |
| WO | 2011060394 | A1 | 5/2011 |
| WO | 2011060395 | A1 | 5/2011 |
| WO | WO2012165956 | * | 12/2012 |

OTHER PUBLICATIONS

Boguszewski; J. Comb. Chem. 2004, 6, 32-34.*
PCT International Search Report issued for PCT/US2013/051110 dated Feb. 28, 2014.
Chou, et al., "Reversible inhibitor of p97, DBeQ, impairs both ubiquitin-dependent and autophagic protein clearance pathways", Proc Natl Acad Sci U S A., 108(12), Mar. 22, 2011, 4834-4839.
Ding, et al., "Linking of Autophagy to Ubiquitin-Proteasome System is Important for the Regulation of Endoplasmic Reticulum Stress and Cell Viability", American Journal of Pathology, 171(2), Aug. 2007, 513-524.
Spruce, et al., "Small molecule antagonists of the sigma-1 receptor cause selective release of the death program in tumor and self-reliant cells and inhibit tumor growth in vitro and in vivo", Cancer Research, 64 (14), Jul. 14, 2004, 4875-4886.
Tsaytler, et al., "Selective Inhibition of a Regulatory Subunit of Protein Phosphatase 1 Restores Proteostasis", Science 332, Mar. 2, 2011, 91-94.
European Search Report issued for European Patent Application No. 13819583.9 dated Nov. 30, 2015.

* cited by examiner

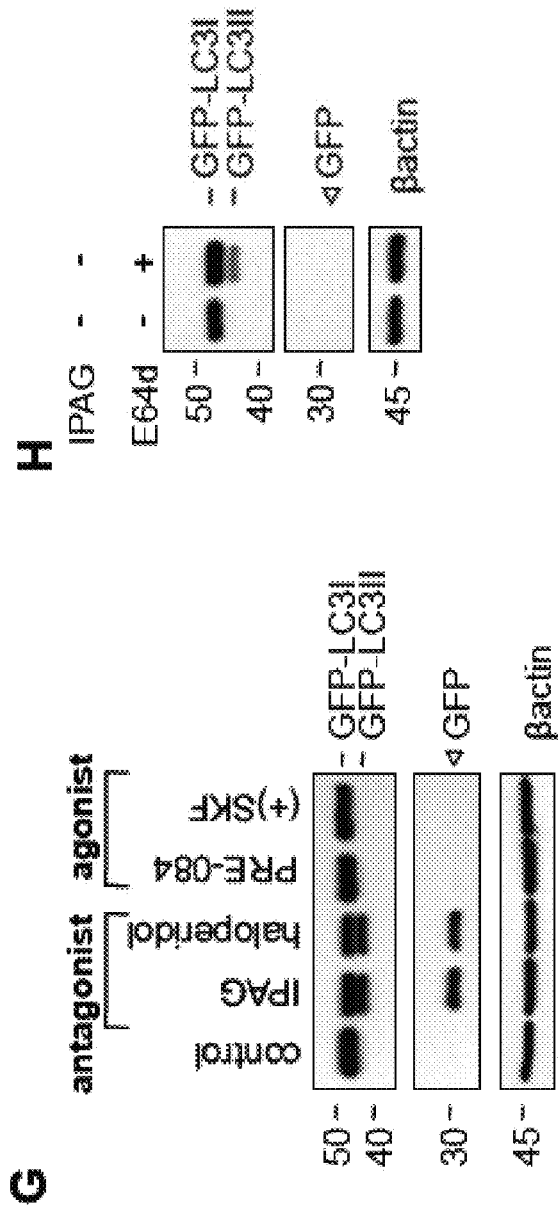
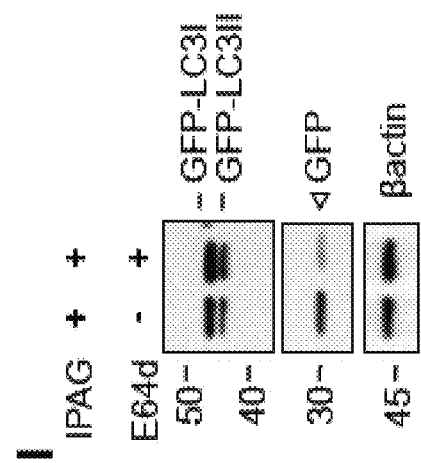
Figures 4G-4I

A

| Drug | Selectivity | |
|---|---|---|
| (+) pentazocine | Sigma1 | agonist |
| (+) SKF10047 | Sigma1 | agonist |
| PRE084 | Sigma1 | agonist |
| BD 1047 | Sigma1 > 2 | antagonist |
| Haloperidol | Sigma1 + 2 | antagonist |
| Rimcazole | Sigma2 > 1 | antagonist |
| IPAG | Sigma1 > 2 | antagonist |

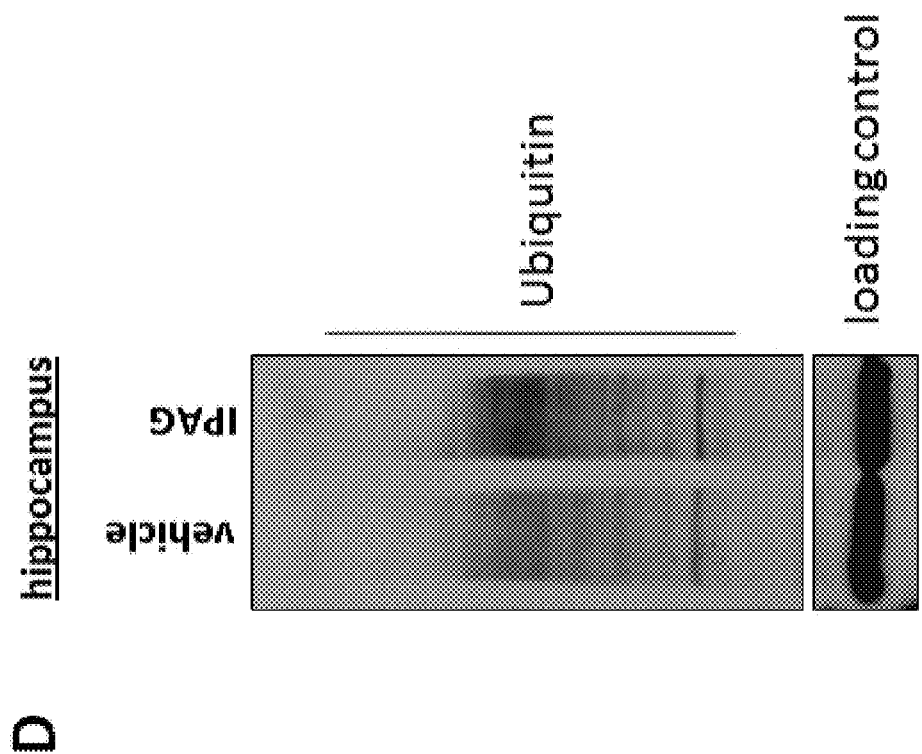

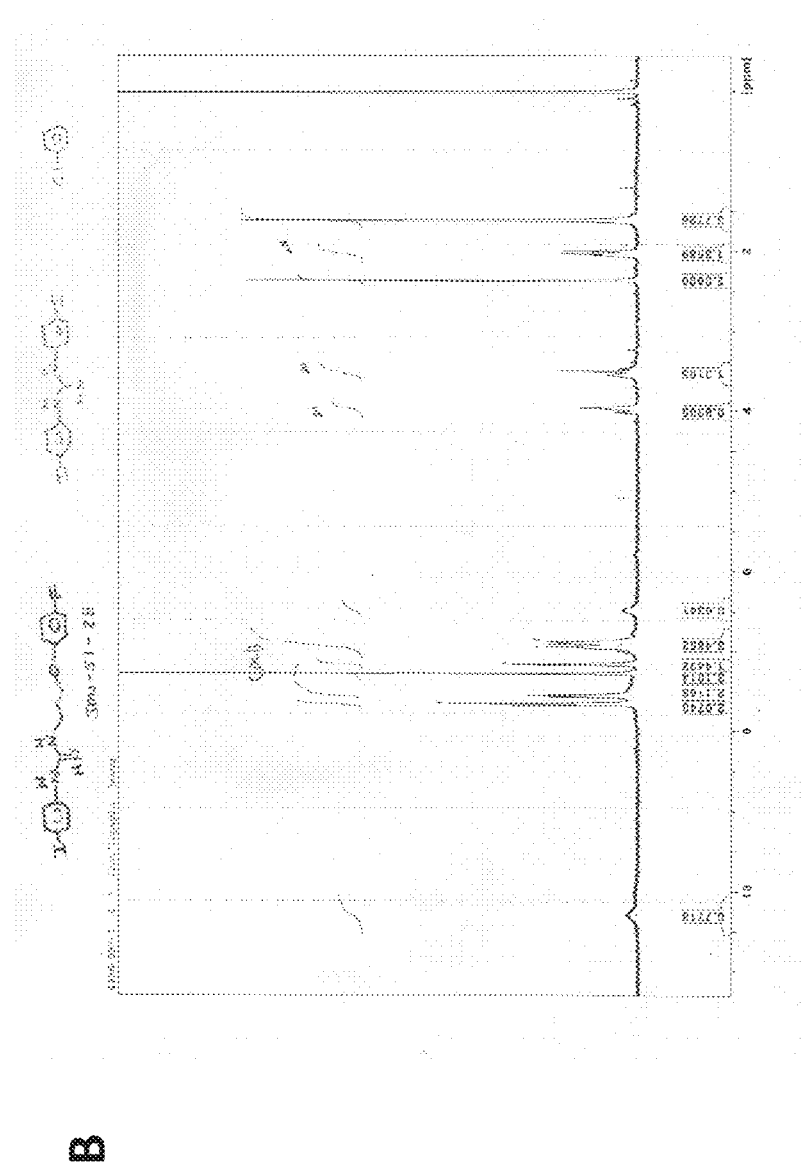
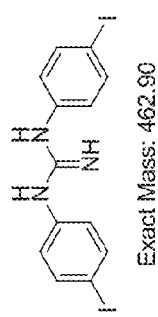
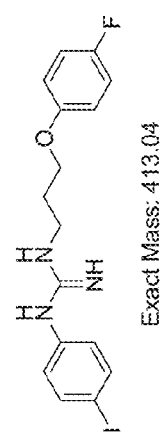
Figure 54B

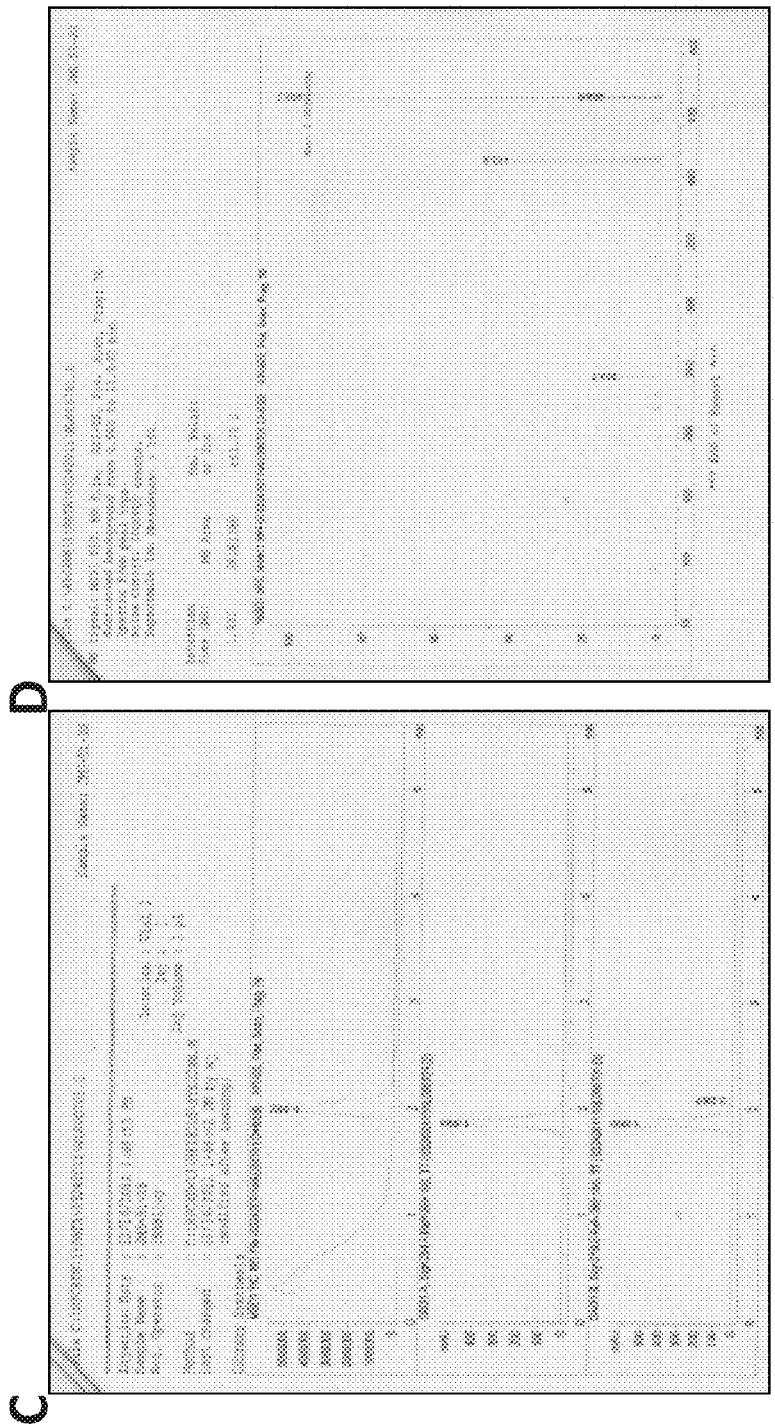
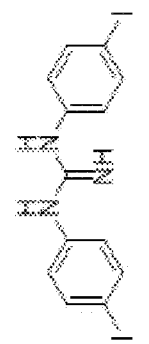
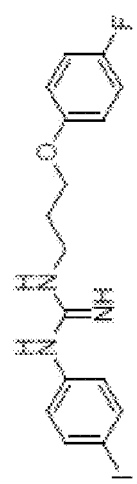
Figures 54C-54D

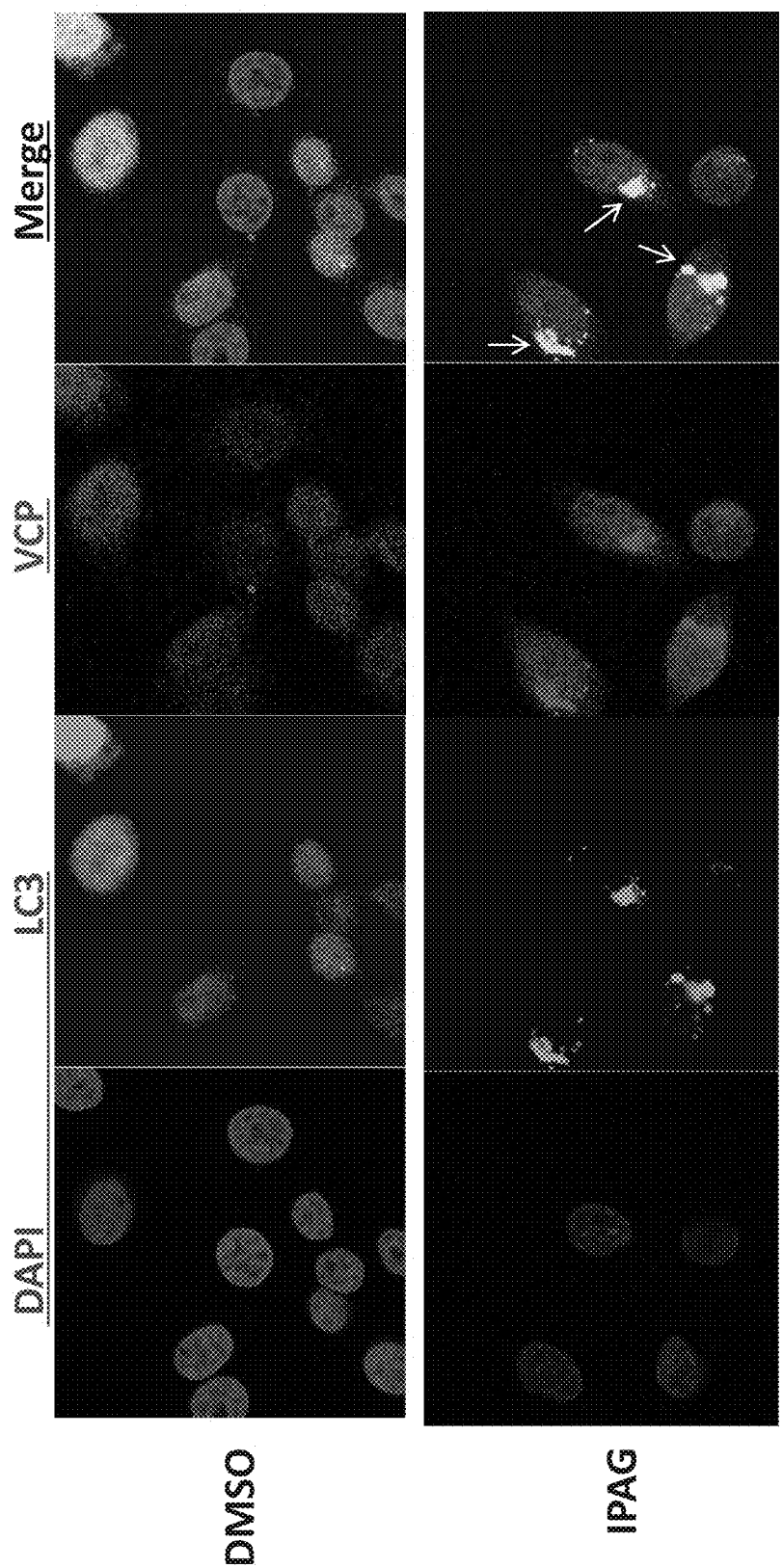

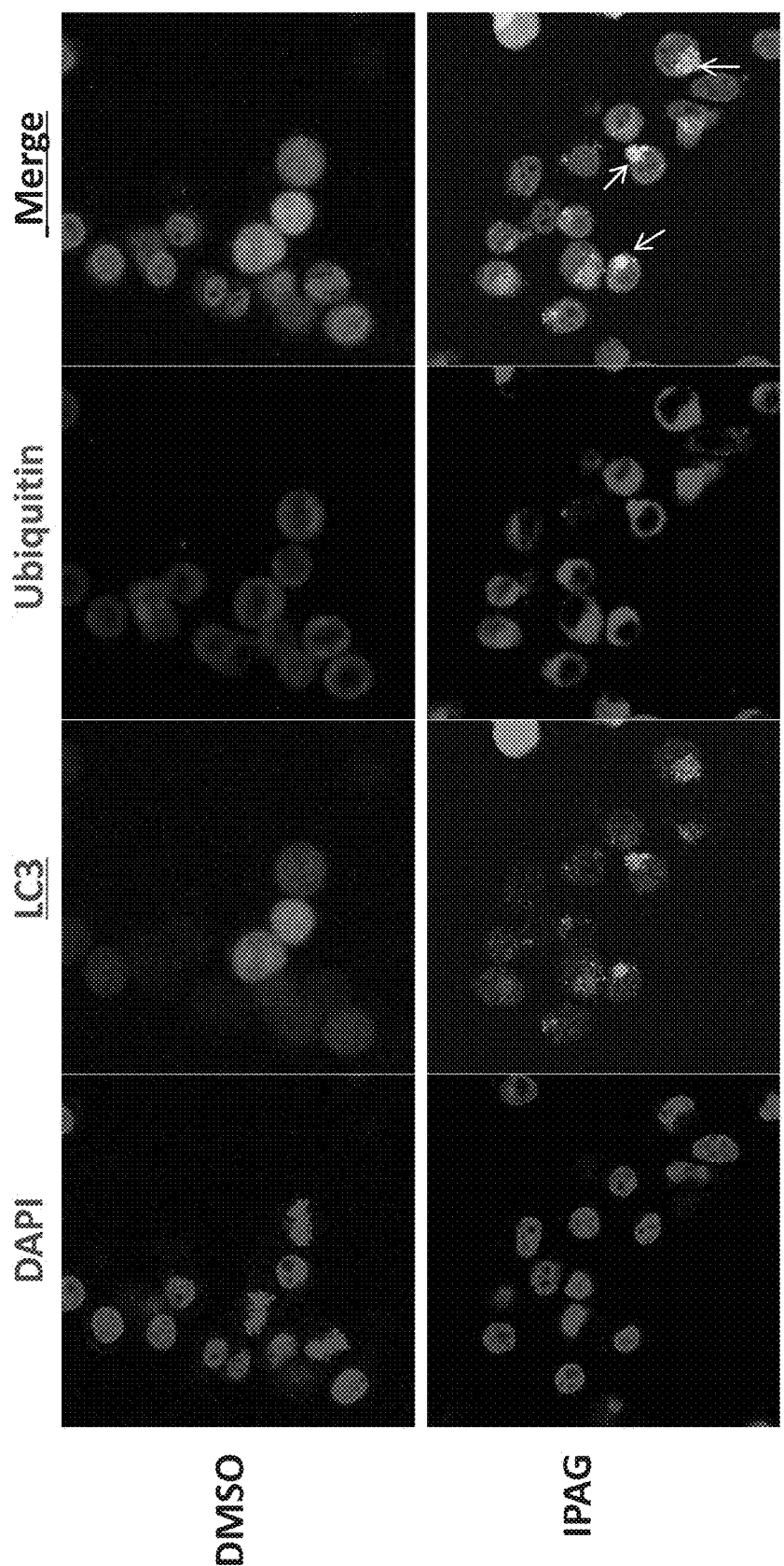

SIGMA RECEPTOR LIGANDS AND METHODS OF MODULATING CELLULAR PROTEIN HOMEOSTASIS USING SAME

CROSS-REFERENCE TO RELATED APPLICATIONS

The present application is a 35 U.S.C. §371 national phase application of, and claims priority to, PCT Application No. PCT/US2013/051110, filed Jul. 18, 2013, which claims priority under 35 U.S.C. §119(e) to U.S. Provisional Patent Application No. 61/673,565, filed Jul. 19, 2012, all of which applications are incorporated herein by reference in their entireties.

BACKGROUND OF THE INVENTION

In eukaryotic cells the endoplasmic reticulum (ER) is the primary site of synthesis, folding, and assembly of secreted and integral membrane proteins and their macromolecular complexes (Mu et al., 2008, Cell 134:769-781; Marciniak et al., 2006, Physiol. Rev. 2006:1133-1149; Ron et al., 2007, Nat. Rev. Mol. Cell Biol. 519-529). Maintenance of ER protein homeostasis relies on the timely convergence of multiple pathways that detect homeostatic protein concentration thresholds and control the ebb-and-flow of ER proteins (Mu et al., 2008, Cell 134:769-781; Marciniak et al, 2006, Physiol. Rev. 2006:1133-1149; Ron et al., 2007, Nat. Rev. Mol. Cell Biol. 519-529; Jonikas et al. 2009, Science 323:1693-1697). This process is driven by an intricate network of molecular chaperones and transcription factors. Disruption of ER homeostasis activates stress response pathways including the unfolded protein response (UPR) (Marciniak et al, 2006, Physiol. Rev. 2006:1133-1149; Ron et al., 2007, Nat. Rev. Mol. Cell Biol. 519-529; Kim et al., 2008, Nat. Rev. Drug Discov. 7:1013-1030; Xu et al., 2005, J. Clin. Invest. 2656-2664).

The mammalian UPR comprises at least two phases: an initial alarm phase, followed by a cytoprotective, adaptive phase in which UPR factors are upregulated to enhance the cellular capacity to process increased concentrations of unfolded protein (Marciniak et al, 2006, Physiol. Rev. 2006:1133-1149; Ron et al., 2007, Nat. Rev. Mol. Cell Biol. 519-529; Kim et al., 2008, Nat. Rev. Drug Discov. 7:1013-1030; Xu et al., 2005, J. Clin. Invest. 2656-2664). Imbalanced or altered capacity to respond to ER stress has been implicated in various diseases and disorders (Marciniak et al, 2006, Physiol. Rev. 2006:1133-1149; Kim et al., 2008, Nat. Rev. Drug Discov. 7:1013-1030; Ma et al., 2004, Nat. Rev. Cancer 4:966-977). Protracted ER stress can overwhelm the UPR, leading to autophagy as a secondary survival response (Ron et al., 2007, Nat. Rev. Mol. Cell Biol. 519-529; Bernales et al., 2006, PLoS Biol. 4:e423; Ogata et al., 2006, Mol. Cell Biol. 26:9220-9231; Yorimitsu et al., 2006, J. Biol. Chem. 281: 30299-30304). Although the relationship between ER stress, unfolded protein response, and autophagy remains unclear, growing evidence suggests that these responses are likely integrated signaling pathways that modulate cell survival and growth (Ron et al., 2007, Nat. Rev. Mol. Cell Biol. 519-529, He et al., 2009, Annu. Rev. Genet. 43:67-93, Hoyer-Hansen et al., 2007, Cell Death Differ. 14:1576-1582).

Autophagy describes a set of bulk cellular degradation pathways in which large aggregates of misfolded proteins and damaged cellular components, including damaged organelles, are sequestered into membrane bound vesicles called autophagosomes and subsequently targeted for lysosomal degradation (He et al., 2009, Annu. Rev. Genet. 43:67-93; Levine et al., 2004, Dev. Cell 6:463-477). Complete autophagy comprises autophagosome fusion with lysosomes to form autolysosomes, wherein the sequestered proteins and lipids are subsequently degraded by autophagic degradation or flux (He et al., 2009, Annu. Rev. Genet. 43:67-93; Levine et al., 2004, Dev. Cell 6:463-477). Autophagy occurs under basal conditions in many tissues and is involved in cellular differentiation and development. It is also activated or hyperactivated in conditions of nutrient starvation and cellular stress (Levine et al., 2004, Dev. Cell 6:463-477, Mizushima et al., 2008, Nature 451:1069-1075), to maintain energy levels and to sequester and remove damaged and cytotoxic cellular components (Levine et al., 2004, Dev. Cell 6:463-477; Mizushima et al., 2008, Nature 451:1069-1075). Thus, autophagy plays important roles in cellular homeostasis and disease prevention, and defective autophagy has been implicated in neurodegenerative disease and cancer (Levine et al., 2008, Cell 132:27-42; Mizushima et al., 2008, Nature 451: 1069-1075; White et al., 2009, Clin. Cancer Res. 15:5308-5316).

Autophagy has been shown to influence tumor cell growth and tumorigenesis (Levine et al., 2008, Cell 132:27-42; White et al., 2009, Clin. Cancer Res. 15:5308-5316; Degenhardt et al., 2006, Cancer Cell 10:304-312; Mathew et al., 2007, Nat. Rev. Cancer 7:961-967). Autophagy may serve a cytoprotective role in cancer cells (Levine et al., 2008, Cell 132:27-42; Mizushima et al., 2008, Nature 451:1069-1075; White et al., 2009, Clin. Cancer Res. 15:5308-5316; Degenhardt et al., 2006, Cancer Cell 10:304-312). Several antineoplastic agents have been shown to induce autophagy (Rubinsztein et al., 2007, Rev. Drug Discov. 6:304-312). However, in many cases it remains unclear whether cell death occurs by autophagy, whether cell death is associated with autophagy, or whether autophagy is a survival response to cytotoxic chemotherapy (Levine et al., 2004, Dev. Cell 6:463-477; Levine et al., 2008, Cell 132:27-42; White et al., 2009, Clin. Cancer Res. 15:5308-5316; Hippert et al., 2006, Cancer Res. 66:9349-9351). Emerging data suggest that autophagy participates in integrated responses to cellular stress that determine cell death versus survival. The proteins and pathways that regulate these integrated stress responses are just beginning to be defined (Ron et al., 2007, Nat. Rev. Mol. Cell Biol. 519-529; Kim et al., 2008, Nat. Rev. Drug Discov. 7:1013-1030, Levine et al., 2004, Dev. Cell 6:463-477; Rubinsztein et al., 2006, Neuron 54:9349-9351).

Sigma receptors, first proposed 30 years ago (Martin et al., 1976, J. Pharmacol. Exp. Ther. 197:517-532), are distinct from classical opioid receptors (Su, 1982, J. Pharmacol. Exp. Ther. 223:284-290). Binding studies suggest at least two Sigma receptor subtypes, of which only the Sigma receptor (hereinafter "Sigma1") has been cloned, whereas the identity of Sigma2 remains unclear (Hanner et al., 1996, Proc. Natl. Acad. Sci. U.S.A. 93:8072-8077; Vilner et al., 1995, Cancer Res. 55:408-413). Sigma1 is highly conserved among mammals (greater than 80% amino acid identity), but shares no significant homology with any traditional receptor family or other mammalian protein (White et al., 2009, Clin. Cancer Res. 15:5308-5316; Mathew, et al., 2007, Nat. Rev. Cancer 7:961-967). Cloned Sigma1 is a 26 kilodalton integral membrane protein (Hanner et al., 1996, Proc. Natl. Acad. Sci. U.S.A. 93:8072-8077; Pal et al., 2007, Mol. Pharmacol. 72:921-933; Aydar et al., 2007, Neuron 34:399-410; Hayashi et al., 2007, Cell 131:596-610). It is found primarily in the ER, and can translocate to the plasma membrane, other organelles, and endoplasmic membrane microdomains (Hanner et al., 1996, Proc. Natl. Acad. Sci. U.S.A. 93:8072-8077; Aydar et al., 2007, Neuron 34:399-410; Hayashi et al., 2007, Cell 131:596-610; Hayashi et al., 2003, J. Pharmacol. Exp. Ther. 306:718-725; Palmer et al., 2007, Cancer Res. 67:11166-11175). Sigma receptors are highly expressed in tumor cell lines, including prostate and breast adenocarcinoma (Vilner et al., 1995, Cancer Res. 55:408-413; Berthosis et al., 2003, Br. J. Cancer 88:438-446; Piergentili et al., J. Med. Chem. 53:1261-1269). Some Sigma ligands are reported as antitumor agents (Berthosis et al., 2003, Br. J. Cancer 88:438-446; Vilner et al., 1995, J. Neurosci. 15:117-134). Interestingly, putative Sigma antagonists, but not agonists, inhibit prostate carcinoma proliferation in vitro and inhibit tumor growth in tumor xenograft experiments (Berthosis et al., 2003, Br. J. Cancer 88:438-446; Spruce et al., 2004, Cancer Res. 64:4875-4886). Recent work has described Sigma ligand-induced cell death by lysosomal destabilization and oxidative stress.

There are numerous examples of clinically used compounds that bind Sigma1 with high affinity and thus are considered Sigma1 ligands, such as haloperidol, a widely used antipsychotic that also binds D2 receptors with similar affinity and whose anti-psychotic properties are primarily understood as D2 mediated (Seeman, et al., 1975, Science 188:1217-1219; Seeman et al., 1976, Nature 261:717-719), and the hallucinogen N,N-dimethyltryptamine, hypothesized to be an endogenous Sigma1 regulator (Fontanilla et al., 2009, Science 323:934-937). Sigma receptors have proved to be highly attractive pharmacological targets for the treatment of various pathologies, such as neuropathic pain (de la Puente et al., 2009, Pain 145:294-303), depression (Skuza, 2003, Pol. J. Pharmacol. 55:923-934), cocaine abuse (Matsumoto et al., 2003, Eur. J. Pharmacol. 469:1-12), epilepsy (Lin et al., 1997, Med. Res. Rev. 17:537-572), psychosis (Rowley et al., 2001, J. Med. Chem. 44:477-501), and Alzheimer's and Parkinson's disease (Maurice et al., 1997, Prog. Neuro-Psychopharmacol. Biol. Psychiatry 21:69-102; Marrazzo et al., 2005, NeuroReport 16:1223-1226). Recent reports demonstrate a genetic link between the Sigma1 receptor gene (SIGMAR1) and Amyotrophic lateral sclerosis (ALS) (Al-Saif et al., 2011, Ann Neurol. 70(6):913-9), as well as Frontotemporal Lobar Degeneration (FTLD) (Luty et al., 2010, Ann Neurol. 2010 68(5):639-49). Moreover, Sigma1 antagonists and Sigma2 agonists may be useful as anticancer agents and selective tumor imaging agents (Akhter et al., 2008, Nucl. Med. Biol. 35:29-34; Tu et al., 2007, J. Med. Chem. 50:3194-3204).

Sigma1 can function as a molecular chaperone at the ER-mitochondrion interface at least in certain model cell lines (Hayashi & Su, 2007, Cell 131(3):596-610). However, the physiological role of Sigma receptors as well as their role in neurodegenerative disease and cancer remains unclear. In vitro, treatment with a Sigma antagonist results in apoptotic cell death following prolonged treatment, with Sigma ligand time-action and dose-response, depending on the Sigma antagonist and cell line (Berthosis et al., 2003, Br. J. Cancer 88:438-446; Piergentili et al., J. Med. Chem. 53:1261-1269; Spruce et al., 2004, Cancer Res. 64:4875-4886; Vilner et al., 1995, J. Neurosci. 15:117-134). Yet, a mechanistic understanding of the Sigma1 receptor system remains elusive.

Most prostate cancer patients become unresponsive to initially effective hormone- and chemotherapy as prostate tumor cells eventually adapt and develop resistance. Treatment with Sigma antagonists leads to apoptotic cell death of both androgen-sensitive and androgen-insensitive prostate cancer cells (Berthosis et al., 2003, Br. J. Cancer 88:438-446; Spruce et al., 2004, Cancer Res. 64:4875-4886). Although some insight has been gained into how prostate cancer cells develop such resistance, currently there are few alternatives to treat hormone refractory (castration resistant) prostate cancer. Emerging therapies to treat intractable, advanced prostate cancers target protein processing and chaperone pathways that maintain prostate tumor growth and survival.

There is a need in the art to identify compounds useful in the treatment of intractable, advanced cancers. Such compounds may target protein processing, protein synthesis, protein folding, protein transport, protein localization, protein assembly into functional macromolecular complexes, and related chaperone pathways, all of which may help maintain tumor growth, survival and metastasis. The present invention addresses this unmet need.

BRIEF SUMMARY OF THE INVENTION

The present invention includes a composition comprising at least one compound selected from the group consisting of:
(i) a compound of Formula (I):

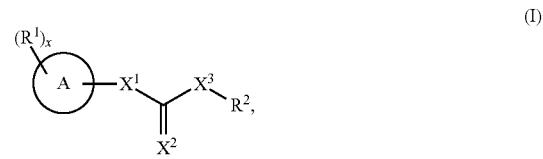

wherein:
ring A is a monocyclic or bicyclic aryl or a monocyclic or bicyclic heteroaryl ring, and wherein the aryl or heteroaryl ring is optionally substituted with 0-4 $R^1$ groups;
each occurrence of $R^1$ is independently selected from the group consisting of —$C_1$-$C_6$ alkyl, —$C_1$-$C_6$ fluoroalkyl, —$C_1$-$C_6$ heteroalkyl, F, Cl, Br, I, —CN, —$NO_2$, —$OR^3$, —$SR^3$, —S(=O)$R^3$, —S(=O)$_2R^3$, —NHS(=O)$_2R^3$, —C(=O)$R^3$, —OC(=O)$R^3$, —$CO_2R^3$, —$OCO_2R^3$, —CH($R^3$)$_2$, —N($R^3$)$_2$, —C(=O)N($R^3$)$_2$, —OC(=O)N($R^3$)$_2$, —NHC(=O)NH($R^3$), —NHC(=O)$R^3$, —NHC(=O)$OR^3$, —C(OH)($R^3$)$_2$, and —C($NH_2$)($R^3$)$_2$;
each occurrence of $R^2$ is independently selected from the group consisting of H, $C_1$-$C_6$ alkyl, $C_1$-$C_6$ heteroalkyl, and —$C_1$-$C_3$ alkyl-($C_3$-$C_6$ cycloalkyl), wherein the alkyl, heteroalkyl or cycloalkyl group is optionally substituted with 0-5 $R^1$ groups, or $X^3$ and $R^2$ combine to form a ($C_3$-$C_7$)heterocycloalkyl group, optionally substituted with 0-2 $R^1$ groups;
each occurrence of $R^3$ is independently selected from the group consisting of H, $C_1$-$C_6$ alkyl, $C_1$-$C_6$ heteroalkyl, aryl, and —$C_1$-$C_3$ alkyl-($C_3$-$C_6$ cycloalkyl), wherein the alkyl, heteroalkyl, aryl, or cycloalkyl group is optionally substituted with 0-5 $R^1$ groups;
$X^1$ is —$CH_2$—, —S—, —O— or —(NR$^2$)—;
$X^2$ is —$CH_2$, =S, =O or =NR$^2$; and
$X^3$ is —S—, —O—, or —NR$^2$—; and
(ii) a compound of Formula (II):

wherein;
$R^A$ is selected from the group consisting of

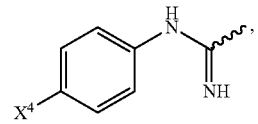

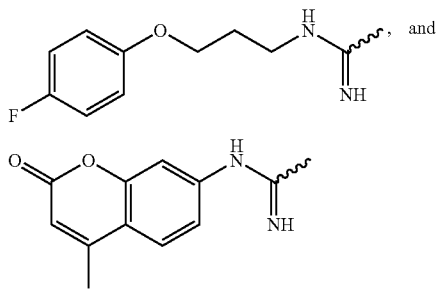

$X^4$ is selected from the group consisting of F, Cl, Br, and I; and $R^B$ is selected from the group consisting of:

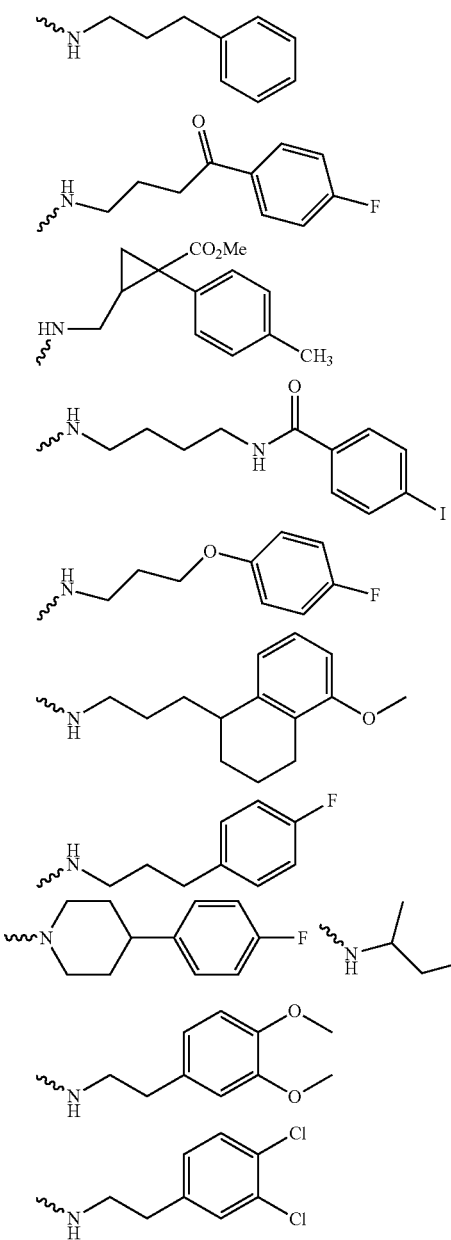

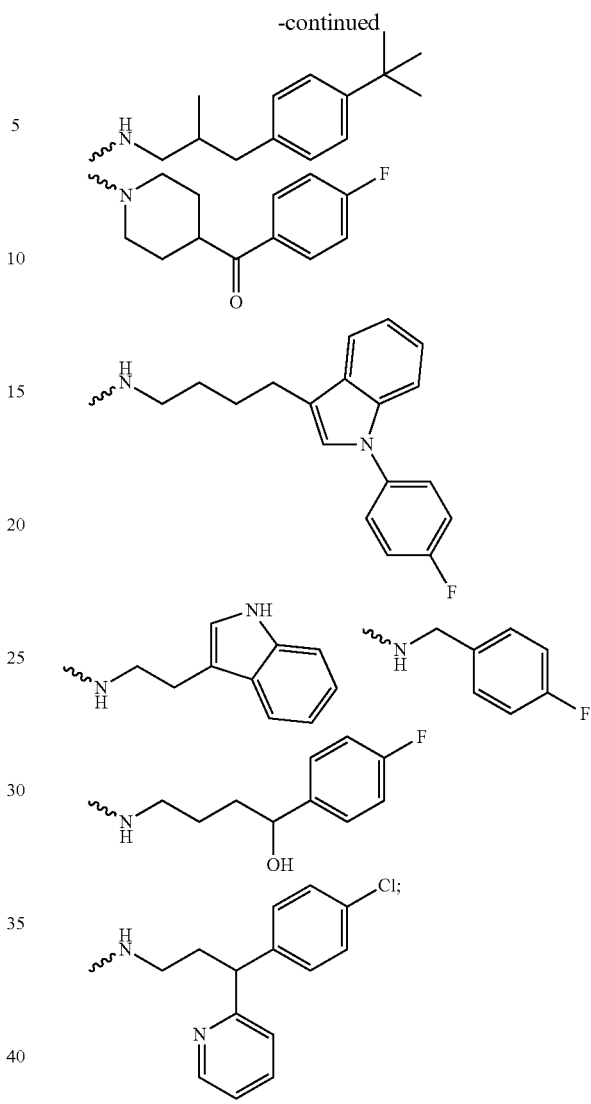

(iii) a salt, solvate, or N-oxide thereof; and any combinations thereof.

In one embodiment, in Formula (I) ring A is a monocyclic aryl or monocyclic heteroaryl ring optionally substituted with 0-4 $R^1$ groups. In another embodiment, in Formula (I) ring A is phenyl optionally substituted with 0-4 $R^1$ groups. In yet another embodiment, in Formula (I) $X^1$ and $X^3$ are both —NH—, and $X^2$ is =NH.

In yet another embodiment, the compound of Formula (I) is selected from the group consisting of 1-(3-(4-fluorophenoxy)propyl)-3-(4-iodophenyl)guanidine (Compound A), 1-(3-(4-fluorophenoxy)propyl)-3-(4-methoxyphenyl)guanidine (Compound B), 1-(n-propyl)-3-(4-iodophenyl)guanidine (Compound C), 1-(n-propyl)-3-(4-methoxyphenyl)guanidine (Compound D), 1-(3-(4-fluorophenoxy)propyl)-3-(4-trifluoromethylphenyl)guanidine (Compound F), 1-(3-(4-fluorophenoxy)propyl)-3-(4-chlorophenyl)guanidine (Compound G), a salt, solvate or N-oxide thereof, and any combinations thereof.

In yet another embodiment, the compound of Formula (II) is selected from the group consisting of, 1,3-bis(3-(4-fluorophenoxy)propyl)guanidine (Compound E), 1-(3-(4-fluorophenoxy)propyl)-3-(4-methyl-2-oxo-2H-chromen-7-yl)guanidine) (Compound H), a salt, solvate or N-oxide thereof, and any combinations thereof.

The present invention also includes a composition comprising at least one compound of Formula (III):

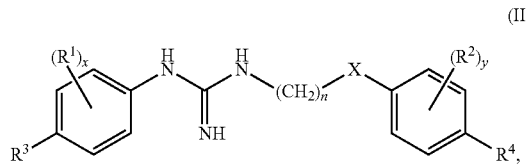

wherein within Formula (III);

each occurrence of $R^1$ and $R^2$ is independently selected from the group consisting of —$C_1$-$C_6$ alkyl, —$C_1$-$C_6$ fluoroalkyl, —$C_1$-$C_6$ heteroalkyl, F, Cl, Br, I, —CN, —$NO_2$, —$OR^5$, —$SR^5$, —S(=O)$R^5$, —S(=O)$_2R^5$, —NHS(=O)$_2R^5$, —C(=O)$R^5$, —OC(=O)$R^5$, —$CO_2R^5$, —$OCO_2R^5$, —CH($R^5$)$_2$, —N($R^5$)$_2$, —C(=O)N($R^5$)$_2$, —OC(=O)N($R^5$)$_2$, —NHC(=O)NH($R^5$), —NHC(=O)$R^5$, —NHC(=O)$OR^5$, —C(OH)($R^5$)$_2$, and —C($NH_2$)($R^5$)$_2$;

$R^3$ is selected from the group consisting of —$C_1$-$C_6$ alkyl, —$C_1$-$C_6$ fluoroalkyl, —$C_1$-$C_6$ alkoxy, F, Cl, Br, and I;

$R^4$ is selected from the group consisting of —$C_1$-$C_6$ alkyl, —$C_1$-$C_6$ alkoxy, F, Cl, Br, and I;

each occurrence of $R^5$ is independently selected from the group consisting of H, $C_1$-$C_6$ alkyl, $C_1$-$C_6$ heteroalkyl, aryl, and —$C_1$-$C_3$ alkyl-($C_3$-$C_6$ cycloalkyl), wherein the alkyl, heteroalkyl, aryl, or cycloalkyl group is optionally substituted;

X is selected from the group consisting of $CH_2$, C=O, or O;

n is an integer from 1-3;

x is an integer from 0-4; and y is an integer from 0-4;

a salt, solvate, or N-oxide thereof, and any combinations thereof.

In one embodiment, the compound of Formula (III) is selected from the group consisting of 1-(3-(4-fluorophenoxy)propyl)-3-(4-iodophenyl)guanidine (Compound A), 1-(3-(4-fluorophenoxy)propyl)-3-(4-methoxyphenyl)guanidine (Compound B), 1-(3-(4-fluorophenoxy)propyl)-3-(4-trifluoromethylphenyl)guanidine (Compound F), 1-(3-(4-fluorophenoxy)propyl)-3-(4-chlorophenyl)guanidine (Compound G), a salt, solvate or N-oxide thereof, and any combinations thereof.

The compositions of the present invention may include certain embodiments. In one embodiment, the composition further comprises a pharmaceutically acceptable carrier. In another embodiment, the composition further comprises at least one additional therapeutic agent that inhibits the ubiquitin proteasome system (UPS) or autophagic survival pathway. In yet another embodiment, the therapeutic agent is selected from the group consisting of growth factor receptor inhibitors, monoclonal antibodies against growth factor receptors, hormone receptor antagonists, autophagy modulators, ER stress response inhibitors, proteasome inhibitors, p97/VCP inhibitors and any combinations thereof.

In yet another embodiment, the therapeutic agent is selected from the group consisting of octapeptide, somatostatin, analoguem, lanreotide, angiopeptin, dermopeptin, octreotide, pegvisomant, 3-methyladenine, chloroquine, hydroxychloroquine, wortmannin, eeyarestatin I, salubrinal, versipelostatin, 2H-isoindole-2-carboxylic acid, 4-fluoro-1,3-dihydro-, (2R,6S,12Z,13aS,14aR,16aS)-14a-[[(cyclopropylsulfonyl)amino]carbonyl]-6-[[(1,1-dimethylethoxy)carbonyl]amino]-1,2,3,5,6,7,8,9,10,11,13a,14,14a,15,16,16a-hexadecahydro-5,16-dioxocyclopropa[e]pyrrolo[1,2-a][1,4]diazacyclopentadecin-2-yl ester (Danoprevir), adamantane-acetyl-(6-aminohexanoyl)3-(leucinyl)3-vinyl-(methyl)-sulfone, N-acetyl-L-leucyl-L-leucyl-L-methional, N-[(phenylmethoxy)carbonyl]-L-leucyl-N-[(1S)-1-formyl-3-methylbutyl]-L-leucinamide, (2R,3S,4R)-3-hydroxy-2-[(1S)-1-hydroxy-2-methylpropyl]-4-methyl-5-oxo-2-pyrrolidinecarboxy-N-acetyl-L-cysteine thioester, N—[N—(N-acetyl-L-leucyl)-L-leucyl]-L-norleucine, lactacystin, 4-(2-aminoethyl)benzenesulfonyl fluoride hydrochloride, (S)-1-carboxy-2-phenyl]-carbamoyl-arg-val-arginal, bovine pancreatic trypsin inhibitor, [(2S,2R)-3-amino-2-hydroxy-4-phenylbutanoyl]-L-leucine, N—[(S)-1-carboxy-isopentyl)-carbamoyl-alpha-(2-iminohexahydro-4-(S)-pyrimidyl]-L-glycyl-L-phenylalaninal, ethylenediamine-tetraacetic acid disodium salt dehydrate, acetyl-leucyl-leucyl-arginal, isovaleryl-val-val-AHMHA-ala-AHMHA where AHMHA=(3S,4S)-4-amino-3-hydroxy-6-methylheptanoic acid, N-alpha-L-rhamnopyranosyloxy (hydroxyphosphinyl)-L-leucyl-L-tryptophan, phenylmethanesulfonyl fluoride, bortezomib, carfilzomib, ONX 0912, NPI-0052, CEP-18770, MLN9708, disulfiram, epigallocatechin-3-gallate, salinosporamide A, PI3K inhibitors, lapatinib, rapamycin, rapalogs, HSP inhibitors, androgen receptor inhibitors, conjugation products of Sigma ligands with targeting components, a salt thereof, and any combinations thereof.

The present invention also includes a method of preventing, treating or ameliorating a Sigma receptor-related disorder or disease in a subject in need thereof. The method comprises administering to the subject an effective amount of a therapeutic composition comprising at least one compound selected from the group consisting of:

(i) a compound of Formula (I):

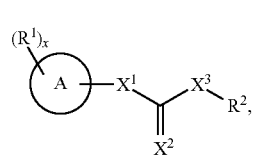

wherein:

ring A is a monocyclic or bicyclic aryl or a monocyclic or bicyclic heteroaryl ring, and wherein the aryl or heteroaryl ring is optionally substituted with 0-4 $R^1$ groups;

each occurrence of $R^1$ is independently selected from the group consisting of —$C_1$-$C_6$ alkyl, —$C_1$-$C_6$ fluoroalkyl, —$C_1$-$C_6$ heteroalkyl, F, Cl, Br, I, —CN, —$NO_2$, —$OR^3$, —$SR^3$, —S(=O)$R^3$, —S(=O)$_2R^3$, —NHS(=O)$_2R^3$, —C(=O)$R^3$, —OC(=O)$R^3$, —$CO_2R^3$, —$OCO_2R^3$, —CH($R^3$)$_2$, —N($R^3$)$_2$, —C(=O)N($R^3$)$_2$, —OC(=O)N($R^3$)$_2$, —NHC(=O)NH($R^3$), —NHC(=O)$R^3$, —NHC(=O)$OR^3$, —C(OH)($R^3$)$_2$, and —C($NH_2$)($R^3$)$_2$;

each occurrence of $R^2$ is independently selected from the group consisting of H, $C_1$-$C_6$ alkyl, $C_1$-$C_6$ heteroalkyl, and —$C_1$-$C_3$ alkyl-($C_3$-$C_6$ cycloalkyl), wherein the alkyl, heteroalkyl or cycloalkyl group is optionally substituted with 0-5 $R^1$ groups, or $X^3$ and $R^2$ combine to form a ($C_3$-$C_7$)heterocycloalkyl group, optionally substituted with 0-2 $R^1$ groups;

each occurrence of $R^3$ is independently selected from the group consisting of H, $C_1$-$C_6$ alkyl, $C_1$-$C_6$ heteroalkyl, aryl, and —$C_1$-$C_3$ alkyl-($C_3$-$C_6$ cycloalkyl), wherein the alkyl, heteroalkyl, aryl, or cycloalkyl group is optionally substituted with 0-5 $R^1$ groups;

$X^1$ is —$CH_2$—, —S—, —O— or —(N$R^2$)—;

$X^2$ is =$CH_2$, =S, =O or =N$R^2$; and $X^3$ is —S—, —O—, or —N$R^2$—; and (ii) a compound of Formula (II):

$$R^A\text{—}R^B \quad (II),$$

wherein;

$R^A$ is selected from the group consisting of

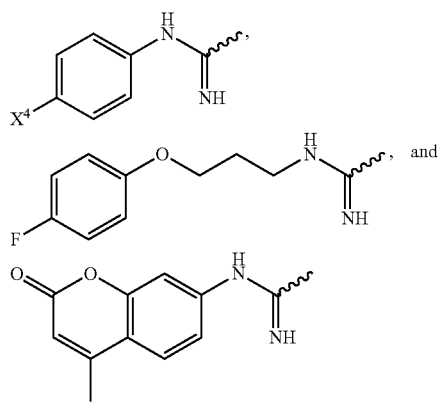

$X^4$ is selected from the group consisting of F, Cl, Br, and I; and $R^B$ is selected from the group consisting of:

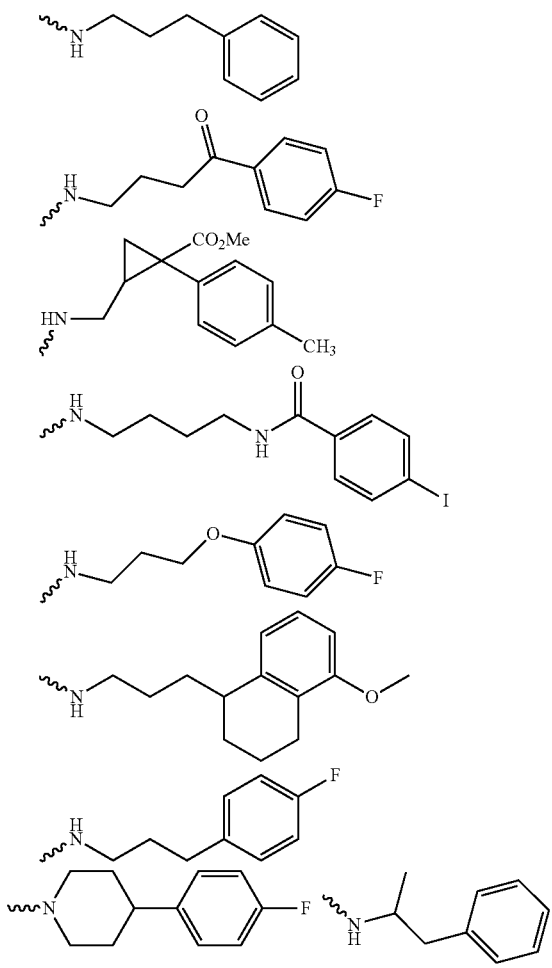

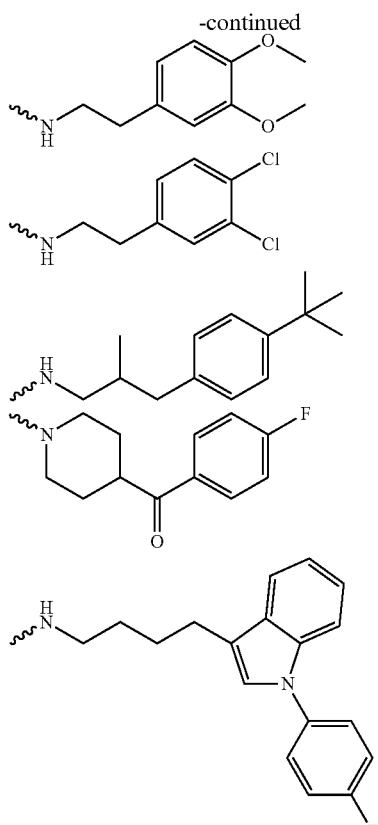

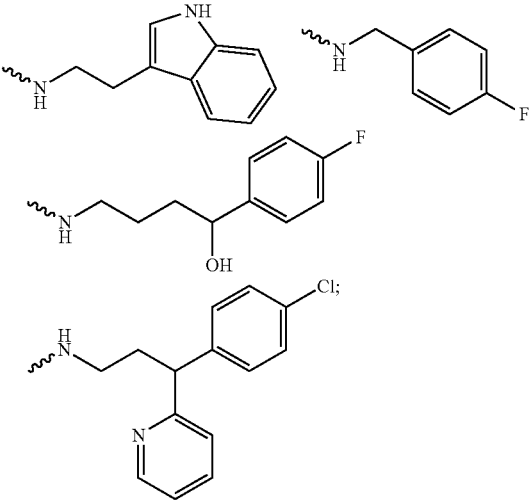

(iii) haloperidol, IPAG, PB28, rimcazole, BD1063, BD1047, PRE084, NE100, (+)-SKF10047, (+)-pentazocine,
(iv) a salt, solvate, or N-oxide thereof; and
any combinations thereof.

In one embodiment, the compound of Formula (I) is selected from the group consisting of 1-(3-(4-fluorophenoxy)propyl)-3-(4-iodophenyl)guanidine (Compound A), 1-(3-(4-fluorophenoxy)propyl)-3-(4-methoxyphenyl)guanidine (Compound B), 1-(n-propyl)-3-(4-iodophenyl)guanidine (Compound C), 1-(n-propyl)-3-(4-methoxyphenyl)guanidine (Compound D), 1-(3-(4-fluorophenoxy)propyl)-3-(4-trifluoromethylphenyl)guanidine (Compound F), 1-(3-(4-fluorophenoxy)propyl)-3-(4-chlorophenyl)guanidine (Compound G), a salt, solvate or N-oxide thereof, and any combinations thereof.

In one embodiment, the compound of Formula (II) is selected from the group consisting of, 1,3-bis(3-(4-fluorophenoxy)propyl)guanidine (Compound E), 1-(3-(4-fluorophenoxy)propyl)-3-(4-methyl-2-oxo-2H-chromen-7-yl) guanidine) (Compound H), a salt, solvate or N-oxide thereof, and any combinations thereof.

The present invention also includes a method of preventing, treating or ameliorating a Sigma receptor-related disorder or disease in a subject in need thereof. The method comprises administering to the subject an effective amount of a therapeutic composition comprising at least one compound selected from the group consisting of:

(i) a compound of Formula (III):

$$(III)$$

$$(R^1)_x \quad \underset{R^3}{\text{phenyl}} - \underset{H}{N} - \underset{NH}{\overset{\|}{C}} - \underset{H}{N} - (CH_2)_n - X - \underset{R^4}{\text{phenyl}} (R^2)_y$$

wherein within Formula (III);

each occurrence of $R^1$ and $R^2$ is independently selected from the group consisting of —$C_1$-$C_6$ alkyl, —$C_1$-$C_6$ fluoroalkyl, —$C_1$-$C_6$ heteroalkyl, F, Cl, Br, I, —CN, —$NO_2$, —$OR^5$, —$SR^5$, —S(=O)$R^5$, —S(=O)$_2R^5$, —NHS(=O)$_2R^5$, —C(=O)$R^5$, —OC(=O)$R^5$, —$CO_2R^5$, —$OCO_2R^5$, —CH($R^5$)$_2$, —N($R^5$)$_2$, —C(=O)N($R^5$)$_2$, —OC(=O)N($R^5$)$_2$, —NHC(=O)NH($R^5$), —NHC(=O)$R^5$, —NHC(=O)O$R^5$, —C(OH)($R^5$)$_2$, and —C($NH_2$)($R^5$)$_2$;

$R^3$ is selected from the group consisting of —$C_1$-$C_6$ alkyl, —$C_1$-$C_6$ fluoroalkyl, —$C_1$-$C_6$ alkoxy, F, Cl, Br, and I;

$R^4$ is selected from the group consisting of —$C_1$-$C_6$ alkyl, —$C_1$-$C_6$ alkoxy, F, Cl, Br, and I;

each occurrence of $R^5$ is independently selected from the group consisting of H, $C_1$-$C_6$ alkyl, $C_1$-$C_6$ heteroalkyl, aryl, and —$C_1$-$C_3$ alkyl-($C_3$-$C_6$ cycloalkyl), wherein the alkyl, heteroalkyl, aryl, or cycloalkyl group is optionally substituted;

X is selected from the group consisting of $CH_2$, C=O, or O;

n is an integer from 1-3;

x is an integer from 0-4; and y is an integer from 0-4;

(ii) haloperidol, IPAG, PB28, rimcazole, BD1063, BD1047, PRE084, NE100, (+)-SKF10047, (+)-pentazocine;

(iii) a salt, solvate, or N-oxide thereof; and any combinations thereof.

In one embodiment, the compound of Formula (III) is selected from the group consisting of 1-(3-(4-fluorophenoxy)propyl)-3-(4-iodophenyl)guanidine (Compound A), 1-(3-(4-fluorophenoxy)propyl)-3-(4-methoxyphenyl)guanidine (Compound B), 1-(3-(4-fluorophenoxy)propyl)-3-(4-trifluoromethylphenyl)guanidine (Compound F), 1-(3-(4-fluorophenoxy)propyl)-3-(4-chlorophenyl)guanidine (Compound G), a salt, solvate or N-oxide thereof, and any combinations thereof.

The methods of the present invention may include certain embodiments. In one embodiment, the Sigma receptor-related disease or disorder is selected from the group comprising cancer, neuropathic pain, depression, substance abuse, epilepsy, psychosis, Alzheimer's disease, Parkinson's disease, frontotemporal lobar degeneration, amyotrophic lateral sclerosis, and any combinations thereof. In another embodiment, the cancer is selected from the group consisting of prostate cancer, liver cancer, pancreas cancer, CNS tumors, breast cancer, neuroblastoma, leukemia, and any combinations thereof. In yet another embodiment, the disease or disorder is cancer and further wherein the administering of the therapeutic composition to the subject causes degradation of at least one growth factor receptor in the subject's cancer. In yet another embodiment, the cancer comprises breast cancer or prostate cancer. In yet another embodiment, the prostate cancer comprises castrate-sensitive or castrate-insensitive prostate cancer. In yet another embodiment, the at least one growth factor receptor comprises EGFR, HER2, HER3, p95HER2, androgen receptor, and any combinations thereof. In yet another embodiment, the Sigma receptor is Sigma1. In yet another embodiment, the subject is a mammal. In yet another embodiment, the mammal is a human.

The present invention also includes a method of preventing, treating or ameliorating a Sigma receptor-related disorder or disease in a subject in need thereof. The method comprises administering to the subject an effective amount of a Sigma receptor-modulating compound, wherein the method further comprises administering to the subject at least one additional therapeutic agent that inhibits the ubiquitin proteasome system (UPS) or autophagic survival pathway.

In one embodiment, the Sigma receptor-modulating compound is a Sigma receptor antagonist. In another embodiment, the Sigma receptor is Sigma1. In yet another embodiment, the Sigma receptor-modulating compound and the additional therapeutic agent are co-administered. In yet another embodiment, the Sigma receptor-modulating compound and the additional therapeutic agent are co-formulated. In yet another embodiment, the Sigma receptor-modulating compound and the additional therapeutic agent are administered at separate times. In yet another embodiment, administering the Sigma receptor-modulating compound to the subject allows for administering a lower dose of the therapeutic agent to the subject, as compared to the dose of the therapeutic agent alone that is required to achieve similar results in preventing, treating or ameliorating the Sigma receptor-related disorder or disease in the subject. In yet another embodiment, the Sigma-receptor related disorder or disease is cancer. In yet another embodiment, the cancer is selected from the group consisting of prostate cancer, liver cancer, pancreas cancer, breast cancer, neuroblastoma, CNS tumors, leukemia, and any combinations thereof In one embodiment, the Sigma receptor-modulating compound is selected from the group consisting of:

(i) a compound of Formula (I):

$$(I)$$

$$(R^1)_x \quad \underset{}{\text{A}} - X^1 - \underset{X^2}{\overset{X^3}{\|}} - R^2,$$

wherein:

ring A is a monocyclic or bicyclic aryl or a monocyclic or bicyclic heteroaryl ring, and wherein the aryl or heteroaryl ring is optionally substituted with 0-4 $R^1$ groups;

each occurrence of $R^1$ is independently selected from the group consisting of —$C_1$-$C_6$ alkyl, —$C_1$-$C_6$ fluoroalkyl, —$C_1$-$C_6$ heteroalkyl, F, Cl, Br, I, —CN, —$NO_2$, —$OR^3$, —$SR^3$, —S(=O)$R^3$, —S(=O)$_2R^3$, —NHS(=O)$_2R^3$, —C(=O)$R^3$, —OC(=O)$R^3$, —$CO_2R^3$, —$OCO_2R^3$, —CH($R^3$)$_2$, —N($R^3$)$_2$, —C(=O)N($R^3$)$_2$, —OC(=O)N($R^3$)$_2$, —NHC(=O)NH($R^3$), —NHC(=O)$R^3$, —NHC(=O)O$R^3$, —C(OH)($R^3$)$_2$, and —C(NH$_2$)($R^3$)$_2$;

each occurrence of $R^2$ is independently selected from the group consisting of H, $C_1$-$C_6$ alkyl, $C_1$-$C_6$ heteroalkyl, and —$C_1$-$C_3$ alkyl-($C_3$-$C_6$ cycloalkyl), wherein the alkyl, heteroalkyl or cycloalkyl group is optionally substituted with 0-5 $R^1$ groups, or $X^3$ and $R^2$ combine to form a ($C_3$-$C_7$)heterocycloalkyl group, optionally substituted with 0-2 $R^1$ groups;

each occurrence of $R^3$ is independently selected from the group consisting of H, $C_1$-$C_6$ alkyl, $C_1$-$C_6$ heteroalkyl, aryl, and —$C_1$-$C_3$ alkyl-($C_3$-$C_6$ cycloalkyl), wherein the alkyl, heteroalkyl, aryl, or cycloalkyl group is optionally substituted with 0-5 $R^1$ groups;

$X^1$ is —CH$_2$—, —S—, —O— or —(N$R^2$)—;
$X^2$ is =CH$_2$, =S, =O or =N$R^2$; and
$X^3$ is —S—, —O—, or —N$R^2$—; and (ii) a compound of Formula (II):

$$R^A—R^B \quad (II),$$

wherein;

$R^A$ is selected from the group consisting of

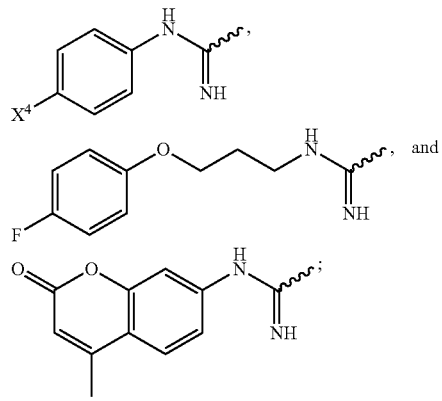

$X^4$ is selected from the group consisting of F, Cl, Br, and I; and $R^B$ is selected from the group consisting of:

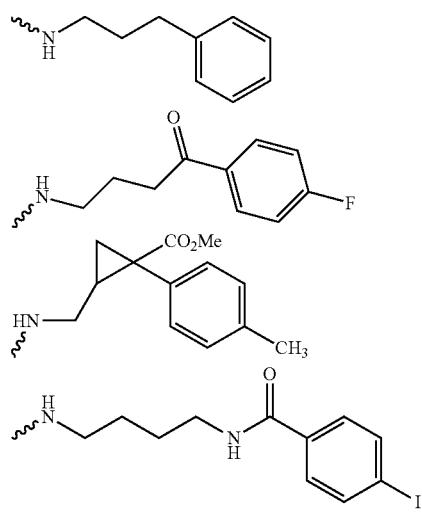

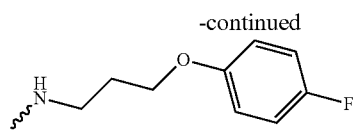
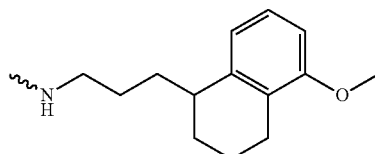
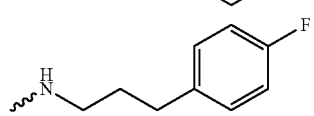
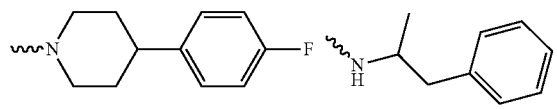
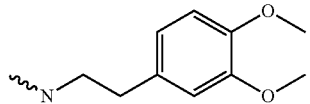
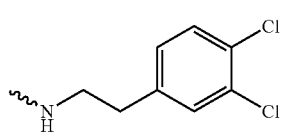
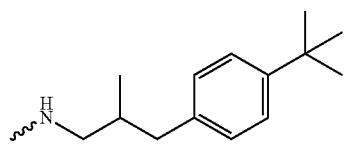
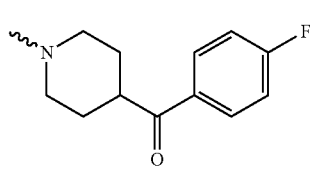
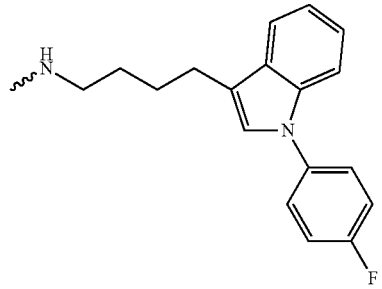
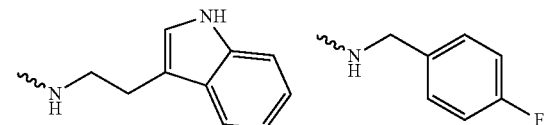
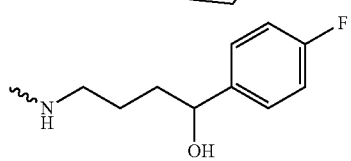

-continued

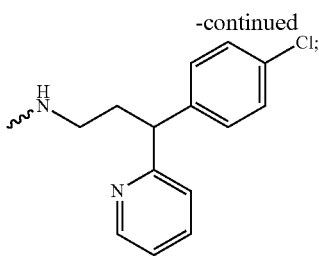

(iii) haloperidol, IPAG, PB28, rimcazole, BD1063, BD147, PRE084, NE100, (+)-SKF10047, (+)-pentazocine;
(iv) a salt, solvate, or N-oxide thereof; and
any combinations thereof.

In another embodiment, the compound of Formula (I) is selected from the group consisting of 1-(3-(4-fluorophenoxy) propyl)-3-(4-iodophenyl)guanidine (Compound A), 1-(3-(4-fluorophenoxy)propyl)-3-(4-methoxyphenyl)guanidine (Compound B), 1-(n-propyl)-3-(4-iodophenyl)guanidine (Compound C), 1-(n-propyl)-3-(4-methoxyphenyl)guanidine (Compound D), 1-(3-(4-fluorophenoxy)propyl)-3-(4-trifluoromethylphenyl)guanidine (Compound F), 1-(3-(4-fluorophenoxy)propyl)-3-(4-chlorophenyl)guanidine (Compound G), a salt, solvate or N-oxide thereof, and any combinations thereof.

In yet another embodiment, the compound of Formula (II) is selected from the group consisting of, 1,3-bis(3-(4-fluorophenoxy)propyl)guanidine (Compound E), 1-(3-(4-fluorophenoxy)propyl)-3-(4-methyl-2-oxo-2H-chromen-7-yl) guanidine) (Compound H), a salt, solvate or N-oxide thereof, and any combinations thereof.

In one embodiment, the Sigma receptor-modulating compound is selected from the group consisting of:
(i) a compound of Formula (III):

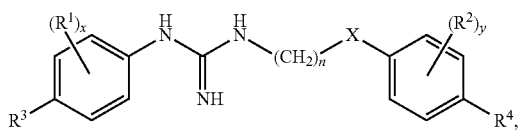

(III)

wherein within Formula (II);
each occurrence of $R^1$ and $R^2$ is independently selected from the group consisting of —$C_1$-$C_6$ alkyl, —$C_1$-$C_6$ fluoroalkyl, —$C_1$-$C_6$ heteroalkyl, F, Cl, Br, I, —CN, —$NO_2$, —$OR^5$, —$SR^5$, —S(=O)$R^5$, —S(=O)$_2R^5$, —NHS(=O)$_2R^5$, —C(=O)$R^5$, —OC(=O)$R^5$, —$CO_2R^5$, —$OCO_2R^5$, —CH($R^5$)$_2$, —N($R^5$)$_2$, —C(=O)N($R^5$)$_2$, —OC(=O)N($R^5$)$_2$, —NHC(=O)NH($R^5$), —NHC(=O)$R^5$, —NHC(=O)$OR^5$, —C(OH)($R^5$)$_2$, and —C($NH_2$)($R^5$)$_2$;
$R^3$ is selected from the group consisting of —$C_1$-$C_6$ alkyl, —$C_1$-$C_6$ fluoroalkyl, —$C_1$-$C_6$ alkoxy, F, Cl, Br, and I;
$R^4$ is selected from the group consisting of —$C_1$-$C_6$ alkyl, —$C_1$-$C_6$ alkoxy, F, Cl, Br, and I;
each occurrence of $R^5$ is independently selected from the group consisting of H, $C_1$-$C_6$ alkyl, $C_1$-$C_6$ heteroalkyl, aryl, and —$C_1$-$C_3$ alkyl-($C_3$-$C_6$ cycloalkyl), wherein the alkyl, heteroalkyl, aryl, or cycloalkyl group is optionally substituted;
X is selected from the group consisting of $CH_2$, C=O, or O;
n is an integer from 1-3;
x is an integer from 0-4; and
y is an integer from 0-4;

(ii) haloperidol, IPAG, PB28, rimcazole, BD1063, BD1047, PRE084, NE100, (+)-SKF10047, (+)-pentazocine;
(iii) a salt, solvate, or N-oxide thereof; and
any combinations thereof.

In one embodiment, the compound of Formula (III) is selected from the group consisting of 1-(3-(4-fluorophenoxy) propyl)-3-(4-iodophenyl)guanidine (Compound A), 1-(3-(4-fluorophenoxy)propyl)-3-(4-methoxyphenyl)guanidine (Compound B), 1-(3-(4-fluorophenoxy)propyl)-3-(4-trifluoromethylphenyl)guanidine (Compound F), 1-(3-(4-fluorophenoxy)propyl)-3-(4-chlorophenyl)guanidine (Compound G), a salt, solvate or N-oxide thereof, and any combinations thereof.

In one embodiment, the therapeutic agent is selected from the group consisting of growth factor receptor inhibitors, monoclonal antibodies against growth factor receptors, hormone receptor antagonists, autophagy modulators, ER stress response inhibitors, proteasome inhibitors, and any combinations thereof.

In one embodiment, the therapeutic agent is selected from the group consisting of octapeptide, somatostatin, analoguem, lanreotide, angiopeptin, dermopeptin, octreotide, pegvisomant, 3-methyladenine, chloroquine, hydroxychloroquine, wortmannin, eeyarestatin I, salubrinal, versipelostatin, 2H-isoindole-2-carboxylic acid, 4-fluoro-1,3-dihydro-, (2R, 6S,12Z,13aS,14aR,16aS)-14a-[[(cyclopropylsulfonyl) amino]carbonyl]-6-[[(1,1-dimethylethoxy)carbonyl]amino]-1,2,3,5,6,7,8,9,10,11,13a,14,14a,15,16,16a-hexadecahydro-5,16-dioxocyclopropa[e]pyrrolo[1,2-a][1,4] diazacyclopentadecin-2-yl ester (Danoprevir), adamantaneacetyl-(6-aminohexanoyl)3-(leucinyl)3-vinyl-(methyl)-sulfone, N-acetyl-L-leucyl-L-leucyl-L-methional, N-[(phenylmethoxy)carbonyl]-L-leucyl-N-[(1S)-1-formyl-3-methylbutyl]-L-leucinamide, (2R,3S,4R)-3-hydroxy-2-[(1S)-1-hydroxy-2-methylpropyl]-4-methyl-5-oxo-2-pyrrolidinecarboxy-N-acetyl-L-cysteine thioester, N—[N—(N-acetyl-L-leucyl)-L-leucyl]-L-norleucine, lactacystin, 4-(2-aminoethyl)benzenesulfonyl fluoride hydrochloride, (S)-1-carboxy-2-phenyl]-carbamoyl-arg-val-arginal, bovine pancreatic trypsin inhibitor, [(2S,2R)-3-amino-2-hydroxy-4-phenylbutanoyl]-L-leucine, N—[(S)-1-carboxy-isopentyl]-carbamoyl-alpha-(2-iminohexahydro-4-(S)-pyrimidyl]-L-glycyl-L-phenylalaninal, ethylenediamine-tetraacetic acid disodium salt dehydrate, acetyl-leucyl-leucyl-arginal, isovaleryl-val-val-AHMHA-ala-AHMHA where AHMHA=(3S, 4S)-4-amino-3-hydroxy-6-methylheptanoic acid, N-alpha-L-rhamnopyranosyloxy (hydroxyphosphinyl)-L-leucyl-L-tryptophan, phenylmethanesulfonyl fluoride, bortezomib, carfilzomib, ONX 0912, NPI-0052, CEP-18770, MLN9708, disulfiram, epigallocatechin-3-gallate, salinosporamide A, PI3K inhibitors, lapatinib, rapamycin, rapalogs, heat shock protein (HSP) inhibitors, androgen receptor inhibitors, conjugation products of Sigma ligands with targeting components, a salt thereof, and any combinations thereof.

In one embodiment, the subject is a mammal. In another embodiment, the mammal is a human.

The present invention also includes a method of modulating cellular protein homeostasis in a subject in need thereof. The method comprises administering to the subject an effective amount of a Sigma receptor-modulating compound, whereby cellular protein homeostasis in the subject is modulated.

In one embodiment, the Sigma receptor-modulating compound is a Sigma receptor antagonist. In another embodiment, the Sigma receptor is Sigma1. In yet another embodiment, the Sigma receptor-modulating compound and the additional therapeutic agent are co-administered. In yet another embodiment, the Sigma receptor-modulating compound and the additional therapeutic agent are co-formulated. In yet another embodiment, the Sigma receptor-modulating compound and the additional therapeutic agent are administered at separate times.

In one embodiment, the Sigma receptor-modulating compound is selected from the group consisting of:
(i) a compound of Formula (I):

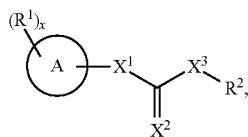
(I)

wherein:
ring A is a monocyclic or bicyclic aryl or a monocyclic or bicyclic heteroaryl ring, and wherein the aryl or heteroaryl ring is optionally substituted with 0-4 $R^1$ groups;
each occurrence of $R^1$ is independently selected from the group consisting of —$C_1$-$C_6$ alkyl, —$C_1$-$C_6$ fluoroalkyl, —$C_1$-$C_6$ heteroalkyl, F, Cl, Br, I, —CN, —$NO_2$, —$OR^3$, —$SR^3$, —$S(=O)R^3$, —$S(=O)_2R^3$, —$NHS(=O)_2R^3$, —$C(=O)R^3$, —$OC(=O)R^3$, —$CO_2R^3$, —$OCO_2R^3$, —$CH(R^3)_2$, —$N(R^3)_2$, —$C(=O)N(R^3)_2$, —$OC(=O)N(R^3)_2$, —$NHC(=O)NH(R^3)$, —$NHC(=O)R^3$, —$NHC(=O)OR^3$, —$C(OH)(R^3)_2$, and —$C(NH_2)(R^3)_2$;
each occurrence of $R^2$ is independently selected from the group consisting of H, $C_1$-$C_6$ alkyl, $C_1$-$C_6$ heteroalkyl, and —$C_1$-$C_3$ alkyl-($C_3$-$C_6$ cycloalkyl), wherein the alkyl, heteroalkyl or cycloalkyl group is optionally substituted with 0-5 $R^1$ groups, or $X^3$ and $R^2$ combine to form a ($C_3$-$C_7$)heterocycloalkyl group, optionally substituted with 0-2 $R^1$ groups;
each occurrence of $R^3$ is independently selected from the group consisting of H, $C_1$-$C_6$ alkyl, $C_1$-$C_6$ heteroalkyl, aryl, and —$C_1$-$C_3$ alkyl-($C_3$-$C_6$ cycloalkyl), wherein the alkyl, heteroalkyl, aryl, or cycloalkyl group is optionally substituted with 0-5 $R^1$ groups;
$X^1$ is —$CH_2$—, —S—, —O— or —($NR^2$)—;
$X^2$ is =$CH_2$, =S, =O or =$NR^2$; and
$X^3$ is —S—, —O—, or —$NR^2$—; and
(ii) a compound of Formula (II):

$R^A$—$R^B$ (II), wherein;

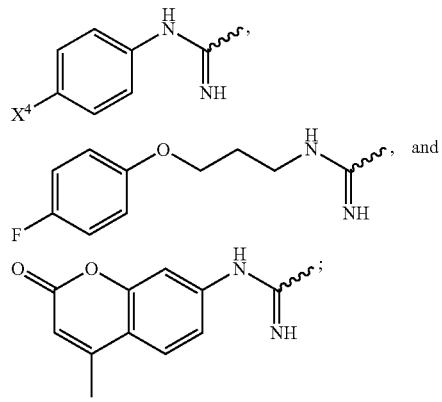

$X^4$ is selected from the group consisting of F, Cl, Br, and I; and $R^B$ is selected from the group consisting of:

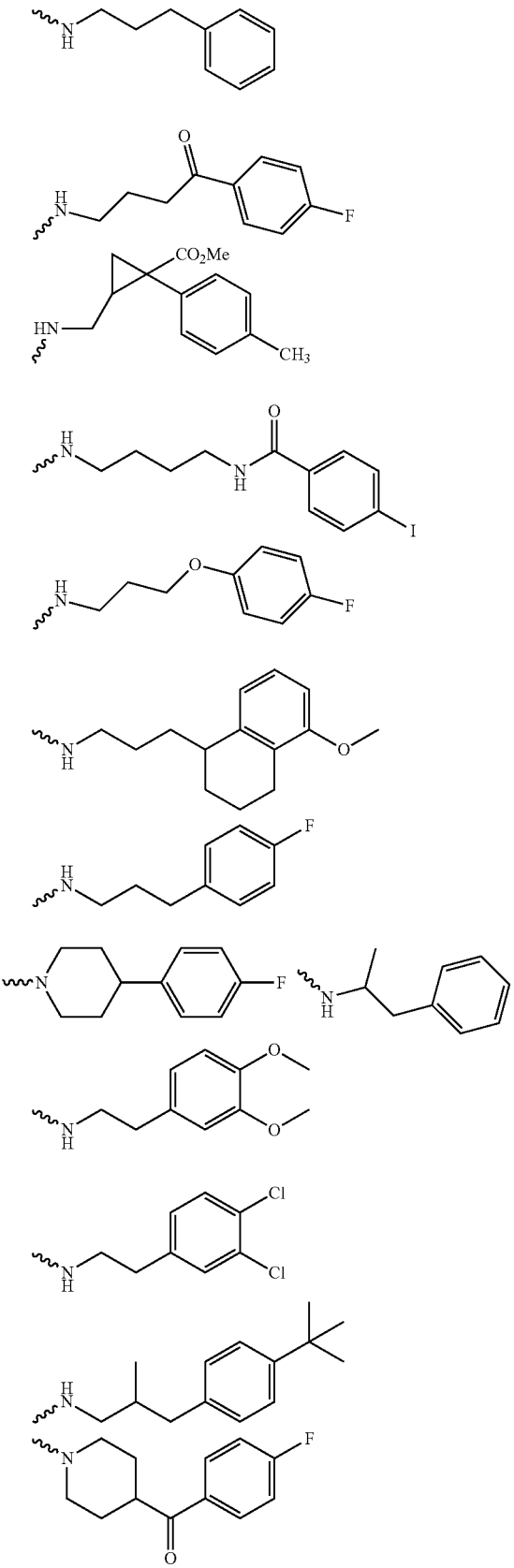

-continued

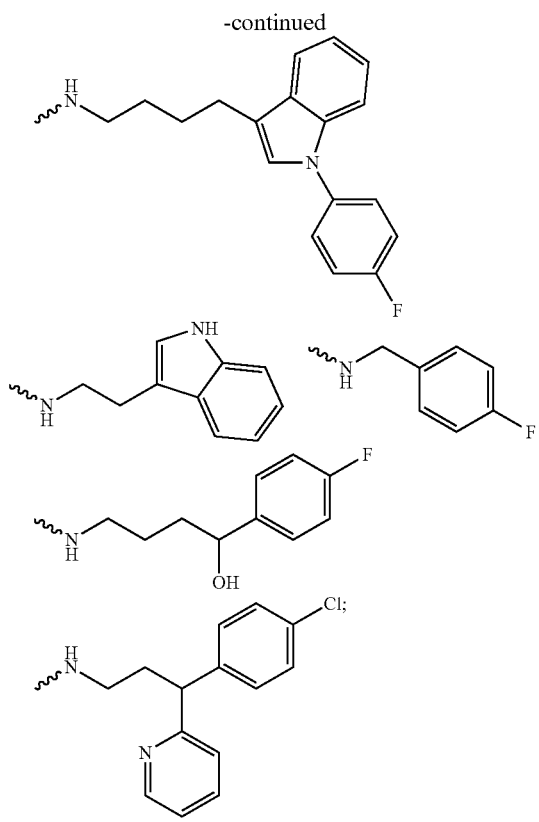

(iii) haloperidol, IPAG, PB28, rimcazole, BD1063, BDI47, PRE084, NE100, (+)-SKF0047, (+)-pentazocine;
(iv) a salt, solvate, or N-oxide thereof; and
any combinations thereof.

In another embodiment, the compound of Formula (I) is selected from the group consisting of 1-(3-(4-fluorophenoxy)propyl)-3-(4-iodophenyl)guanidine (Compound A), 1-(3-(4-fluorophenoxy)propyl)-3-(4-methoxyphenyl)guanidine (Compound B), 1-(n-propyl)-3-(4-iodophenyl)guanidine (Compound C), 1-(n-propyl)-3-(4-methoxyphenyl)guanidine (Compound D), 1-(3-(4-fluorophenoxy)propyl)-3-(4-trifluoromethylphenyl)guanidine (Compound F), 1-(3-(4-fluorophenoxy)propyl)-3-(4-chlorophenyl)guanidine (Compound G), a salt, solvate or N-oxide thereof, and any combinations thereof.

In yet another embodiment, the compound of Formula (II) is selected from the group consisting of, 1,3-bis(3-(4-fluorophenoxy)propyl)guanidine (Compound E), 1-(3-(4-fluorophenoxy)propyl)-3-(4-methyl-2-oxo-2H-chromen-7-yl)guanidine) (Compound H), a salt, solvate or N-oxide thereof, and any combinations thereof.

In one embodiment, the Sigma receptor-modulating compound is selected from the group consisting of:
(i) a compound of Formula (III):

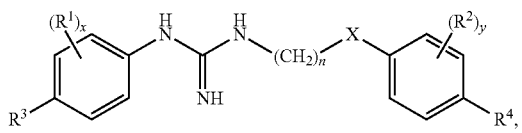

(III)

wherein within Formula (III);
each occurrence of $R^1$ and $R^2$ is independently selected from the group consisting of —$C_1$-$C_6$ alkyl, —$C_1$-$C_6$ fluoroalkyl, —$C_1$-$C_6$ heteroalkyl, F, Cl, Br, I, —CN, —$NO_2$, —$OR^5$, —$SR^5$, —S(=O)$R^5$, —S(=O)$_2R^5$, —NHS(=O)$_2R^5$, —C(=O)$R^5$, —OC(=O)$R^5$, —$CO_2R^5$, —$OCO_2R^5$, —CH($R^5$)$_2$, —N($R^5$)$_2$, —C(=O)N($R^5$)$_2$, —OC(=O)N($R^5$)$_2$, —NHC(=O)NH($R^5$), —NHC(=O)$R^5$, —NHC(=O)$OR^5$, —C(OH)($R^5$)$_2$, and —C($NH_2$)($R^5$)$_2$;
$R^3$ is selected from the group consisting of —$C_1$-$C_6$ alkyl, —$C_1$-$C_6$ fluoroalkyl, —$C_1$-$C_6$ alkoxy, F, Cl, Br, and I;
$R^4$ is selected from the group consisting of —$C_1$-$C_6$ alkyl, —$C_1$-$C_6$ alkoxy, F, Cl, Br, and I;
each occurrence of $R^5$ is independently selected from the group consisting of H, $C_1$-$C_6$ alkyl, $C_1$-$C_6$ heteroalkyl, aryl, and —$C_1$-$C_3$ alkyl-($C_3$-$C_6$ cycloalkyl), wherein the alkyl, heteroalkyl, aryl, or cycloalkyl group is optionally substituted;
X is selected from the group consisting of $CH_2$, C=O, or O;
n is an integer from 1-3;
x is an integer from 0-4; and
y is an integer from 0-4;
(ii) haloperidol, IPAG, PB28, rimcazole, BD1063, BD1047, PRE084, NE100, (+)-SKF10047, (+)-pentazocine;
(iii) a salt, solvate, or N-oxide thereof; and
any combinations thereof.

In one embodiment, the compound of Formula (III) is selected from the group consisting of 1-(3-(4-fluorophenoxy)propyl)-3-(4-iodophenyl)guanidine (Compound A), 1-(3-(4-fluorophenoxy)propyl)-3-(4-methoxyphenyl)guanidine (Compound B), 1-(3-(4-fluorophenoxy)propyl)-3-(4-trifluoromethylphenyl)guanidine (Compound F), 1-(3-(4-fluorophenoxy)propyl)-3-(4-chlorophenyl)guanidine (Compound G), a salt, solvate or N-oxide thereof, and any combinations thereof.

In one embodiment, the subject is afflicted with a neurodegenerative disease. In another embodiment, the neurodegenerative disease comprises Parkinson's disease, frontotemporal lobar degeneration, amyotrophic lateral sclerosis, or any combinations thereof. In yet another embodiment, the subject is a mammal. In yet another embodiment, the mammal is a human.

BRIEF DESCRIPTION OF THE DRAWINGS

The following detailed description of preferred embodiments of the invention are better understood when read in conjunction with the appended drawings. For the purpose of illustrating the invention, there are shown in the drawings embodiments that are presently preferred. It should be understood, however, that the invention is not limited to the precise arrangements and instrumentalities of the embodiments shown in the drawings.

FIGS. 1A-1B, illustrates prostate adenocarcinoma cell death induced by Sigma1 antagonists. FIG. 1A is a graph illustrating Sigma ligand-mediated decrease in cell number measured by Alamar blue assay: dose-response analysis of DU145 cells treated with Sigma antagonist (haloperidol) or agonist (PRE084) for 3 days and compared to control (DMSO treated). FIG. 1B is a graph illustrating PC3 cell death quantitated by trypan blue exclusion assay following treatment with 5 μM Sigma antagonist (haloperidol) or agonist (PRE084) for up to three days and compared to control (DMSO treated) cell culture. Quantitated cell death was presented as the percentage of trypan blue positive cells per drug treated population. Salient cell death occurred following ~24-48 hours of treatment with the Sigma antagonist.

FIGS. 2A-2B, is a set of flowcharts illustrating a model for Sigma antagonist-mediated tumor cell death. FIG. 2A is a flowchart illustrating that Sigma antagonists induce endoplasmic reticulum (ER) stress, resulting in a sequence of adaptive or cytoprotective responses comprising UPR and autophagy, wherein UPR induces autophagy as a cytoprotective response. FIG. 2B is a flowchart illustrating that, when the cytoprotective response of autophagy is overwhelmed, the cell undergoes apoptosis.

FIG. 4, comprising FIGS. 4A-4I, illustrates autophagosome formation and autophagic flux associated with Sigma antagonist treatment. FIG. 4A is an image of a gel illustrating the finding that treatment of MDA-MB-468 breast adenocarcinoma cells for 24 hours with 10 μM Sigma antagonists (IPAG, haloperidol, PB28, rimcazole), but not agonists (PRE-084, (+)-SKF10047, (+)-pentazocine), resulted in a salient induction of LC3II levels. Size markers indicate kilodaltons (kDa). FIG. 4B is a series of photographs illustrating translocation of GFP-tagged LC3 (GFP-LC3) into autophagosomes in Sigma ligand treated MDA-MB-468 (GFP-LC3) cells. Cells were treated for 24 hours with 10 μM IPAG, haloperidol, PB28, rimcazole, and with 50 μM PRE-084, (+)-SKF10047, (+)-pentazocine. (+)-SKF10047 is abbreviated as (+)-SKF and (+)-pentazocine is abbreviated as (+)-PTZ. FIG. 4C is a graph illustrating dose-responsive translocation of GFP-LC3 into autophagosomes. GFP-LC3 punctae were quantitated in MDA-MB-468 (GFP-LC3) cells treated for 24 hours with increasing concentrations of antagonists and agonists. Histograms represent data from at least four determinations, presented as the mean number±S.E.M of punctae per cell at the indicated doses of drug. Drug $EC_{50}$±S.E.M. values are indicated. Data are representative of at least 10 fields and 300 cells for each drug concentration. $P<0.001$ for all antagonists compared to agonists; $P<0.05$ for IPAG and haloperidol compared to PB28 and rimcazole. FIG. 4D is an image of a gel illustrating accumulation of LC3II in presence of E64d. Cell lysates were evaluated after 18 hours of cotreatment of E64d (20 μg/ml) with IPAG (10 μM). FIG. 4E is a graph illustrating effects of haloperidol (10 μM) combined with E64d. FIG. 4F is a graph illustrating effects of IPAG combined with E64d. The histograms in FIGS. 4E-4F illustrate quantitations of the ratio of LC3II band density in treated over DMSO control lanes, and the data are presented as the fold induction in LC3II band density compared to control (DMSO alone) (n=4, *$P<0.05$). Note that no histogram bar is shown for DMSO alone as this condition is set as the control, baseline. FIG. 4G a gel illustrating that cleavage of GFP-LC3 was used to further evaluate autophagic flux. MDA-MB-468 (GFP-LC3) cells were treated for 24 hours with the indicated Sigma ligands. FIG. 4H is an image of a gel illustrating that there was no accumulation of GFP-LC3II in the absence of IPAG and E64d. FIG. 4I is an image of a gel illustrating accumulation of GFPLC3II and diminished GFP by combined treatment with IPAG (10 μM) and E64d (20 μg/ml).

FIGS. 5A-5C, illustrates the finding that Sigma1 antagonist-mediated autophagy is Sigma1 dependent. MDA-MB-468 (GFP-LC3) cells were treated for 24 hours with 10 μM IPAG, 72 hours following transfection with either control or Sigma1 siRNA. FIG. 5A is an image of an immunoblot confirming that siRNA-mediated knockdown of Sigma1 was evaluated post-transfection and post-treatment in MDA-MB-468 (GFP-LC3) cells. Levels of GFP-LC3 cleavage were determined by GFP immunoblot. Data are representative of three determinations. FIG. 5B is a representative image of GFP-LC3 puncta formation in MDA-MB-468 (GFP-LC3) cells treated for 24 with 10 μM IPAG. FIG. 5C is a graph illustrating quantitation of GFP-LC3 puncta formation in MDA-MB-468 (GFP-LC3) cells treated for 24 with 10 μM IPAG.

FIGS. 6A-6F, illustrates dose-responsive induction of UPR by Sigma1 antagonist. MDA-MB-468 cells were treated for 24 hours with increasing doses of IPAG (1 to 20 μM). FIG. 6A is an image of a gel illustrating induction of LC3II protein levels. FIG. 6B is an image of a gel illustrating induction of GRP78/BiP protein levels. FIG. 6C is an image of a gel illustrating phosphorylation of p38MAPK (Thr180/Tyr182). FIG. 6D is an image of a gel illustrating induction of IRE1α protein levels and phosphorylation of JNK (Thr183/Tyr185). FIG. 6E is an image of a gel illustrating induction of ATF4 protein levels and phosphorylation of eIF2α (Ser51). FIG. 6F is a graph illustrating quantification of autophagosomes and UPR marker induction following 24-hour treatment with 1 μM IPAG. Data generated from at least three independent determinations, and are presented as mean fold induction over DMSO treated control. Error bars represent the standard error of the mean. *$P<0.05$, ***$P<0.001$.

FIGS. 7A-7E, illustrates the time-course of Sigma1 antagonist-induced UPR. Time-course of Sigma1 antagonist-induced ER stress was evaluated by immunoblot analysis of UPR markers. Cells were treated for indicated times with 10 μM IPAG. FIG. 7A is an image of a gel illustrating induction of IRE1α protein levels and phosphorylation of JNK (Thr183/Tyr185). FIG. 7B is an image of a gel illustrating induction of ATF4 protein levels and phosphorylation of eIF2α (Ser51). FIG. 7C is an image of a gel illustrating phosphorylation of p38MAPK (Thr180/Tyr182). FIG. 7D is an image of a gel illustrating induction of GRP78/BiP protein levels. FIG. 7E is an image of a graph illustrating time-action histogram of autophagosome formation in MDA-MB-468 (GFP-LC3). Data are representative of at least 10 fields and 300 cells for each drug concentration. $P<0.001$ for 24 hour IPAG treatment compared to 0 hour (basal), 1 hour, and 6 hour; $P<0.05$ for 24 hour compared to 12 hour IPAG treatment.

FIGS. 8A-8D, illustrates the finding that the inhibition of Sigma1 antagonist mediated UPR inhibits autophagy. FIG. 8A is an image of an immunoblot illustrating IRE1αsiRNA knockdown, 48-72 hours post-transfection. Knockdown of IRE1α abrogates IPAG mediated induction of GFP-LC3 cleavage. FIG. 8B comprises representative images of siRNA mediated knockdown of IRE1α and ATF4 abrogate GFP-LC3 punctae formation. FIG. 8C is a graph quantifying siRNA mediated knockdown of IRE1α and the abrogation of GFP-LC3 punctae formation by ATF4. Figure D is a graph illustrating that JNK inhibitor, SP610250, abrogates IPAG mediated punctae formation. MDA-MB-468 (GFP-LC3) cells were treated for 24 hours with a combination of IPAG (10 μM) and JNK inhibitor SP610250 (20 μM).

FIGS. 9A-9C, illustrates inhibition of Sigma1 antagonist-associated autophagy by Beclin1 RNAi. Beclin1 or control siRNA was transfected 72 hours prior to treatment with Sigma1 antagonists. Cells were treated for 24 hours with 10 μM of the indicated Sigma1 antagonists (IPAG, haloperidol). FIG. 9A illustrates representative images of MDA-MB-468 (GFP-LC3) cells treated as described above. FIG. 9B is a graph illustrating quantification of images as mean number of GFP-LC3 punctae per cell. Data are representative of at least 10 fields and 200 cells for each treatment condition. FIG. 9C is an image of an immunoblot confirming siRNA knockdown of Beclin1 and inhibition of Sigma1 antagonist-mediated GFP-LC3 cleavage in Beclin knockdown cells.

FIG. 10, comprising FIG. 10A is a graph illustrating the time-course of Sigma1 antagonist-induced cell death. MDA-MB-468 cells were treated for 24 and 48 hours with 10 µM IPAG (antagonist), and compared to cells treated with 10 µM PRE-084 (agonist) or DMSO (control) for the same time period. Cell death is measured by trypan blue exclusion, and is presented as the percentage of dead cells in a counted population. Data are from at least 4 determinations (***$P<0.001$). FIG. 10B is an image of an immunoblot demonstrating Caspase 3 (Asp 175) cleavage (cCaspase) following 48 hours of IPAG treatment. PRE-084 is abbreviated as PRE. FIG. 10C is a graph illustrating Sigma1 antagonist (IPAG) induced cell death in Beclin1 knockdown cells, 72 hours following transfection of Beclin1 siRNA. Data are from at least 4 determinations. FIG. 10D is an image of an immunoblot confirming siRNA mediated Beclin1 knockdown and demonstrating IPAG induced apoptosis by cleavage of Caspase 3 (cCaspase) and PARP (cPARP). FIG. 10E illustrates Sigma1 antagonist-induced cell death measured in IRE1α knockdown cells. Cells were treated for 24 hours with 10 uM IPAG, 72 hours following transfection of IRE1αsiRNA. Cell death was quantitated as in FIG. 10A. FIG. 10F is an image of an immunoblot illustrating apoptotic cell death was confirmed by immunoblot detection of cleaved Caspase 3 (cCaspase) and cleaved PARP (cPARP) as in FIG. 10D.

FIGS. 12A-12B, illustrates the finding that chemical inhibition of autophagy accelerates Sigma1 antagonist mediated cell death. MDA-MB-468 cells were treated for 24 hours with DMSO (control), 10 µM IPAG (Sigma antagonist), or 5 mM 3-methyladenine (3-MA, autophagy inhibitor), or a combination of IPAG and 3-MA. FIG. 12A is a graph illustrating quantitation of GFP-LC3 punctae per cell. Data were quantitated from four determinations, and are presented as mean±S.E.M. FIG. 12B is a graph illustrating cell death measured by trypan blue exclusion. Cell death, above control levels, was observed at 24 hours only when the IPAG and 3-MA were combined. Statistical significance was determined by one-way ANOVA, followed by Bonferroni's Post-test.

FIG. 13A is an image of a silver stain gel illustrating Sigma1-HA-$His_6$ associated proteins isolated by tandem-affinity purification from MDA-MB-468 breast adenocarcinoma cells. Approximately 80 proteins associated (i.e., co-purified) with Sigma1. FIG. 13B is a pie chart illustrating Sigma1-associated protein profile determined by MUD-Pit LC-MS/MS. 80% of Sigma1-associated proteins were involved in cellular processes directly relevant to ER protein homeostatis, cell survival, and death.

FIGS. 16A-16B, illustrates Sigma antagonist associated autophagy. FIG. 16A illustrates representative images of the translocation of GFP-tagged LC3 (LC3-GFP) into autophagosomes in a control (DMSO) group and a haloperidol-treated group (10 µM, antagonist). FIG. 16B is an image of a gel illustrating increased levels of the microtubule-associated protein light chain 3BII isoform (CL3BII), which is a broadly used indicator of activated autophagy. Treatment with 10 µM of haloperidol for 24 hours resulted in a salient induction of LC3BII levels.

FIG. 26, comprising FIGS. 26A-26B, illustrates six prototypical Sigma receptor ligands. FIG. 26A is a list illustrating the six prototypic Sigma receptor ligands selected for their selectivity, Sigma1 or Sigma2 or both, and their putative pharmacological activity as an agonist or antagonist. FIG. 26B illustrates the corresponding chemical structures of the Sigma receptor ligands. All compounds shown here are commercially available.

FIGS. 27A-27C, illustrates the finding that Sigma receptor antagonists inhibit proliferation of both estrogen receptor-positive and -negative cells. In vitro cell proliferation was quantitated by Alamar blue reduction. The anti-proliferative effects of six drug concentrations of the indicated drugs were quantitated after 4 days of treatment. In these breast adenocarcinoma cell cultures, Sigma1 agonists (+)-pentazocine and (+)-SKF10047 (data shown for the latter) were ineffective at concentrations as high as 0.1M. Sigma1 antagonists IPAG and rimcazole inhibited cell proliferation with comparable potencies in all cell lines. FIG. 27A is a graph illustrating that tamoxifen, IPAG, and rimcazole inhibited cell proliferation with similar potencies in the estrogen receptor positive breast tumor cell (MCF-7) culture. FIG. 27B is a graph illustrating that tamoxifen, IPAG, and rimcazole inhibited cell proliferation with similar potencies in the estrogen receptor positive breast tumor cell (T47D) culture. FIG. 27C is a graph illustrating that the Sigma antagonists IPAG and rimcazole also inhibited cell proliferation of the estrogen receptor negative MDA-MB-468 cells with similar potencies. Other Sigma1 antagonists, BD1063, BD1047, and haloperidol also inhibited cell proliferation (data not shown). Data are representative of 3 experiments performed in duplicate.

FIGS. 30A-30B, illustrates that Sigma1 antagonists mediate cell cycle arrest. Treatment with Sigma1 antagonist, IPAG, results in accumulation of breast adenocarcinoma cells in G1 phase of the cell cycle. FIG. 30A is a graph illustrating the percentage of G1, S, and G2 phase cells in T47D cells treated for 24 hours with DMSO (vehicle control), 1 μM IPAG (Sigma1 antagonist), or 10 μM (+)SKF-10047 (Sigma1 agonist). FIG. 30B is a graph illustrating the percentage of G1, S, and G2 phase cells in MDA-MB-468 cells treated for 24 hours with DMSO (vehicle control), 10 μM IPAG (Sigma1 antagonist), or 10 μM (+)-SKF-10047 (Sigma1 agonist). In contrast to IPAG treatment, control (DMSO) and (+)-SKF10047 (SKF) treated cells did not present significant difference in cell cycle profile.

FIGS. 31A-31E, shows that Sigma1 antagonists diminish tumor cell size in a dose and time responsive manner. FIG. 31A is a differential interference contrast (DIC) image of MDA-MB-468 breast adenocarcinoma cells treated for ~20 hours with DMSO (drug vehicle control), 10 μM IPAG (antagonist) or 10 μM PRE084 (agonist). A twenty-micron bar is shown in each image. Data are presented as mean±SEM. FIG. 31B is a graph illustrating the finding that IPAG diminished the mean cell size (FSC-H) of MDA-MB-468 breast tumor cells in a time-responsive manner. The mean FSC-H of 370±5 at to decreased to 323±4 after 24 hours of IPAG treatment and to 267±2 after 48 hours of treatment. Two-tailed t-tests were performed to determine statistical significance. For IPAG treatment compared to control (DMSO) and Sigma agonists (SKF and PRE084), P=0.0002 at d1 and P=0.00013 at d2. Data were generated from three to five independent determinations for each time-point. Flow cytometry was used to measure mean cell size (mean FSC-H) of T-47D breast adenocarcinoma cells. FIG. 31C is a bar graph illustrating T-47D cells treated for 24 hours with 10 μM indicated Sigma ligand. IPAG and BD 1047 (Sigma1 antagonists) diminished cell size from a mean FSC-H of 412±5 for control (DMSO) cells versus 341±7 and 381±8 for IPAG and BD1047 treated cells, respectively. Both Sigma1 putative agonists, (+)-SKF10047 (SKF) and PRE-084, did not alter cell size. Data represent 5 independent determinations (*P<0.05, *P<0.001). FIG. 31D is a bar graph illustrating how IPAG (antagonist) decreases cell size in a dose responsive manner. T-47D were treated for 24 h with 1 and 10 μM IPAG, and mean FSC-H was measured. FIG. 31E is a graph illustrating that T47D cell size decreases over time. T-47D cells were treated for a total of 48 hours with 10 μM of the indicated Sigma ligands. IPAG treatment decreased the mean FSC-H of G1 phase T-47D from 412±5 to 331±3 and 300±2 at 24 hours (d1) and 48 hours (d2) of drug treatment. Neither Sigma1 agonist, (+)-SKF10047 and PRE084, altered cell size. These data were generated from at least three independent experiments. Two-tailed t-tests were performed to determine statistical significance. For IPAG treatment compared to control (DMSO) and Sigma1 agonists (SKF and PRE084), P=0.0002 at d1 and P<0.0001 at d2. For FIGS. 31B-31E**, the mean FSC-H was determined for each cell cycle population (i.e., G1, S, G2/M), and data is shown for G1 phase cells. S and G2/M phase cells responded similarly (data not shown).

FIGS. 32A-32B, illustrates induction of unfolded protein response (UPR) associated with Sigma1 antagonist treatment. FIG. 32A comprises images of immunoblots of MDA-MB-468 breast adenocarcinoma cells treated with 10 μM Sigma1 antagonist (IPAG) for the indicated times, up to 24 hours. Total cell lysates were resolved by SDS-PAGE and immunoblotted for UPR markers IRE1α, GRP78/BiP, GRP94, and ORP150. The higher migrating IRE1α band was consistent with the phosphorylated form (P-IRE1α). FIG. 32B is a series of images of immunoblots illustrating a range of tumor cell lines treated for ~24 hours with 10 μM IPAG (Sigma1 antagonist) or 10 μM PRE084 (Sigma1 agonist). Increased levels of GRP78/BiP (BiP) was an indicator of UPR. Cell lines include: breast adenocarcinoma (MDAMB468, MCF-7, T47D), prostate adenocarcinoma (DU145, PC3), hepatocellular carcinoma (HepG2), pancreatic adenocarcinoma (Panc1).

FIGS. 33A-33D, illustrates the finding that Sigma1 antagonist treatment mediated translation arrest. FIG. 33A is an image of an immunoblot of T-47D cells treated for 20 hours with 10 μM of Sigma1 antagonists, IPAG and haloperidol (HPL), or the agonists, PRE-084 and (+)SKF10047, followed by a 1 hour pulse with [$^{35}$S]-methionine and cysteine to measure new protein synthesis. Detergent soluble protein extracts were resolved by 10% SDS-PAGE, transferred onto PVDF filter and analyzed for

[$^{35}$S]-labeled protein content following 3 day exposure to autoradiograph film and subsequently immunoblotted to detect Sigma1 and β actin levels. FIG. 31B is an image of an immunoblot of T-47D cells treated for 20 hours with 10 µM of the indicated Sigma ligands, IPAG (antagonist) and PRE084 (agonist); levels of phosphothreonine 389-p70S6Kinase (P-S6K) and phosphoserine 65-4E-BP1 (P-4E-BP) were evaluated by immunoblot. FIG. 33C is an image of an immunoblot of the time-course of changes in P-S6K and P-4E-BP1 levels in response to treatment with 10 µM IPAG for the indicated time periods. FIG. 33D is an image of an immunoblot illustrating that translation arrest was further confirmed by immunoblot detection of phospho-serine 209-eIF4E (P-eIF4E) and phosphoserine 51-eIF2α (P-eIF2α) under the same conditions described in FIG. 33C above.

FIGS. 34A-34B, illustrates the finding that Sigma1 antagonist treatment is associated with an increased level of ubiquitylated proteins. FIG. 34A is an image of an immunoblot of MDA-MB-468 breast adenocarcinoma cells treated with 10 µM Sigma1 antagonist (IPAG) for the indicated times, up to 24 hours. Total cell lysates were resolved by SDS-PAGE and immunoblotted with a poly-ubiquitin antibody P4D1. FIG. 34B is an image of an immunoblot of HepG2 hepatocellular carcinoma cells treated for 20 hours with 10 µM of indicated Sigma1 ligands. Immunoblots revealed increased levels of ubiquitylated proteins (detected with the P4D1 anti-poly-ubiquitin antibody).

FIG. 35, comprising FIG. 35A is an image of an immunoblot illustrating increased levels of poly-ubiquitylated (poly-Ub) proteins in response to haloperidol (Haldol) treatment. FIG. 35B is an image of an immunoblot illustrating translation arrest markers phospho-Ser 209-eIF4E (P-eIF4E) and phosphoThr 389-p70S6Kinase (P-S6K). FIG. 35C is a graph illustrating the quantification of bands in FIG. 35B. FIG. 35D is an image of an immunoblot illustrating levels of poly-ubiquitylated (poly-Ub) proteins in the hippocampus in response to treatment with vehicle or IPAG.

FIGS. 36A-36C, illustrates Sigma1 antagonist associated autophagy. FIG. 36A, comprises representative images of translocation of GFP-tagged LC3 (LC3-GFP) into autophagosomes in MDA-MB-468 (MDA468) breast adenocarcinoma cells. Only antagonist-treated MDA-MB-468 cells presented LC3-GFP translocation to autophagosomes: 10 µM IPAG (antagonist) and 10 µM PRE084 (agonist). Similar results were obtained with haloperidol (antagonist) and (+)SKF-10047 (agonist) (not shown). The images are representative of at least 80 fields for each treatment condition. FIG. 36B is an image of an immunoblot illustrating the finding that formation of GFP-LC3II the formation of GFP-LC3 positive punctae, an indicator of autophagosome formation. Protein extracts from MDA-MB-468 cells stably transfected with and expressing GFP-LC3, treated for 24 hours with 10 µM of the indicated Sigma1 ligand. FIG. 36C comprises images of immunoblots illustrating that increased levels of the microtubule associated protein light chain 3BII isoform (LC3BII) is another broadly used indicator of activated autophagy. Treatment of a range of tumor cell lines with 10 µM IPAG for 24 hours resulted in a salient induction of LC3BII levels, whereas PRE084 did not significantly alter basal autophagy. Similar results were obtained with haloperidol and (+)SKF-10047 (not shown).

Legend: MCF-7 (breast adenocarcinoma), T47D (breast adenocarcinoma), DU145 (prostate adenocarcinoma), PC3 (prostate adenocarcinoma), HepG2 (hepatocellular carcinoma), and Panc1 (pancreatic adenocarcinoma).

Figure 37:
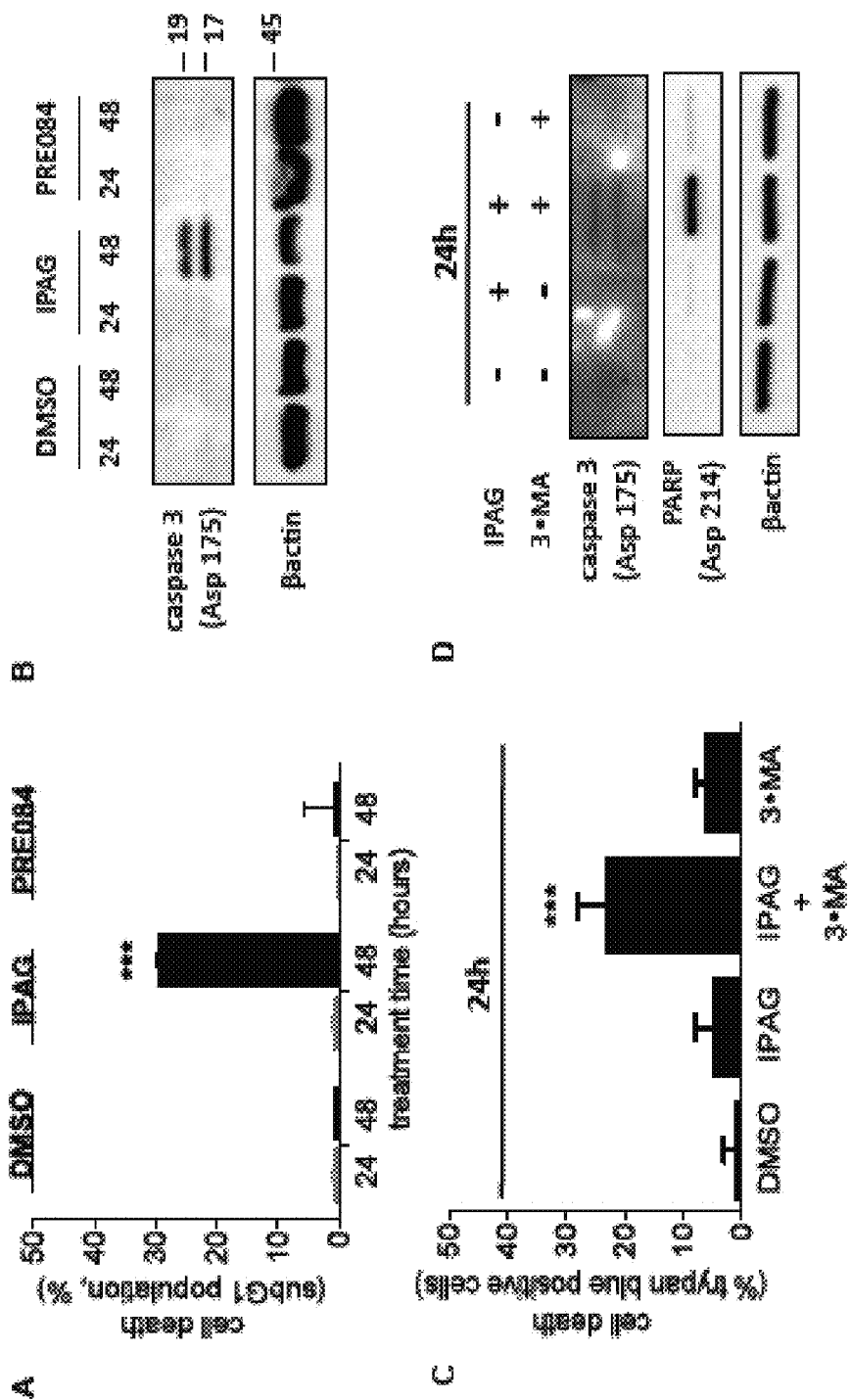

FIG. 37, comprising FIGS. 37A-37D, illustrates that inhibition of autophagy accelerates and/or potentiates Sigma1 antagonist induced apoptosis. FIG. 37A is a graph illustrating the time-course of Sigma antagonist-induced cell death as measured by flow cytometry. MDA-MB-468 cells were treated with DMSO (control), 10 µM IPAG (antagonist), or 10 µM PRE084 (agonist), fixed and stained with propidium iodide for DNA content analysis. The subG1 population was quantified and used as a measure of cell death. Data are from 4 independent determinations. FIG. 37B is an image of a Western blot of caspase 3 (Asp175) cleavage. IPAG induced apoptotic cell death occurred at the 48 hour treatment time point. FIG. 37C is a graph illustrating DA-MB-468 cells treated for 24 hours with a combination of IPAG (10 µM) and autophagy inhibitor 3-methyladenine (3-MA, 5 mM). Cell death was measured by trypan blue exclusion. FIG. 37D is an image of an immunoblot confirming apoptotic cell death by detection of cleaved caspase 3 (Asp175) and cleaved PARP (Asp214). Cell death was observed at 24 hours only when the Sigma antagonist and autophagy inhibitor were combined. For FIGS. 37A-37C, statistical significance was determined by two-way ANOVA followed by Bonferroni post-test, ***$P<0.001$.

Figure 38:
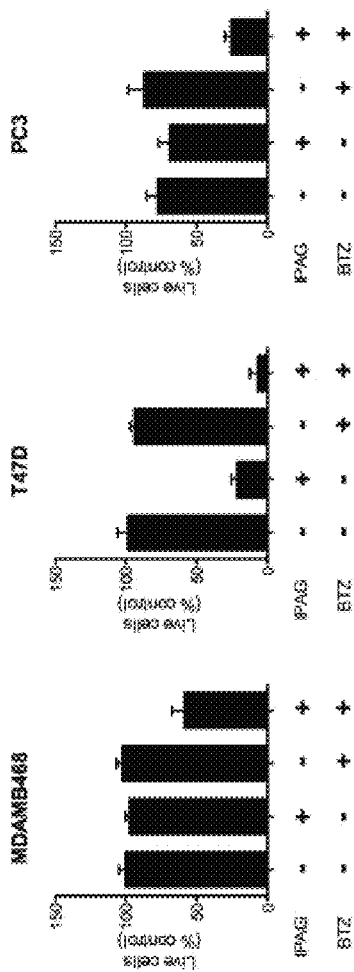

FIG. 38 is a series of graphs illustrating Sigma receptor antagonist potentiates bortezomib-induced adenocarcinoma cell death. In vitro cell proliferation and cell death were quantified by Alamar blue reduction. To evaluate potentiation of proteasome inhibitor (bortezomib)-induced cell death by IPAG, MDA-MB-468 cells were treated for 20 hours with a 10 µM IPAG or 0.01 µM bortezomib alone or both drugs combined. Cell death was confirmed by trypan blue exclusion assay (data not shown). Data are representative of an experiment performed in triplicate.

Figure 39:
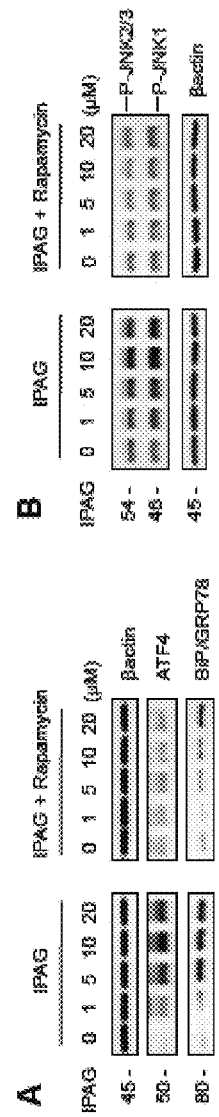

FIG. 39, comprising FIGS. 39A-39B, illustrates that rapamycin modulates response to Sigma1 antagonist mediated endoplasmic reticulum stress. MDA-MB-468 breast adenocarcinoma were treated for 20 hours with the indicated concentration of IPAG (Sigma1 antagonist) alone or in combination with 0.1 µM Rapamycin. FIG. 39A is a series of images of immunoblots evaluating levels of unfolded protein response (UPR) markers, ATF4 and BiP. FIG. 39B is a series of images of immunoblots evaluating levels of phospho-JNK. This suggests that enhancement of mTOR-mediated macroautophagy may mitigate Sigma1 antagonist induced ER stress.

Figure 40:
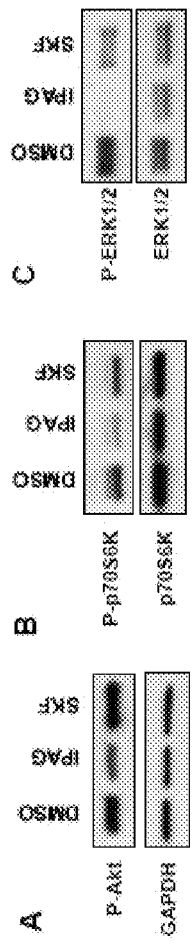

FIG. 40, comprising FIGS. 40A-40C, illustrates Sigma1 antagonist modulation of Akt, S6K, and ERK phosphorylation. MDA-MB-468 breast tumor cells were treated for 24 hours with 10 µM IPAG (Sigma1 antagonist) or (+)SKF-10047 (SKF, Sigma1 agonist). Treated cells were harvested and cellular proteins were extracted with a buffer containing 1% Sodium Dodecyl Sulfate (SDS) and deoxycholate (DOC), supplemented with phosphatase and protease inhibitors. FIG. 40A is an image of an immunoblot illustrating Akt phosphorylation. Whereas Akt phosphorylation at serine 473 decreased 3-fold in IPAG treated cells, (+)-SKF10047 treatment did not alter Akt phosphorylation. Akt phosphorylation at threonine 308 was not altered in any of the samples (not shown). Equivalent loading was confirmed with an anti-GAPDH antibody. FIG. 40B is an image of an immunoblot illustrating phosphorylation. Phosphorylation of mTOR substrate, p70S6K at threonine 389 decreased 3-fold in IPAG, but not SKF treated cells. Total p70S6K was immunoblotted as a loading control. FIG. 40C is an immunoblot illustrating that p44/42 ERK1/2phosphorylation at threonine 202 and tyrosine 204 was abrogated by 24 hour treatment with IPAG. Data shown is representative of two independent experiments.

Figure 41:
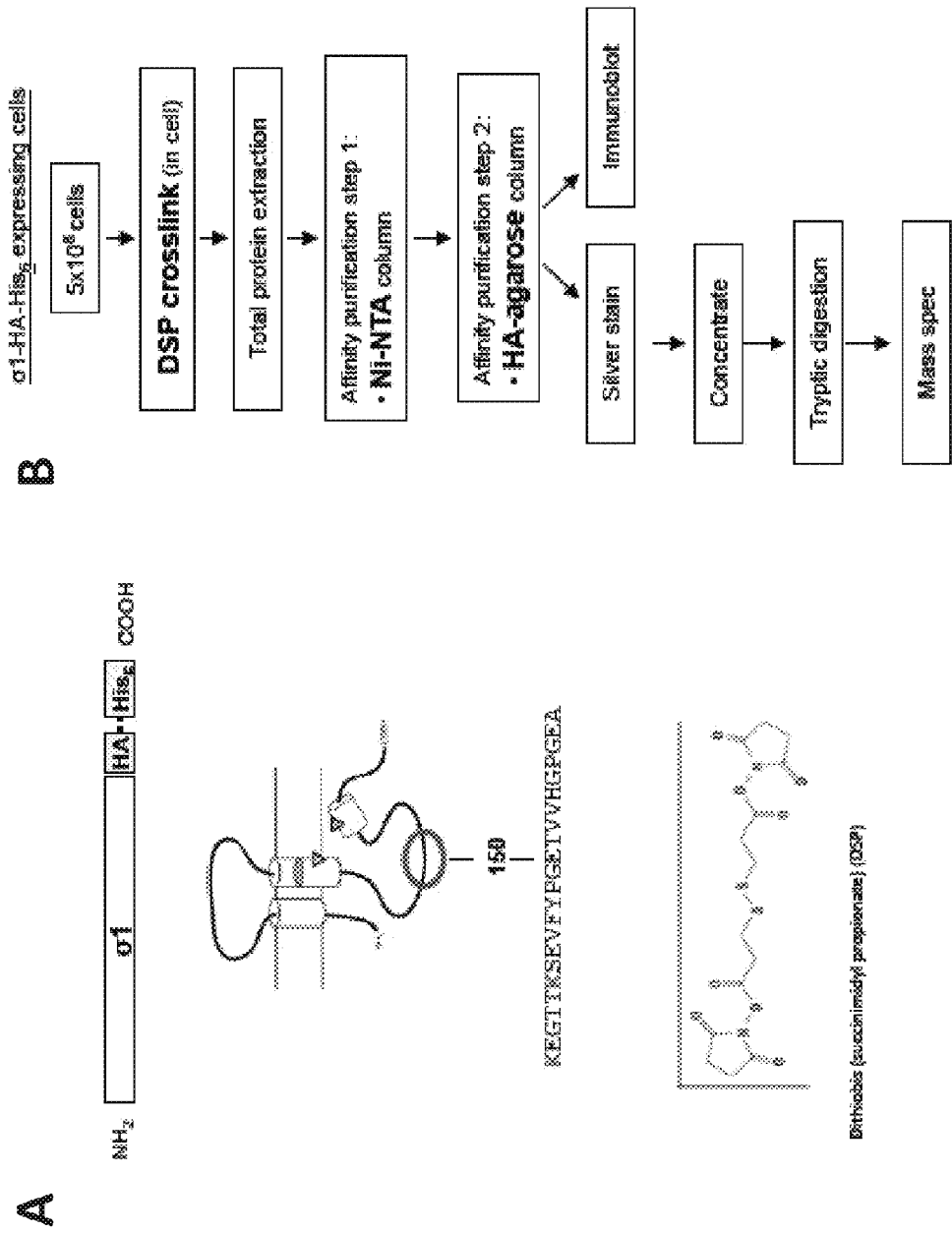

FIG. 41, comprising FIGS. 41A-41B, illustrates work-flow schematics for the identification of Sigma1 associated proteins. FIG. 41A illustrates putative topology of Sigma1. A homobifunctional cross-linking agent, dithio-bis(succinimidyl propionate) (DSP), was used for intracellular cross-linking of Sigma1 associated proteins to either of the two lysine residues of Sigma1. Amino acid residue E150 is indicated. FIG. 41B is a flow chart illustrating a dual affinity purification scheme to isolate and identify Sigma1-HA-His6 associated proteins.

Figure 42:
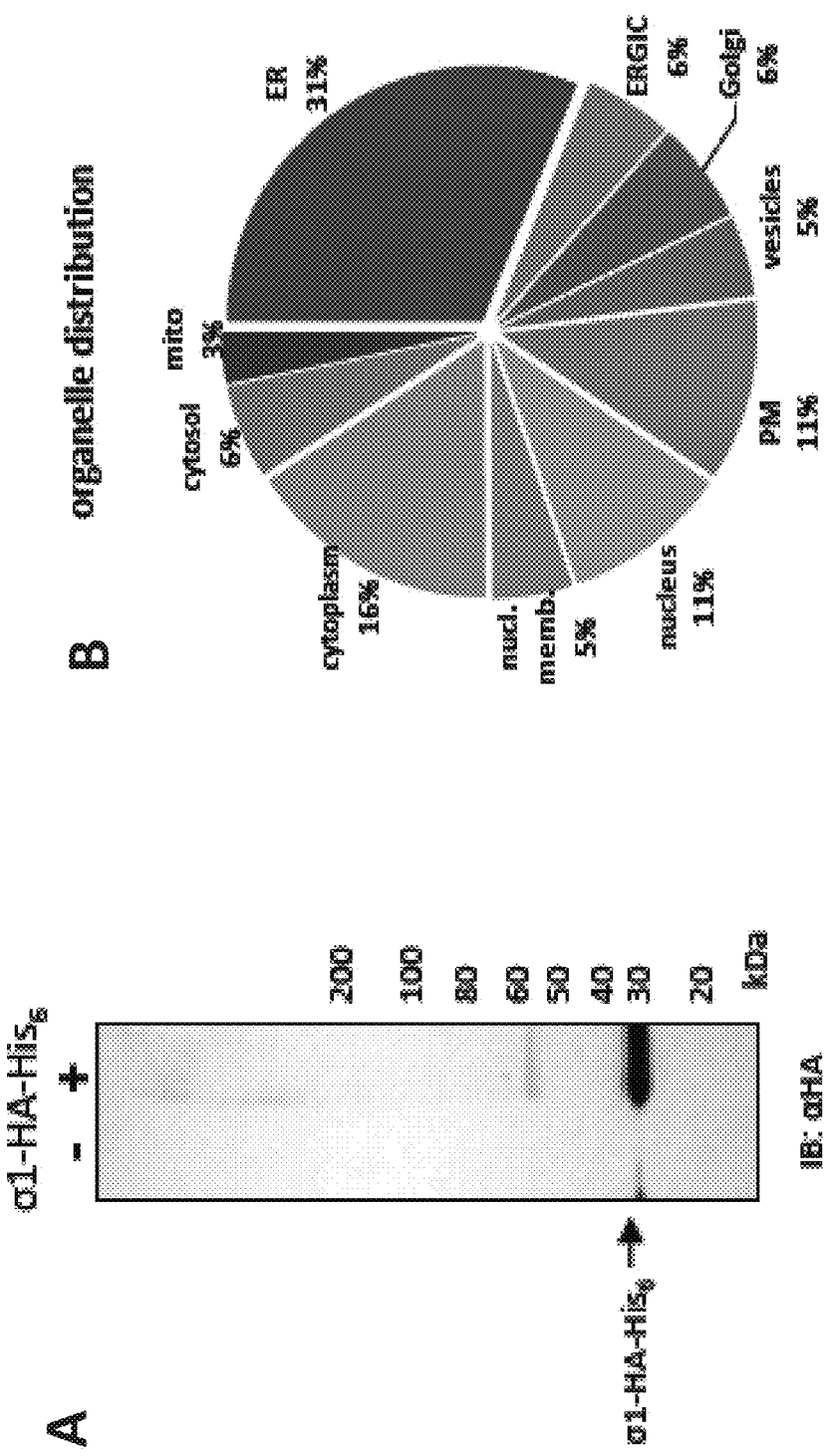

FIG. 42, comprising FIGS. 42A-42B, illustrates Sigma1 associated proteins in a breast tumor cell line. FIG. 42A is a Western blot of dual affinity purified Sigma1-HA-His6 sample, immunoblotted with a rabbit anti-hemagglutinin (HA) epitope, HRP conjugated antibody. The HA-agarose affinity column was made with a mouse monoclonal anti-HA antibody. FIG. 42B is a pie chart illustrating organelle distribution of Sigma1 associated proteins. The identified proteins were not restricted to a single functional category, nor were they exclusively located in indicated organelles. In nearly all cases, the Sigma1 associated proteins existed in multiple organelles and in multiple cellular processes. LC/MS analysis subsequent to subcellular fractionation may provide more information concerning Sigma1 associated protein interactions and responses to Sigma ligand treatment. Legend: ER. endoplasmic reticulum; ERGIC, ER-Golgi intermediate compartment; PM, plasma membrane.

Figure 43:
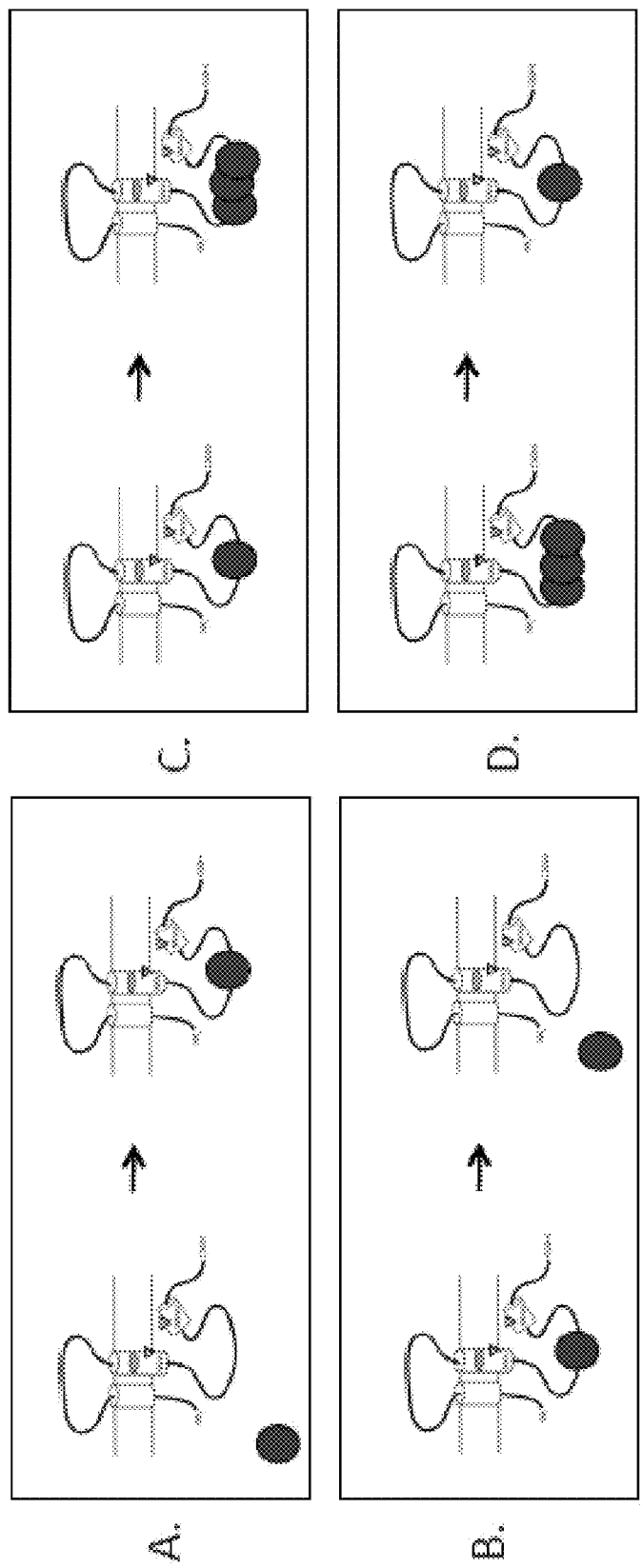

FIG. 43, comprising FIGS. 43A-43D, illustrates a proposed model for a mechanism of Sigma1-mediated actions. FIG. 43A is a model illustrating Sigma1-HA-His6 quantal association. FIG. 43B is a model illustrating quantal dissociation. FIG. 43C is a model illustrating graded gain of association. FIG. 43D is a model illustrating graded loss of association. The Sigma1 "receptor" has no known intrinsic enzymatic or signaling function. Sigma1 may function as a novel molecular chaperone, and Sigma1 antagonists may induce ER stress by altering its physical association with partner proteins. Putative Sigma1 ligand binding sites are indicated by triangles ($\Delta$), which are distinct from IDR protein binding.

Figure 44:
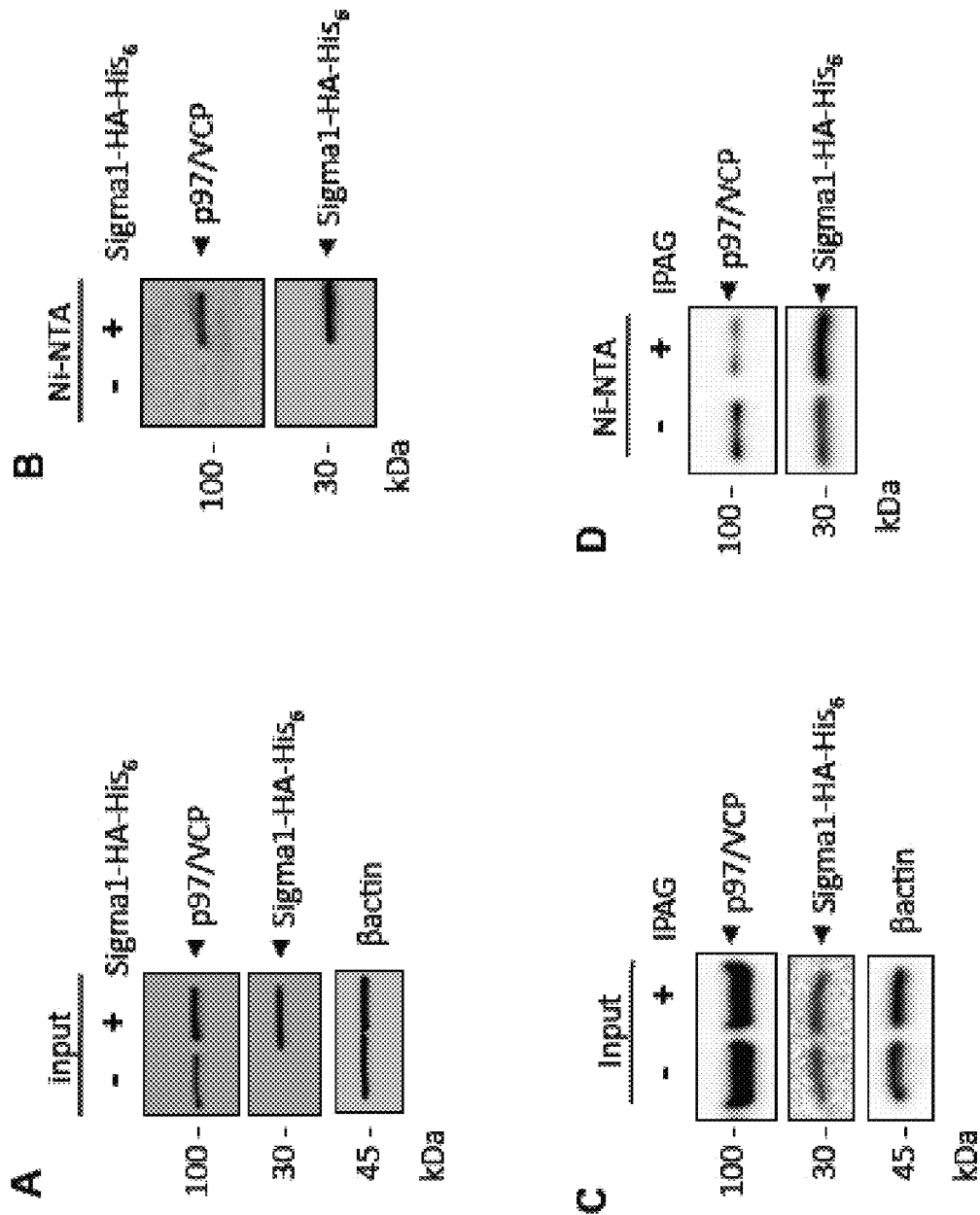

FIG. 44, comprising FIGS. 44A-44D, illustrates the finding that p97/VCP is a Sigma1 associated protein. A novel assay was developed to evaluate Sigma1 ligand modulation of Sigma1 functions involving protein-protein interactions. FIG. 44A is an image of an immunoblot confirming expression of p97/VCP and Sigma1-HA-His6 in detergent soluble cell extracts added to Ni-NTA resin (input). FIG. 44B is an image of an immunoblot relating to eluate from a Ni-NTA affinity purified fraction. Co-isolation/co-purification of p97/VCP was accomplished with Sigma1-HA-His6, which was isolated/purified by Ni-NTA. No p97/VCP was detected in an eluate fraction from Ni-NTA purified from protein extracts of non-transfected, parental cells that did not express Sigma1-HA-His6 (−). FIG. 44C is an image of an immunoblot confirming expression of p97/VCP and Sigma1-HA-His6 in detergent-soluble cell extracts from MDA-MB-468 breast adenocarcinoma cells treated for 12 hours with 10 μM IPAG (Sigma1 putative antagonist); the extracts were added to Ni-NTA resin (input). FIG. 44D is an image of an immunoblot illustrating eluate from a Ni-NTA affinity purified fraction. Co-isolation/co-purification of p97/VCP was accomplished with Sigma1-HA-His6, which was isolated/purified by Ni-NTA. Lower levels of Sigma1-associated p97/VCP were detected in eluate fraction from Ni-NTA purified from protein extracts of MDA-MB-468 cells treated for 12 hours with 10 μM IPAG (Sigma1 putative antagonist). Molecular mass is presented in kilodaltons (kDa).

Figure 45:
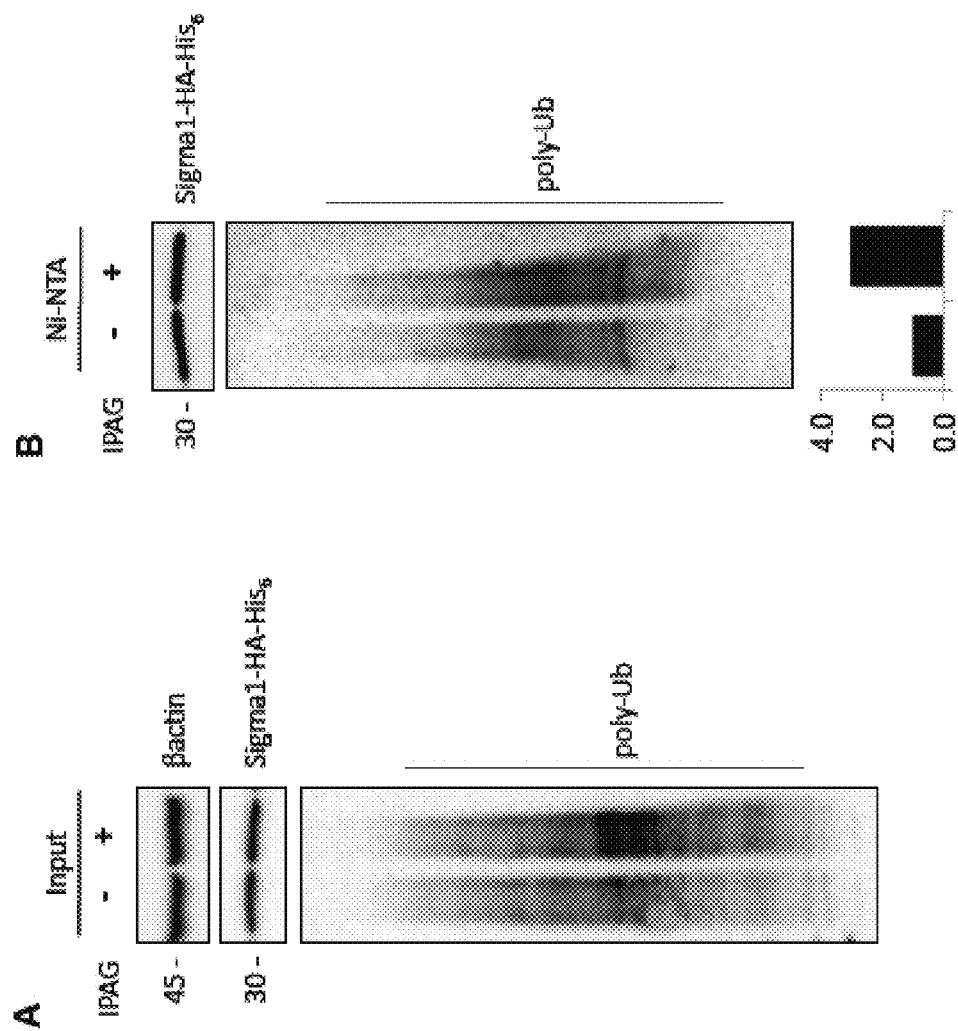

FIG. 45, comprising FIGS. 45A-45B, illustrates the finding that ubiquitylated proteins are bound to Sigma1. A novel assay was developed to evaluate Sigma1 ligand modulation of Sigma functions involving association with ubiquitylated proteins. FIG. 45A is an image of an immunoblot confirming expression of Sigma1-HA-His6 and induction of ubiquitylated protein levels in detergent soluble cell extracts added to Ni-NTA resin (input) from MDA-MB-468 breast adenocarcinoma cells treated for 12 hours with 10 μM IPAG (Sigma1 putative antagonist). FIG. 45B is an image of an immunoblot of eluate from a Ni-NTA affinity purified fraction. Co-isolation/co-purification of poly-ubiquitylated proteins with Sigma1-HA-His6 were isolated/purified by Ni-NTA. Increased levels of Sigma1-associated ubiquitylated proteins were detected in an eluate fraction from Ni-NTA purified from protein extracts of MDA-MB-468 cells treated for 12 hours with 10 μM IPAG (Sigma1 putative antagonist). Molecular mass is presented in kilodaltons (kDa).

Figure 46:
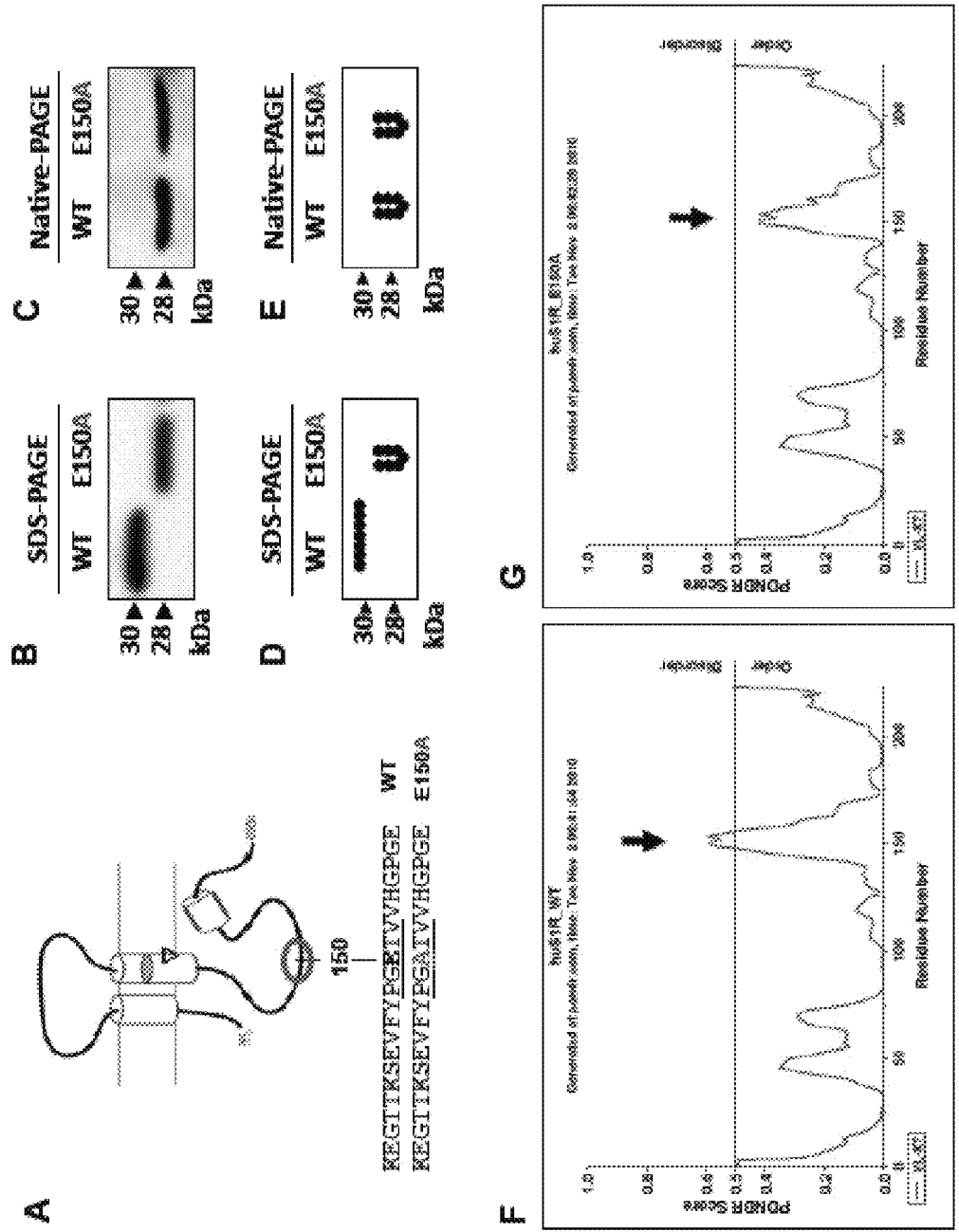

FIG. 46, comprising FIGS. 46A-46G, illustrates bioinformatics prediction and mutational analysis of an intrinsically disordered region in the Sigma1 cytoplasmic tail. FIG. 46A is a schematic illustration of Sigma1 membrane topology. The amino acid sequence surrounding residue 150 is shown at the bottom. This sequence also corresponds to synthetic blocking peptides that have been generated against this region. FIG. 46B is an image of a denaturing SDS-PAGE gel of WT and mutant Sigma1 from HEK293T transient transfectant cell lysates. Apparent molecular mass ($M_r$) is presented in kilodaltons (kDa). FIG. 46C is a native PFO-PAGE of same cell lysates. FIG. 46D is an illustration of conformational differences between wild type and mutant Sigma1 predicted in FIG. 46A. and revealed by SDS-PAGE. FIG. 46E is an illustration of conformational differences between wild type and mutant Sigma1 predicted in FIG. 46A and revealed by PFO-PAGE. FIG. 46F is a graph illustrating that intrinsic disorder in the Sigma1 using PONDR VL-XT (URL and reference) indicates a short intrinsically disordered region (IDR) within the murine Sigma carboxy-terminal tail, corresponding to residues underlined in FIG. 46A. The black downward arrow points to disordered region. FIG. 46G is a graph illustrating the finding that E150A mutation resulted in loss of intrinsic disorder.

Figure 47:
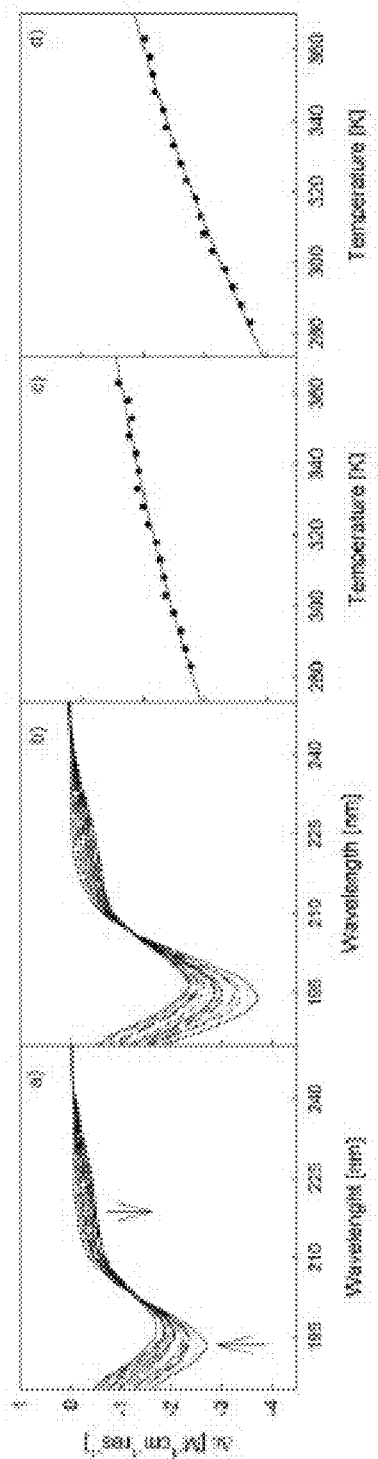

FIG. 47 illustrates the UVCD spectral analysis of Sigma1 C-tail peptide. The intrinsically disordered region in the Sigma1 cytoplasmic tail was examined through the temperature-dependent ultraviolet circular dichroism (UVCD) spectra of (a) the native Sigma1 peptide residues 137-159 and (b) the corresponding mutant Sigma1 peptide (E150A). The arrows indicate the increasing temperature from 283-363K. Panels (c) and (d) show the negative maximal dichroism ($\Delta\epsilon_{193nm}$) obtained from the UVCD spectra plotted as a function of temperature for the native and mutant peptide, respectively.

Figure 48:
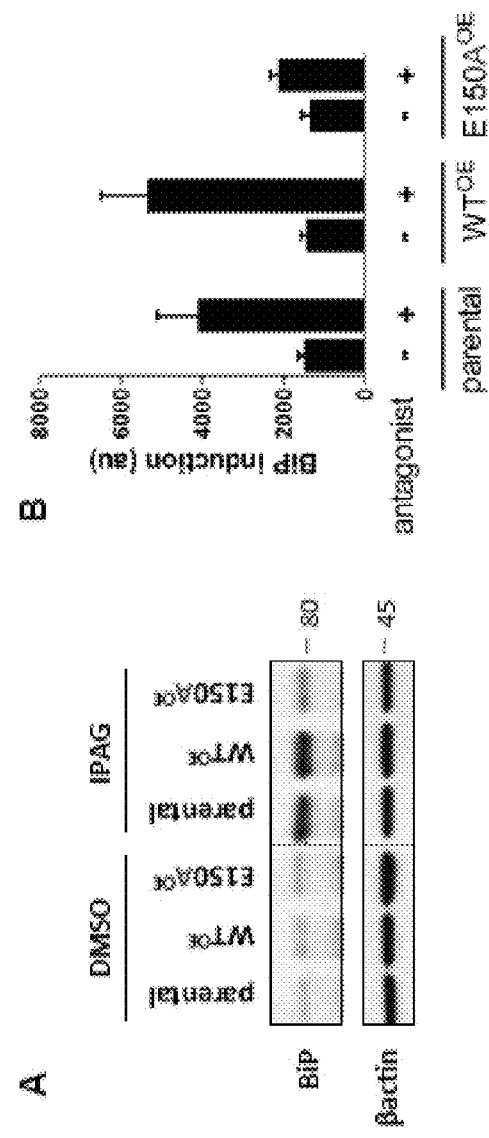

FIG. 48, comprising FIGS. 48A-48B, illustrates the finding that the Sigma1 IDR mutant abrogates ligand mediated induction of ER stress, and can be used as a tool to evaluate aspects of Sigma1 ligand mediated ER stress response. HEK293T cells were stably transfected with Sigma1-HA-His$_6$ (WT$^{OE}$) or Sigma1E150A-HA-His$_6$ (E150A$^{OE}$) and treated for ~16 hours with DMSO or 10 μM IPAG (Sigma1 "antagonist"). FIG. 48A is a series of images of immunoblots of GRP78/BiP (BiP), a marker of unfolded protein response and endoplasmic reticulum (ER) stress. FIG. 48B is a graph illustrating the quantification of BiP induction from three determinations.

Figure 49:
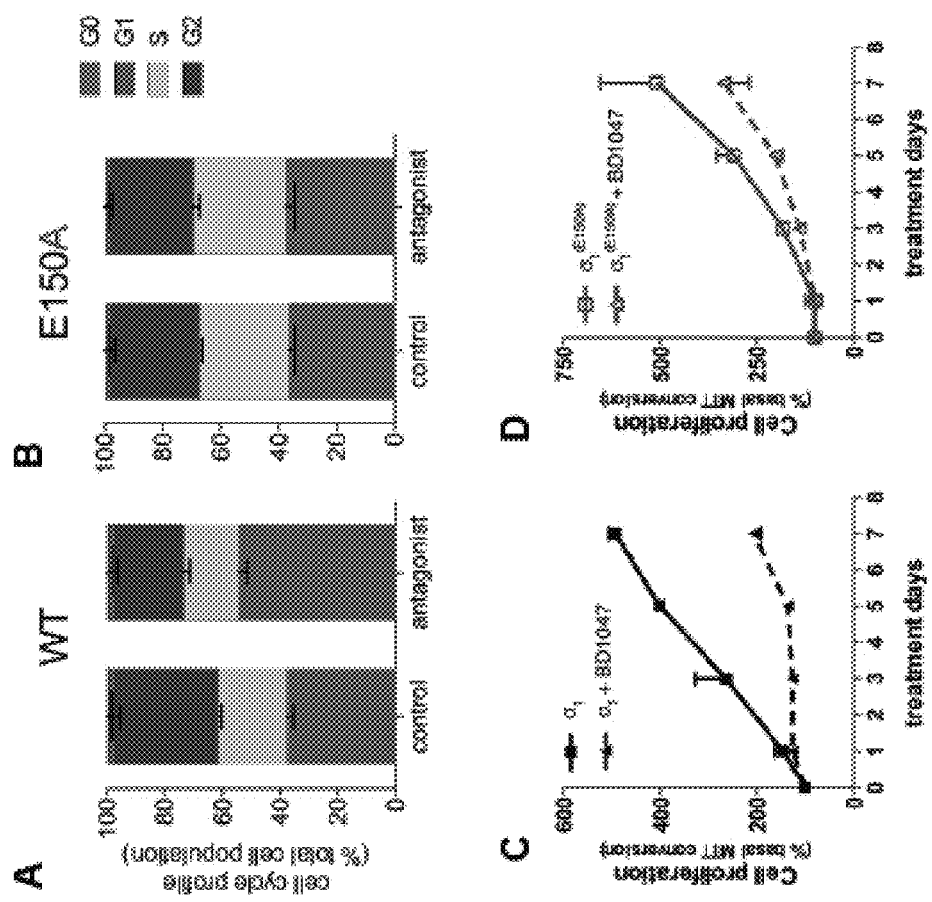

FIG. 49, comprising FIGS. 49A-49D, illustrates the finding that a point mutation in Sigma1 cytoplasmic tail inhibited the response to Sigma1 antagonists mediated cell cycle arrest, and may be used as a novel tool to evaluate Sigma ligand modulation of cell cycle and proliferation. Treatment with a Sigma1 antagonist resulted in accumulation of cells in G1 phase of the cell cycle. FIG. 49A is a graph illustrating the percentage of G1, S, and G2 phase cells in T47D cells treated for 24 hours with DMSO (vehicle control), 1 µM IPAG (Sigma1 antagonist), or 10 µM (+)-SKF-10047 (Sigma1 agonist). FIG. 49B is a graph illustrating the percentage of G1, S, and G2 phase cells in MDA-MB-468 cells treated for 24 hours with DMSO (vehicle control), 10 µM IPAG (Sigma1 antagonist), or 10 µM (+)SKF-10047 (Sigma1 agonist). In contrast to IPAG treatment, control (DMSO) and (+)SKF10047 (SKF) treated cells did not present significant difference in cell cycle profile. FIG. 49C is a graph illustrating ligand-mediated changes to cell proliferation measured by MTT assay. Proliferation of parental, wild-type, Sigma1 expressing cells was measured in standard cell culture medium and compared to proliferation in medium (solid black line) containing 10 µM BD1047 (Sigma1 antagonist, broken black line). MTT assay was performed at the indicated time points (treatment days). FIG. 49D is a graph illustrating proliferation of E150A mutant (σ1E150A) expressing cells measured in standard cell culture medium and compared to proliferation in medium (solid line) containing 10 µM BD1047 (Sigma1 antagonist, broken line).

Figure 50:
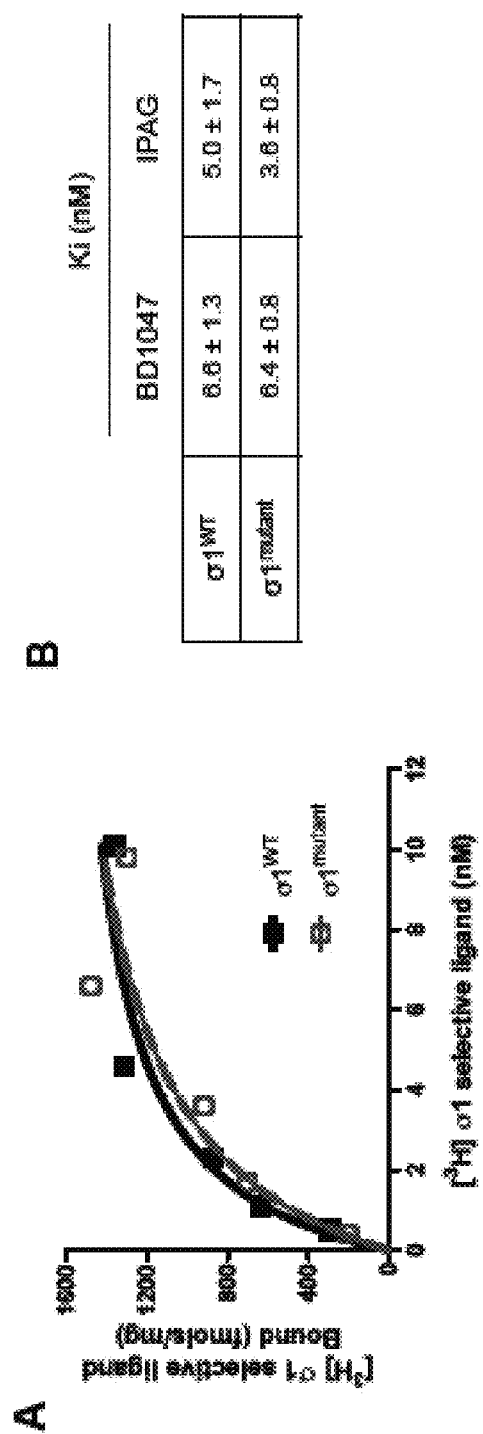

FIG. 50, comprising FIGS. 50A-50B, illustrates the finding that the binding of Sigma1 small molecule ligands were not altered by cytoplasmic tail mutation, and may be used as a tool to evaluate post-ligand-binding steps mediated by Sigma1 ligand-receptor interactions. FIG. 50A is a graph illustrating [$^3$H]-(+)-pentazocine (selective Sigma1 ligand) binding saturation. FIG. 50B illustrates the results of [$^3$H]-(+)-pentazocine competition binding. Binding was performed with [$^3$H]-(+)-pentazocine (3 nM) in HEK cell membranes from Sigma1-HA transfected cells (clone 320-3-3), Sigma1 mutated (E150A-HA) cells (clone 167-11-7) and Sigma1 mutated (E150K-HA) cells (clone 320-32-12). Despite the profound effect of the mutation on the inhibition of cell proliferation, the E150A mutation did not alter 3H-Sigma ligand binding.

Figure 51:
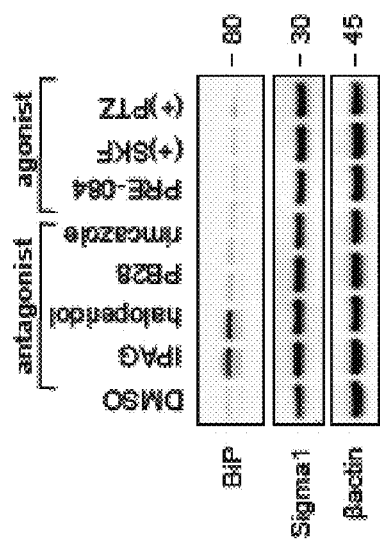

FIG. 51 is an immunoblot illustrating the finding that Sigma1 ligand treatment is associated with ER stress. MDA-MB-468 breast adenocarcinoma cells were treated for ~16 hours with DMSO control, IPAG (10 µM), haloperidol (10 µM), PB28 (20 µM), rimcazole (20 µM), PRE084 (20 µM), (+)SKF10047 [(+)SKF, (20 µM)], or (+)pentazocine [(+)PTZ, 20 µM]. Detergent-soluble total cell extracts were resolved by 10% SDS-PAGE and immunoblotted to detect levels of GRP78/BiP (BiP), Sigma1, and βactin (loading control). Putative Sigma1 "antagonist" and "agonist" are indicated.

Figure 52:
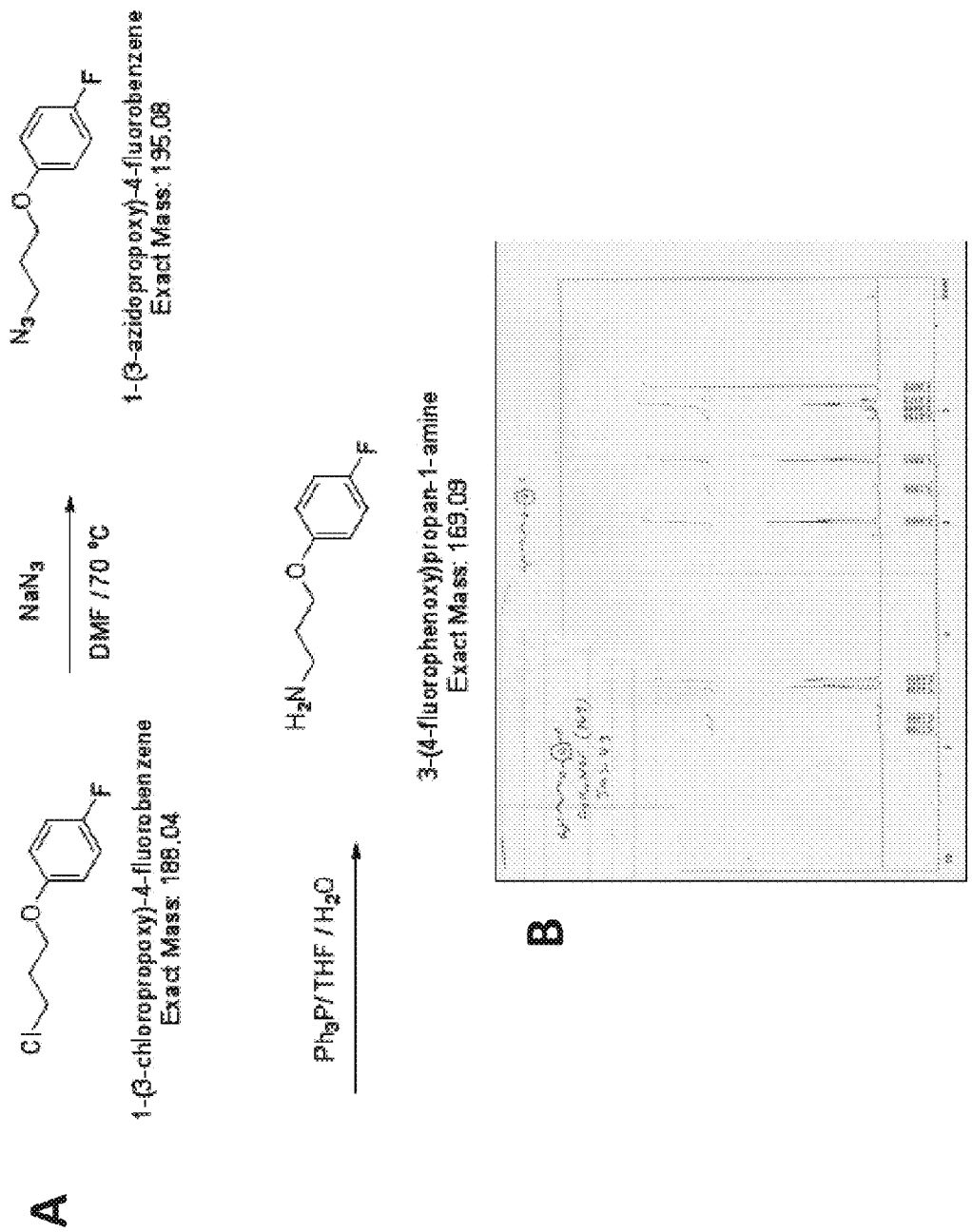

FIG. 52, comprising FIGS. 52A-52B, illustrates 3-(4-fluorophenoxy)propan-1-amine, which can act as a haloperidol amine surrogate. FIG. 52A is a scheme illustrating the synthesis of 3-(4-fluorophenoxy)propan-1-amine, beginning with 1-(3-chloropropoxy)-4-fluorobenzene. FIG. 52B illustrates the $^1$H NMR spectrum of 3-(4-fluorophenoxy)propan-1-amine.

Figure 53:
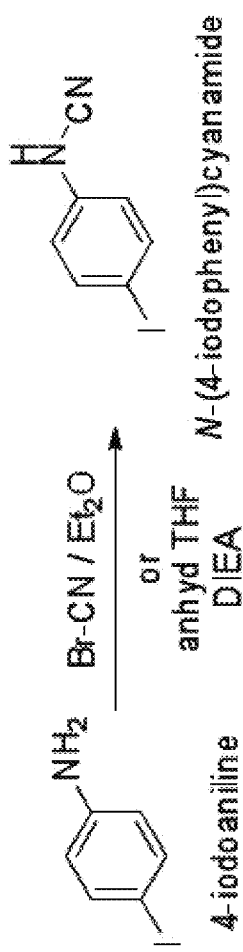

FIG. 53 is a synthetic scheme illustrating a general synthetic strategy toward the synthesis of N-(4-iodophenyl)cyanamide.

Figure 54A:
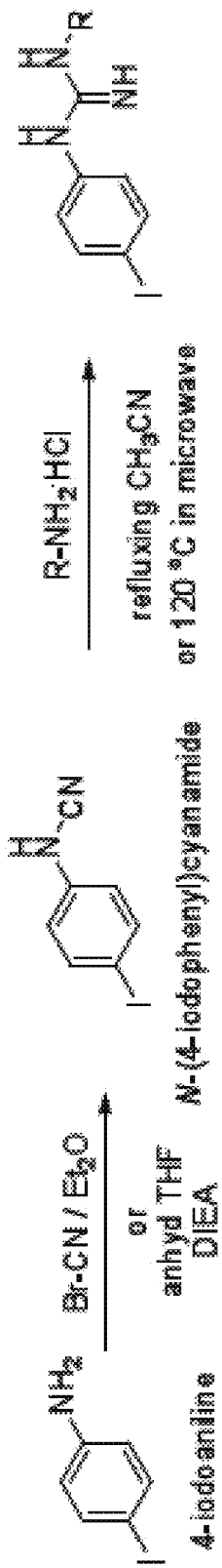

FIG. 54, comprising FIGS. 54A-54D, illustrates a synthetic strategy toward guanidines. FIG. 54A is a scheme illustrating a general synthesis of guanidines. FIG. 54B is the $^1$H NMR spectrum illustrating formation of symmetric and non-symmetric 4-iodophenyl guanidines (structures are pictured below the spectrum). FIG. 54C is the HPLC trace for the mixture of non-symmetric guanidine and dimer. FIG. 54D is the MS trace for the mixture of non-symmetric guanidine and dimer.

Figure 55:
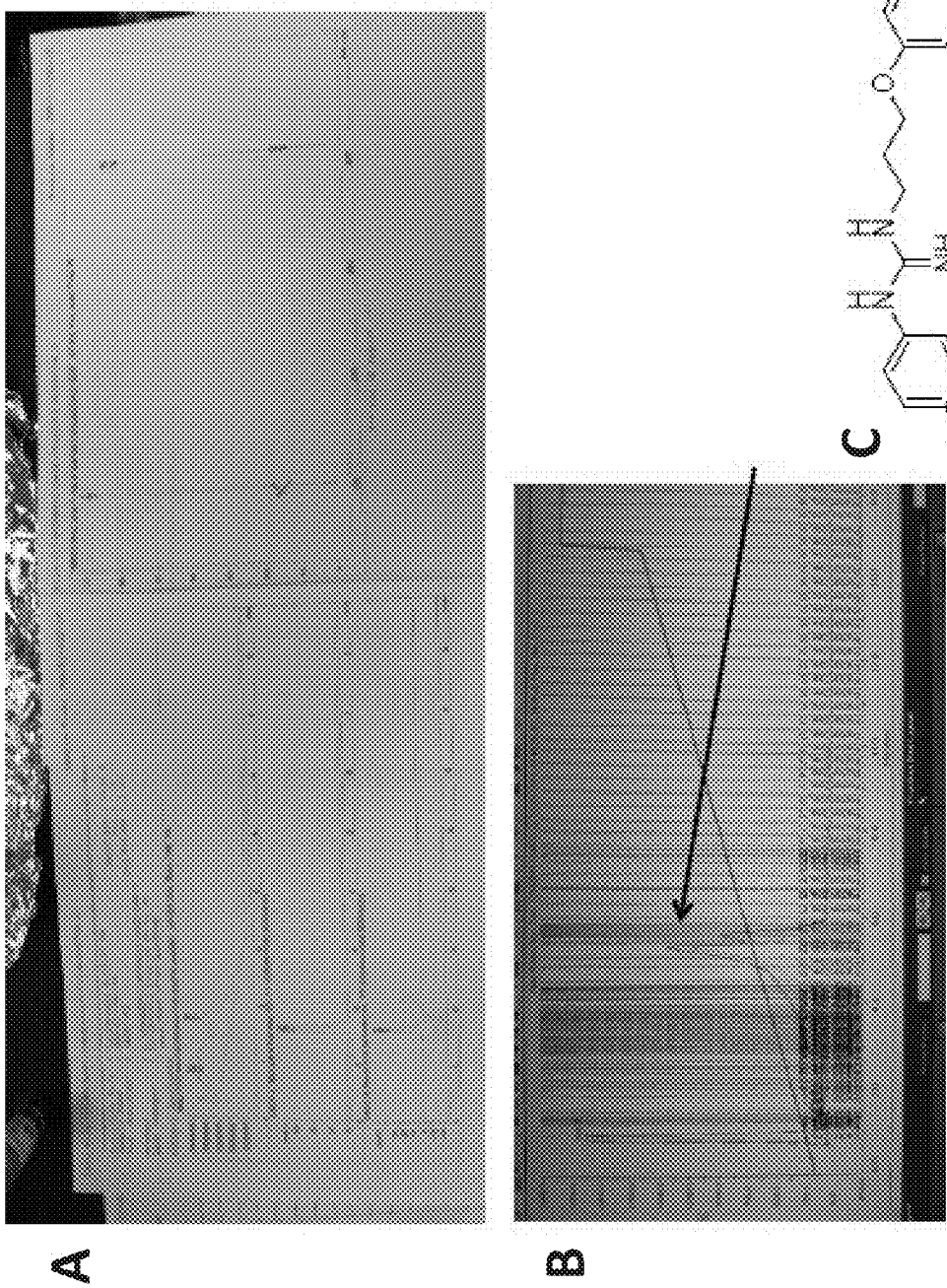

FIG. 55, comprising FIGS. 55A-55C, illustrates the HPLC purification of 1-3-(4-fluorophenoxy)propyl)-3-(4-iodophenyl)guanidine for testing.

FIG. 55A illustrates the HPLC trace of the purified compound. FIG. 55B is a trace of the HPLC fractions. The pure fraction is highlighted (black arrow). FIG. 55C is the structure of 1-3-(4-fluorophenoxy)propyl)-3-(4-iodophenyl)guanidine.

Figure 56:
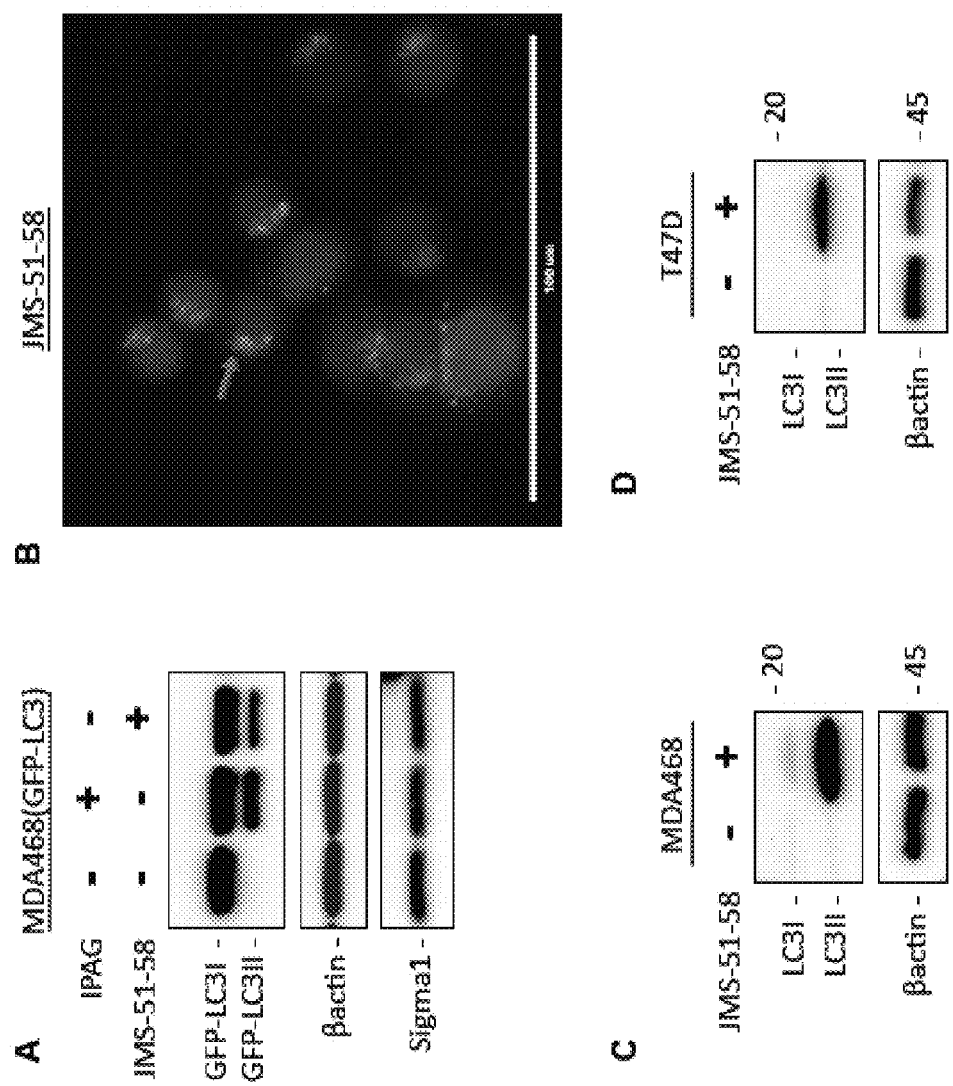

FIG. 56, comprising FIGS. 56A-56D, illustrates the finding that the novel Sigma1 ligand, JMS-51-58 [1-3-(4-fluorophenoxy)propyl)-3-(4-iodophenyl)guanidine], induced autophagy. FIG. 56A is an immunoblot illustrating MDA-MB-468 breast adenocarcinoma cells stably transfected with GFP-LC3 (green fluorescent protein tagged light chain 3, an autophagy marker) treated for ~16 hours with 10 µM IPAG or 10 µM 1-3 JMS-51-58. The appearance of GFP-LC3II was an indication of autophagosome formation. FIG. 56B is an image illustrating formation of autophagosomes (GFP-LC3 punctae) in MDA468 (GFP-LC3) treated with 10 µM JMS-51-58 as in FIG. 56A. The arrow points to an example of GFP-LC3-positive autophagosomes. The white bar at the bottom of the image indicates 100 µm. FIG. 56C is an image of an immunoblot illustrating the appearance of endogenous LC3II, a marker of autophagosome formation, in MDA-MB-468 breast adenocarcinoma cells treated for 16 hours with 10 µM of JMS-51-58. FIG. 56D is an image of an immunoblot illustrating the appearance of endogenous LC3II, a marker of autophagosome formation, in T47D breast adenocarcinoma cells treated for 16 hours with 10 µM JMS-51-58.

Figure 57:
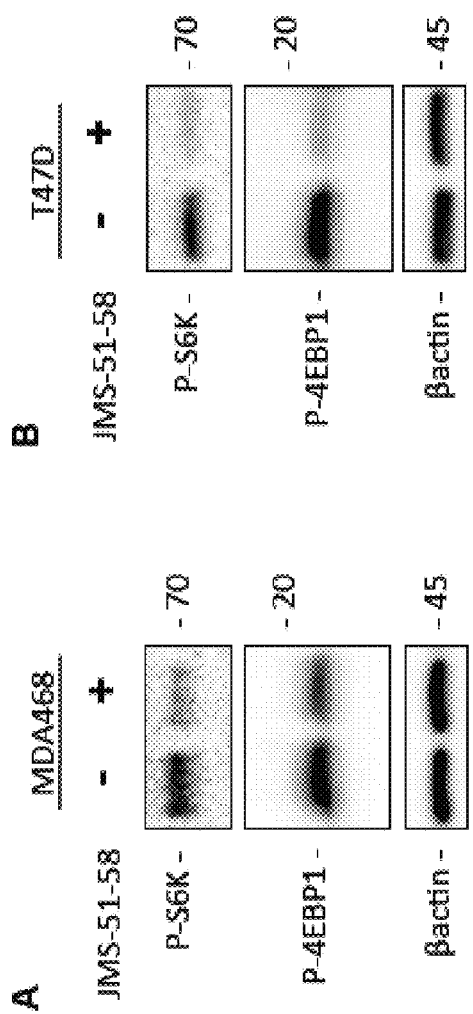

FIG. 57, comprising FIGS. 57A-57B, illustrates the finding that the novel Sigma1 ligand, JMS-51-58, mediated translational arrest. FIG. 57A is an image of an immunoblot illustrating MDA-MB-468 breast adenocarcinoma cells treated for 16 hours with 10 µM of JMS-51-58. FIG. 57B is an image of an immunoblot illustrating T47D breast adenocarcinoma cells treated for 16 hours with 10 µM of JMS-51-58. The levels of phosphothreonine 389-p70S6Kinase (P-S6K) and phosphoserine 65-4E-BP1 (P-4E-BP1) were evaluated by immunoblot. Decreased levels of both phosphoprotein levels indicated diminished protein synthesis.

Figure 58:
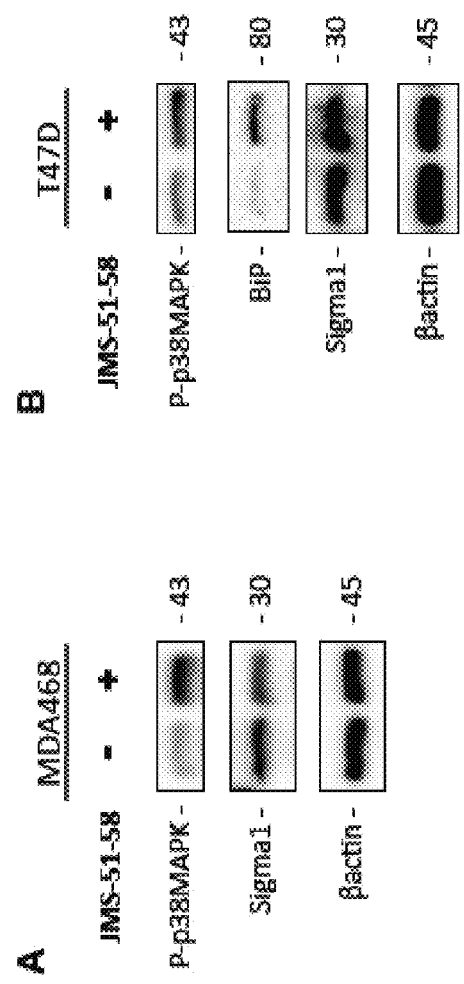

FIG. 58, comprising FIGS. 58A-58B, illustrates the finding that the novel Sigma1 ligand JMS-51-58 mediated ER stress response. FIG. 58A is an image of an immunoblot of MDA-MB-468 breast adenocarcinoma cells treated for 16 hours with 10 µM JMS-51-58. FIG. 58B is an image of an immunoblot of T47D breast adenocarcinoma cells treated for 16 hours with 10 µM JMS-51-58. The levels of phospho-Thr 180/Tyr 182 p38MAPK (P-p38MAPK) and GRP78/BiP and were evaluated by immunoblot.

Figure 59:
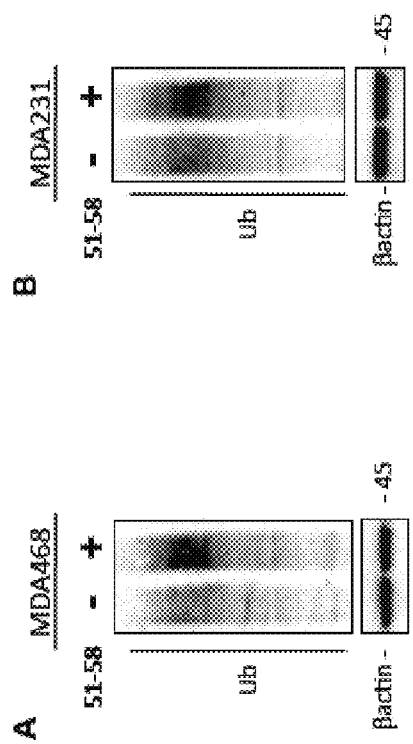

FIG. 59, comprising FIGS. 59A-59B, illustrates the finding that the novel Sigma1 ligand JMS-51-58 modulated the ubiquitin proteasome system. FIG. 59A is an image of an immunoblot evaluating the levels of poly-ubiquitylated proteins of MDA-MB-468 breast adenocarcinoma treated for 16 hours with 10 µM of JMS-51-58. FIG. 59B is an image of an immunoblot evaluating the levels of poly-ubiquitylated proteins of MDA-MB-231 breast adenocarcinoma cells treated for 16 hours with 10 µM of JMS-51-58. The levels of poly-ubiquitylated proteins were evaluated by immunoblot. JMS-51-58 treatment resulted in increased ubiquitylated protein levels compared to the DMSO control.

Figure 60:
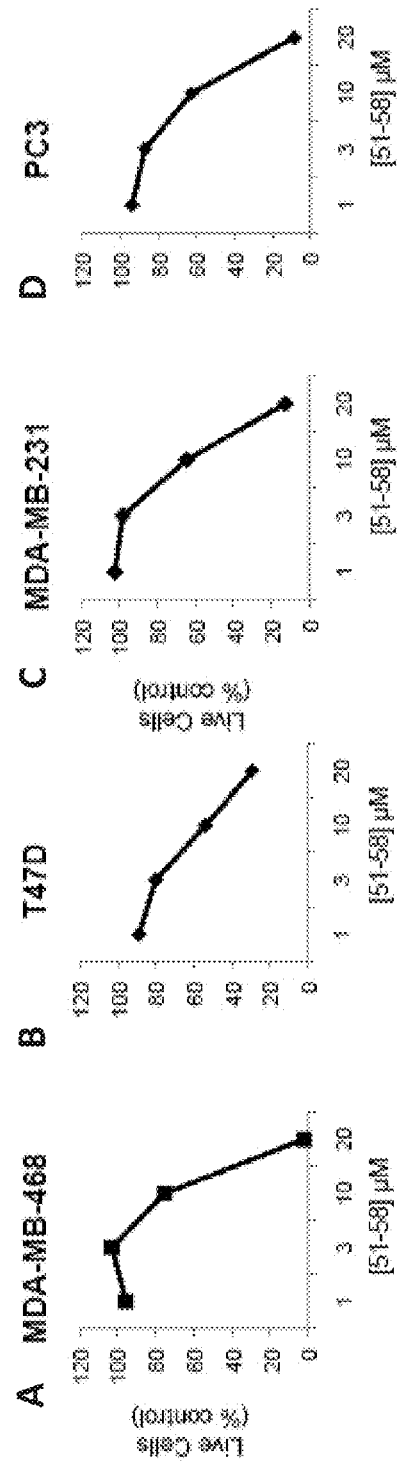

FIG. 60, comprising FIGS. 60A-60D, illustrates the finding that the novel Sigma1 ligand JMS-51-58 inhibited tumor cell proliferation. In vitro cell proliferation was quantified by Alamar blue assay. The anti-proliferative effects of four drug concentrations of novel Sigma1 small molecule ligand JMS-51-$2^{nd}$-58 were quantified after 40-70 hours of treatment. Data are representative of an experiment formed in triplicate for each cell line. FIG. 60A is a graph illustrating cell death in MDA-MB-468 breast adenocarcinoma cell cultures. FIG. 60B is a graph illustrating cell death in T47D breast adenocarcinoma cell cultures. FIG. 60C is a graph illustrating cell death in MDA-MB-231 breast adenocarcinoma cell cultures. FIG. 60D is a graph illustrating cell death in PC3 prostate adenocarcinoma cell cultures.

Figure 61:
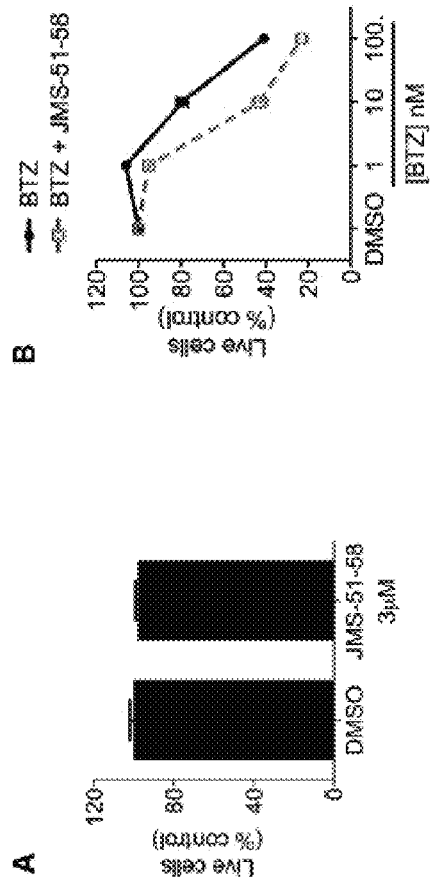

FIG. 61, comprising FIGS. 61A-61B, is a set of graphs illustrating the finding that the novel Sigma1 ligand JMS-51-58 potentiated proteasome inhibitor mediated inhibition of tumor cell proliferation. In vitro cell proliferation was quantified by Alamar blue assay. The anti-proliferative effects of four drug concentrations of novel Sigma1 small molecule ligand JMS-51-58, were quantified after ~70 hours of treatment of MDA-MB-231 breast adenocarcinoma cell cultures. FIG. 61A is a graph illustrating that in MDA-MB-231 cell culture, 3 µM of JMS-51-58 did not alter cell proliferation or rates of cell death. FIG. 61B is a graph illustrating that the sub-lethal dose of JMS-51-58 potentiated the cell proliferation inhibiting effects of bortezomib (BTZ). Note the shift to the left of the dose-response curve (broken line). Data are representative of an experiment performed in triplicate.

Figure 62:
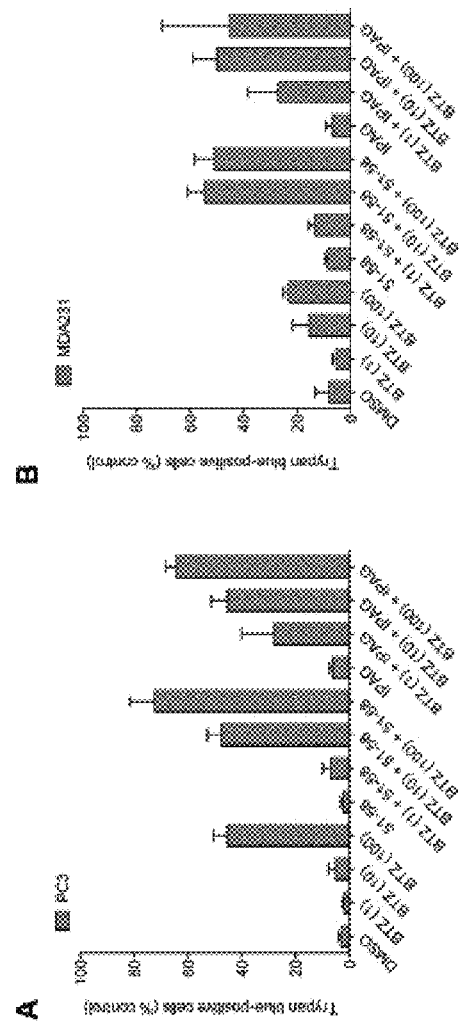

FIG. 62, comprising FIGS. 62A-62B, is a set of graphs illustrating the finding that the novel Sigma1 ligand JMS-51-58 potentiated proteasome inhibitor mediated tumor cell death. In vitro cell death was quantified by Trypan blue exclusion assay. To evaluate potentiation of proteasome inhibitor (bortezomib)-induced cell death by JMS-51-58, MDA-MB-468 cells were treated for 20 hours with JMS-51-58 (10 µM) alone, bortezomib (1 nM, 10 nM, 100 nM) alone or both drugs combined. Treatment with IPAG (10 µM) alone or combined with bortezomib (1 nM, 10 nM, 100 nM) was performed in parallel. Data are representative of an experiment performed in triplicate.

Figure 63:
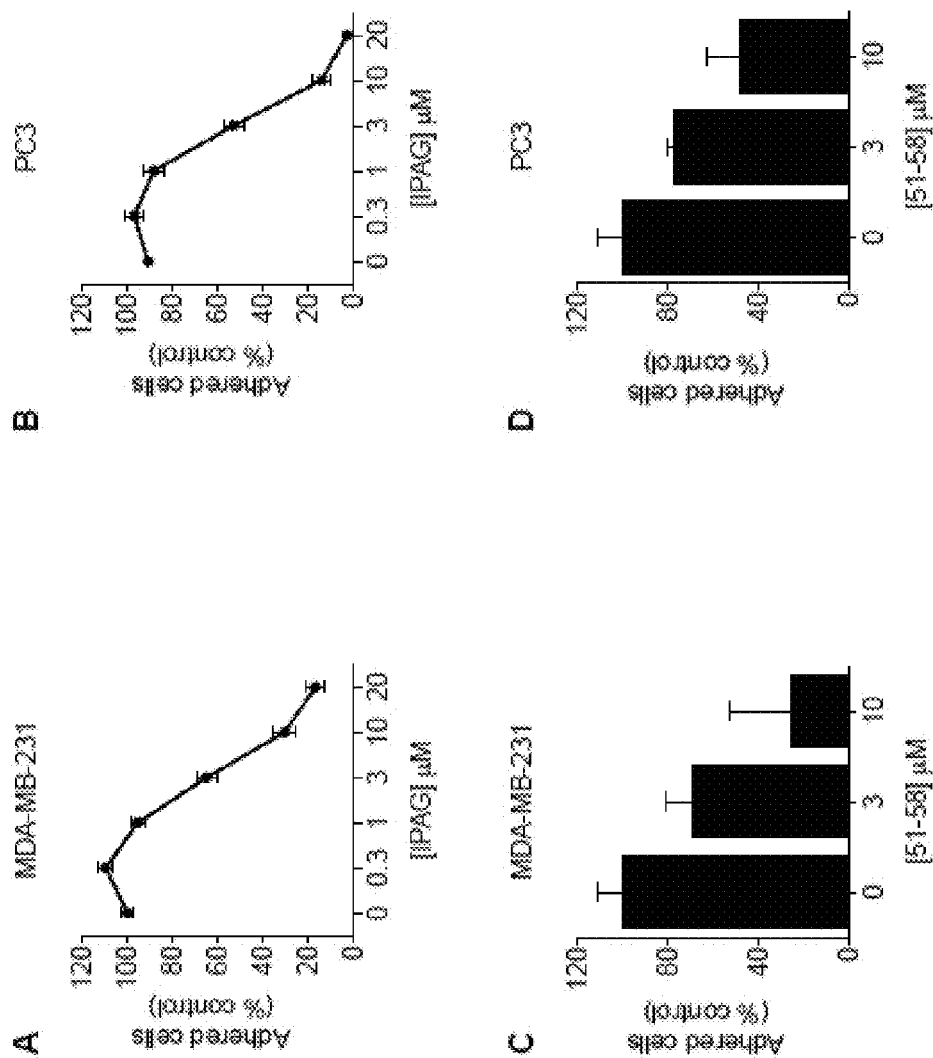

FIG. 63, comprising FIGS. 63A-63D, illustrates the finding that the novel Sigma1 ligand JMS-51-58 inhibited adhesion of metastatic breast and prostate adenocarcinoma cell lines, revealing its potential for use as an inhibitor of tumor cell metastasis. In vitro cell adhesion was quantified by Alamar blue assay. MDA-MB-231 and PC3 cells were detached with 0.25% trypsin+2 mM EDTA and reseeded onto 96 well plates. At the time of cell seeding, IPAG (Sigma1 putative antagonist) was added at the indicated doses to wells containing adenocarcinoma cells. The suspended cells were allowed to sediment and adhere for 16 hours in the presence of drug. Subsequently, the culture medium was removed by aspiration, each well washed once with 0.2 ml PBS (without calcium and magnesium), and Alamar blue assay was performed to quantify the number of live cells adhered to the surface of each well. FIG. 63A is a graph illustrating cell adherence in MDA-MB-231 breast adenocarcinoma cells. FIG. 63B is a graph illustrating cell adherence in PC3 prostate adenocarcinoma cells. The same procedure was performed using the indicated concentrations of JMS-51-58. FIG. 63C is a graph illustrating cell adherence in MDA-MB-231 breast adenocarcinoma cells. FIG. 63D is a graph illustrating cell adherence in PC3 prostate adenocarcinoma cells. Standard deviation bars are shown.

Figure 64:
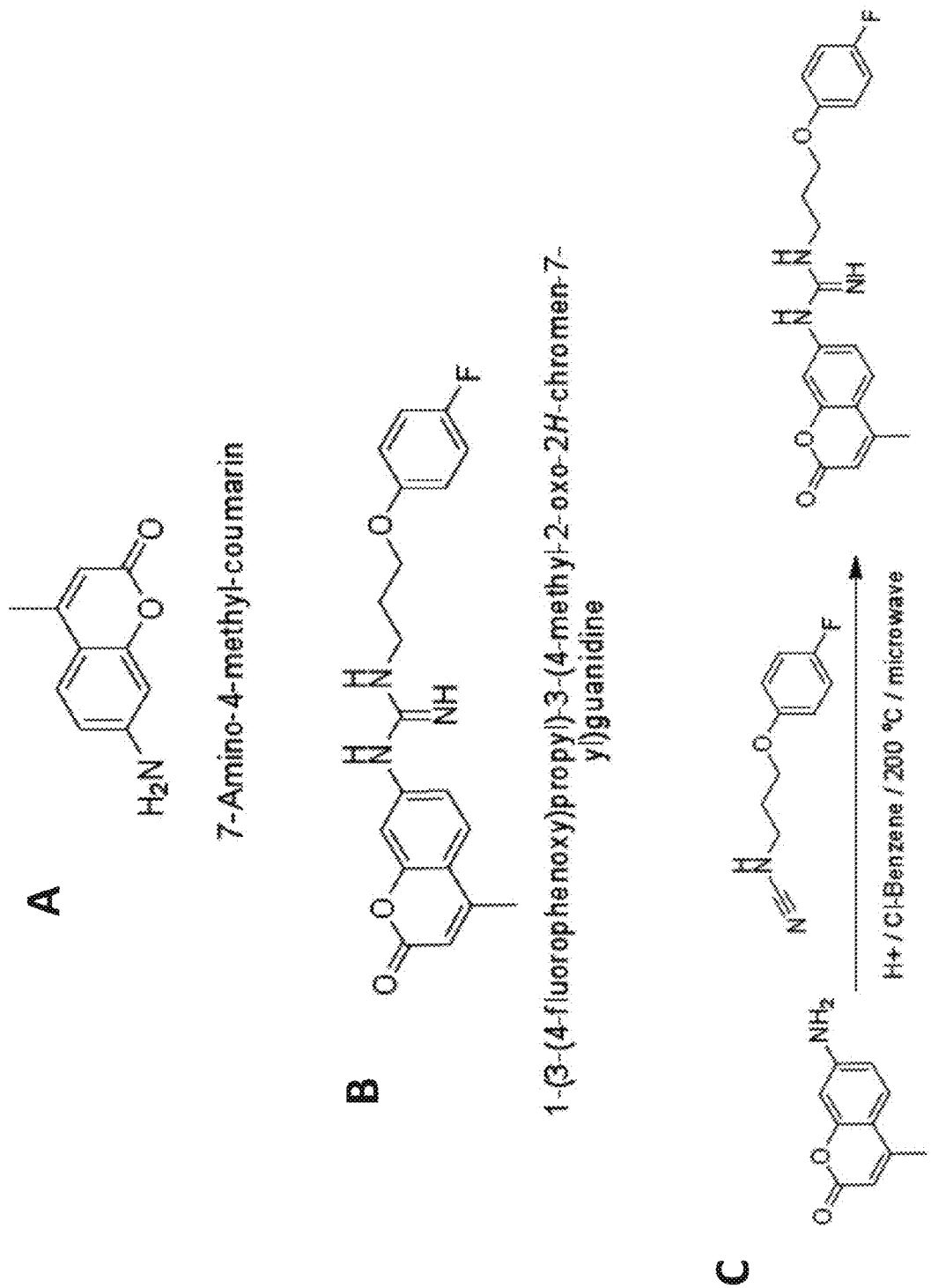

FIG. 64, comprising FIGS. 64A-64C, illustrates the incorporation of fluorophores into Sigma ligands for use as novel fluorescent probes to study biological phenomena in living cells. FIG. 64A is the structure of 7-amino-4-methyl coumarin, a fluorescent dye. FIG. 64B is the structure of a fluorescent probe (a Sigma1 ligand comprising a fluorophore) useful to study Sigma receptor biology in living cells. FIG. 64C is a scheme illustrating the synthesis of the fluorescent probe.

Figure 65:
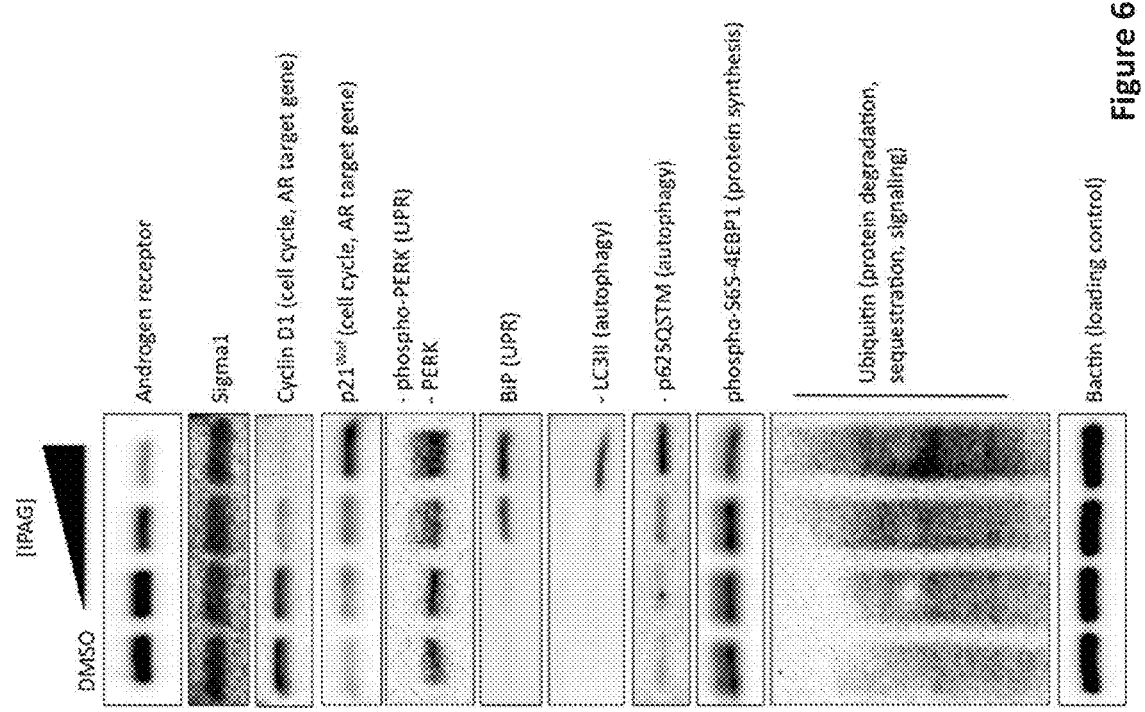

FIG. 65 illustrates the modulation of androgen receptor levels in prostate cancer by a Sigma1 antagonist. Androgen receptor (AR) positive prostate adenocarcinoma cell line, LNCaP, was treated with increasing doses (1-10 µM) of Sigma1 antagonist, IPAG, for 16 hours and subsequently cells were harvested, and proteins were extracted and immunoblotted to evaluate Sigma1 ligand mediated changes in AR protein levels, changes in protein levels AR responsive genes (Cyclin D1, p21), induction of UPR (band migration shift of PERK, increased levels of BiP), induction of autophagy (appearance of LC3II, increased levels of p62SQSTM), changes in protein synthesis (in this case, absence of changes in protein synthesis marker phospho-4EBP1), and increased levels of ubiquitylated proteins. βactin served as a loading control.

Figures 66A, 66B, 66C, 66D:
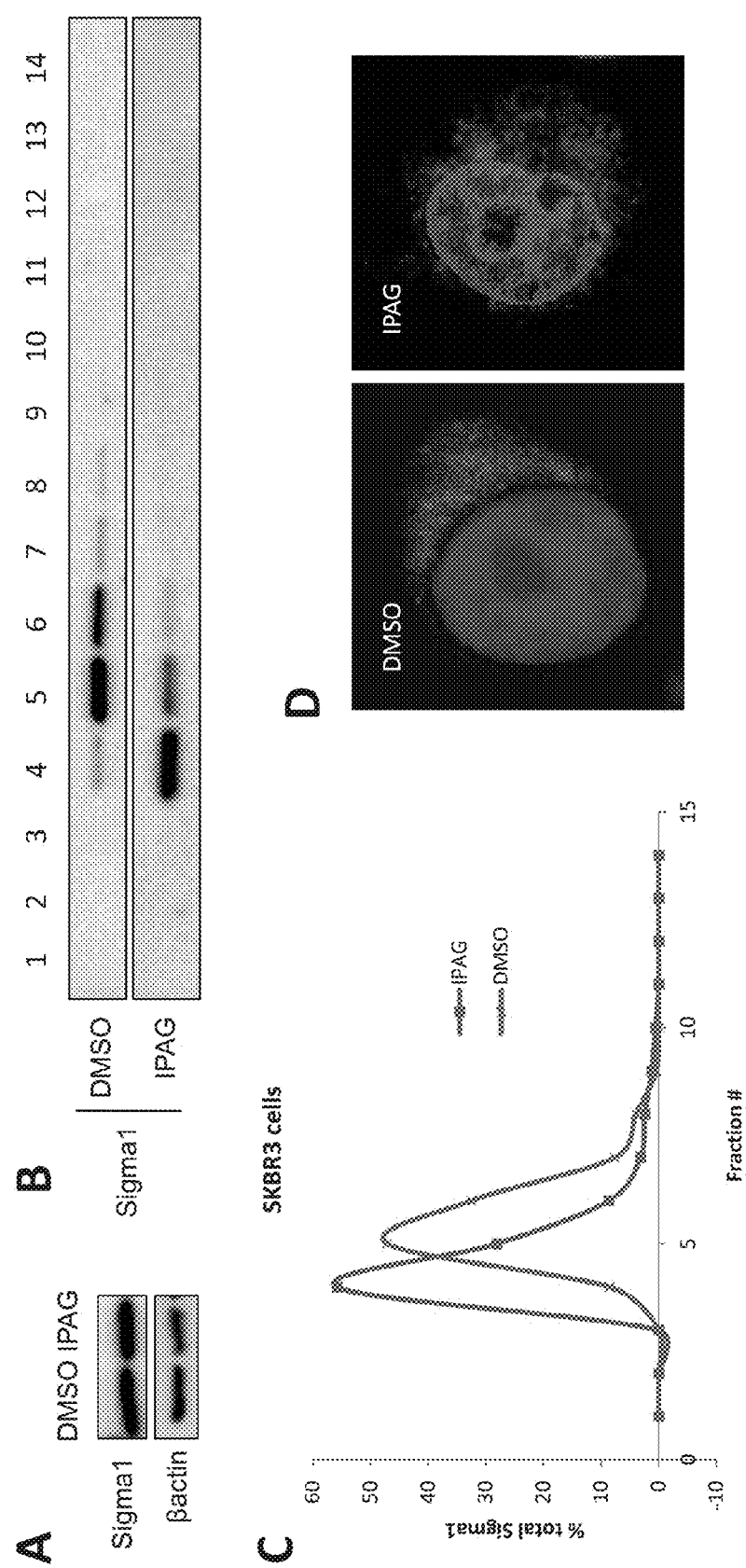
Figure 66E:
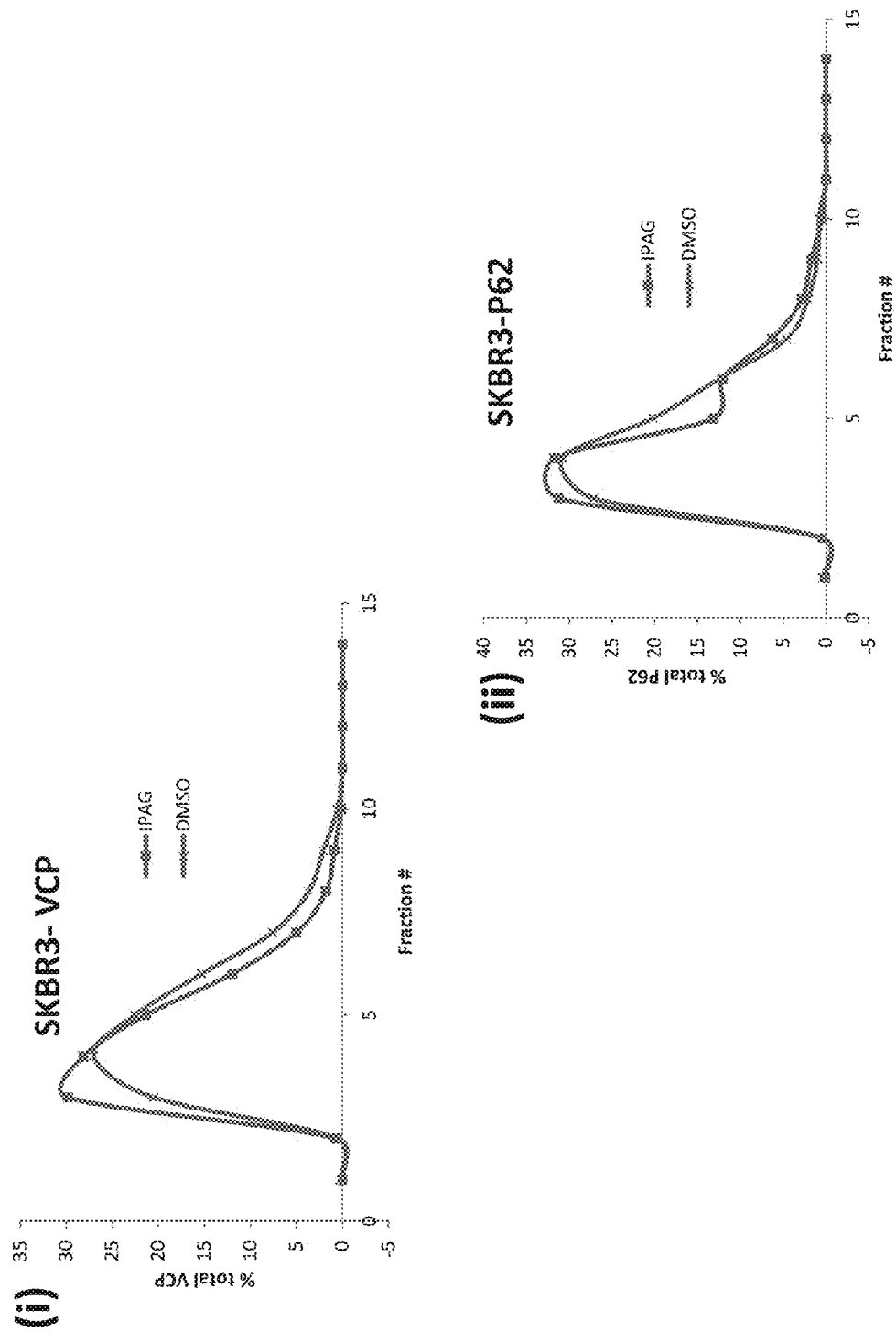
Figure 66G:
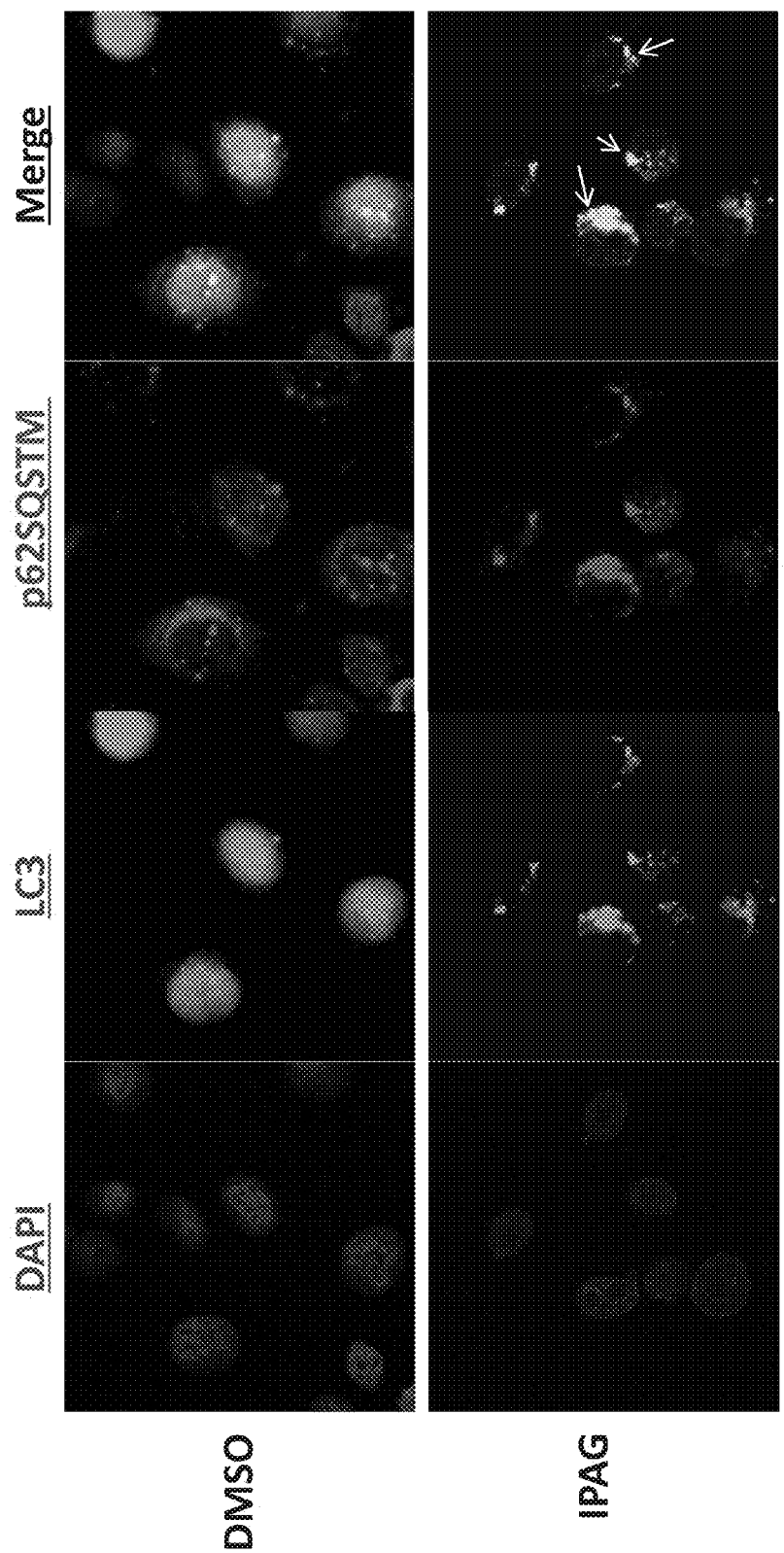
Figure 66H:
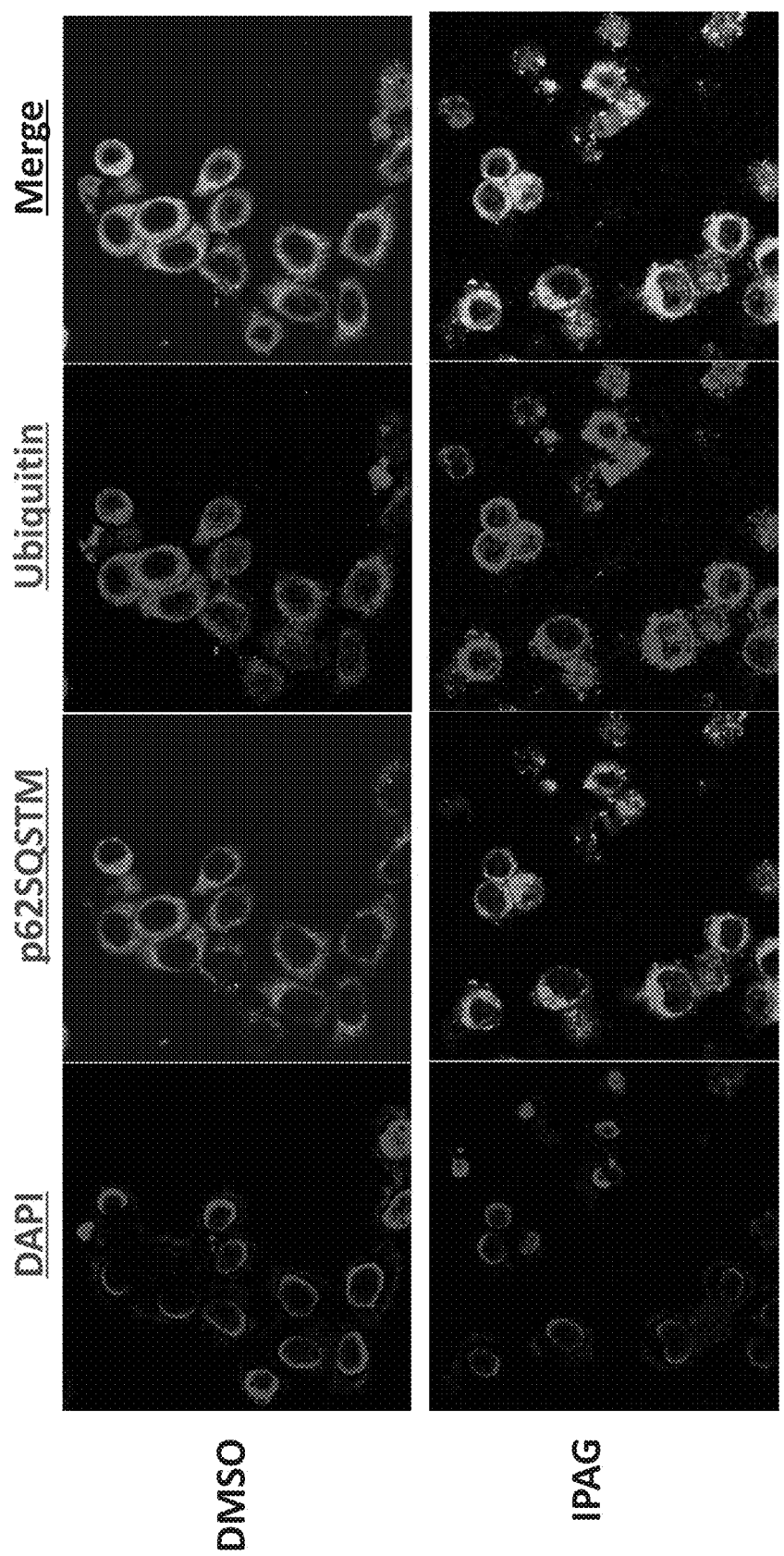

FIG. 66, comprising FIGS. 66A-66H, illustrates the non-limiting mechanism(s) of Sigma1 ligand actions, wherein Sigma ligand treatment induces differential localization of Sigma1. FIG. 66A is an immunoblot that illustrates that Sigma1 steady-state protein levels do not change in response to IPAG treatment. FIG. 66B is an immunoblot of the fractions collected from biochemical sub-cellular fractionation assay. This immunoblot demonstrates that Sigma1 distribution is altered in response to IPAG treatment. FIG. 66C is a graph illustrating quantification of bands in FIG. 66B. FIG. 66D is a set of images of confocal immunofluorescence microscopy of Sigma1 in SKBR3 cells treated for 12-16 hours with IPAG. Green signal indicated Sigma1, blue signal (DAPI) indicated nucleus. FIG. 66E is a set of graphs illustrating quantification of fractions collected from biochemical sub-cellular fractionation assay performed using SKBR3 cells. Red line represents fractionation following 12-16 hour treatment with IPAG, the blue line represents fractionation of 12-16 hour DMSO (vehicle (control) treated cells. Graph (i): Quantification of VCP fractionation immunoblot. Graph (ii): Quantification of p62SQSTM fractionation immunoblot. FIG. 66F is a set of confocal microscopy images, with evidence of co-localization of p97/VCP (VCP) and autophagosome marker GFP-LC3II (LC3). This confocal image demonstrated presence of VCP in autophagosomes (indicated by white arrows in merged image, lower right panel). FIG. 66G is a set of confocal microscopy images, with evidence of co-localization of p62SQSTM and autophagosome marker GFP-LC3II (LC3). This confocal image demonstrates presence of p62SQSTM in autophagosomes (indicated by white arrows in merged image, lower right panel). p62SQSTM is an adaptor protein for the transport and incorporation of ubiquitylated proteins into autophagosomes. Functional and physical association with LC3II and functional interaction with VCP are reported in the literature. FIG. 66H is a set of confocal microscopy images, with evidence of co-localization of poly-ubiquitylated proteins and p62SQSTM. This confocal image demonstrated presence of poly-ubiquitylated proteins in autophagosomes that contain p62SQSTM. The ubiquitin-p62SQSTM co-localization and distribution pattern changed subsequent to IPAG treatment. The data illustrated here support the finding that treatment of a cell with an ER stress inducing Sigma ligand (e.g., IPAG) did not alter total Sigma1 receptor levels, but did alter the subcellular localization of Sigma1, with Sigma1 redistributed and concentrated in the ER. Sigma1 functional related and physical associated proteins were redistributed to the other parts of the cell, especially into autophagosome. Further, prolonged ER stress induced by IPAG treatment caused cancer cell death. This is consistent with data presented in FIGS. 43-44, wherein changes in protein associations were observed in response to Sigma ligand treatment.

Figure 67A:
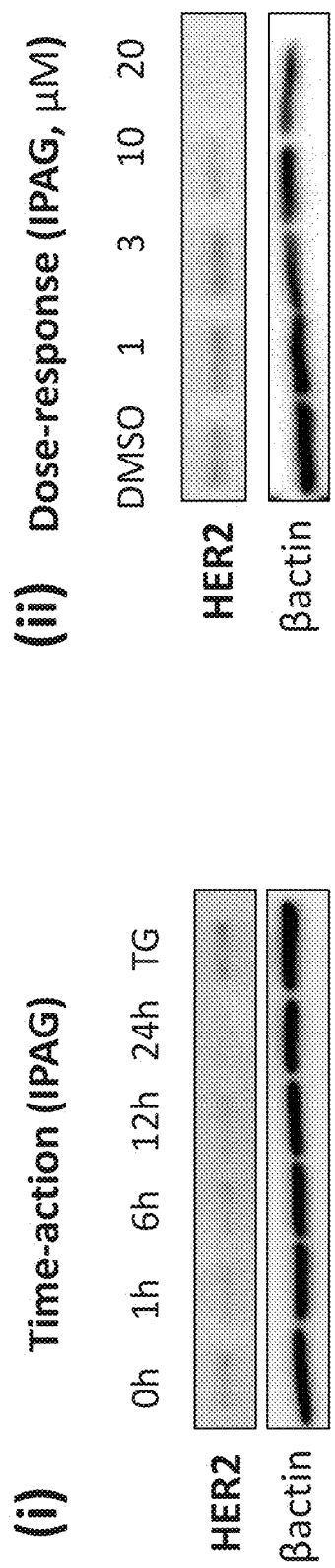
Figure 67B:
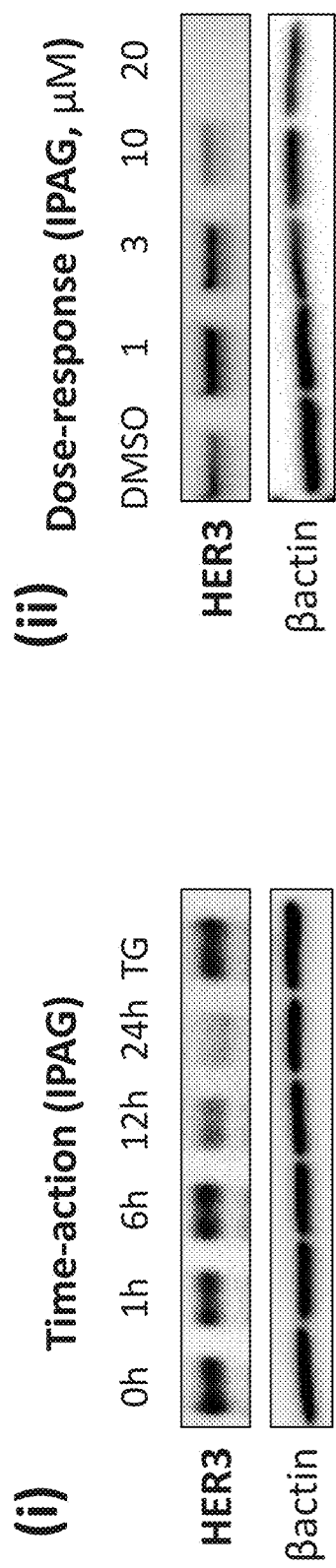
Figure 67C:
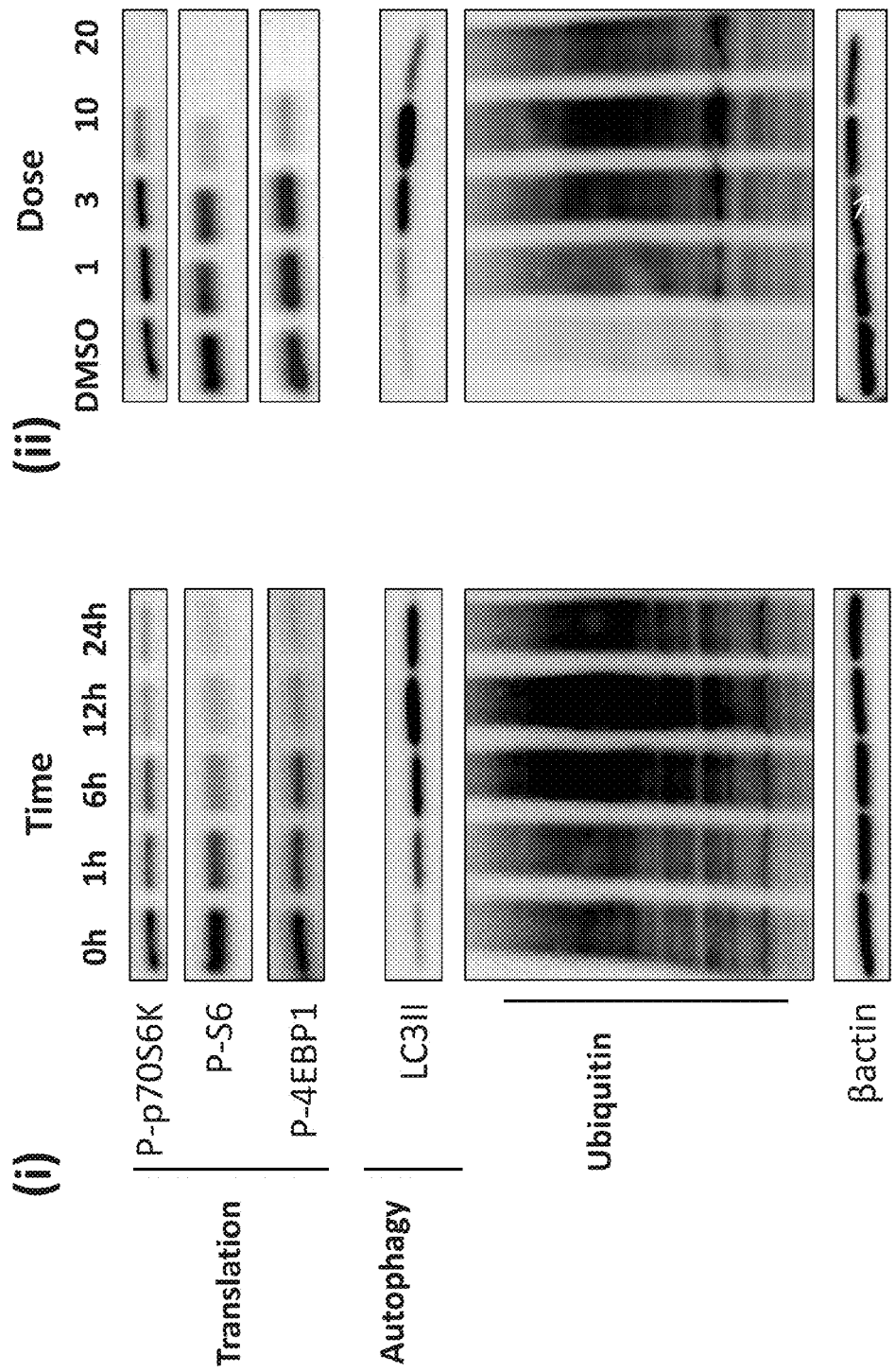
Figure 67D:
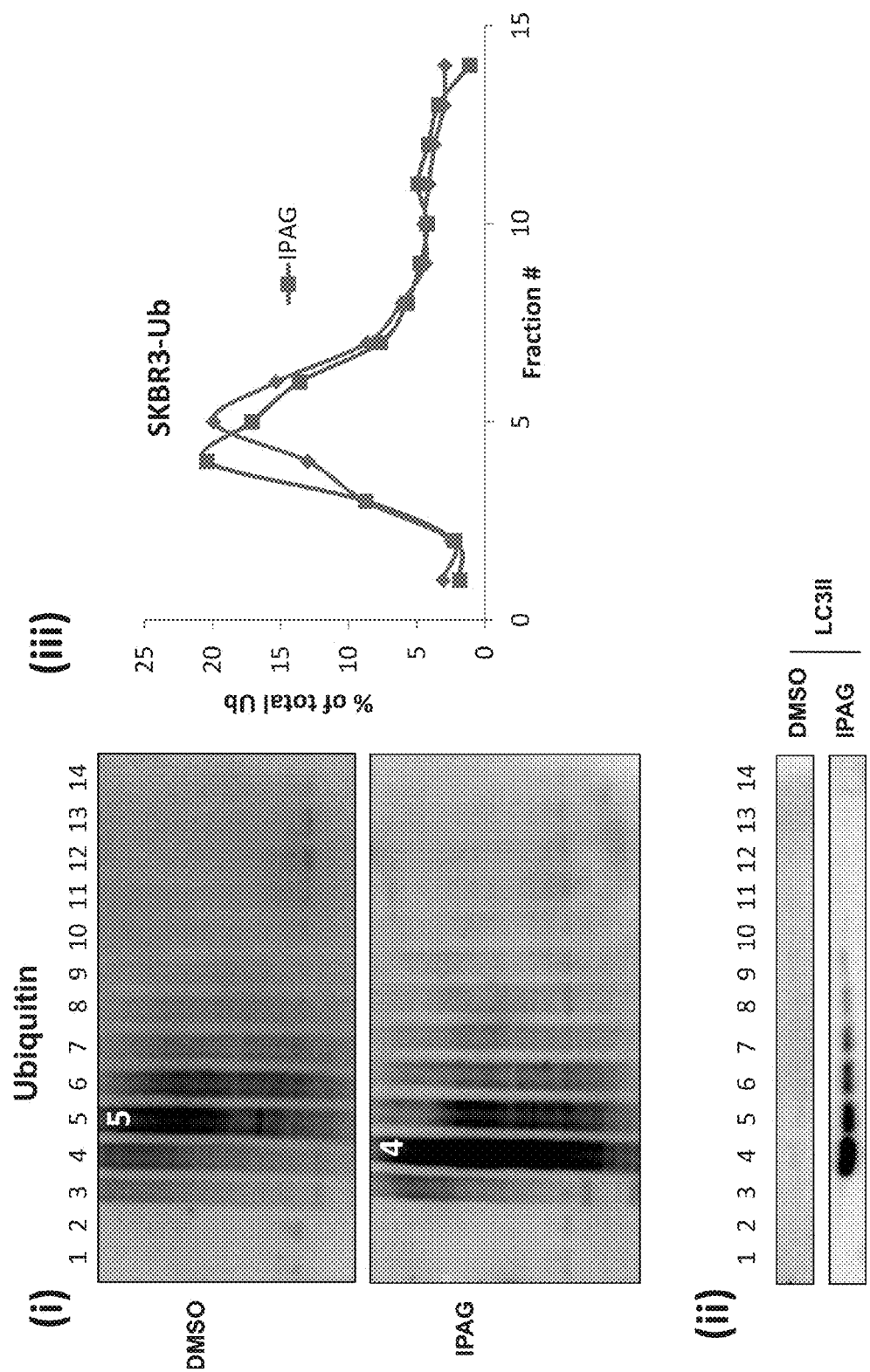
Figure 67E:
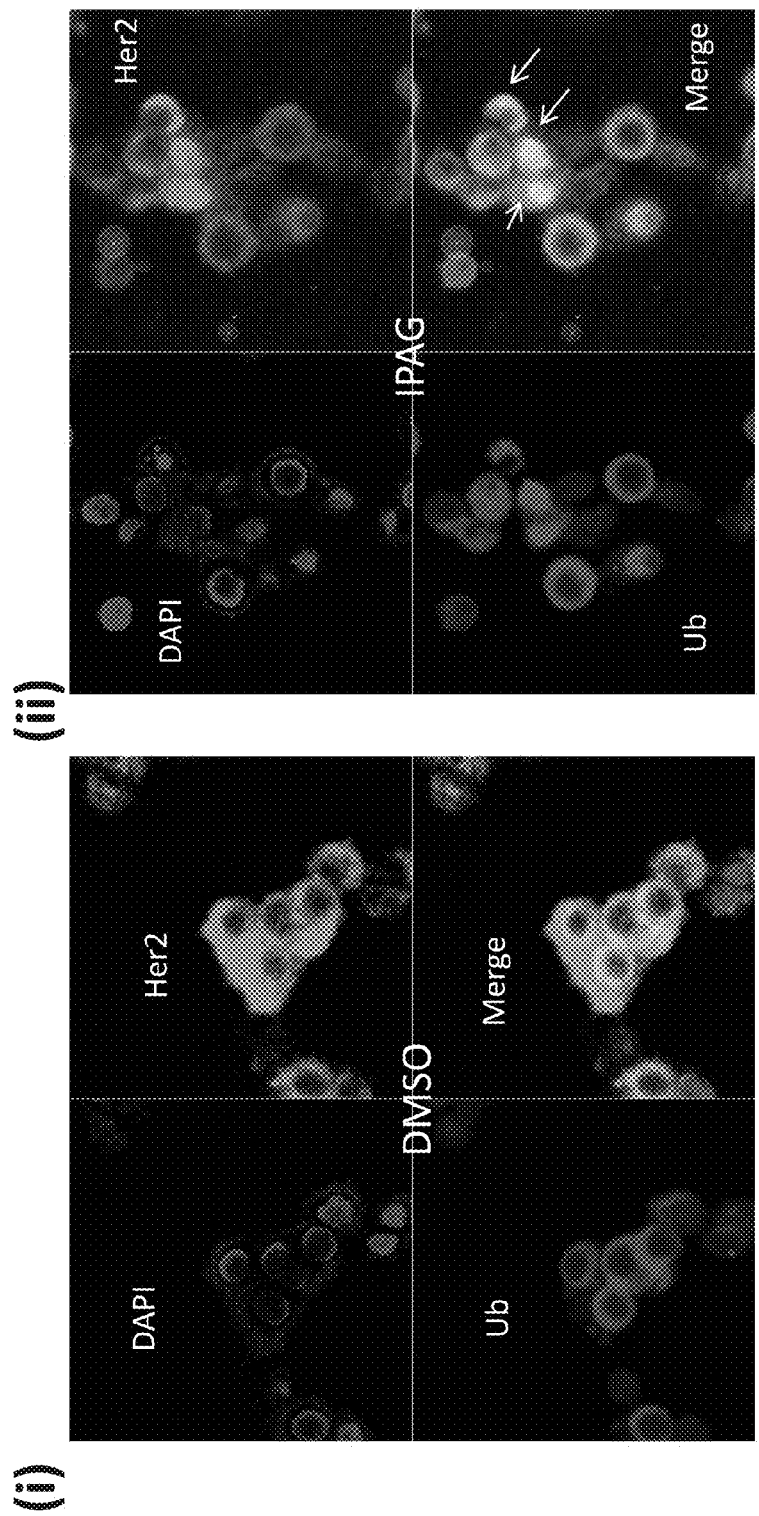
Figure 67F:
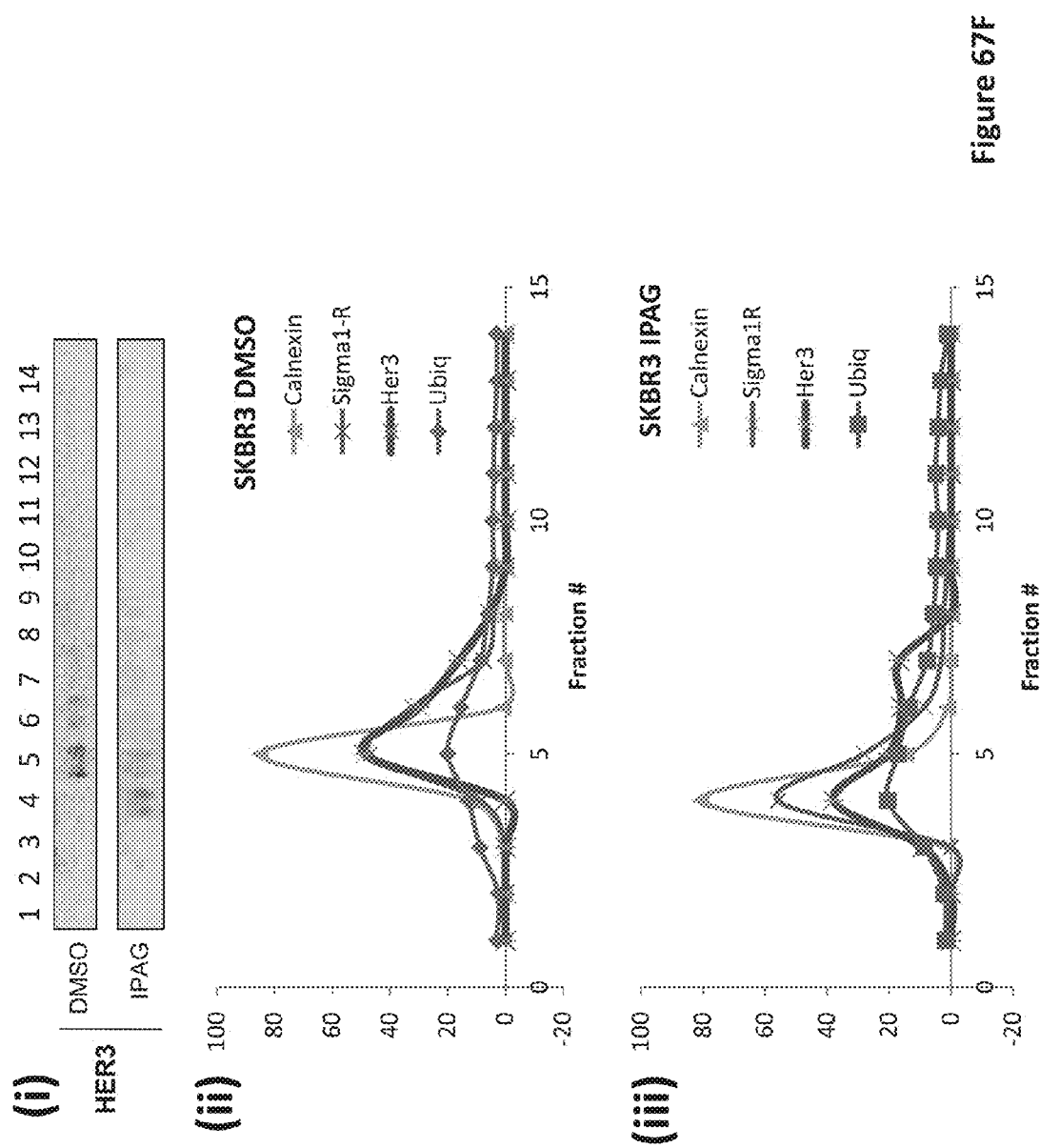

FIG. 67, comprising FIGS. 67A-67F, illustrates the finding that Sigma1 ligands may be used to modulate (in this case, decrease) the levels of growth factor receptors such as HER2 and HER3 in breast cancer cells, in the absence of detectable cell death. IPAG time and dose-dependently causes decreased levels of HER2/3 in SkBr-3 cells. Short exposure to IPAG or lower dosage induces ubiquitin-mediated autophagosomal degradation of HER2/3. Prolonged IPAG treatment or higher dosage caused translational arrest. At later stage, a combined effect of autophagosomal degradation and translational arrest significantly reduced HER2/3 level in SkBr-3 cells. FIG. 67A is a set of immunoblots of HER2 following treatment with IPAG. Detergent soluble whole-cell lysates were solved by denaturing SDS-PAGE. (i) 1-to-24 hour (h) treatment with 10 µM IPAG or 11 µM thapsigargin (TG). (ii) Following 12 hour treatment with 1, 3, 10, 20 µM IPAG. FIG. 67B is a set of immunoblots of HER3 following treatment with IPAG. Detergent soluble whole-cell lysates were solved by denaturing SDS-PAGE. (i) 1-to-24 hour (h) treatment with 10 µM IPAG or 1 µM thapsigargin (TG). (ii) Following 12 hour treatment with 1, 3, 10, 20 µM IPAG. FIG. 67C is a set of immunoblots of detergent soluble whole-cell lysates solved by denaturing SDS-PAGE. (i) Immunoblot of translational regulation, autophagy, and protein ubiquitylation markers following 1-to-24 hour (h) treatment with 10 µM IPAG. (ii) Immunoblot to evaluate drug dose-response—12 hour treatment with 1, 3, 10, 20 µM IPAG—using the same markers indicated in (i). FIG. 67D is a series of immunoblot of the fractions collected from biochemical sub-cellular fractionation assay performed using SKBR3 cells. (i) This immunoblot demonstrates that the intracellular distribution of ubiquitylated proteins is altered in response to IPAG treatment. Note salient shift in band intensity from predominantly fraction 4-6 in control (DMSO) treated cells compared to fraction 3-5 in IPAG treated cells. (ii) Fractions in which autophagosome marker LC3II is found correlates with ubiquitylated proteins in (i). (iii) Quantification of bands in (i). FIG. 67E is a series of confocal microscopy images, with evidence of co-localization of HER2 and ubiquitin (Ub). This confocal image demonstrated decreased levels of HER2 in response to IPAG treatment (intensity of green signal in DMSO upper right compared to IPAG upper right panel) and concentrated co-localization of Ub and HER2 subsequent to IPAG treatment (indicated by white arrows in merged image, lower right panel). FIG. 67F illustrates biochemical subcellular fractionation. (i) Immunoblot of HER3 in cell lysate fractions from SKBR3 following 16 hour (h) treatment with 10 µM IPAG. (ii) Quantification of HER3 band in DMSO (vehicle control) treated conditions. (iii) Quantification of HER3 band in IPAG treated conditions.

FIG. 68 is a series of confocal microscopy image illustrating the evidence of co-localization of poly-ubiquitylated proteins and autophagosome marker GFP-LC3II (LC3). This confocal image demonstrates presence of poly-ubiquitylated proteins in autophagosomes (indicated by white arrows in merged image, lower right panel).

Figure 69:
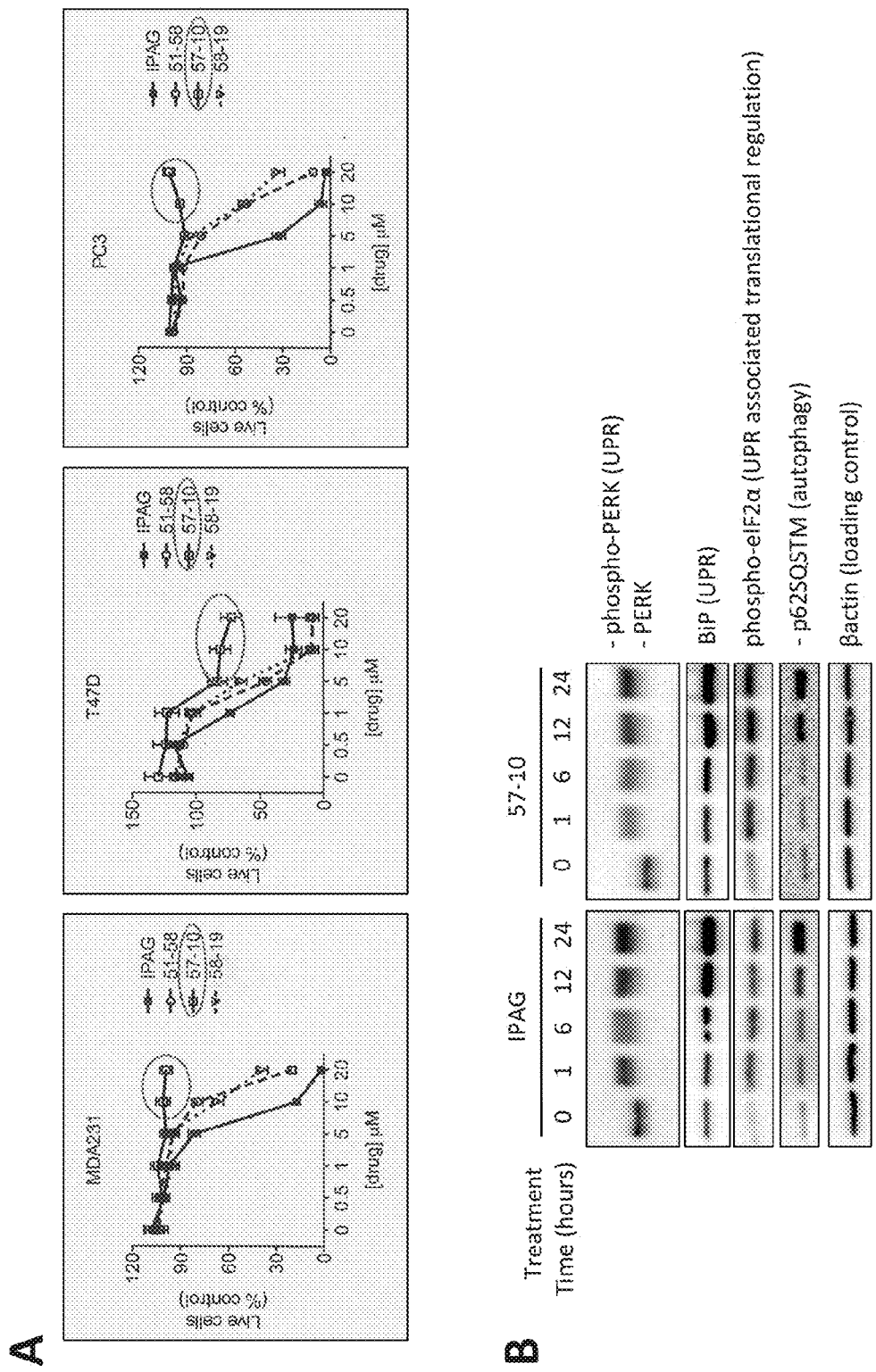

FIG. 69, comprising FIGS. 69A-69B, illustrates the finding that Sigma1 ligand, JMS-57-10, mediates UPR, modulates protein translation, and autophagy in the absence of cell death. (FIG. 69A) Alamar blue assay used to quantify the relative number of viable cells (live cells) following 72 hours of treatment with a range of doses of the indicated Sigma1 ligands. Red circle highlights effects of treatment with JMS-57-10 (57-10). Note that for all three cell lines, JMS-57-10 did not elicit appreciable cell death under these conditions. Therefore, the decrease in the relative % of live cells observed for T47D represents inhibited cell proliferation. (FIG. 69B) Immunoblot to evaluate induction of UPR, translational regulation, and autophagy in response to IPAG and JMS-57-10 (57-10).

Figure 70:
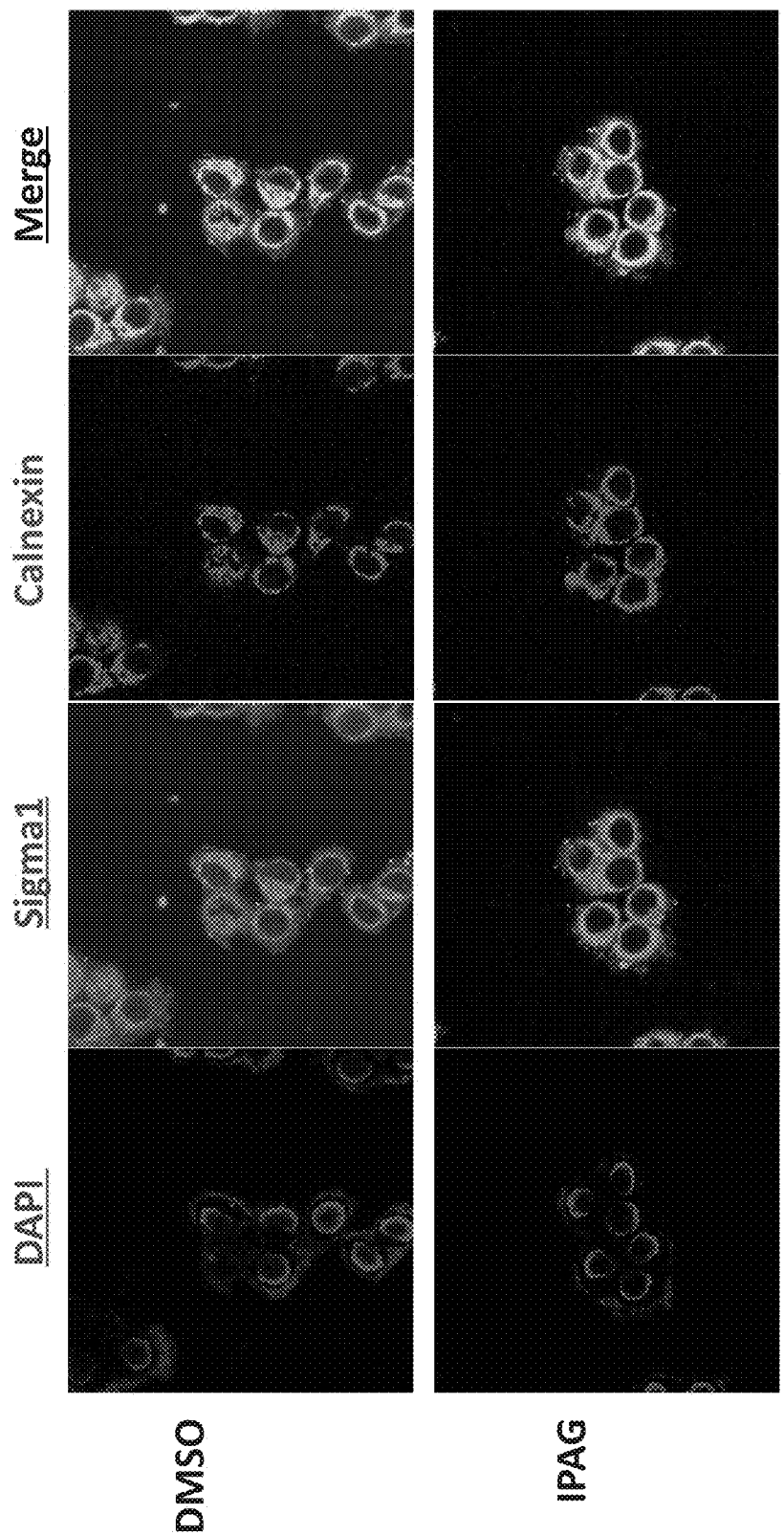

FIG. 70 is a series of confocal microscopy images illustrating the finding that Sigma1 is present in predominantly in the ER of SKBR3 breast cancer cells. Confocal immunofluorescence microscopy demonstrated co-localization of Sigma1 and calnexin, a resident endoplasmic reticulum (ER) protein. The result indicated that Sigma1 remained ER localized, albeit with apparently different distribution pattern, in cells treated for 12-16 hours with IPAG. Yellow signal (merge) indicated co-localization.

Figure 71:
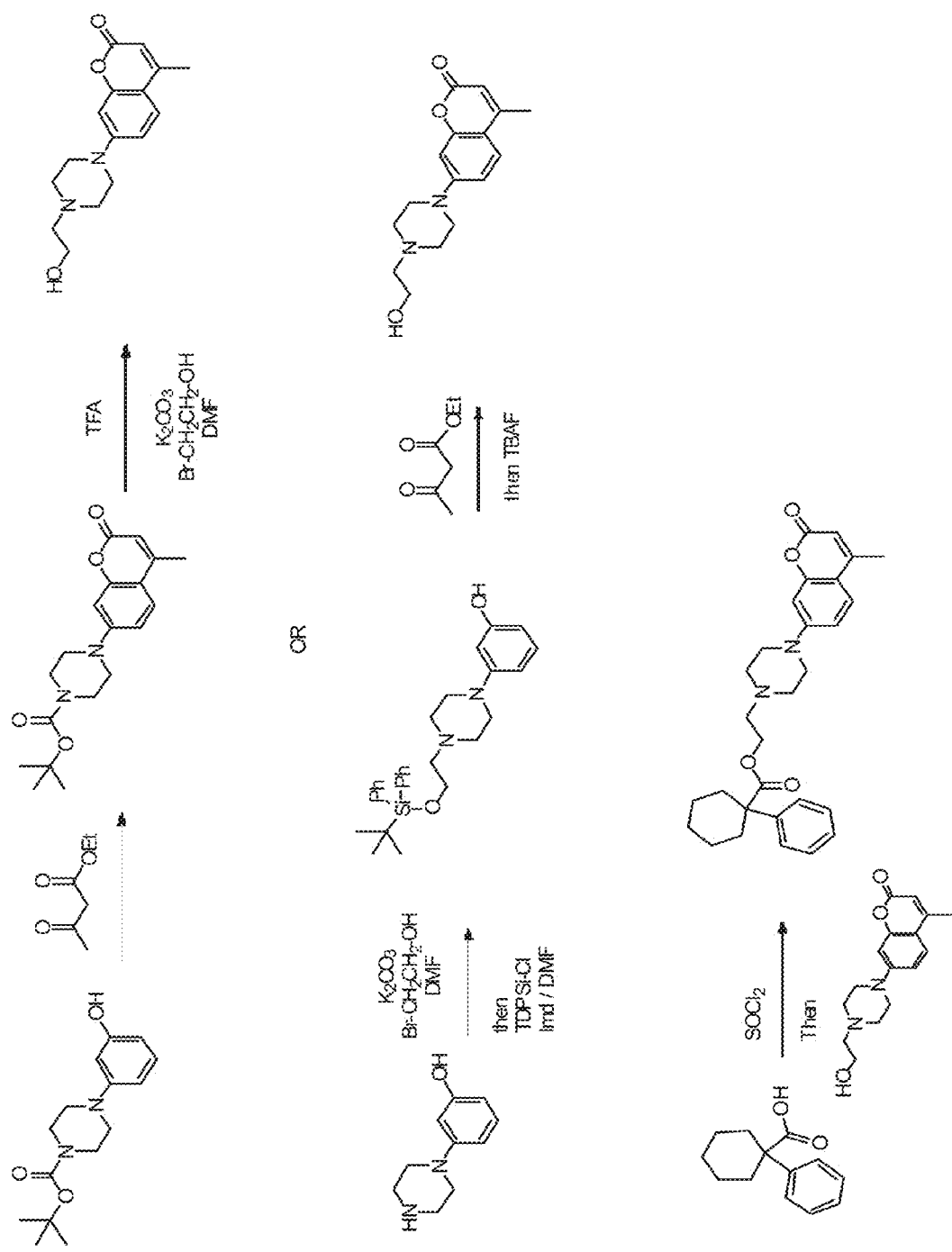

FIG. 71 is a synthetic scheme illustrating the synthesis of 2-(4-(4-methyl-2-oxo-2H-chromen-7-yl)piperazin-1-yl) ethyl 1-phenylcyclohexanecarboxylate, a fluorescent probe useful in the invention.

Figure 72:
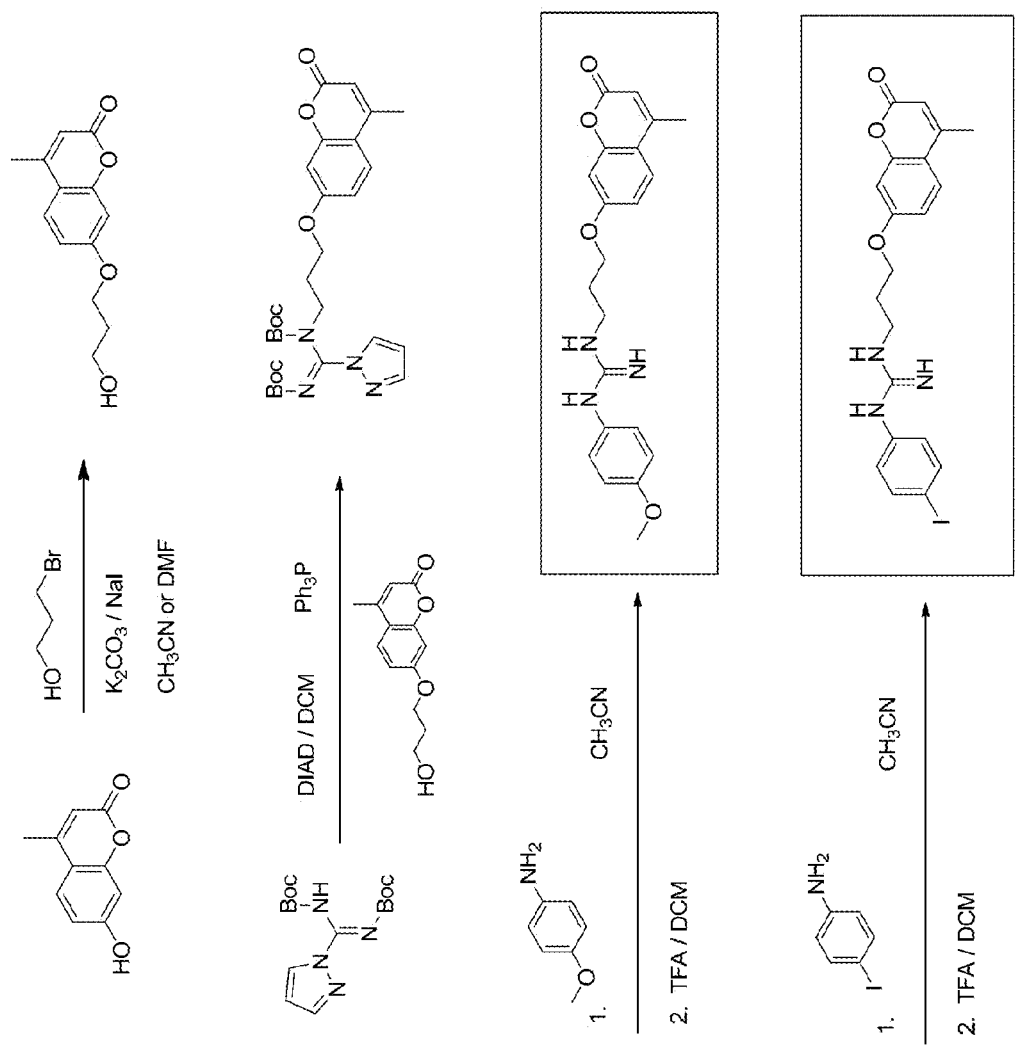

FIG. 72 is a synthetic scheme illustrating the synthesis of 1-(4-methoxyphenyl)-3-(3-((4-methyl-2-oxo-2H-chromen-7-yl)oxy)propyl)guanidine and 1-(4-iodophenyl)-3-(3-((4-methyl-2-oxo-2H-chromen-7-yl)oxy)propyl)guanidine, fluorescent probes useful in the invention.

DETAILED DESCRIPTION OF THE INVENTION

The present invention relates to the unexpected discovery of novel compounds that bind to and modulate the activity of the Sigma receptor. These compounds are useful in the treatment of Sigma receptor-related diseases and disorders, either alone or in combination with at least one additional therapeutic agent. In one embodiment, the Sigma modulator of the invention is a Sigma antagonist, inverse agonist or agonist. In another embodiment, the Sigma modulator of the invention is a Sigma antagonist. In yet another embodiment, the Sigma receptor is a Sigma1 receptor (also known as Sigma1).

The present invention includes novel methods of treating, ameliorating or preventing a Sigma receptor-related disease or disorder using the compounds of the invention. In one embodiment, the Sigma receptor-related disease or disorder is selected from the group comprising cancer, neuropathic pain, depression, substance abuse, epilepsy, psychosis, Alzheimer's disease, Parkinson's disease, frontotemporal lobar degeneration (FTLD), amyotrophic lateral sclerosis (ALS) and combinations thereof. In another embodiment, the cancer is selected from the group consisting of prostate cancer, liver cancer, pancreas cancer, CNS tumors (including brain tumors), breast cancer, neuroblastoma, leukemia, and combinations thereof.

The present invention also includes novel methods of treating, ameliorating or preventing a Sigma receptor-related disease or disorder using the compounds of the invention in combination with therapeutic agents that target the UPR and/or autophagic survival pathways. In a preferred embodiment, the Sigma receptor-related disease or disorder is cancer.

Compounds useful within the methods of the invention include the compounds of Formula (I) and Formula (II) as described elsewhere herein, as well as any compound known to be a Sigma antagonist, agonist or inverse agonist, such as but not limited to haloperidol, IPAG, PB28, rimcazole, BD1063, BD1047, PRE084, NE100, (+)-SKF10047, (+)-pentazocine, and any combinations thereof. The invention contemplates using any of these compounds to modulate cellular protein synthesis, processing, and/or degradation in a subject in need thereof.

In one aspect, the compounds of the invention are useful in the treatment of cancers and neurodegenerative disorders wherein cellular functions can be selectively targeted by Sigma ligands.

As illustrated herein (FIG. 69), a compound of the invention was shown not to be cytotoxic to several tumor cell lines tested. Despite this lack of cytotoxicity, the compound still induced UPR. The compounds of the invention may thus be used to treat a neurodegenerative disease and other pathologies and disorders wherein modulation of protein homeostasis (such as synthesis, folding, processing, or degradation of proteins) could be beneficial.

As illustrated in FIG. 66, treatment of a cell with an ER stress inducing Sigma ligand (e.g., IPAG) did not alter Sigma1 levels, but did alter the subcellular localization of Sigma1. Consistently, as illustrated herein (FIGS. 43-44), changes in protein associations were observed in response to Sigma ligand treatment. In an embodiment, ligand mediated changes to Sigma1 partner protein associations and corresponding/consequent changes in Sigma1 subcellular localization may provide the basis for biochemical mechanism studies to establish Sigma ligand structure-activity-relationships.

As illustrated in FIG. 67, Sigma1 ligands modulate (in this case, decrease) the levels of growth factor receptors such as HER2 and HER3 in breast cancer cells, in the absence of detectable cell death. In one embodiment, a compound of the invention may be used to treat cancer in a subject in need thereof, wherein administering of the compound to the subject causes degradation of a growth factor receptor in the tumor cells. In another embodiment, the growth factor receptor comprises EGFR (epidermal growth factor receptor), HER2, HER3, p95HER2 (truncated form of HER2), androgen receptor, or any combinations thereof. In yet another embodiment, the cancer comprises breast cancer or prostate cancer. In yet another embodiment, the prostate cancer comprises castration-sensitive or castration-insensitive prostate cancer. Sigma ligands may thus be used as selective cytotoxics or selective inhibitors of cell growth without cytotoxicity. This broadens the utility of Sigma ligands beyond simple cytotoxic agents, and it demonstrates the potential versatility of the compounds of the invention.

DEFINITIONS

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "abnormal," when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics that are normal or expected for one cell or tissue type might be abnormal for a different cell or tissue type.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a symptom of the disease or disorder, the frequency with which such a symptom is experienced by a patient, or both, is reduced.

As used herein, the term "Sigma" refers to the Sigma1 receptor (Sigma1), Sigma2 receptor (Sigma2), any splice variant thereof or any isoform thereof.

As used herein, a "Sigma receptor modulator" is a compound that binds to the Sigma receptor and modifies the activity or biological function of the receptor as compared to the activity or biological function of the receptor in the absence of the modulator. The modulator may be a receptor agonist, which is able to activate the receptor and cause a biological response that is enhanced over the baseline activity of the unbound receptor. The modulator may be a partial agonist, which does not activate the receptor thoroughly and causes a biological response that is smaller in magnitude compared to those of full agonists. The modulator may be a receptor antagonist, which binds to the receptor but does not activate it, resulting in receptor blockage and inhibiting the binding of other agonists. An antagonist does not diminish the baseline intracellular response in the absence of an agonist. The modulator may be an inverse agonistic, which reduces the activity of the receptor by inhibiting its constitutive activity.

The terms "patient," "subject," "individual," and the like are used interchangeably herein, and refer to any animal, or cells thereof whether in vitro or in situ, amenable to the methods described herein. In a non-limiting embodiment, the patient, subject or individual is a human.

A "therapeutic" treatment is a treatment administered to a subject who exhibits signs of pathology, for the purpose of diminishing or eliminating those signs.

As used herein, the term "treatment" or "treating" is defined as the application or administration of a therapeutic agent, i.e., a compound of the invention (alone or in combination with another pharmaceutical agent), to a patient, or application or administration of a therapeutic agent to an isolated tissue or cell line from a patient (e.g., for diagnosis or ex vivo applications), who has a condition contemplated herein, a symptom of a condition contemplated herein or the potential to develop a condition contemplated herein, with the purpose to cure, heal, alleviate, relieve, alter, remedy, ameliorate, improve or affect a condition contemplated herein, the symptoms of a condition contemplated herein or the potential to develop a condition contemplated herein. Such treatments may be specifically tailored or modified, based on knowledge obtained from the field of pharmacogenomics.

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary and topical administration.

The phrase "therapeutically effective amount," as used herein, refers to an amount that is sufficient or effective to prevent or treat (delay or prevent the onset of, prevent the progression of, inhibit, decrease or reverse) a disease or condition associated with the Sigma receptor, including alleviating symptoms of such diseases.

As used herein, the terms "effective amount," "pharmaceutically effective amount" and "therapeutically effective amount" refer to a nontoxic but sufficient amount of an agent to provide the desired biological result. That result may be reduction and/or alleviation of the signs, symptoms, or causes of a disease, or any other desired alteration of a biological system. An appropriate therapeutic amount in any individual case may be determined by one of ordinary skill in the art using routine experimentation.

An "effective amount" of a delivery vehicle is that amount sufficient to effectively bind or deliver a compound.

As used herein, the term "potency" refers to the dose needed to produce half the maximal response ($ED_{50}$).

As used herein, the term "efficacy" refers to the maximal effect ($E_{max}$) achieved within an assay.

As used herein, the term "PRE084" refers to 2-morpholin-4-ylethyl 1-phenylcyclohexane-1-carboxylate or a salt thereof.

As used herein, the term "BD1047" refers to N'-[2-(3,4-dichlorophenyl)ethyl]-N,N,N'-trimethylethane-1,2-diamine or a salt thereof.

As used herein, the term "BD1063" refers to 1-[2-(3,4-dichlorophenyl)ethyl]-4-methylpiperazine or a salt thereof.

As used herein, the term "haloperidol" refers to 4-[4-(4-chlorophenyl)-4-hydroxy-1-piperidyl]-1-(4-fluorophenyl)-butan-1-one or a salt thereof.

As used herein, the term "(+)-SKF10047" refers to [2S-(2α,6α,11R*]-1,2,3,4,5,6-hexahydro-6,11-dimethyl-3-(2-propenyl)-2,6-methano-3-benzazocin-8-ol or a salt thereof.

As used herein, the term "(+)-pentazocine" refers to (+)-[2S-(2,6,11R*)]-1,2,3,4,5,6-hexahydro-6,1-dimethyl-3-(3-methyl-2-butenyl)-2,6-methano-3-benzazocin-8-ol or a salt thereof.

As used herein, the term "rimcazole" refers to 9-{3-[(3R,5S)-3,5-dimethylpiperazin-1-yl]propyl}-9H-carbazole or a salt thereof.

As used herein, the term "PB28" refers to 1-cyclohexyl-4-[3-(5-methoxy-1,2,3,4-tetra-hydronaphthalen-1-yl)propyl] piperazine or a salt thereof.

As used herein, the term "IPAG" refers to 1-(4-iodophenyl)-3-(2-adamantyl)guanidine or a salt thereof.

As used herein, the term "NE100" refers to 4-methoxy-3-(2-phenylethoxy)-N,N-dipropylbenzeneethanamine hydrochloride or a salt thereof.

As used herein, the term "E64d" refers to (2S,3S)-trans-epoxysuccinyl-L-leucylamido-3-methylbutane ethyl ester or a salt thereof.

As used herein, the term "methyladenine" refers to 3-methyladenine or a salt thereof.

As used herein, the term "tamoxifen" refers to (Z)-2-[4-(1,2-diphenylbut-1-enyl)phenoxy]-N,N-dimethylethanamine or a salt thereof.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the language "pharmaceutically acceptable salt" refers to a salt of the administered compounds prepared from pharmaceutically acceptable non-toxic acids, including inorganic acids, organic acids, solvates, hydrates, or clathrates thereof. Examples of such inorganic acids are hydrochloric, hydrobromic, hydroiodic, nitric, sulfuric, phosphoric, acetic, hexafluorophosphoric, citric, gluconic, benzoic, propionic, butyric, sulfosalicylic, maleic, lauric, malic, fumaric, succinic, tartaric, amsonic, pamoic, p-tolunenesulfonic, and mesylic. Appropriate organic acids may be selected, for example, from aliphatic, aromatic, carboxylic and sulfonic classes of organic acids, examples of which are formic, acetic, propionic, succinic, camphorsulfonic, citric, fumaric, gluconic, isethionic, lactic, malic, mucic, tartaric, para-toluenesulfonic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic (besylate), stearic, sulfanilic, alginic, galacturonic, and the like. Furthermore, pharmaceutically acceptable salts include, by way of non-limiting example, alkaline earth metal salts (e.g., calcium or magnesium), alkali metal salts (e.g., sodium-dependent or potassium), and ammonium salts.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the term "alkyl," by itself or as part of another substituent means, unless otherwise stated, a straight or branched chain hydrocarbon having the number of carbon atoms designated (i.e. $C_{1-6}$ means one to six carbon atoms) and including straight, branched chain, or cyclic substituent groups. Examples include methyl, ethyl, propyl, isopropyl, butyl, isobutyl, tert-butyl, pentyl, neopentyl, hexyl, and cyclopropylmethyl. Most preferred is $(C_1-C_6)$alkyl, particularly ethyl, methyl, isopropyl, isobutyl, n-pentyl, n-hexyl and cyclopropylmethyl.

As used herein, the term "substituted alkyl" means alkyl as defined above, substituted by one, two or three substituents selected from the group consisting of halogen, —OH, alkoxy, —NH$_2$, —N(CH$_3$)$_2$, —C(=O)OH, trifluoromethyl, —C≡N, —C(=O)O(C$_1$-C$_4$)alkyl, —C(=O)NH$_2$, —SO$_2$NH$_2$, —C(=NH)NH$_2$, and —NO$_2$, preferably containing one or two substituents selected from halogen, —OH, alkoxy, —NH$_2$, trifluoromethyl, —N(CH$_3$)$_2$, and —C(=O) OH, more preferably selected from halogen, alkoxy and —OH. Examples of substituted alkyls include, but are not limited to, 2,2-difluoropropyl, 2-carboxycyclopentyl and 3-chloropropyl.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—CH$_2$—CH$_2$—CH$_3$, —CH$_2$—CH$_2$—CH$_2$—OH, —CH$_2$—CH$_2$—NH—CH$_3$, —CH$_2$—S—CH$_2$—CH$_3$, and —CH$_2$CH$_2$—S(=O)—CH$_3$. Up to two heteroatoms may be consecutive, such as, for example, —CH$_2$—NH—OCH$_3$, or —CH$_2$—CH$_2$—S—S—CH$_3$ As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy(isopropoxy) and the higher homologs and isomers. Preferred are $(C_1-C_3)$ alkoxy, particularly ethoxy and methoxy.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "cycloalkyl" refers to a mono cyclic or polycyclic non-aromatic radical, wherein each of the atoms forming the ring (i.e. skeletal atoms) is a carbon atom.

In one embodiment, the cycloalkyl group is saturated or partially unsaturated. In another embodiment, the cycloalkyl group is fused with an aromatic ring. Cycloalkyl groups include groups having from 3 to 10 ring atoms. Illustrative examples of cycloalkyl groups include, but are not limited to, the following moieties:

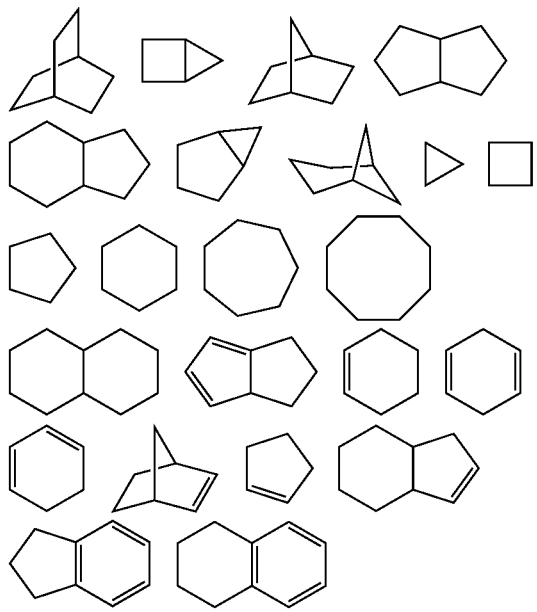

Monocyclic cycloalkyls include, but are not limited to, cyclopropyl, cyclobutyl, cyclopentyl, cyclohexyl, cycloheptyl, and cyclooctyl. Dicyclic cycloalkyls include, but are not limited to, tetrahydronaphthyl, indanyl, and tetrahydropentalene. Polycyclic cycloalkyls include adamantine and norbornane. The term cycloalkyl includes "unsaturated nonaromatic carbocyclyl" or "nonaromatic unsaturated carbocyclyl" groups, both of which refer to a nonaromatic carbocycle as defined herein, which contains at least one carbon carbon double bond or one carbon carbon triple bond.

As used herein, the term "heterocycloalkyl" or "heterocyclyl" refers to a heteroalicyclic group containing one to four ring heteroatoms each selected from O, S and N. In one embodiment, each heterocycloalkyl group has from 4 to 10 atoms in its ring system, with the proviso that the ring of said group does not contain two adjacent O or S atoms. In another embodiment, the heterocycloalkyl group is fused with an aromatic ring. In one embodiment, the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In one embodiment, the heterocycle is a heteroaryl.

An example of a 3-membered heterocycloalkyl group includes, and is not limited to, aziridine. Examples of 4-membered heterocycloalkyl groups include, and are not limited to, azetidine and a beta lactam. Examples of 5-membered heterocycloalkyl groups include, and are not limited to, pyrrolidine, oxazolidine and thiazolidinedione. Examples of 6-membered heterocycloalkyl groups include, and are not limited to, piperidine, morpholine and piperazine. Other nonlimiting examples of heterocycloalkyl groups are:

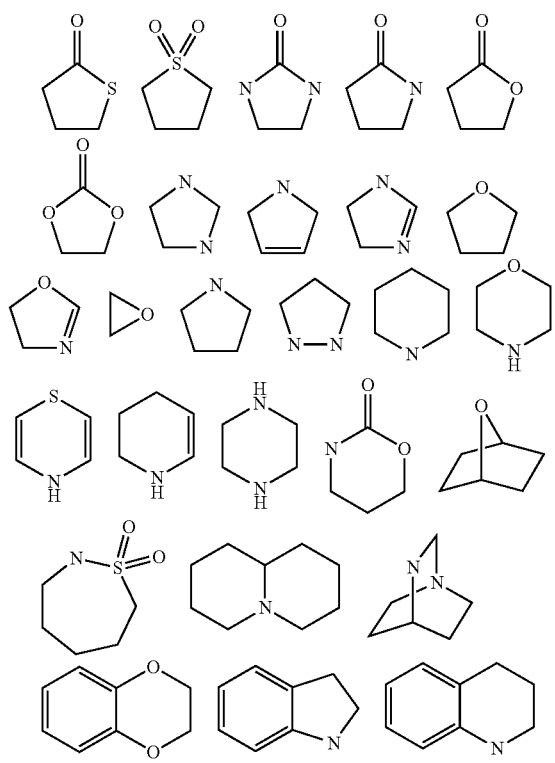

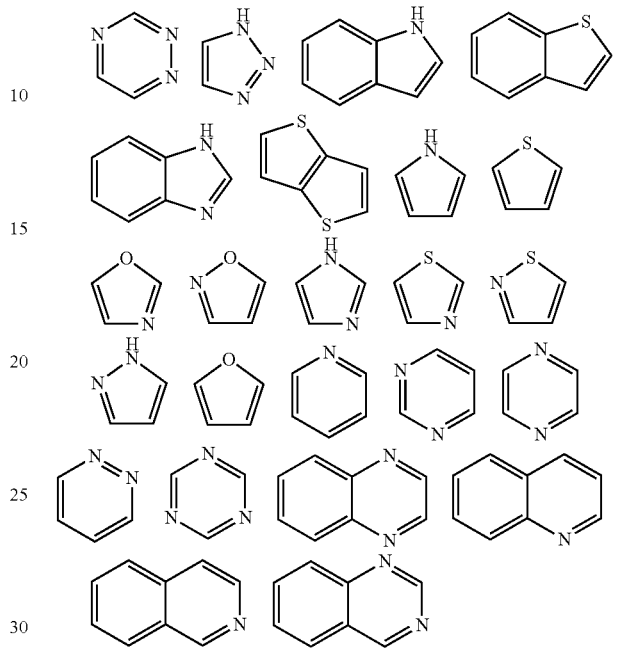

Examples of non-aromatic heterocycles include monocyclic groups such as aziridine, oxirane, thiirane, azetidine, oxetane, thietane, pyrrolidine, pyrroline, pyrazolidine, imidazoline, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin, and hexamethyleneoxide.

As used herein, the term "aromatic" refers to a carbocycle or heterocycle with one or more polyunsaturated rings and having aromatic character, i.e. having (4n+2) delocalized a (pi) electrons, where n is an integer.

As used herein, the term "aryl," employed alone or in combination with other terms, means, unless otherwise stated, a carbocyclic aromatic system containing one or more rings (typically one, two or three rings), wherein such rings may be attached together in a pendent manner, such as a biphenyl, or may be fused, such as naphthalene. Examples of aryl groups include phenyl, anthracyl, and naphthyl. Preferred examples are phenyl and naphthyl, most preferred is phenyl.

As used herein, the term "aryl-($C_1$-$C_3$)alkyl" means a functional group wherein a one- to three-carbon alkylene chain is attached to an aryl group, e.g., —$CH_2CH_2$-phenyl. Preferred is aryl-$CH_2$— and aryl-$CH(CH_3)$—. The term "substituted aryl-($C_1$-$C_3$)alkyl" means an aryl-($C_1$-$C_3$)alkyl functional group in which the aryl group is substituted. Preferred is substituted aryl($CH_2$)—. Similarly, the term "heteroaryl-($C_1$-$C_3$)alkyl" means a functional group wherein a one to three carbon alkylene chain is attached to a heteroaryl group, e.g., —$CH_2CH_2$-pyridyl. Preferred is heteroaryl-($CH_2$)—. The term "substituted heteroaryl-($C_1$-$C_3$)alkyl" means a heteroaryl-($C_1$-$C_3$)alkyl functional group in which the heteroaryl group is substituted. Preferred is substituted heteroaryl-($CH_2$)—.

As used herein, the term "heteroaryl" or "heteroaromatic" refers to a heterocycle having aromatic character. A polycyclic heteroaryl may include one or more rings that are partially saturated. Examples include the following moieties:

Examples of heteroaryl groups also include pyridyl, pyrazinyl, pyrimidinyl (particularly 2- and 4-pyrimidinyl), pyridazinyl, thienyl, furyl, pyrrolyl (particularly 2-pyrrolyl), imidazolyl, thiazolyl, oxazolyl, pyrazolyl (particularly 3- and 5-pyrazolyl), isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl. Examples of polycyclic heterocycles and heteroaryls include indolyl (particularly 3-, 4-, 5-, 6- and 7-indolyl), indolinyl, quinolyl, tetrahydroquinolyl, isoquinolyl (particularly 1- and 5-isoquinolyl), 1,2,3,4-tetrahydroisoquinolyl, cinnolinyl, quinoxalinyl (particularly 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (particularly 3-, 4-, 5-, 6- and 7-benzofuryl), 2,3-dihydrobenzofuryl, 1,2-benzisoxazolyl, benzothienyl (particularly 3-, 4-, 5-, 6-, and 7-benzothienyl), benzoxazolyl, benzothiazolyl (particularly 2-benzothiazolyl and 5-benzothiazolyl), purinyl, benzimidazolyl (particularly 2-benzimidazolyl), benzotriazolyl, thioxanthinyl, carbazolyl, carbolinyl, acridinyl, pyrrolizidinyl, and quinolizidinyl.

As used herein, the term "substituted" means that an atom or group of atoms has replaced hydrogen as the substituent attached to another group. The term "substituted" further refers to any level of substitution, namely mono-, di-, tri-, tetra-, or penta-substitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two.

As used herein, the term "optionally substituted" means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

In one embodiment, the substituents are independently selected from the group consisting of oxo, halogen, —CN, —NH$_2$, —OH, —NH(CH$_3$), —N(CH$_3$)$_2$, alkyl (including straight chain, branched and/or unsaturated alkyl), substituted or unsubstituted cycloalkyl, substituted or unsubstituted heterocycloalkyl, fluoro alkyl, substituted or unsubstituted heteroalkyl, substituted or unsubstituted alkoxy, fluoroalkoxy, —S-alkyl, S(=O)$_2$alkyl, —C(=O)NH[substituted or unsubstituted alkyl, or substituted or unsubstituted phenyl], —C(=O)N[H or alkyl]$_2$, —OC(=O)N[substituted or unsubstituted alkyl]$_2$, —NHC(=O)NH[substituted or unsubstituted alkyl, or substituted or unsubstituted phenyl], —NHC(=O)alkyl, —N[substituted or unsubstituted alkyl]C(=O)[substituted or unsubstituted alkyl], —NHC(=O)[substituted or unsubstituted alkyl], —C(OH)[substituted or unsubstituted alkyl]$_2$, and —C(NH$_2$)[substituted or unsubstituted alkyl]$_2$. In another embodiment, by way of example, an optional substituent is selected from oxo, fluorine, chlorine, bromine, iodine, —CN, —NH$_2$, —OH, —NH(CH$_3$), —N(CH$_3$)$_2$, —CH$_3$, —CH$_2$CH$_3$, —CH(CH$_3$)$_2$, —CF$_3$, —CH$_2$CF$_3$, —OCH$_3$, —OCH$_2$CH$_3$, —OCH(CH$_3$)$_2$, —OCF$_3$, —OCH$_2$CF$_3$, —S(=O)$_2$—CH$_3$, —C(=O)NH$_2$, —C(=O)—NHCH$_3$, —NHC(=O)NHCH$_3$, —C(=O)CH$_3$, and —C(=O)OH. In yet one embodiment, the substituents are independently selected from the group consisting of C$_{1-6}$ alkyl, —OH, C$_{1-6}$ alkoxy, halo, amino, acetamido, oxo and nitro. In yet another embodiment, the substituents are independently selected from the group consisting of C$_{1-6}$ alkyl, C$_{1-6}$ alkoxy, halo, acetamido, and nitro. As used herein, where a substituent is an alkyl or alkoxy group, the carbon chain may be branched, straight or cyclic, with straight being preferred.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention relates to the unexpected discovery of novel compounds that bind to and modulate the activity of the Sigma receptor. In one embodiment, the Sigma receptor modulators of the invention are Sigma receptor antagonists. In another embodiment, the Sigma receptor is selected from the group consisting of Sigma1, Sigma2 and a combination thereof. In yet another embodiment, the Sigma receptor is Sigma1.

The compounds of the invention may be used to treat Sigma receptor-related diseases and disorders, such as but not limited to cancer, neuropathic pain, depression, substance abuse, epilepsy, psychosis, Alzheimer's disease, Parkinson's disease, frontotemporal lobar degeneration (FTLD), amyotrophic lateral sclerosis (ALS) and combinations thereof. The cancer may be selected from the group consisting of prostate cancer, liver cancer, pancreas cancer, breast cancer, neuroblastoma, leukemia, CNS cancers (including brain tumors), and combinations thereof. In one embodiment, the therapeutic effect elicited by the compounds of the invention is mediated by the Sigma receptor. In another embodiment, the therapeutic effect elicited by the compounds of the invention is not mediated by the Sigma receptor.

Without wishing to be limited by theory, protein homeostasis/"proteostasis" (i.e., maintenance of proper protein synthesis, processing, folding. transport, assembly, and degradation) modulating properties of the compounds of the invention allow then to be used in the treatment of any disease in which protein homeostasis is disrupted (e.g., neurodegenerative diseases) or in which this process is especially crucial (e.g., cancer). In one embodiment, the compound of the invention crosses the blood-brain barrier. In another embodiment, the compound of the invention does not cross the blood-brain barrier.

In a non-limiting aspect, the present invention relates to the unexpected discovery that Sigma1 antagonists induces ER stress (such as translation arrest, unfolded protein response (UPR), or autophagy) and activates the unfolded protein response (UPR) in a dose and time responsive manner. As demonstrated herein, autophagy was engaged following extended treatment with Sigma1 antagonists, suggesting that protracted UPR results in autophagy as a secondary response. In fact, UPR activation preceded autophagosome formation and autophagy preceded apoptosis in Sigma1 antagonist-treated cells. Inhibition of Sigma1 antagonist-induced UPR or autophagy accelerated Sigma1 antagonist-mediated apoptosis. Therefore, as demonstrate herein, the combination of a Sigma1 antagonist with an agent targeting the UPR and/or autophagic survival pathways provides a novel and efficacious approach to treat, ameliorate or prevent cancer. In one embodiment, the compounds of the present invention induce endoplasmic reticulum (ER) stress, such as, but are not limited to, translation arrest, unfolded protein response (UPR), autophagy, and combinations thereof. In another embodiment, the compounds of the present invention modulate cellular protein ubiquitylation, including but not being limited to ER associated proteasomal degradation (ERAD). As demonstrate herein, the Sigma ligand, IPAG, induced a novel, ubiquitin-selective autophagy in breast cancer cell lines.

The present invention includes a composition comprising at least one compound of the invention, wherein the composition optionally further comprise at least one additional therapeutic agent. The present invention also includes a composition comprising a Sigma receptor-modulating compound and at least one additional therapeutic agent. In one embodiment, the additional therapeutic agent targets the UPR and/or autophagic survival pathway. In another embodiment, the additional therapeutic agent binds to and modulates the Sigma receptor. In yet another embodiment, the additional therapeutic agent is a chemotherapeutic and/or hormone therapy agent.

Examples of additional therapeutic agents contemplated within the invention include, but are not limited to, growth factor receptor inhibitors, monoclonal antibodies against growth factor receptors (e.g., Traztuzumab), hormone receptor antagonists (e.g., androgen receptor inhibitors), autophagy modulators (such as rapamycin and its analogs or "rapalogs"), ER stress response inhibitors, proteasome inhibitors, p97/VCP inhibitors (e.g., DBeQ and derivatives thereof—Chou et al., 2011, Proc. Natl. Acad. Sci. USA 108(12):4834-9), and combinations thereof. Non-limiting examples of additional therapeutic agents contemplated within the invention include octapeptide, somatostatin, analoguem, lanreotide, angiopeptin, dermopeptin, octreotide, pegvisomant, 3-methyladenine, chloroquine, hydroxychloroquine, wortmannin, eeyarestatin I, salubrinal, versipelostatin, 2H-isoindole-2-carboxylic acid, 4-fluoro-1,3-dihydro-(2R,6S,12Z,13aS,14aR,16aS)-14a-[[(cyclopropylsulfonyl)amino]carbonyl]-6-[[(1,1-dimethylethoxy)carbonyl]amino]-1,2,3,5,6,7,8,9,10,11,13a,14,14a,15,16,16a-hexadecahydro-5,16-dioxocyclopropa[e]pyrrolo[1,2-a][1,4]diazacyclopentadecin-2-yl ester (Danoprevir), adamantane-acetyl-(6-aminohexanoyl)3-(leucinyl)3-vinyl-(methyl)-sulfone, N-acetyl-L-leucyl-L-leucyl-L-methional, N-[(phenylmethoxy)carbonyl]-L-leucyl-N-[(1S)-1-formyl-3-methylbutyl]-L-leucinamide, (2R,3S,4R)-3-hydroxy-2-[(1S)-1-hydroxy-2-methylpropyl]-4-methyl-5-oxo-2-pyrrolidinecarboxy-N-acetyl-L-cysteine thioester, N—[N—(N-acetyl-L-leucyl)-L-leucyl]-L-norleucine, lactacystin, 4-(2-aminoethyl)benzenesulfonyl fluoride hydrochloride, (S)-1-carboxy-2-phenyl]-carbamoyl-Arg-Val-arginal, bovine pancreatic trypsin inhibitor, [(2S,2R)-3-amino-2-hydroxy-4-phenylbutanoyl]-L-leucine, N—[(S)-1-carboxy-isopentyl)-carbamoyl-alpha-(2-iminohexahydro-4-(S)-pyrimidyl]-L-glycyl-L-phenylalaninal, ethylenediamine-tetraacetic acid disodium salt dehydrate, acetyl-leucyl-leucyl-arginal, isovaleryl-Val-Val-AHMHA-Ala-AHMHA where AHMHA=(3S,4S)-4-amino-3-hydroxy-6-methylheptanoic acid, N-alpha-L-rhamnopyranosyloxy-(hydroxyphosphinyl)-L-leucyl-L-tryptophan, phenylmethanesulfonyl fluoride, bortezomib, carfilzomib, ONX 0912, NPI-0052, CEP-18770, MLN9708, disulfiram, epigallocatechin-3-gallate, salinosporamide A, PI3K inhibitors, lapatinib, rapamycin and rapalogs, heat shock protein (HSP) inhibitors (e.g., geldanamycin and derivatives such as 17-AAG), androgen receptor inhibitors (e.g., MDV3100, ARN-509), and conjugation products of Sigma ligands with targeting components such as Herceptin/Traztuzumab (e.g., Trastuzumab-emtansine, T-DM1, is an antibody-drug conjugate comprising the antibody trastuzumab (Herceptin) linked to the cytotoxin mertansine—Niculescu-Duvaz, 2010, Curr. Opin. Mol. Ther. 12(3):350-60).

The compounds of the present invention, used alone or in combination with at least one additional therapeutic agent (e.g., those that target the ubiquitin proteasome system (UPS) and/or autophagic survival pathways), are useful in the treatment of Sigma receptor-related disorders or diseases. Examples of disorders or diseases contemplated within the invention include, but are not limited to, cancer, neuropathic pain, depression, substance abuse, epilepsy, psychosis, Alzheimer's disease, Parkinson's disease, neurodegeneration, lysosomal storage disease, diseases in which protein folding and processing is altered, and indications wherein the modulation of autophagy may be therapeutically beneficial. In a preferred embodiment, the disease is cancer.

In one embodiment, the compounds of the present invention have improved drug-like properties over compounds known in the art to bind to and modulate the Sigma receptor. In another embodiment, the compounds of the present invention do not cross the blood-brain barrier. In yet another embodiment, the compounds of the present invention cross the blood-brain barrier.

The compounds of the present invention include a Sigma ligand probe, which may be used to study biological phenomena in living cells. In one embodiment, the Sigma ligand probe comprises a fluorophore. In another embodiment, the fluorophore is 7-amino-4-methyl coumarin (FIG. 64). In one embodiment, the fluorescent probe is 2-(4-(4-methyl-2-oxo-2H-chromen-7-yl)piperazin-1-yl)ethyl 1-phenylcyclohexan-ecarboxylate. In another embodiment, the fluorescent probe is 1-(4-methoxyphenyl)-3-(3-((4-methyl-2-oxo-2H-chromen-7-yl)oxy)propyl)guanidine. In yet another embodiment, the fluorescent probe is 1-(4-iodophenyl)-3-(3-((4-methyl-2-oxo-2H-chromen-7-yl)oxy)propyl)guanidine. In yet another embodiment, the fluorescent probe is 1-(3-(4-fluorophenoxy)propyl)-3-(4-methyl-2-oxo-2H-chromen-7-yl) guanidine).

The compounds of the present invention may be characterized by pharmacological, cellular, biochemical, in vivo, pharmacokinetics, or pharmacodynamics properties. Preferred examples of characterization studies include, but are not limited to, Sigma1-ligand binding properties, signaling pathway analysis and/or characterization, proteomic analysis of Sigma1 protein associations in response to Sigma ligand treatment, tumor, brain response, and toxicity.

Compounds of the Invention

The compounds of the present invention may be synthesized using techniques well-known in the art of organic synthesis. The starting materials and intermediates required for the synthesis may be obtained from commercial sources or synthesized according to methods known to those skilled in the art.

In one aspect, the compound of the invention is a compound of formula (I), or a salt, solvate, or N-oxide thereof:

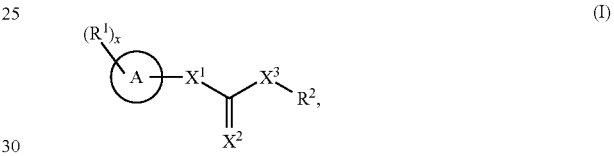

wherein:

ring A is a monocyclic or bicyclic aryl or a monocyclic or bicyclic heteroaryl ring, and wherein the aryl or heteroaryl ring is optionally substituted with 0-4 $R^1$ groups;

each occurrence of $R^1$ is independently selected from the group consisting of —$C_1$-$C_6$ alkyl, —$C_1$-$C_6$ fluoroalkyl, —$C_1$-$C_6$ heteroalkyl, F, Cl, Br, I, —CN, —$NO_2$, —$OR^3$, —$SR^3$, —S(=O)$R^3$, —S(=O)$_2R^3$, —NHS(=O)$_2R^3$, —C(=O)$R^3$, —OC(=O)$R^3$, —$CO_2R^3$, —$OCO_2R^3$, —CH($R^3$)$_2$, —N($R^3$)$_2$, —C(=O)N($R^3$)$_2$, —OC(=O)N($R^3$)$_2$, —NHC(=O)NH($R^3$), —NHC(=O)$R^3$, —NHC(=O)O$R^3$, —C(OH)($R^3$)$_2$, and —C($NH_2$)($R^3$)$_2$;

each occurrence of $R^2$ is independently selected from the group consisting of H, $C_1$-$C_6$ alkyl, $C_1$-$C_6$ heteroalkyl, and —$C_1$-$C_3$ alkyl-($C_3$-$C_6$ cycloalkyl), wherein the alkyl, heteroalkyl or cycloalkyl group is optionally substituted with 0-5 $R^1$ groups, or $X^3$ and $R^2$ combine to form a ($C_3$-$C_7$)heterocycloalkyl group, optionally substituted with 0-2 $R^1$ groups;

each occurrence of $R^3$ is independently selected from the group consisting of H, $C_1$-$C_6$ alkyl, $C_1$-$C_6$ heteroalkyl, aryl, and —$C_1$-$C_3$ alkyl-($C_3$-$C_6$ cycloalkyl), wherein the alkyl, heteroalkyl, aryl, or cycloalkyl group is optionally substituted with 0-5 $R^1$ groups;

$X^1$ is —$CH_2$—, —S—, —O— or —(N$R^2$)—;
$X^2$ is =$CH_2$, =S, =O or =N$R^2$; and
$X^3$ is —S—, —O—, or —N$R^2$—.

In one embodiment, ring A is a monocyclic aryl or monocyclic heteroaryl ring optionally substituted with 0-4 $R^1$ groups. In another embodiment, ring A is unsubstituted. In yet another embodiment, ring A is phenyl or substituted phenyl.

In a preferred embodiment, $X^1$ and $X^3$ are both —NH—, and $X^2$ is =NH.

In another aspect, the compound of the invention is a compound of formula (II), or a salt, solvate, or N-oxide thereof:

wherein;

$R^A$ is selected from the group consisting of

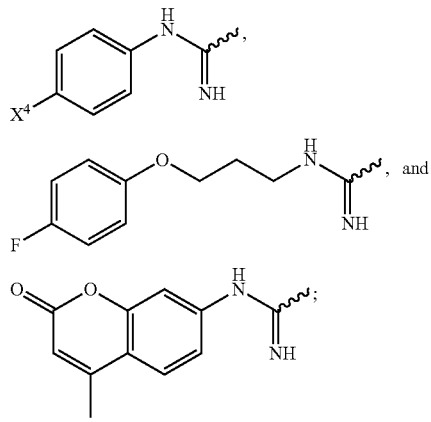

wherein $X^4$ is selected from the group consisting of F, Cl, Br, and I; and $R^B$ is selected from the group consisting of:

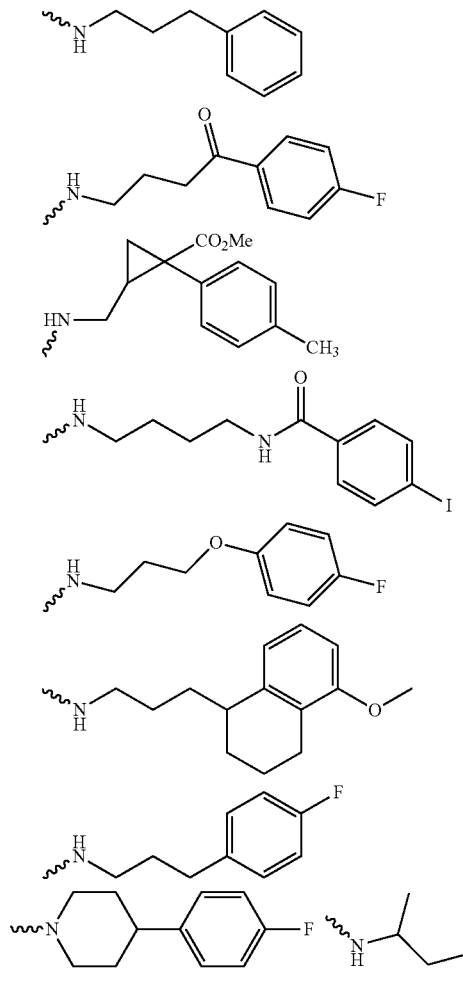

-continued

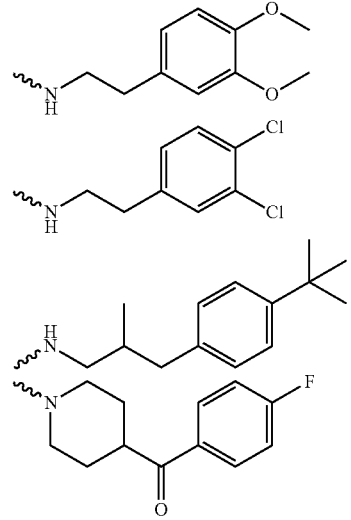

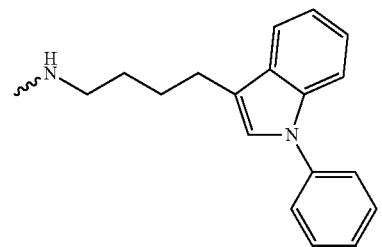

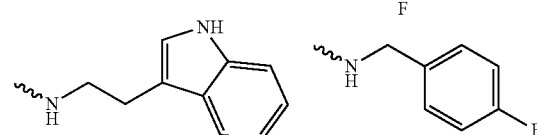

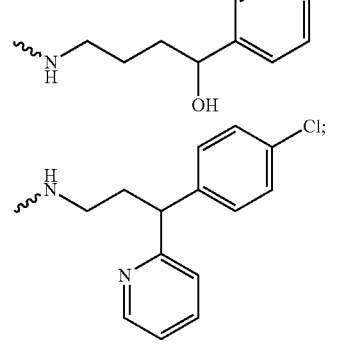

In another aspect, the compound of the invention is a compound of formula (III), or a salt, solvate, or N-oxide thereof:

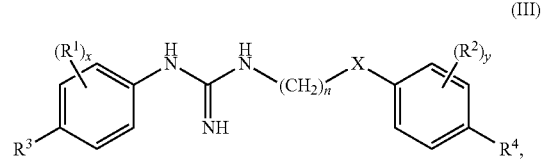

wherein within formula (III);

each occurrence of $R^1$ and $R^2$ is independently selected from the group consisting of —$C_1$-$C_6$ alkyl, —$C_1$-$C_6$ fluoroalkyl, —$C_1$-$C_6$ heteroalkyl, F, Cl, Br, I, —CN, —$NO_2$, —$OR^5$, —$SR^5$, —$S(=O)R^5$, —$S(=O)_2R^5$, —$NHS(=O)_2R^5$, —$C(=O)R^5$, —$OC(=O)R^5$, —$CO_2R^5$, —$OCO_2R^5$, —$CH(R^5)_2$, —$N(R^5)_2$, —$C(=O)N(R^5)_2$, —$OC(=O)N(R^5)_2$, —$NHC(=O)NH(R^5)$, —$NHC(=O)R^5$, —$NHC(=O)OR^5$, —$C(OH)(R^5)_2$, and —$C(NH_2)(R^5)_2$;

$R^3$ is selected from the group consisting of —$C_1$-$C_6$ alkyl, —$C_1$-$C_6$ fluoroalkyl, —$C_1$-$C_6$ alkoxy, F, Cl, Br, and I;

$R^4$ is selected from the group consisting of —$C_1$-$C_6$ alkyl, —$C_1$-$C_6$ alkoxy, F, Cl, Br, and I;

each occurrence of $R^5$ is independently selected from the group consisting of H, $C_1$-$C_6$ alkyl, $C_1$-$C_6$ heteroalkyl, aryl, and —$C_1$-$C_3$ alkyl-($C_3$-$C_6$ cycloalkyl), wherein the alkyl, heteroalkyl, aryl, or cycloalkyl group is optionally substituted.

X is selected from the group consisting of $CH_2$, C=O, or O;

n is an integer from 1-3;

x is an integer from 0-4; and y is an integer from 0-4.

In one embodiment, the compound of the invention is selected from the group consisting of:

1-(3-(4-fluorophenoxy)propyl)-3-(4-iodophenyl)guanidine (Compound A; also known as JMS-51-58 or 51-58);

1-(3-(4-fluorophenoxy)propyl)-3-(4-methoxyphenyl)guanidine (Compound B);

1-(n-propyl)-3-(4-iodophenyl)guanidine (Compound C);

1-(n-propyl)-3-(4-methoxyphenyl)guanidine (Compound D);

1,3-bis(3-(4-fluorophenoxy)propyl)guanidine (Compound E);

1-(3-(4-fluorophenoxy)propyl)-3-(4-trifluoromethylphenyl)guanidine (Compound F);

1-(3-(4-fluorophenoxy)propyl)-3-(4-chlorophenyl)guanidine (Compound G);

1-(3-(4-fluorophenoxy)propyl)-3-(4-methyl-2-oxo-2H-chromen-7-yl)guanidine (Compound H);

a salt, solvate or N-oxide thereof; and any combinations thereof.

Preparation of the Compounds of the Invention

Compounds of Formula (I) may be prepared by the general schemes described herein, using the synthetic method known by those skilled in the art. The following examples illustrate non-limiting embodiments of the invention.

Figure 17:
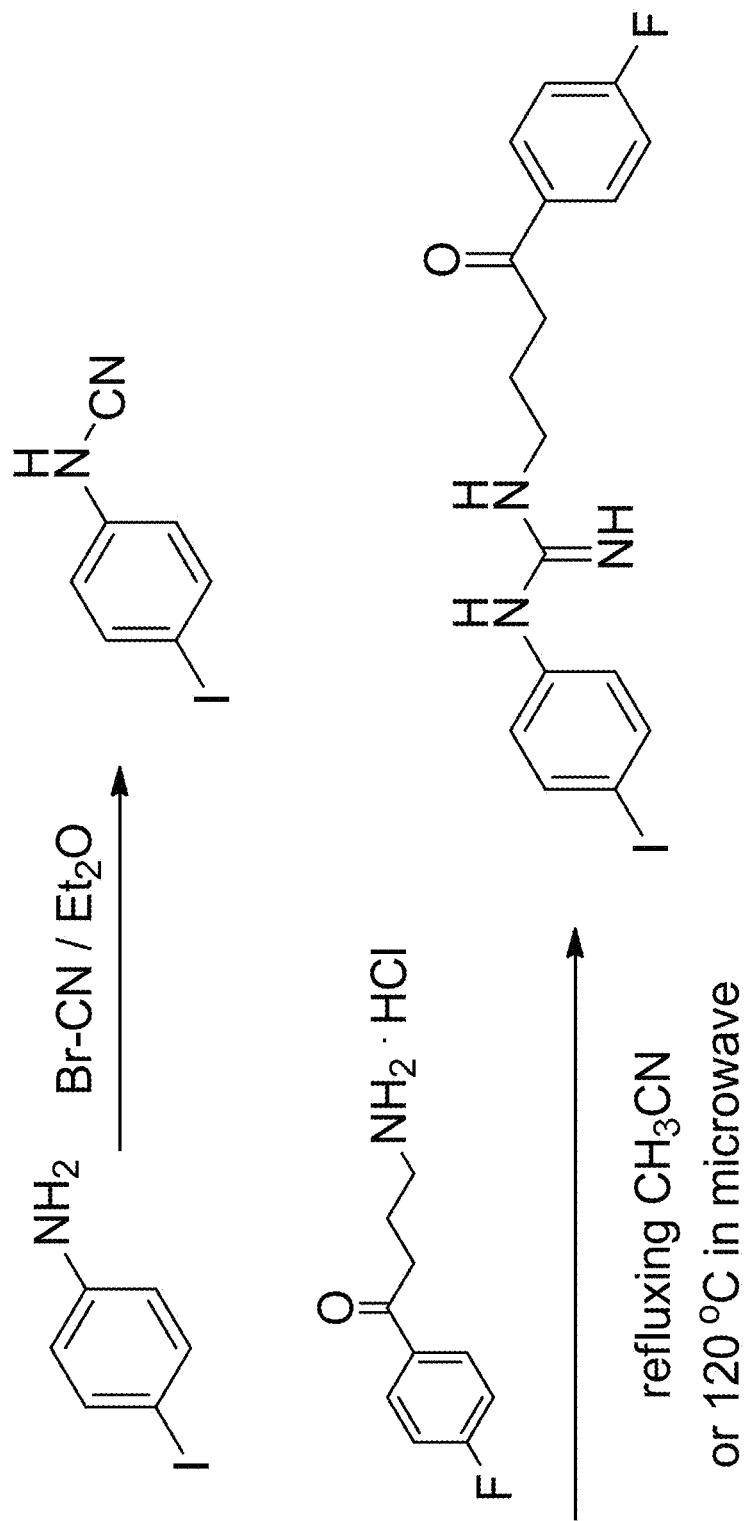
FIG. 17 is a synthetic scheme illustrating a generalized synthetic route toward novel hybrid IPAG-Haloperidol analogs

In a non-limiting embodiment, the synthesis of unsymmetrical N,N'-disubstituted guanidines is accomplished by coupling an aryl cyanamide and an amine (FIG. 17). In one embodiment, the coupling reaction takes place at an elevated temperature ranging from 80° C. to 250° C. An aniline may be converted to an aryl cyanamide with cyanogen bromide in ether. The unsymmetrical N,N'-disubstituted guanidine is then formed by coupling the aryl cyanamide with an amine. Non-limiting examples of coupling methods include heating in acetonitrile at reflux, and heating at 120° C. in a microwave.

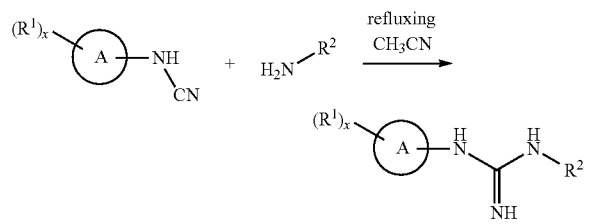

Figure 18:
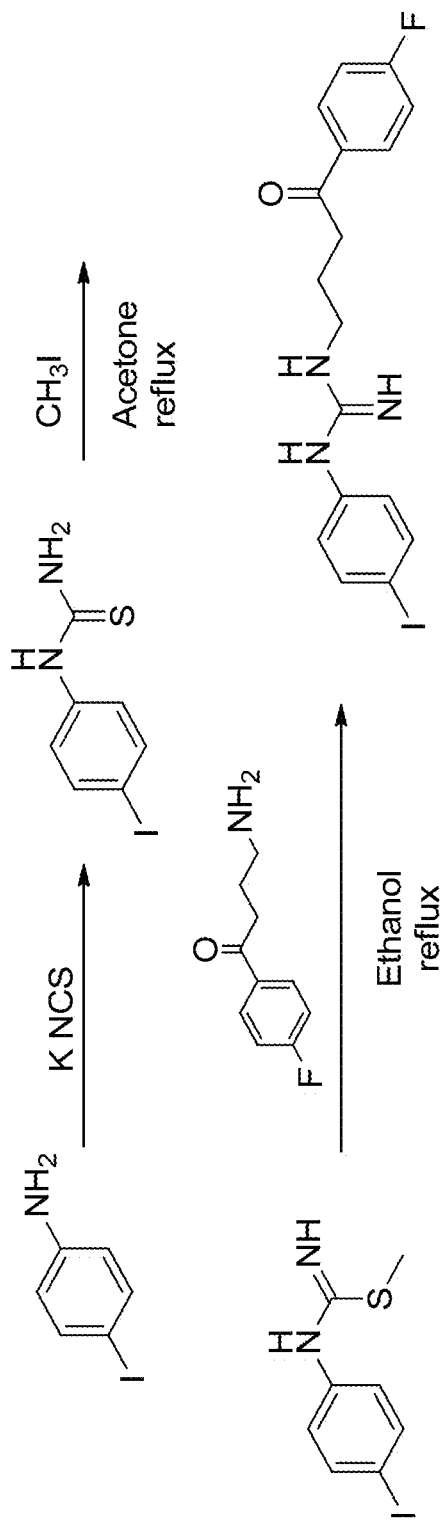
FIG. 18 is a synthetic scheme illustrating an alternative synthesis of N-aryl-N'-substituted guanidines.
Figure 19:
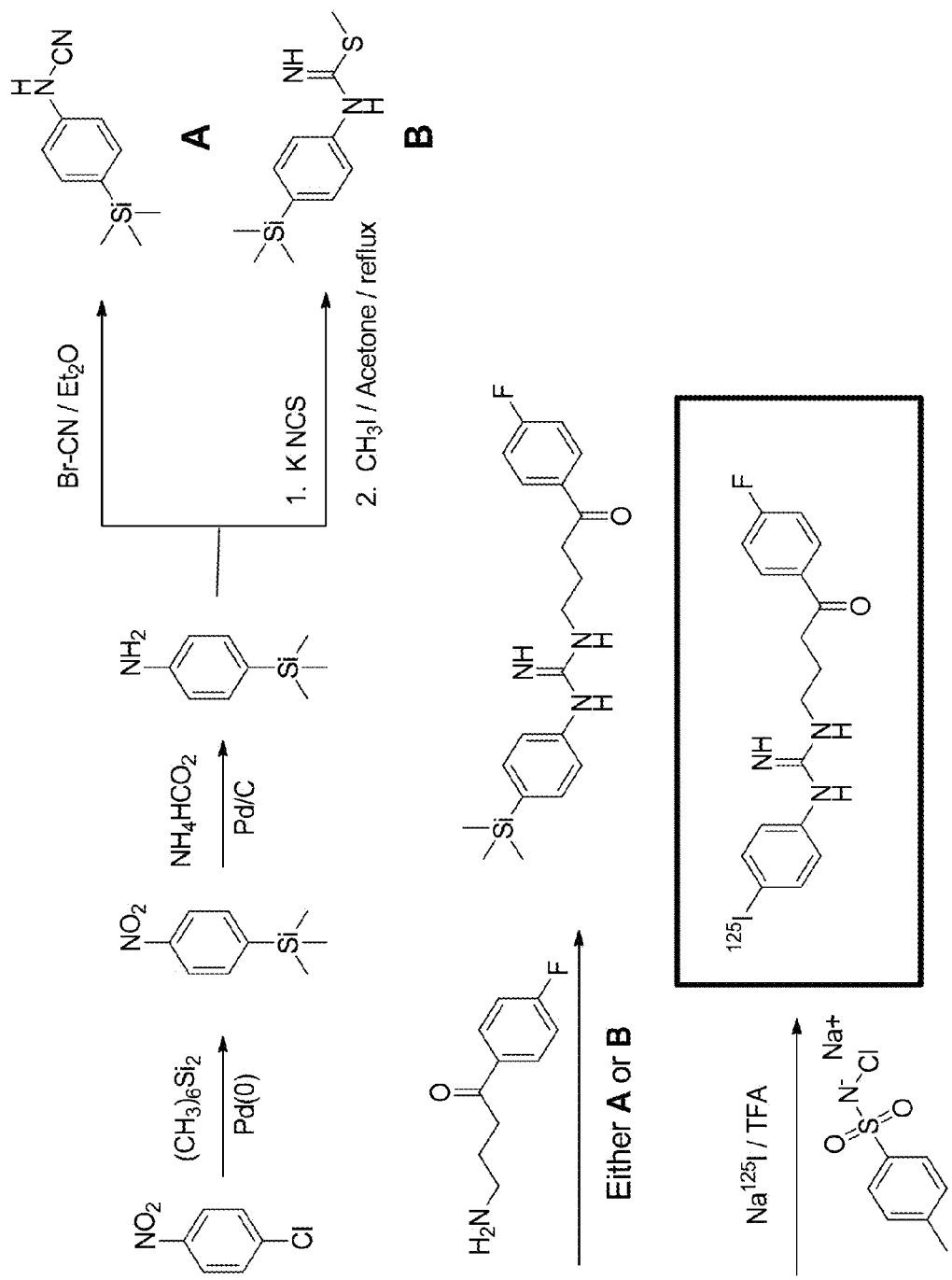
FIG. 19 is a synthetic scheme illustrating a synthesis of radio-labeled hybrid IPAG-haloperidol.
Figure 20:
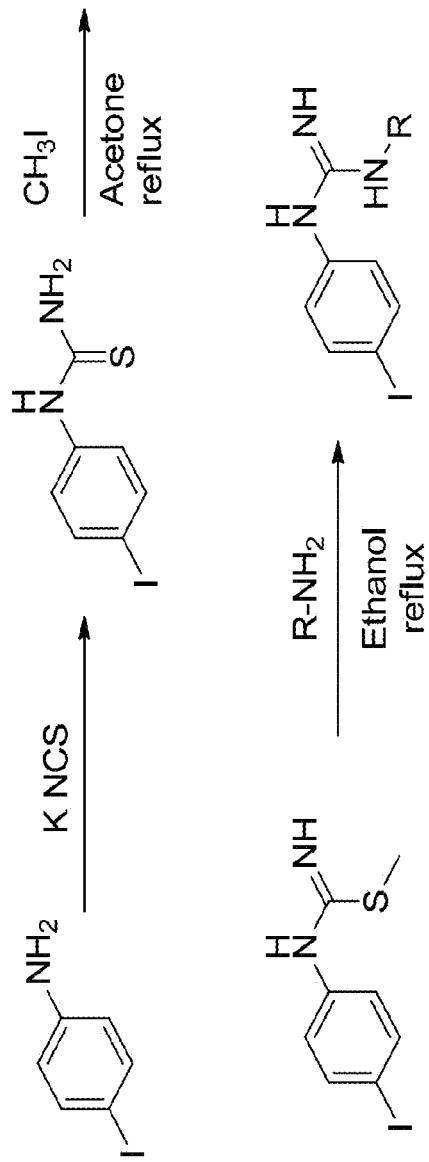
FIG. 20 is a synthetic scheme illustrating a generalized synthetic route toward N-aryl-N'-substituted guanidines.
Figure 21:
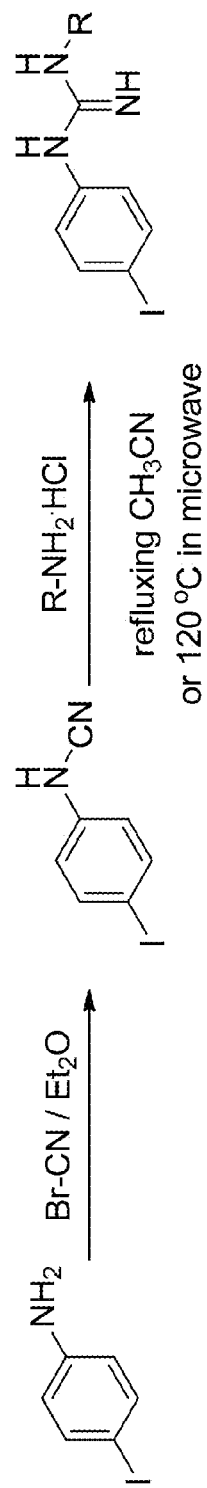
FIG. 21 is a synthetic scheme illustrating an alternative generalized synthetic route toward N-aryl-N'-substituted guanidines.
Figure 22:
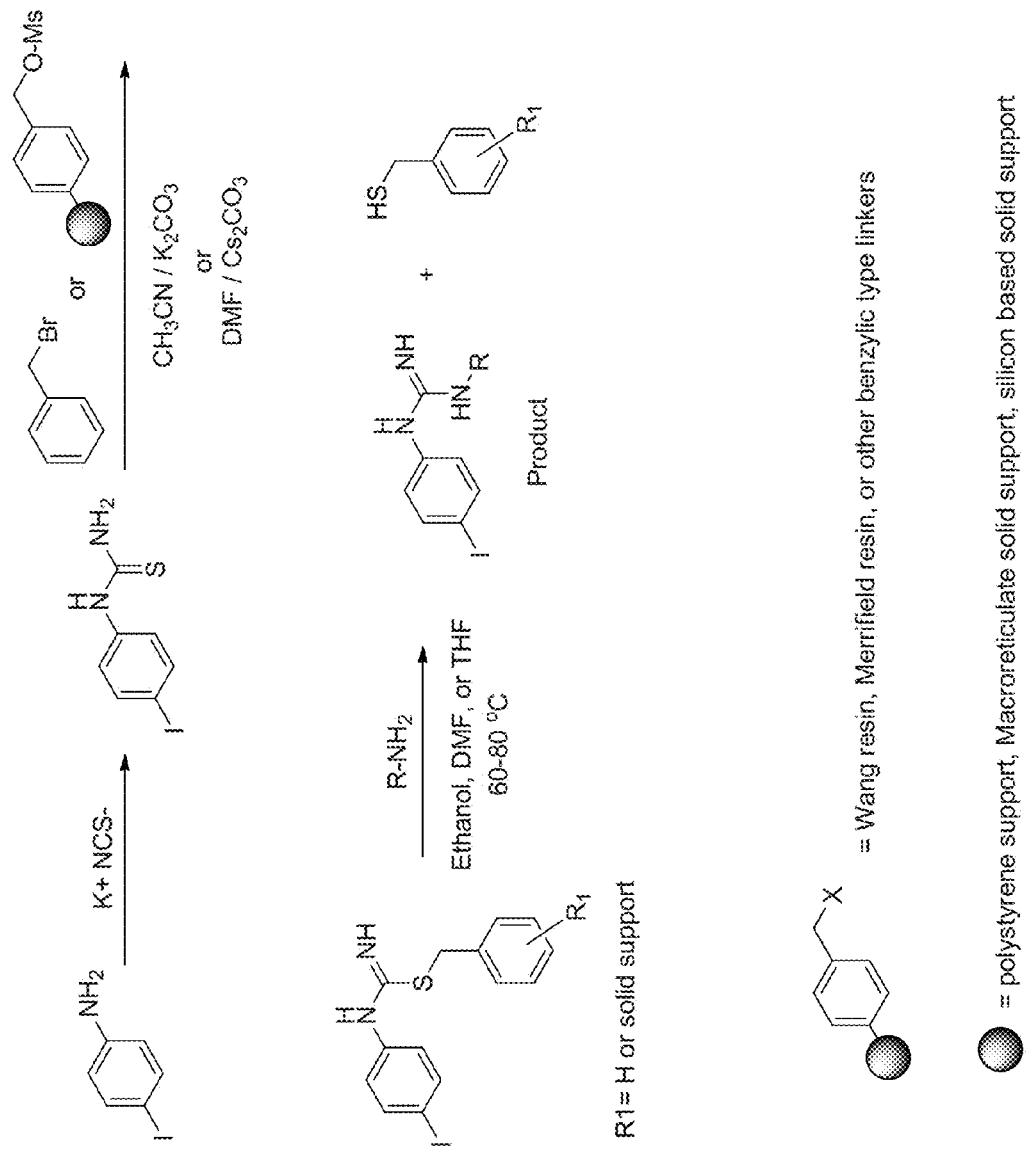
FIG. 22 is a synthetic scheme illustrating a general synthetic route to guanidine precursors using solution or solid phase methods.
Figure 23:
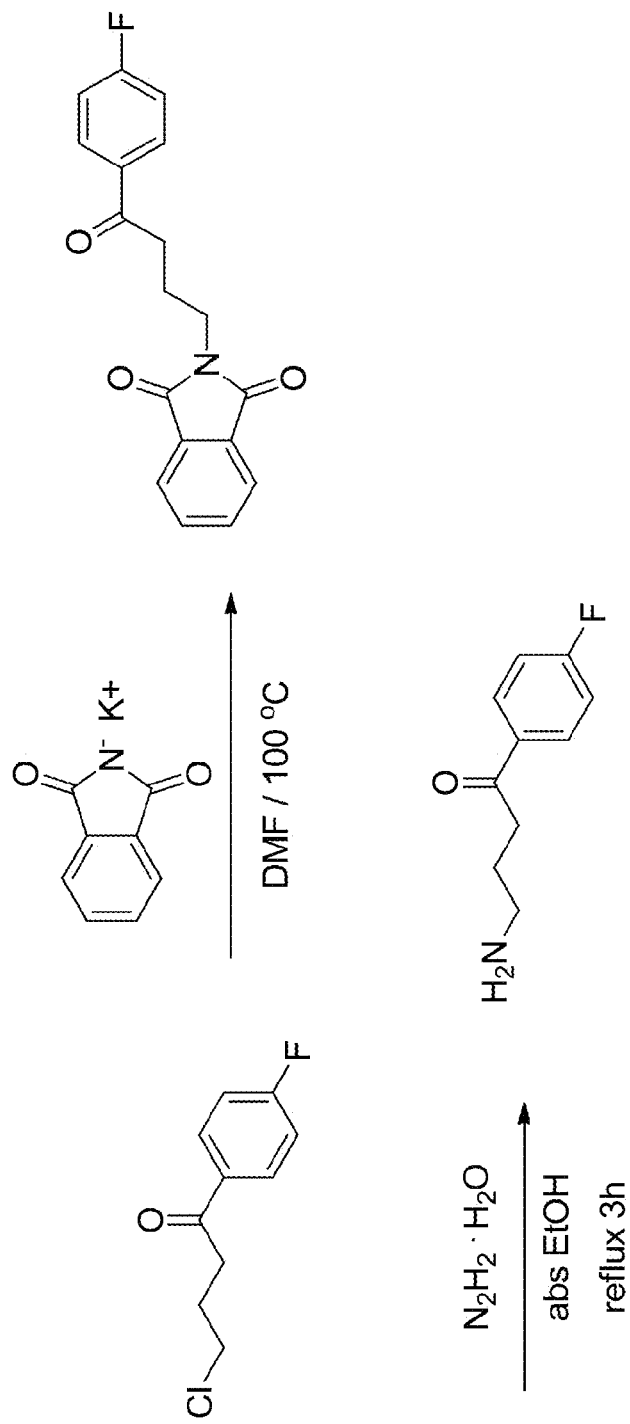
FIG. 23 is a synthetic scheme illustrating the synthesis of haloperidol amine.
Figure 24:
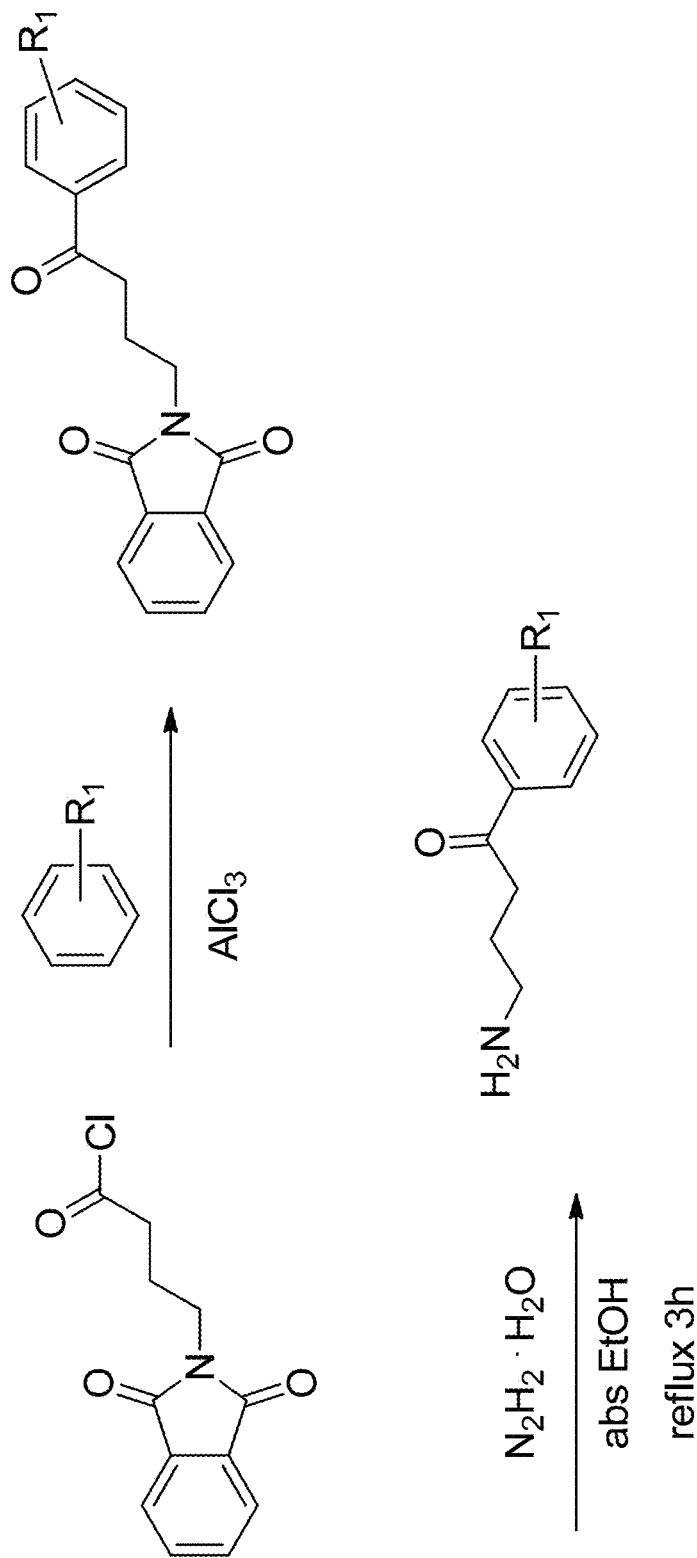
FIG. 24 is a synthetic scheme illustrating the synthesis of haloperidol-like amines.
Figure 25:
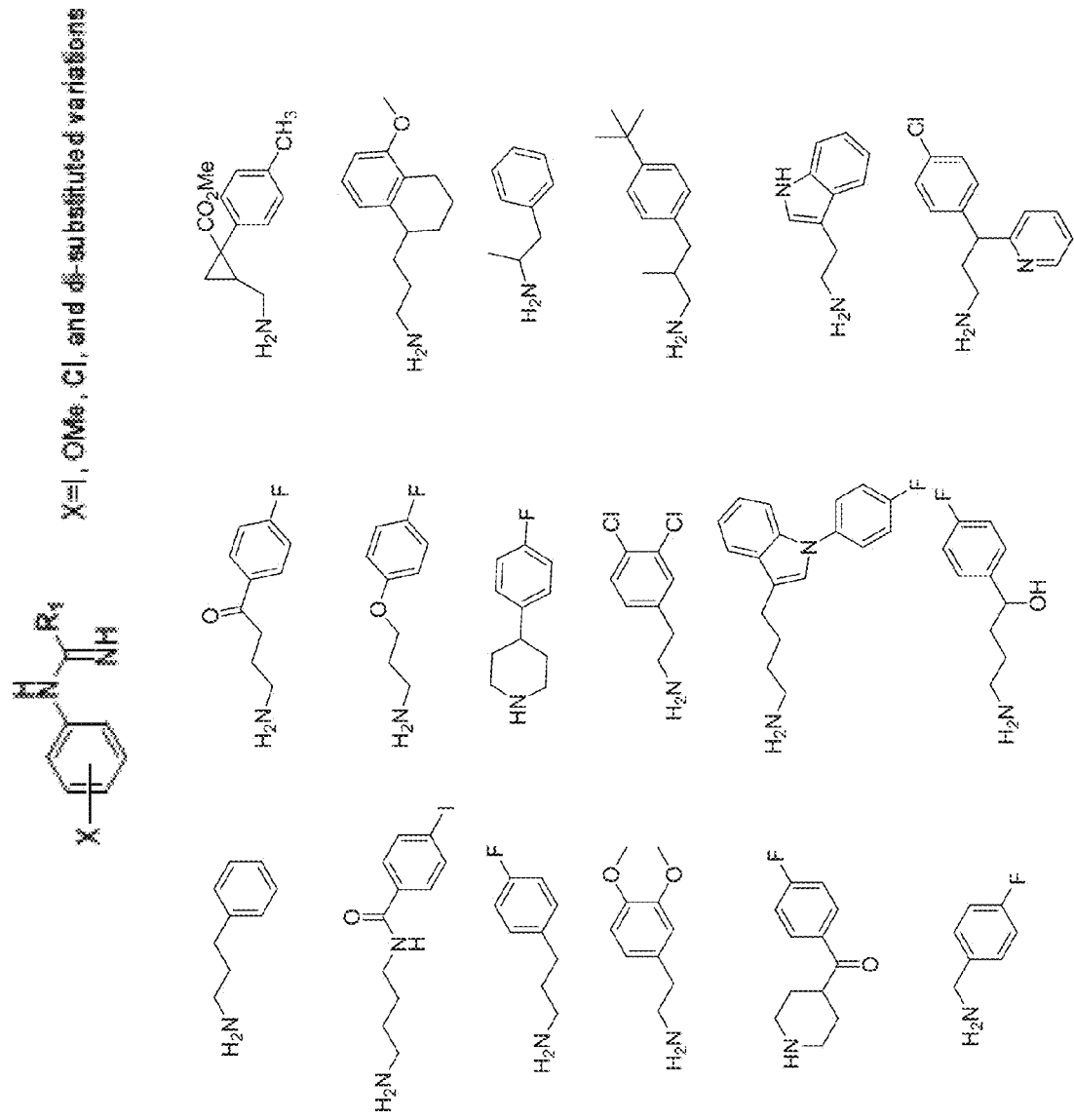
FIG. 25 is a list of representative structures of guanidine Sigma antagonists, with variable groups substituted at $R^1$.

In another non-limiting embodiment, unsymmetrical N,N'-disubstituted guanidines may be synthesized by coupling a benzimidothioate and an amine (FIG. 18). For example, an aniline may be reacted with potassium isothiocyanate to provide a thiourea. The thiourea may then be treated with methyl iodide in acetone heated to reflux, providing the desired benzimidothioate. The unsymmetrical N,N'-disubstituted guanidine may then be formed by coupling the benzimidothioate with an amine. A non-limiting example of a coupling method includes heating in ethanol at reflux.

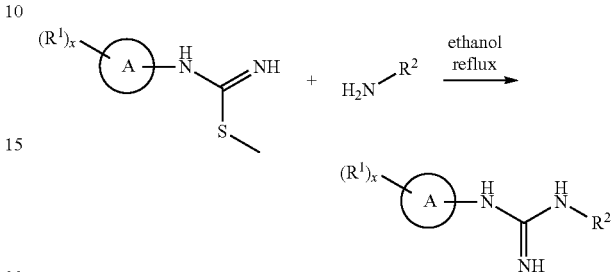

The compounds of the invention may possess one or more stereocenters, and each stereocenter may exist independently in either the R or S configuration. In one embodiment, compounds described herein are present in optically active or racemic forms. It is to be understood that the compounds described herein encompass racemic, optically-active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In one embodiment, a mixture of one or more isomer is utilized as the therapeutic compound described herein. In another embodiment, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

The methods and formulations described herein include the use of N-oxides (if appropriate), crystalline forms (also known as polymorphs), solvates, amorphous phases, and/or pharmaceutically acceptable salts of compounds having the structure of any compound of the invention, as well as metabolites and active metabolites of these compounds having the same type of activity. Solvates include water, ether (e.g., tetrahydrofuran, methyl tert-butyl ether) or alcohol (e.g., ethanol) solvates, acetates and the like. In one embodiment, the compounds described herein exist in solvated forms with pharmaceutically acceptable solvents such as water, and ethanol. In another embodiment, the compounds described herein exist in unsolvated form.

In one embodiment, the compounds of the invention may exist as tautomers. All tautomers are included within the scope of the compounds presented herein.

In one embodiment, compounds described herein are prepared as prodrugs. A "prodrug" refers to an agent that is converted into the parent drug in vivo. In one embodiment, upon in vivo administration, a prodrug is chemically converted to the biologically, pharmaceutically or therapeutically active form of the compound. In another embodiment, a prodrug is enzymatically metabolized by one or more steps or processes to the biologically, pharmaceutically or therapeutically active form of the compound.

In one embodiment, sites on, for example, the aromatic ring portion of compounds of the invention are susceptible to various metabolic reactions.

Incorporation of appropriate substituents on the aromatic ring structures may reduce, minimize or eliminate this metabolic pathway. In one embodiment, the appropriate substituent to decrease or eliminate the susceptibility of the aromatic ring to metabolic reactions is, by way of example only, a deuterium, a halogen, or an alkyl group.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^2H$, $^3H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In one embodiment, isotopically-labeled compounds are useful in drug and/or substrate tissue distribution studies. In another embodiment, substitution with heavier isotopes such as deuterium affords greater metabolic stability (for example, increased in vivo half-life or reduced dosage requirements). In yet another embodiment, substitution with positron emitting isotopes, such as $^{11}C$, $^{18}F$, $^{15}O$ and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In one embodiment, the compounds described herein are labeled by other means, including, but not limited to, the use of chromophores or fluorescent moieties, bioluminescent labels, or chemiluminescent labels.

The compounds described herein, and other related compounds having different substituents are synthesized using techniques and materials described herein and as described, for example, in Fieser & Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4$^{th}$ Ed., (Wiley 1992); Carey & Sundberg, Advanced Organic Chemistry 4th Ed., Vols. A and B (Plenum 2000, 2001), and Green & Wuts, Protective Groups in Organic Synthesis 3rd Ed., (Wiley 1999) (all of which are incorporated by reference for such disclosure). General methods for the preparation of compound as described herein are modified by the use of appropriate reagents and conditions, for the introduction of the various moieties found in the formula as provided herein.

Compounds described herein are synthesized using any suitable procedures starting from compounds that are available from commercial sources, or are prepared using procedures described herein.

In one embodiment, reactive functional groups, such as hydroxyl, amino, imino, thio or carboxy groups, are protected in order to avoid their unwanted participation in reactions. Protecting groups are used to block some or all of the reactive moieties and prevent such groups from participating in chemical reactions until the protective group is removed. In another embodiment, each protective group is removable by a different means. Protective groups that are cleaved under totally disparate reaction conditions fulfill the requirement of differential removal.

In one embodiment, protective groups are removed by acid, base, reducing conditions (such as, for example, hydrogenolysis), and/or oxidative conditions. Groups such as trityl, dimethoxytrityl, acetal and t-butyldimethylsilyl are acid labile and are used to protect carboxy and hydroxy reactive moieties in the presence of amino groups protected with Cbz groups, which are removable by hydrogenolysis, and Fmoc groups, which are base labile. Carboxylic acid and hydroxy reactive moieties are blocked with base labile groups such as, but not limited to, methyl, ethyl, and acetyl, in the presence of amines that are blocked with acid labile groups, such as t-butyl carbamate, or with carbamates that are both acid and base stable but hydrolytically removable.

In one embodiment, carboxylic acid and hydroxy reactive moieties are blocked with hydrolytically removable protective groups such as the benzyl group, while amine groups capable of hydrogen bonding with acids are blocked with base labile groups such as Fmoc. Carboxylic acid reactive moieties are protected by conversion to simple ester compounds as exemplified herein, which include conversion to alkyl esters, or are blocked with oxidatively-removable protective groups such as 2,4-dimethoxybenzyl, while co-existing amino groups are blocked with fluoride labile silyl carbamates.

Allyl blocking groups are useful in the presence of acid- and base-protecting groups since the former are stable and are subsequently removed by metal or pi-acid catalysts. For example, an allyl-blocked carboxylic acid is deprotected with a palladium-catalyzed reaction in the presence of acid labile t-butyl carbamate or base-labile acetate amine protecting groups. Yet another form of protecting group is a resin to which a compound or intermediate is attached. As long as the residue is attached to the resin, that functional group is blocked and does not react. Once released from the resin, the functional group is available to react.

Typically blocking/protecting groups may be selected from:

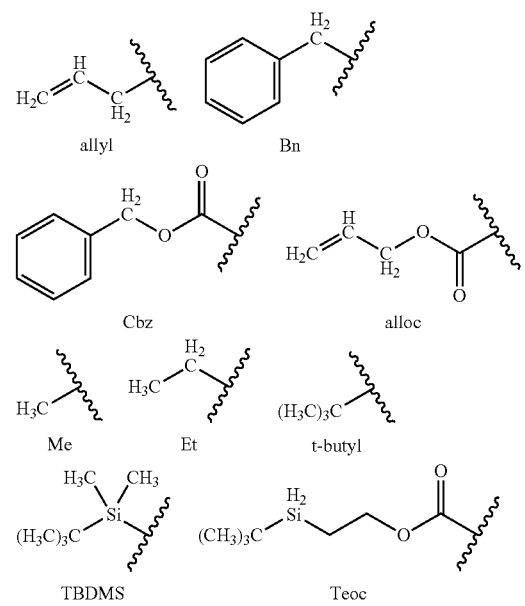

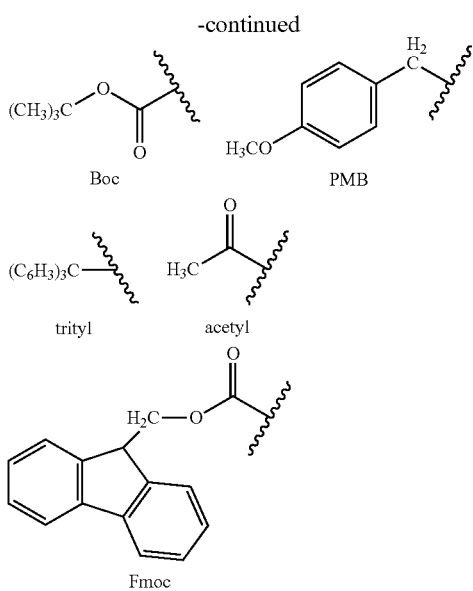

Other protecting groups, plus a detailed description of techniques applicable to the creation of protecting groups and their removal are described in Greene & Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure.

Methods of the Invention

The invention includes a method of treating, ameliorating or preventing a Sigma receptor-related disorder or disease in a subject in need thereof. The method comprises administering to the subject an effective amount of a therapeutic composition comprising a compound of the invention. In one embodiment, the Sigma receptor-related disease or disorder is selected from the group comprising cancer, neuropathic pain, depression, substance abuse, epilepsy, psychosis, Alzheimer's disease, Parkinson's disease, and combinations thereof. In another embodiment, the cancer is selected from the group consisting of prostate cancer, liver cancer, pancreas cancer, breast cancer, CNS tumors (including brain tumors), neuroblastoma, leukemia, and combinations thereof.

The invention also includes a method of treating, ameliorating or preventing a Sigma receptor-related disorder or disease in a subject in need thereof. The method comprises administering to the subject an effective amount of a therapeutic composition comprising a Sigma receptor-modulating compound, and further administering to the subject a therapeutic agent that inhibits the ubiquitin proteasome system (UPS) and/or autophagic survival pathways. In one embodiment, the Sigma receptor-modulating compound is a compound of the invention.

In one embodiment, administering the Sigma receptor-modulating compound to the subject allows for administering a lower dose of the therapeutic agent that inhibits the ubiquitin proteasome system (UPS) and/or autophagic survival pathways, as compared to the dose of the therapeutic agent alone that is required to achieve similar results in treating, ameliorating or preventing the Sigma receptor-related disorder in the subject. In another embodiment, the Sigma receptor-modulating compound and the therapeutic agent are co-administered to the subject.

In yet another embodiment, the Sigma receptor-modulating compound and the therapeutic agent are co-formulated and co-administered to the subject.

In one embodiment, the methods described herein further comprise inhibiting the Sigma receptor. In another embodiment, the methods described herein further comprise modulating the Sigma receptor.

In one embodiment, the subject is a mammal. In another embodiment, the mammal is a human.

Combination Therapies

The compounds of the present invention are intended to be useful in combination with one or more additional compounds. These additional compounds may comprise compounds of the present invention or therapeutic agents known to treat, prevent, or reduce the symptoms or effects of Sigma receptor-related disorders or diseases. Such compounds include, but are not limited to, hormone receptor antagonists, autophagy inhibitors, ER stress response inhibitors, and proteasome inhibitors.

In non-limiting examples, the compounds of the invention may be used in combination with one or more therapeutic agents (or a salt, solvate or prodrug thereof) selected from the group consisting of hormone receptor antagonists, including but are not limited to octapeptide, somatostatin, analoguem, lanreotide, angiopeptin, dermopeptin, octreotide, and pegvisomant;

autophagy inhibitors, including but are not limited to 3-methyladenine, chloroquine, hydroxychloroquine, and wortmannin;

ER stress response inhibitors, including but are not limited to eeyarestatin I, salubrinal, and versipelostatin;

proteasome inhibitors, including but are not limited to 2H-isoindole-2-carboxylic acid, 4-fluoro-1,3-dihydro-(2R,6S,12Z,13aS,14aR,16aS)-14a-[[(cyclopropylsulfonyl)amino]carbonyl]-6-[[(1,1-dimethylethoxy)carbonyl]amino]-1,2,3,5,6,7,8,9,10,11,13a,14,14a,15,16,16a-hexadecahydro-5,16-dioxocyclopropa[e]pyrrolo[1,2-a][1,4]diazacyclopentadecin-2-yl ester (Danoprevir), adamantane-acetyl-(6-aminohexanoyl)3-(leucinyl)3-vinyl-(methyl)-sulfone, N-acetyl-L-leucyl-L-leucyl-L-methional, N-[(phenylmethoxy)carbonyl]-L-leucyl-N-[(1S)-1-formyl-3-methylbutyl]-L-leucinamide, (2R,3S,4R)-3-hydroxy-2-[(1S)-1-hydroxy-2-methylpropyl]-4-methyl-5-oxo-2-pyrrolidinecarboxy-N-acetyl-L-cysteine thioester, N—[N—(N-acetyl-L-leucyl)-L-leucyl]-L-norleucine, lactacystin, 4-(2-aminoethyl)benzenesulfonyl fluoride hydrochloride, (S)-1-carboxy-2-phenyl]-carbamoyl-arg-val-arginal, bovine pancreatic trypsin inhibitor, [(2S,2R)-3-amino-2-hydroxy-4-phenylbutanoyl]-L-leucine, N—[(S)-1-carboxy-isopentyl)-carbamoyl-alpha-(2-iminohexahydro-4-(S)-pyrimidyl]-L-glycyl-L-phenylalaninal, ethylenediamine-tetraacetic acid disodium salt dehydrate, acetyl-leucyl-leucyl-arginal, isovaleryl-val-val-AHMHA-ala-AHMHA where AHMHA=(3S,4S)-4-amino-3-hydroxy-6-methylheptanoic acid, N-alpha-L-rhamnopyranosyloxy(hydroxyphosphinyl)-L-leucyl-L-tryptophan, phenylmethanesulfonyl fluoride, bortezomib, carfilzomib, ONX 0912, NPI-0052, CEP-18770, MLN9708, disulfiram, epigallocatechin-3-gallate, and salinosporamide A; and p97/VCP inhibitors, including but not limited to DBeQ and derivatives thereof.

A synergistic effect may be calculated, for example, using suitable methods such as, for example, the Sigmoid-$E_{max}$ equation (Holford & Scheiner, 1981, Clin. Pharmacokinet. 6:429-453), the equation of Loewe additivity (Loewe & Muischnek, 1926, Arch. Exp. Pathol Pharmacol. 114:313-326) and the median-effect equation (Chou & Talalay, 1984, Adv. Enzyme Regul. 22:27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Administration/Dosage/Formulations

The regimen of administration may affect what constitutes an effective amount. The therapeutic formulations may be administered to the subject either prior to or after the onset of a Sigma-receptor related disorder or disease. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, preferably a mammal, more preferably a human, may be carried out using known procedures, at dosages and for periods of time effective to treat Sigma-receptor related disorders or diseases in the patient. An effective amount of the therapeutic compound necessary to achieve a therapeutic effect may vary according to factors such as the state of the disease or disorder in the patient; the age, sex, and weight of the patient; and the ability of the therapeutic compound to treat Sigma-receptor related disorders or diseases in the patient. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level depends upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of Sigma-receptor related disorders or diseases in a patient.

In one embodiment, the compositions of the invention are formulated using one or more pharmaceutically acceptable excipients or carriers. In one embodiment, the pharmaceutical compositions of the invention comprise a therapeutically effective amount of a compound of the invention and a pharmaceutically acceptable carrier.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it is preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin. In one embodiment, the pharmaceutically acceptable carrier is not DMSO alone.

In one embodiment, the compositions of the invention are administered to the patient in dosages that range from one to five times per day or more. In another embodiment, the compositions of the invention are administered to the patient in range of dosages that include, but are not limited to, once every day, every two, days, every three days to once a week, and once every two weeks. It is readily apparent to one skilled in the art that the frequency of administration of the various combination compositions of the invention varies from individual to individual depending on many factors including, but not limited to, age, disease or disorder to be treated, gender, overall health, and other factors. Thus, the invention should not be construed to be limited to any particular dosage regime and the precise dosage and composition to be administered to any patient is determined by the attending physical taking all other factors about the patient into account.

Compounds of the invention for administration may be in the range of from about 1 µg to about 10,000 mg, about 20 µg to about 9,500 mg, about 40 µg to about 9,000 mg, about 75 µg to about 8,500 mg, about 150 µg to about 7,500 mg, about 200 µg to about 7,000 mg, about 3050 µg to about 6,000 mg, about 500 µg to about 5,000 mg, about 750 µg to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments therebetween.

In some embodiments, the dose of a compound of the invention is from about 1 mg and about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In one embodiment, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of Sigma-receptor related disorders or diseases in a patient.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans)buccal, (trans)urethral, vaginal (e.g., trans- and perivaginally), (intra) nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For oral administration, the compounds of the invention may be in the form of tablets or capsules prepared by conventional means with pharmaceutically acceptable excipients such as binding agents (e.g., polyvinylpyrrolidone, hydroxypropylcellulose or hydroxypropylmethylcellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulphate). If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400). Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e. having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e. drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) melt.

The present invention also includes a multi-layer tablet comprising a layer providing for the delayed release of one or more compounds of the invention, and a further layer providing for the immediate release of a medication for treatment of Parkinson's Disease. Using a wax/pH-sensitive polymer mix, a gastric insoluble composition may be obtained in which the active ingredient is entrapped, ensuring its delayed release.

Parenteral Administration

For parenteral administration, the compounds of the invention may be formulated for injection or infusion, for example, intravenous, intramuscular or subcutaneous injection or infusion, or for administration in a bolus dose and/or continuous infusion. Suspensions, solutions or emulsions in an oily or aqueous vehicle, optionally containing other formulatory agents such as suspending, stabilizing and/or dispersing agents may be used.

Additional Administration Forms

Additional dosage forms of this invention include dosage forms as described in U.S. Pat. Nos. 6,340,475; 6,488,962; 6,451,808; 5,972,389; 5,582,837; and 5,007,790. Additional dosage forms of this invention also include dosage forms as described in U.S. Patent Applications Nos. 20030147952; 20030104062; 20030104053; 20030044466; 20030039688; and 20020051820. Additional dosage forms of this invention also include dosage forms as described in PCT Applications Nos. WO 03/35041; WO 03/35040; WO 03/35029; WO 03/35177; WO 03/35039; WO 02/96404; WO 02/32416; WO 01/97783; WO 01/56544; WO 01/32217; WO 98/55107; WO 98/11879; WO 97/47285; WO 93/18755; and WO 90/11757.

Controlled Release Formulations and Drug Delivery Systems

In one embodiment, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material which provides sustained release properties to the compounds. As such, the compounds for use the method of the invention may be administered in the form of microparticles, for example, by injection or in the form of wafers or discs by implantation.

In one embodiment of the invention, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that mat, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Dosing

The therapeutically effective amount or dose of a compound of the present invention depends on the age, sex and weight of the patient, the current medical condition of the patient and the progression of Sigma-receptor related disorders or diseases in the patient being treated. The skilled artisan is able to determine appropriate dosages depending on these and other factors.

A suitable dose of a compound of the present invention may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

In the case wherein the patient's status does improve, upon the doctor's discretion the administration of the inhibitor of the invention is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced, as a function of the viral load, to a level at which the improved disease is retained. In one embodiment, patients require intermittent treatment on a long-term basis upon any recurrence of symptoms and/or infection.

The compounds for use in the method of the invention may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. Capsid assembly inhibitors exhibiting high therapeutic indices are preferred. The data obtained from cell culture assays and animal studies are optionally used in formulating a range of dosage for use in human. The dosage of such capsid assembly inhibitors lies preferably within a range of circulating concentrations that include the $ED_{50}$ with minimal toxicity. The dosage optionally varies within this range depending upon the dosage form employed and the route of administration utilized.

Those skilled in the art recognizes, or is able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Materials and Methods
Chemicals.

IPAG, haloperidol hydrochloride, rimcazole dihydrochloride, PB28 dihydrochloride, BD1047, BD1063, NE100, PRE-084 hydrochloride, (+)-SKF10047 hydrochloride, and (+)-pentazocine were obtained from Tocris (Minneapolis, Minn.). (+)-Pentazocine was obtained from the National Institute on Drug Abuse (Bethesda, Md.). The cell membrane permeable calpain and cathepsin inhibitor E64d was purchased from Sigma Aldrich (St. Louis, Mo.).

Cell Lines and Transfections.

The cell lines evaluated and/or mentioned herein include: MDA-MB-468, MDA-MB-231, MCF-7, T47D, SKBR3, 4T1, PC3, DU145, LNCaP, Panc1, HepG2, HCT116, BE2C, SH-SY5Y, K562, HEK293T, and NIH3T3. All cell lines are from ATCC. Cells were maintained in a 1:1 mixture of DMEM:F-12 with 4.5 g/liter glucose, 5% FCS, non-essential amino acids and penicillin/streptomycin. Cells were seeded approximately 24 hours prior to start of drug treatment in most assays.

Human beclin1, human ATG5, human p97/VCP, human Sigma1, human IRE1α, human ATF4, and control siRNA were purchased from Santa Cruz Biotechnology. siRNA transfections (10 nmoles per well) were performed with INTERFERin (PolyPlus) or oligofectamine according to manufacturer's procedures (InVitrogen).

Cell Death Assays.

Cell death was evaluated by trypan blue exclusion assay, as well as cleaved caspase 3 (Asp 175) and cleaved PARP (Asp 214) immunoblot. Trypan blue exclusion and propidium iodide staining were used to quantify general cell death and the presence of apoptotic cell death was confirmed by immunoblot. The percentage of dead cells in a given population was determined by quantifying the number of trypan blue positive (dead) cells and dividing by the total number of trypan blue positive and negative cells.

Immunoblots and Antibodies.

Cells were lysed and proteins extracted in a modified RIPA buffer (25 mM Tris-HCl pH 7.6, 150 mM NaCl, 1% NP-40, 1% sodium deoxycholate and 0.1% SDS) supplemented with 10% glycerol (volume/volume), complete protease inhibitor cocktail (Roche), and Halt phosphatase inhibitor cocktail (Pierce). Approximately 10-20 μg of detergent soluble protein were resolved on NOVEX 10-20% polyacrylamide Tris-glycine gels (InVitrogen). Immunoblots were performed in a 20 mM Tris-buffered 137 mM saline solution (pH 7.6) containing 0.1% Tween-20 (polyoxyethylene (20) sorbitan monolaurate) and 5% (weight/volume) blotting grade non-fat dry milk (BioRad). The Lumigen PS-3 enhanced chemiluminescence kit (GE Healthcare) was used to reveal immunoblotted proteins.

The mouse anti-GFP, mouse β-actin, and rabbit Beclin1, mouse ATF4, and all horseradish peroxidase conjugated secondary antibodies were purchased from Santa Cruz Biotechnologies. The rabbit polyclonal LC3, phospo-p38MAPK (Thr180/Tyr182), phospho-SAPK/JNK (Thr183/Tyr185), IRE1α, phospho-eIF2α (Ser51), GRP78/BiP, cleaved Caspase 3 (Asp 175), and cleaved PARP (Asp 214) were all purchased from Cell Signaling Technologies.

Microscopy and Quantitation of Autophagosome Formation.

The human GFP-LC3 expression plasmid, pEGFP-LC3 (a gift from Drs. Grazia Ambrosini and Gary K. Schwartz, MSKCC), was stably transfected into MDA-MB-468 and selected with 0.5 mg/ml G418 sulfate. Stable populations were generated and compared to parental MDA-MB-468 for Sigma1 expression and autophagic and growth inhibitory response to Sigma ligands. GFP-LC3 translocation (punctae formation) was assessed by microscopy in MDA-MB-468 (GFP-LC3) stable cell populations. For microscopy-based experiments, cells were seeded onto Lab-Tek II glass chamber slides (Nalge Nunc International). Following 24 hours of drug treatment, cells were washed with room temperature Dulbecco modified phosphate buffered saline solution, containing calcium and magnesium, and fixed and permeabilized with room temperature Cytofix-Cytoperm solution (BD Biosciences). Images of GFP-LC3 punctae were acquired with a Zeiss Axioplan 2 Imaging widefield microscope using Axiovision LE software. Punctae were counted using the spot quantitation program in the Fluoro-Chem software package (Alpha Innotech) and confirmed in parallel by manual counting. Autophagosome formation in MDAMB-468 (GFP-LC3) cells was quantitated as the mean number of GFP-LC3 punctae per GFP positive cell.

Autophagic Flux Assays

Autophagic flux (turnover of autolysosome cargo) was evaluated using two previously described methods. Lipid conjugated GFP-LC3 translocates to autophagosomes that conditionally fuse with lysosomes, leading to autolysosomal degradation of LC3 and release of GFP in the case of active autophagic flux. In this GFP-LC3 degradation assay, cleaved GFP was detected by immunoblot. Autophagic flux was also verified by inhibiting autolysosomal degradation with the cell permeable calpain and cathepsin inhibitor E64d. In this assay, accumulation of LC3II was an indicator of autophagic flux Statistical Analysis.

Statistical significance was determined by one-way ANOVA followed by Bonferroni's post-test using Prism software (GraphPad).

Example 1

Induction of Dose-Responsive Activation of Autophagy

Figure 11:
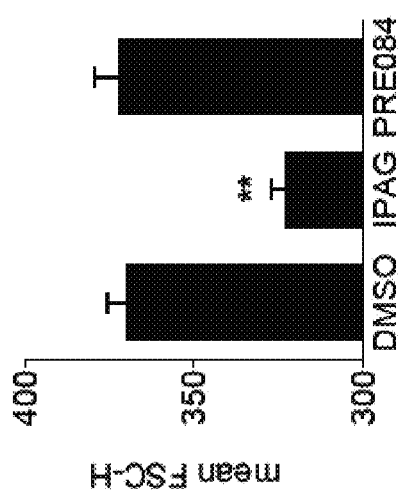
FIG. 11 is a graph illustrating decrease in MDAMB468 cell size associated with the Sigma1 antagonist treatment. MDA-MB-468 cells were treated for 24 hours with DMSO (control), 10 µM IPAG (antagonist), or 10 µM PRE084 (agonist). Cell size was quantitated by flow cytometry, using a Becton Dickinson FACS Calibur flow cytometer with Cell Quest software. The mean forward scatter height (FSC-H) of the G1-phase population was determined as a measure of relative cell size. Single cells were gated away from aggregated cells using an FL2-width versus FL-2 area dot plot. Mean FSC-H±S.E. was calculated from at least 4 independent determinations. For each FSC-H determination, FACS analysis was performed on 10,000 single cells. The mean FSC-H of DMSO (control) and PRE084 treated MDA-MB-468 measured 370±6 and 372±7, respectively, whereas the mean FSC-H of IPAG treated MDA-MB-468 cells was 323±4. ** $P<0.01$ for IPAG compared to DMSO and IPAG compared to PRE084.

MDA-MB-468 and T47D breast adenocarcinoma cells, which natively express Sigma1, were treated with Sigma receptor antagonists or agonists. In all experiments the antagonists, but not agonists, decreased cell size by ~20% after 24 hours of treatment with 10 μM drug (FIG. 11). In view of recent evidence that autophagy plays a role in cell growth, this process was evaluated to determine whether it was activated in Sigma antagonist-treated cells.

Figures 4A, 4B:
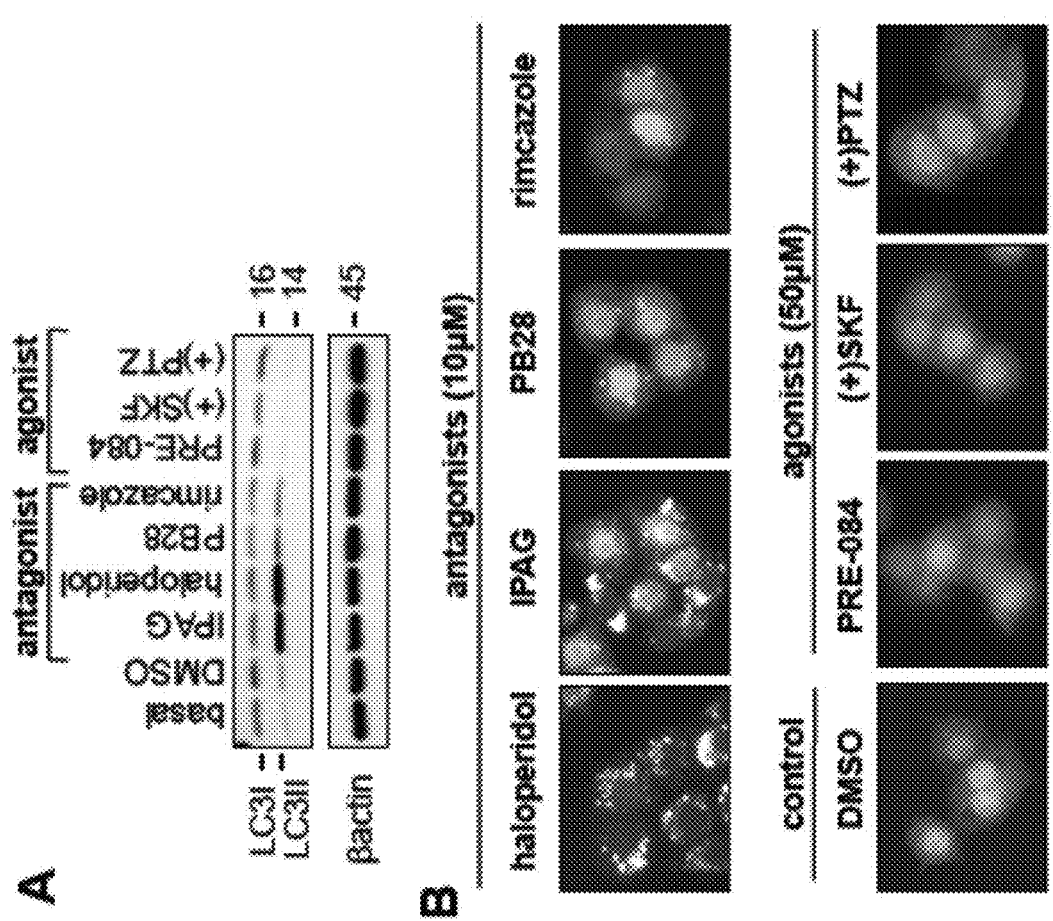

Initially, an established immunoblot-based assay to detect microtubule associated protein light chain 3 (LC3) lipidation was used to test for the activation of autophagy. In these experiments, treatment with Sigma antagonists (IPAG, haloperidol, rimcazole, PB28), but not agonists (PRE-084, (+)-SKF10047, (+)-pentazocine), converted LC3 to LC3II, an indication of LC3 lipid conjugation and autophagosome formation (FIG. 4A). These results were confirmed with a widely used microscopy based assay to visualize and quantify the translocation of an amino-terminal green fluorescent protein tagged LC3 (GFPLC3) into vesicular structures, which appear as GFP-concentrated punctae characteristic of autophagosome formation. Since transient transfections can produce spurious GFP-LC3 aggregates, stable GFP-LC3 transfected populations of MDA-MB-468 (GFP-LC3) were generated. These cells were treated for 24 hours with increasing concentrations of Sigma receptor antagonists and agonists, and were compared to basal and DMSO treated controls (FIGS. 4B & 4C).

Figure 4C:
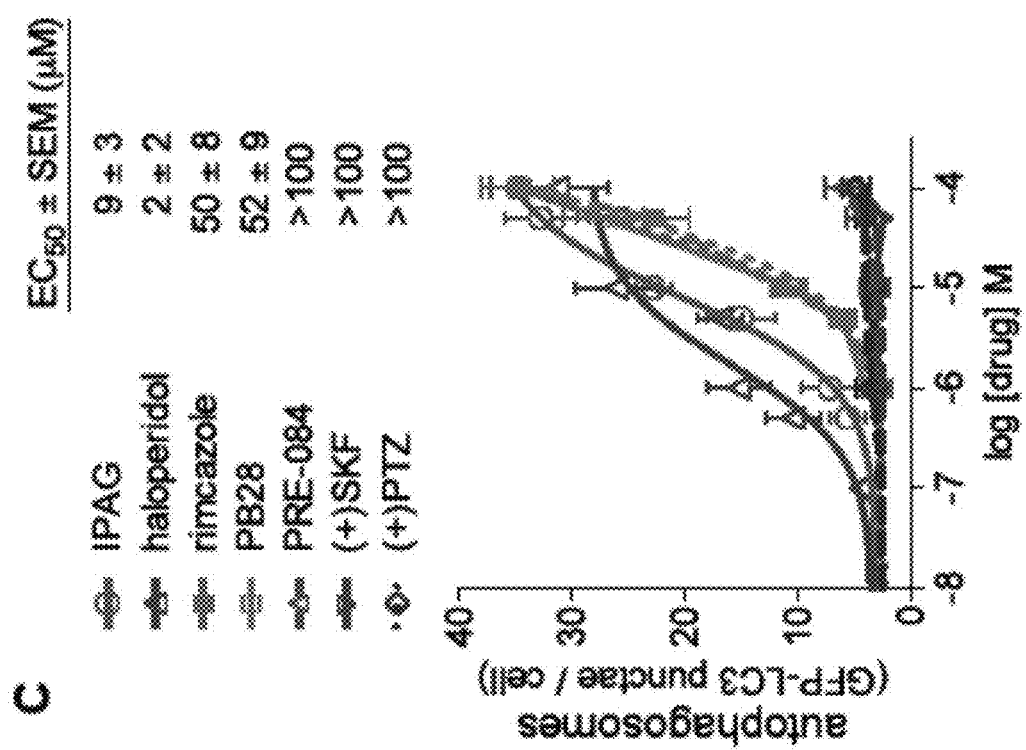

Sigma antagonist-induced autophagosome formation was dose-responsive, with a range of potencies among antagonists (FIG. 4C). Following 24 hours of treatment, precipitous cell death occurred with 40 μM IPAG and haloperidol, and with 100 μM of rimcazole and PB28. The number of punctae per cell produced at these concentrations were set as the maximal autophagosome induction levels (maximum effect, $E_{max}$) in calculating $EC_{50}$ values. The $E_{max}$ of all four antagonists was 30 to 35 punctae per cell, with no significant difference between ligands (FIG. 4C). However, the potency ($EC_{50}$±S.E.M.) of Sigma antagonists IPAG (9±3 μM), haloperidol (2±2 μM), rimcazole (50±8 μM), and PB28 (52±9 μM) varied (FIG. 4C). Basal and DMSO treated cells produced 4±1 and 5±1 punctae per cell, respectively (FIG. 4C). The agonists PRE-084, (+)-SKF10047, and (+)-pentazocine produced no more than 6±2, 5±1, and 6±1 punctae per cell, respectively, at drug concentrations up to 100 μM (FIG. 4C). Thus Sigma receptor antagonist treatment produced autophagosomes in a dose-responsive manner, which reached saturating levels, and this result was consistent with receptor-mediated effects.

Example 2

Inhibition of Sigma1 Antagonist Associated Autophagy by Sigma1 RNAi

Figure 5:
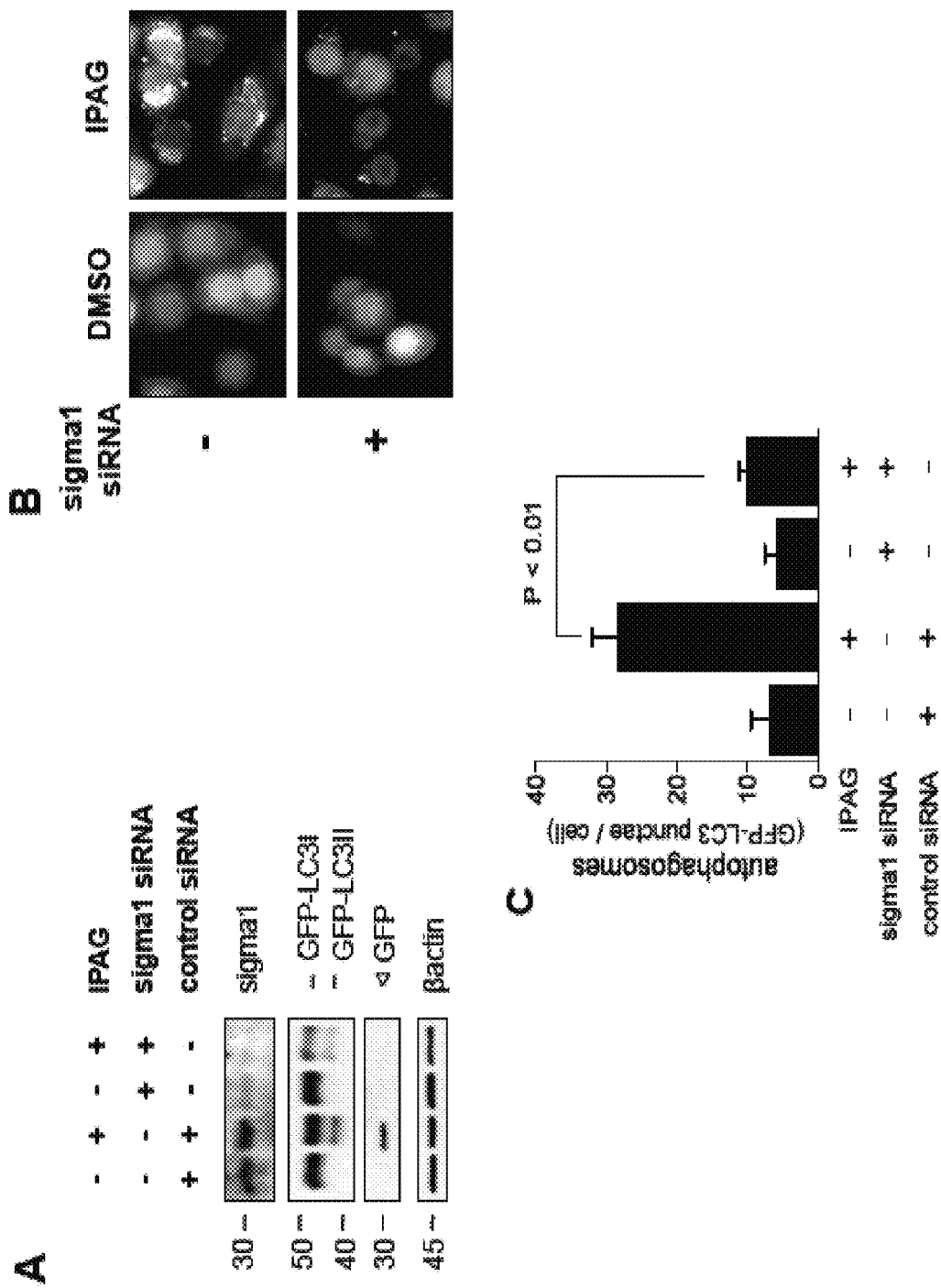
FIG. 5, comprising

To confirm that the Sigma1 antagonist treatment associated autophagy was indeed Sigma1 mediated, siRNA was used to knockdown Sigma1 receptors in MDA-MB-468 (GFP-LC3) cells, and evaluated IPAG induced autophagy (FIG. 5). Significant Sigma1 knockdown was detectable >72 hours after transfection of Sigma1 selective siRNA, suggesting a stable, long protein half-life, consistent with previous reports. Knockdown levels reached approximately 20% of basal levels (FIG. 5A).

Autophagosome formation (GFP-LC3 punctae) and autophagic degradation (GFP-LC3 cleavage) were evaluated. Knockdown of Sigma1 alone did not induce the formation of autophagosomes in the absence of Sigma1 ligands, 6±2 punctae per cell compared to 7±3 punctae per cell in control siRNA transfected cells (FIG. 5C). Treatment with 10 μM IPAG for 20 hours resulted in 28±4 punctae per cell in control siRNA transfected cells and a significant inhibition to 10±2 punctae per cell in Sigma1-knockdown cells (FIG. 5C).

Example 3

Induction of ER Stress and Activation of UPR

Whether Sigma antagonists immediately induce autophagy or whether it is activated downstream of other cellular events was next examined. As Sigma1 is highly enriched in the ER, next examined was whether antagonist treatment could induce ER stress mediated UPR. Components of the IRE1α-JNK1/2 and eIF2α-ATF4 branches of the UPR as well as the UPR-associated ER chaperone, GRP78/BiP, were assayed as indicators of activated UPR.

The stress induced mitogen activated protein kinase p38 (p38MAPK) is a downstream target of the IRE1-TRAF2 (TNF receptor-associated receptor 2)-ASK1 (apoptosis signaling regulated kinase 1) signaling complex that is activated in response to ER stress and subsequently phosphorylates and enhances apoptosis. In addition p38MAPK has a role in the control of basal and starvation-induced autophagy.

Figure 6:
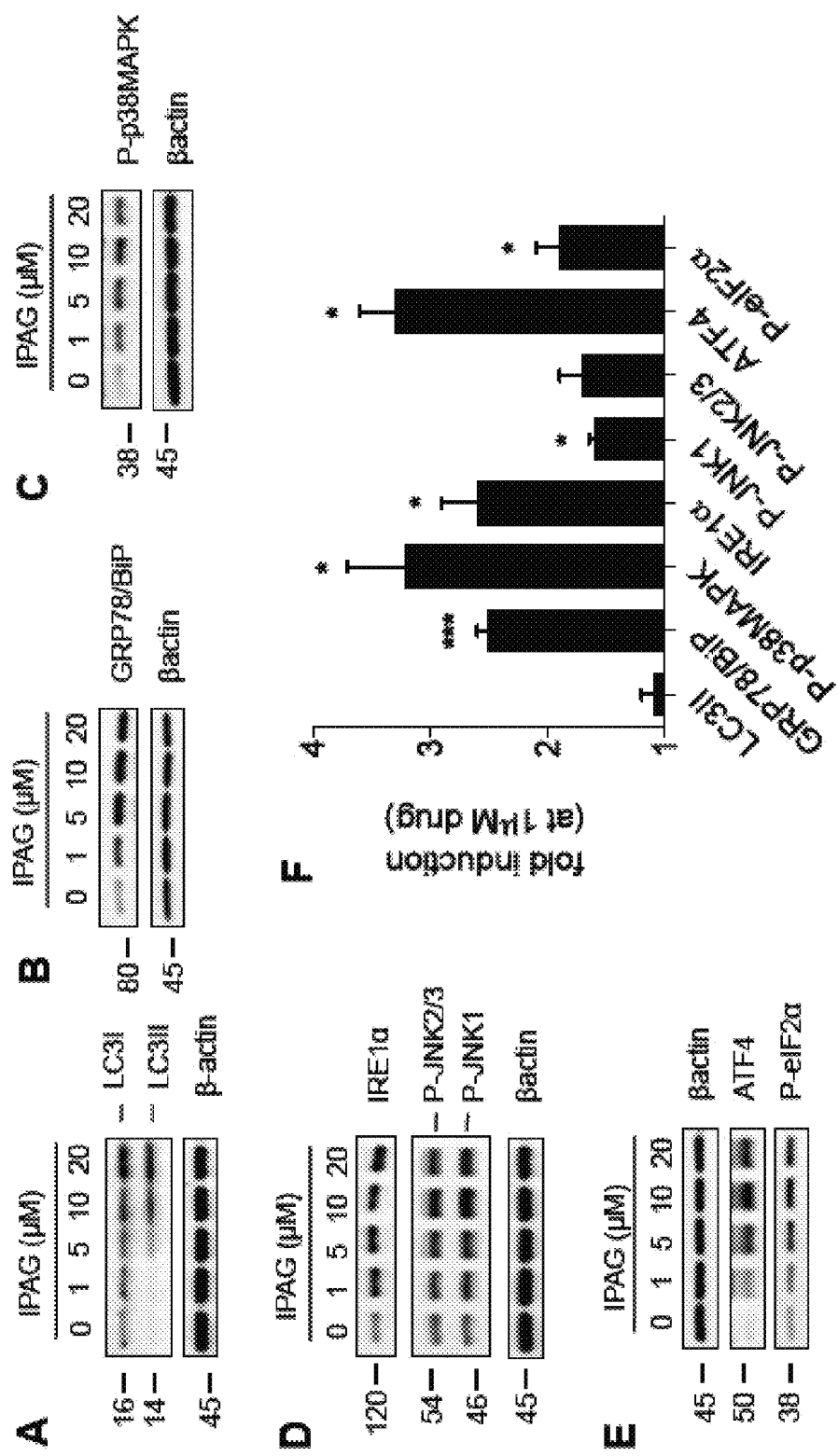
FIG. 6, comprising

All of the above-mentioned markers of ER stress were evaluated following treatment with increasing doses of Sigma ligands in order to compare UPR with the dose-responsive activation of autophagy. Sigma1 antagonist, IPAG, activated the UPR in a dose-responsive manner (FIG. 6). In contrast, Sigma1 agonists did not activate any of these markers (data not shown). Interestingly, the UPR to Sigma1 antagonists induced ER stress occurs at lower doses than the autophagic response (FIG. 6). Indeed, treatment with 1 μM IPAG, a dose that does not produce autophagosomes, resulted in a salient activation of at least seven markers of UPR (FIG. 6). Whereas, the mean $EC_{50}$ of LC3 lipid conjugation (i.e., LC3II induction) was 7 μM, the $EC_{50}$ values for induction of ATF4, IRE1α, GRP78/BiP, and phosphorylation of eIF2α (Ser51), JNK (Thr183/Tyr185), and p38MAPK (Thr180/Tyr182) were 0.5, 0.9, 1.4, 2.3, 1.6, 1.7, and 0.5 μM, respectively. These mean values, generated from two independent determinations indicated that Sigma1 antagonist induction of UPR occurred at 3 to 14 fold lower concentrations than required for autophagosome formation (FIG. 6).

Figure 7:
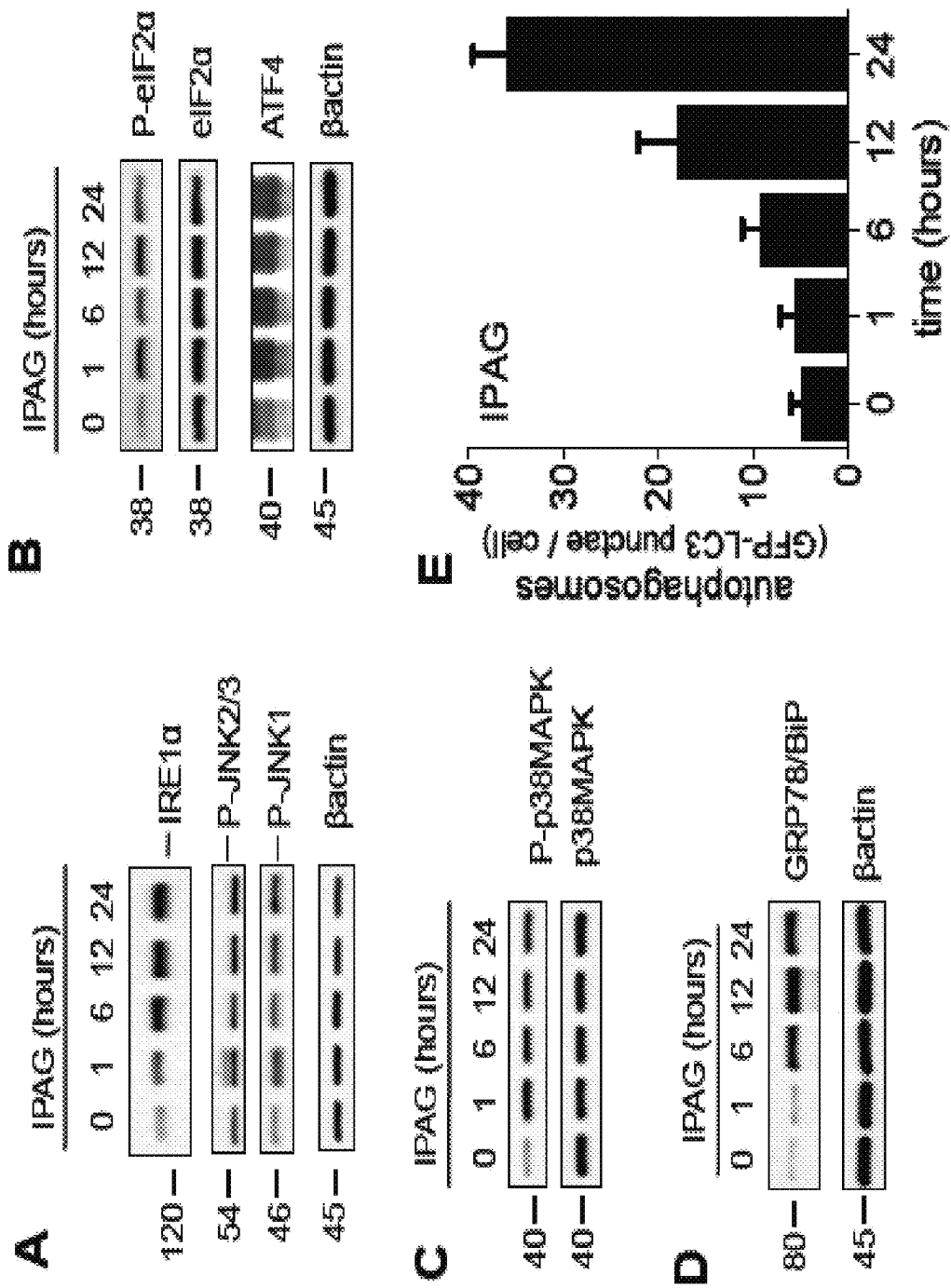
FIG. 7, comprising

Next, whether autophagy occurs prior or subsequent to UPR was examined. Cells were treated with 10 μM IPAG for 1, 6, 12, and 24 hours (FIG. 7). Of the six ER stress and UPR markers evaluated in this experiment, salient induction of 5 was detected by 1 hour of treatment, and one was clearly induced between 1 to 6 hours (FIG. 7A-D). In contrast, significant formation of autophagosomes, measured by GFP-LC3 punctae and LC3II immunoblot, was detected between 6 to 12 hours (FIG. 7E).

Example 4

Inhibition of UPR Prevents Sigma1 Antagonist-Associated Autophagy

Figure 8:
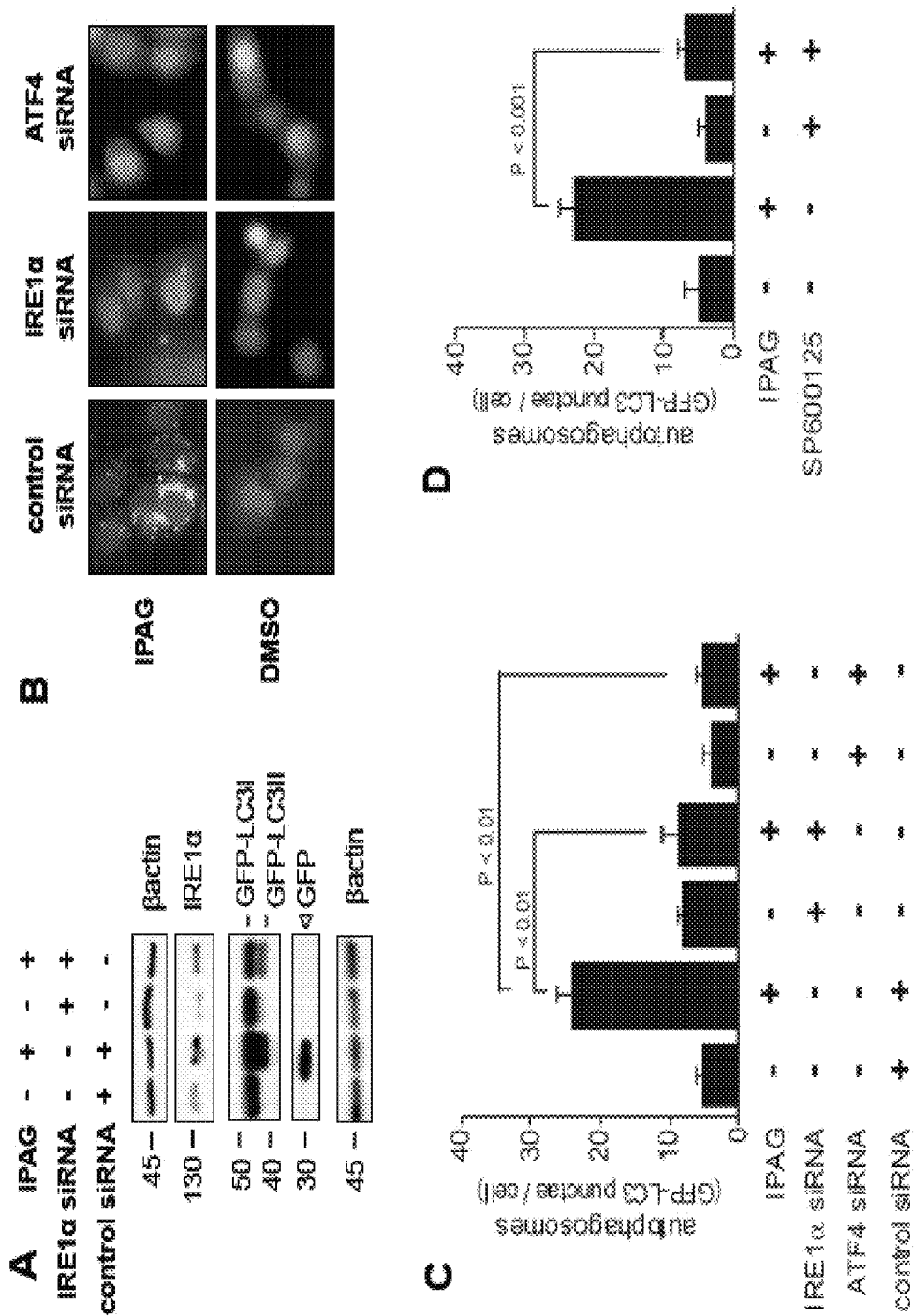
FIG. 8, comprising
Figure 9:
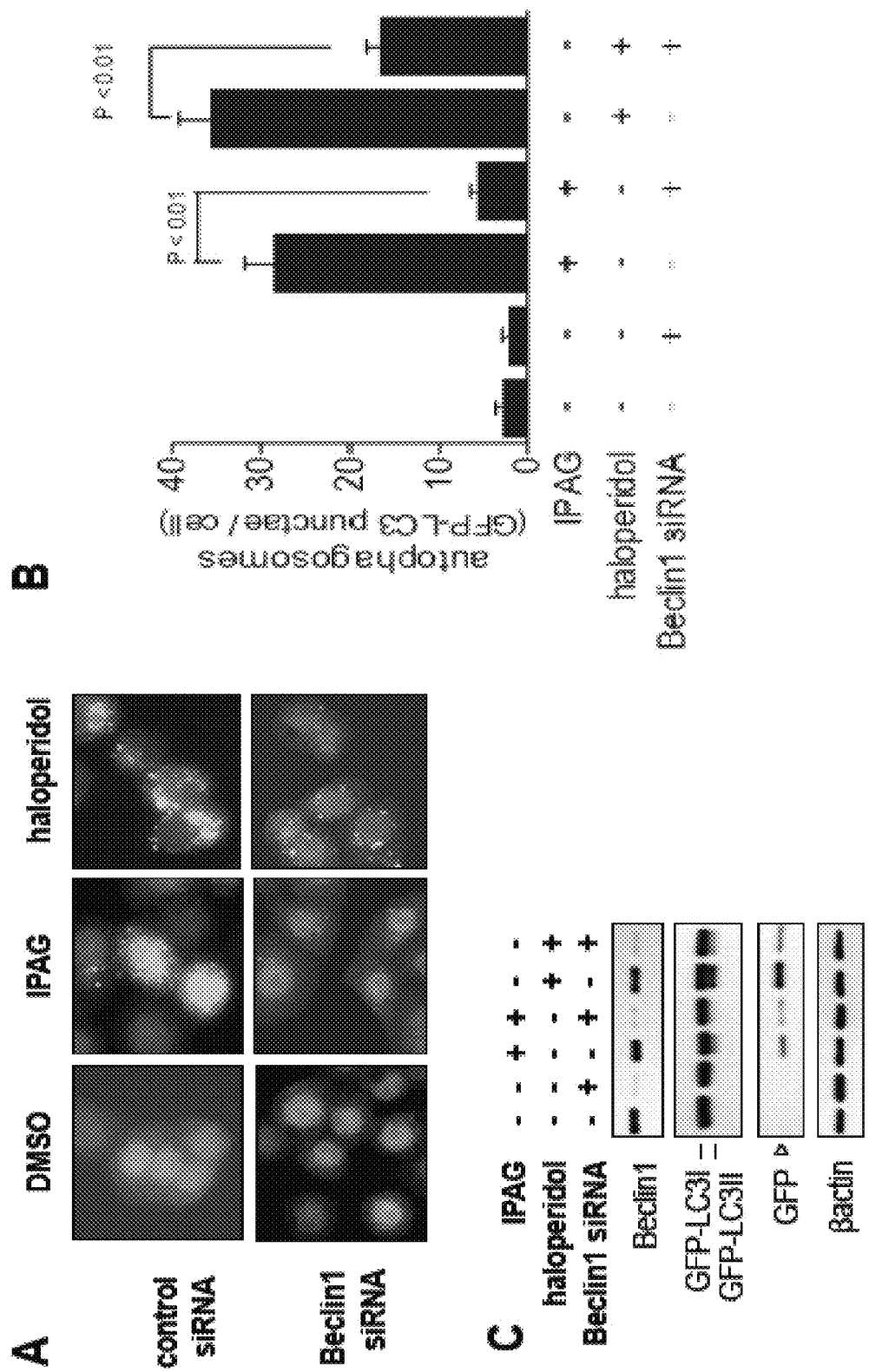
FIG. 9, comprising

The results of the dose response and time-action experiments suggested that ER stress-induced UPR was engaged upstream of autophagy. However, these experiments did not demonstrate that ER stress was required to activate autophagy. To confirm that UPR precedes and is required for Sigma1 antagonist-induced autophagy, UPR was inhibited by siRNA-mediated knockdown of IRE1α or ATF4. In these experiments, 72 hours after transfection of siRNA, MDA-MB-468 cells were treated for 20 hours with 10 μM IPAG (FIG. 8). Knockdown of IRE1α resulted in decreased autophagosome formation and autophagic degradation (FIGS. 8A & 8B). The number of autophagosomes per cell decreased from 24±2 when treated with IPAG to 9±2 when IRE1α was knocked down (FIG. 8C). By knocking down ATF4, IPAG treatment produced 5±1 autophagosomes per cell (FIG. 8C). In addition to knockdown experiments, a chemical inhibitor of c-Jun N-terminal kinase (JNK) signaling, SP600125, was used to inhibit the IRE1α/JNK branch of the UPR. Consistent with IRE1α knockdown, the addition of SP600125 autophagosome formation from 23±2 (IPAG alone) to 7±1 (IPAG and SP600125) in IPAG treated cell cultures (FIG. 8D). Together, these data suggested that Sigma1 antagonist-induced autophagy occurs via UPR activation.

Example 5

Sigma1 Antagonist-Induced Autophagy Required Beclin1

Figure 12:
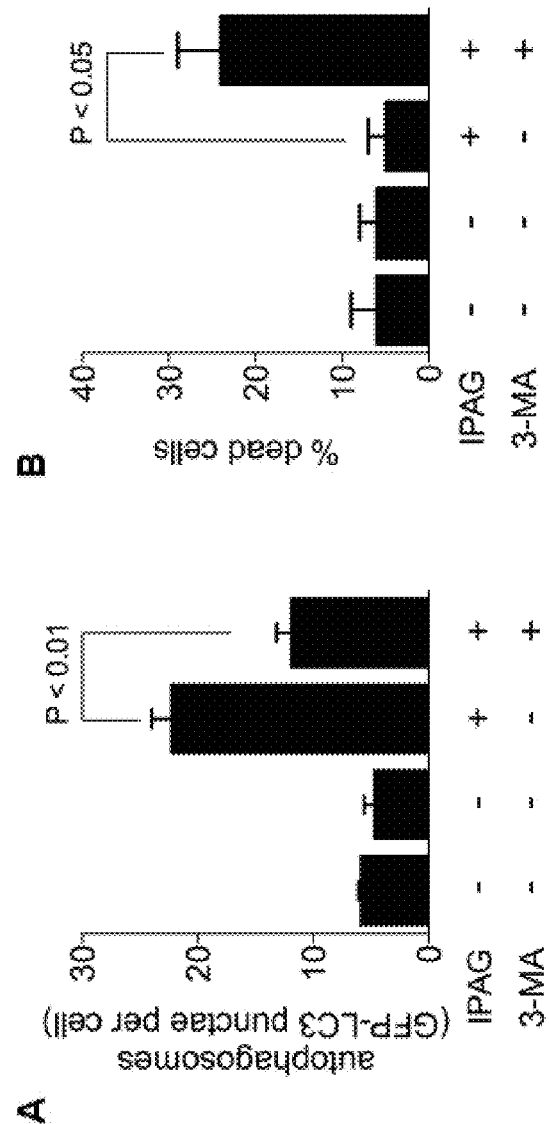
FIG. 12, comprising

To confirm that GFP-positive punctae formation and degradation were indeed products of autophagy, the effects of RNAi mediated knockdown of Beclin1, an essential autophagy protein, were evaluated. Knockdown of Beclin1 significantly inhibited puncta formation, decreasing the mean number of punctae per cell from 28±3 to 6±1 in IPAG treated cells and from 36±4 to 17±1 in haloperidol treated cells (FIG. 8). Sigma1 antagonist induced autophagosome formation was also inhibited by 3-methyladenine (3-MA), a widely used type III phosphatidylinositol 3-kinase inhibitor. Addition of 3-MA (5 mM) decreased the number of IPAG induced punctae per cell from 23±2 to 12±1 (FIG. 12A). Treatment with 5 mM 3-MA alone produced 5±1 punctae per cell, not significantly different than the 4±2 produced in DMSO controls (FIG. 12A).

Example 6

Figures 10A, 10B, 10C, 10D:
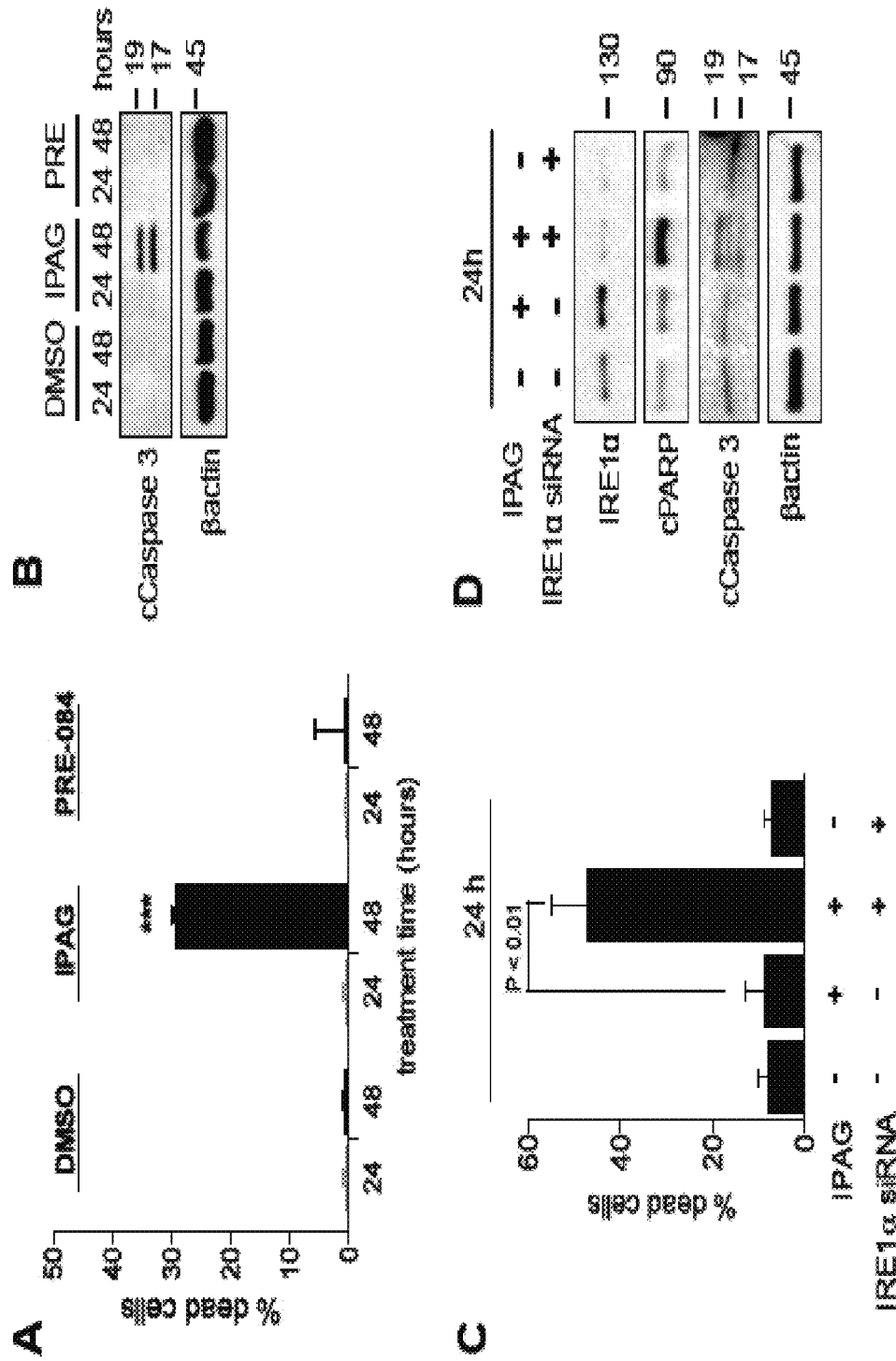
FIGS. 10A-10F, illustrates the finding that inhibition of UPR or autophagy accelerates Sigma antagonist-induced apoptosis.

Inhibition of Sigma1 Antagonist-Induced UPR and Autophagy Accelerated Apoptotic Cell Death The results described above suggested that UPR and autophagy may function as primary and secondary survival responses, respectively, to Sigma1 antagonist-induced ER stress. The proportion of dead MDA-MB-468 cells following 24 hours of treatment with IPAG (10±2%) was not significantly different than DMSO treated (9±1%) control cell cultures (FIG. 10). However, following 48 hours of continuous treatment, 30±2% IPAG treated cells undergo apoptotic cell death (FIG. 10). By 72 hours >75% of IPAG-treated cells died. Consistent with this pattern, whereas control siRNA transfected cells survived 24 hours of IPAG (9±4%), inhibition of UPR by IRE1α knockdown potentiated the cytotoxic effect of IPAG (47±8%) at the 24-hour treatment time-point (FIGS. 10C-10D). Knockdown of ATF4 also potentiated IPAG induced apoptosis, with 30±9% dead cells per well, whereas ATF4 knockdown alone did not significantly alter cell death rates, with 7±2% dead cells per well. Thus, inhibition of UPR by siRNA knockdown of IRE1α or ATF4 abrogated autophagosome formation (FIG. 8) and potentiated Sigma1 antagonist-mediated apoptotic cell death (FIGS. 10C-10D).

Figures 10E, 10F:
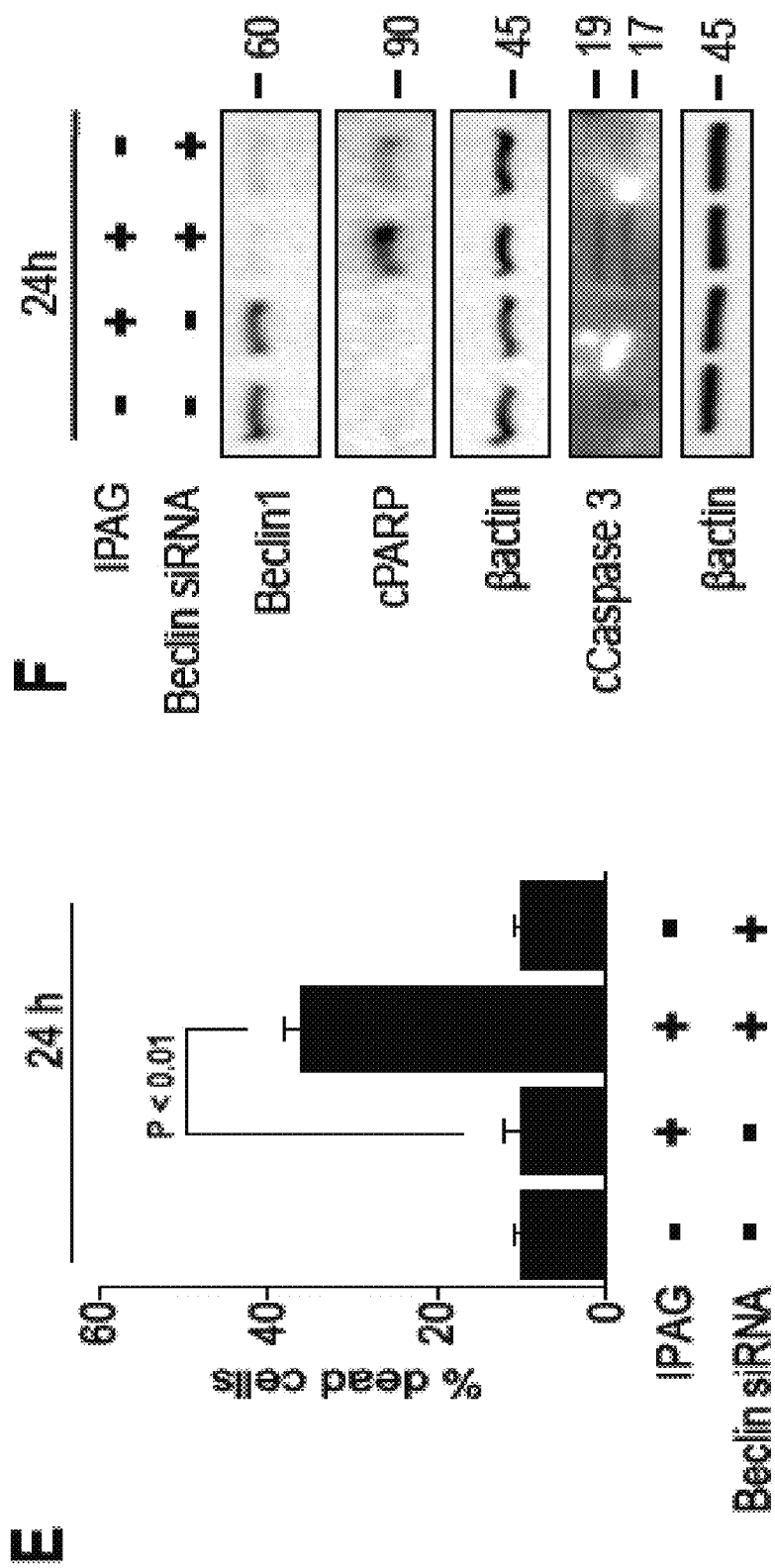

Next, the effects of inhibiting autophagy either by siRNA mediated Beclin1 knockdown or chemical inhibition by 3-methyladenine (3-MA) were evaluated. Whereas treatment with 10 μM IPAG for 24 hours did not induce significant cell death (5±3%) with no evidence of apoptosis, inhibiting autophagosome formation with 3-MA (5 mM) or by siRNA knockdown of Beclin1 resulted in cell death at 24 hours of IPAG treatment, with over 33% dead cells per well (FIGS. 10E-10F). Whereas the percentage of dead cells per well did not significantly differ between 24 hour treatment with IPAG alone (5±2%) or 3-MA alone (6±2%), combined treatment with IPAG and 3-MA potentiated the number of dead cells per well to 24±5% (FIG. 12B).

Example 7

Figure 13:
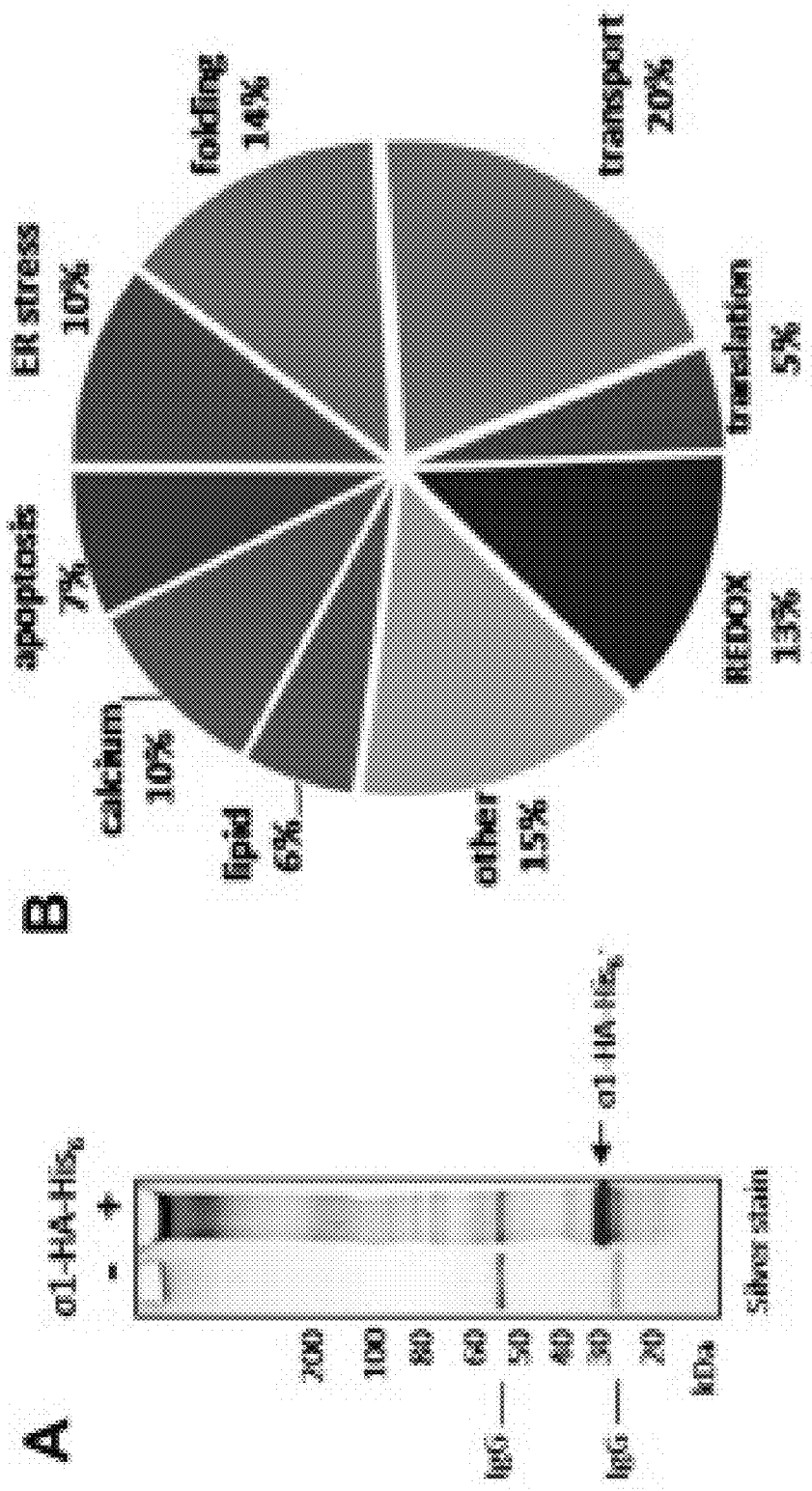
FIG. 13, comprising FIGS. 13A-13B, describes Sigma1 receptor-associated proteins. Experiments involved protein complex purification and identification experiments with dual affinity-tagged Sigma1 with tandem hemagglutin (HA) epitope and six-histidine ($His_6$).

Sigma1 Receptors Associate with Proteins Involved in ER Protein Processing. Cell Growth, and Survival Liquid chromatography-tandem mass spectrometry (LC-MS/MS) techniques and co-immunoprecipitation experiments were performed to identify and confirm Sigma1 associated cellular factors. A plasmid construct containing a dual carboxy-terminal affinity-tagged Sigma1 with tandem hemagglutinin (HA) epitope and six-histidine (His6) tag, Sigma1-HA-His6 was generated. This dual-tagged Sigma1 construct enabled successive highly selective protein purification procedures. Using this approach, a Sigma1-HA-His6 receptor complexes from a range of tumor cell lines, including prostate adenocarcinoma (PC3, DU145), breast adenocarcinoma (MDA-MB-468, MCF-7), neuroblastoma (BE(2)-C) was isolated. Silver staining revealed a number of proteins that co-purified with Sigma1 (FIG. 13). LC-MS/MS analysis of the complex has identified approximately 80 Sigma1-associated proteins. Preliminary data revealed that ~85% of Sigma1-associated proteins are directly associated with ER homeostasis and stress response. Among these associated proteins were GRP78/BiP and GRP94, and at least 12 heat shock family chaperones.

Example 8

Figures 4D, 4E, 4F:
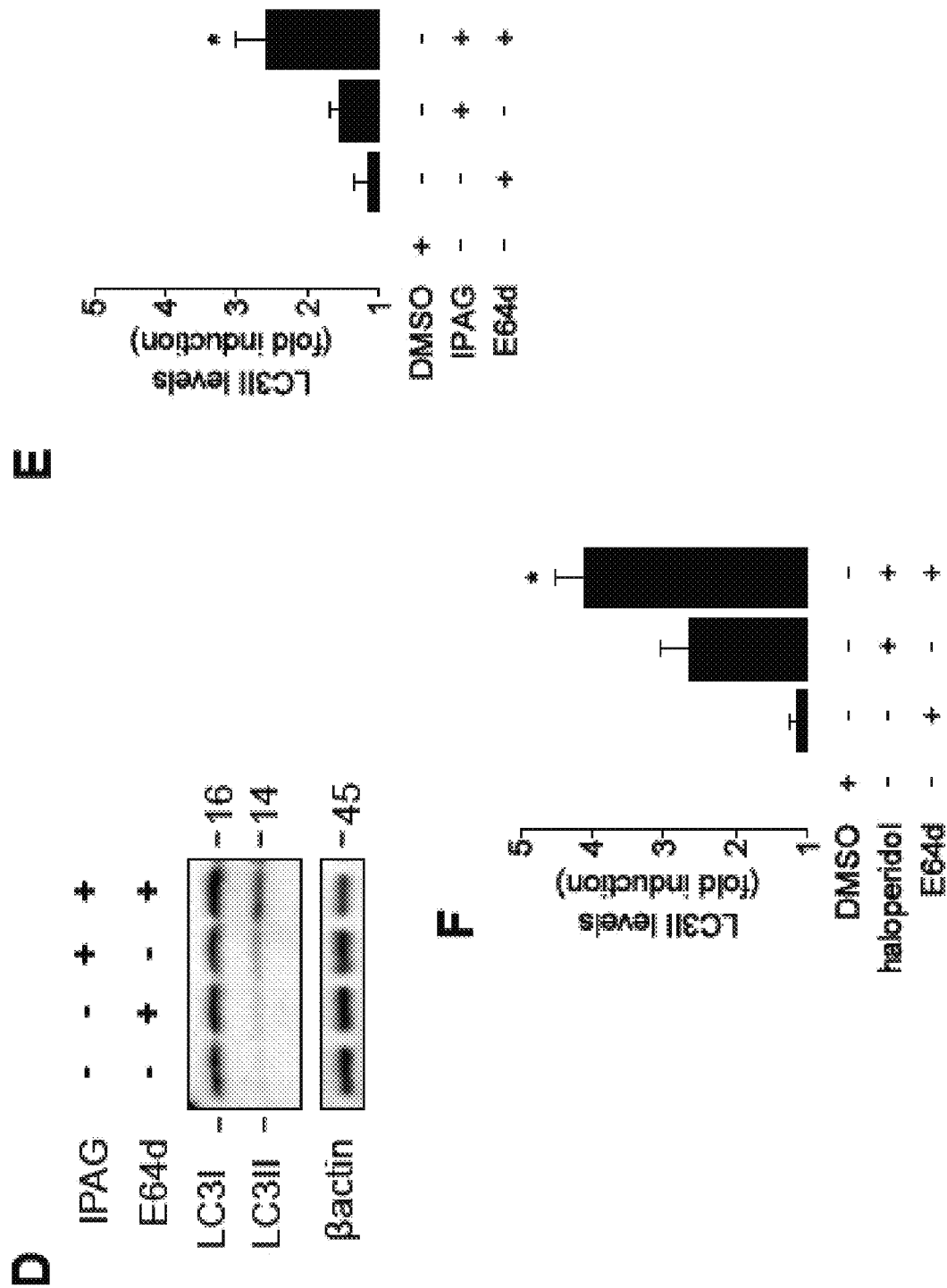
Figure 15:
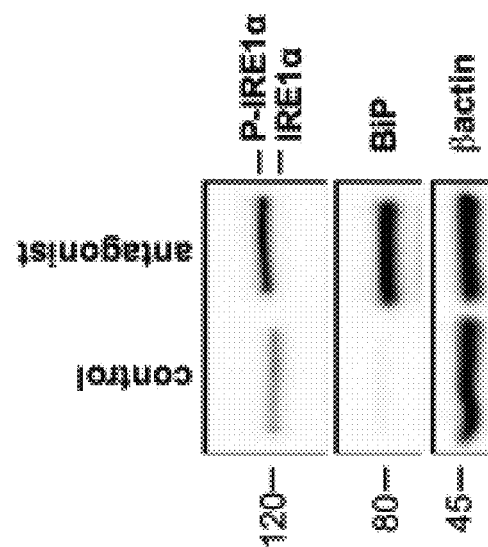
FIG. 15 is an image of an immunoblot illustrating induction of UPR in a prostate cancer cell line. The immunoblot is of cell detergent soluble cell lysate from PC3 prostate adenocarcinoma cells treated for 20 hours with 10 µM haloperidol (antagonist) and compared to DMSO (control) treated cells. P-IRE1α indicates phosphorylated IRE1α. Similar results were obtained with DU145 prostate cancer cells.

Sigma Receptor Antagonist Treatment Induces ER Stress and Activation of the Unfolded Protein Response Consistent with Sigma1 association with ER homeostatic factors, preliminary data with three prostate cancer cell lines (PC3, DU145, LaPC4) revealed an increased level of ubiquitinated proteins with Sigma antagonist treatment, reminiscent of ERAD mediated increase in ubiquitylation (data for haloperidol treatment of PC3 shown in FIG. 4). This might be due to an accumulation of ubiquitylated proteins or due to an increase in ubiquitin ligase activity. Progression of the ER stress response could be monitored by a set of markers, many of which have been directly linked to the UPR. The most extensively investigated sensors that initiate the UPR are IRE1α, PERK, and ATF6, which transduce signals to a cascade of effectors. Many of these UPR 4 effectors function as transcription factors that induce the synthesis of ER chaperones, such as GRP78/BiP and GRP94, involved in maintaining protein homeostasis. Preliminary experiments have found that treatment of PC3 and DU145 PCa cells with Sigma1 antagonists, IPAG and haloperidol, resulted in salient induction of IRE1α and BiP levels (data shown for haloperidol in FIG. 15).

Example 9

Autophagosome Formation and Autophagic Degradation

Figure 16:
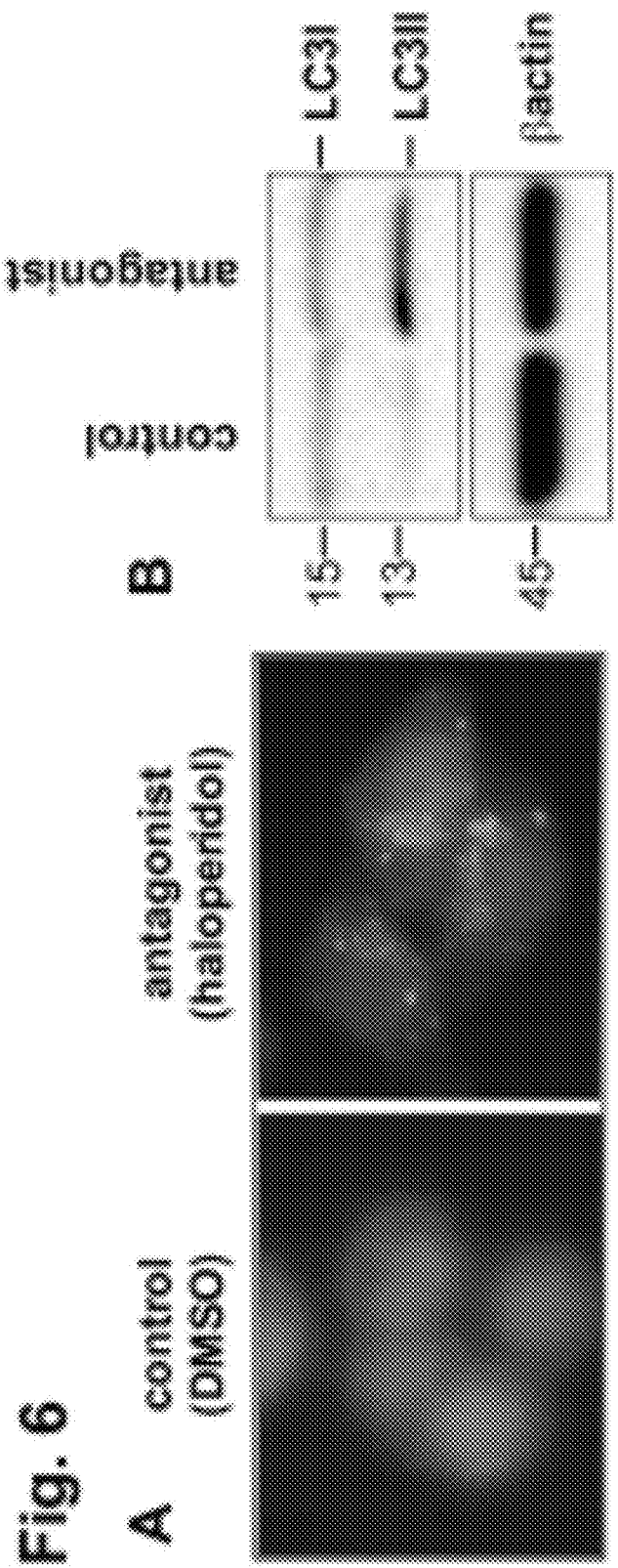
FIG. 16, comprising

Sigma antagonist-induced ER stress led to the activation of autophagy in several tumor cell lines, including PC3 prostate cancer cells (FIG. 16). In preliminary experiments, an immunoblot assay was performed to detect the formation of the lipid-conjugated form of microtubule associated protein light chain 3 (LC3II), a widely used marker of autophagosome formation (FIG. 16). In addition, a well-established and widely used microscopy-based assay was performed which detects the translocation of an amino-terminal green fluorescent protein tagged LC3 (GFP-LC3) into vesicular structures which appear as GFP concentrated punctae characteristic of autophagosome formation, as shown with haloperidol in FIG. 6.

Figure 27:
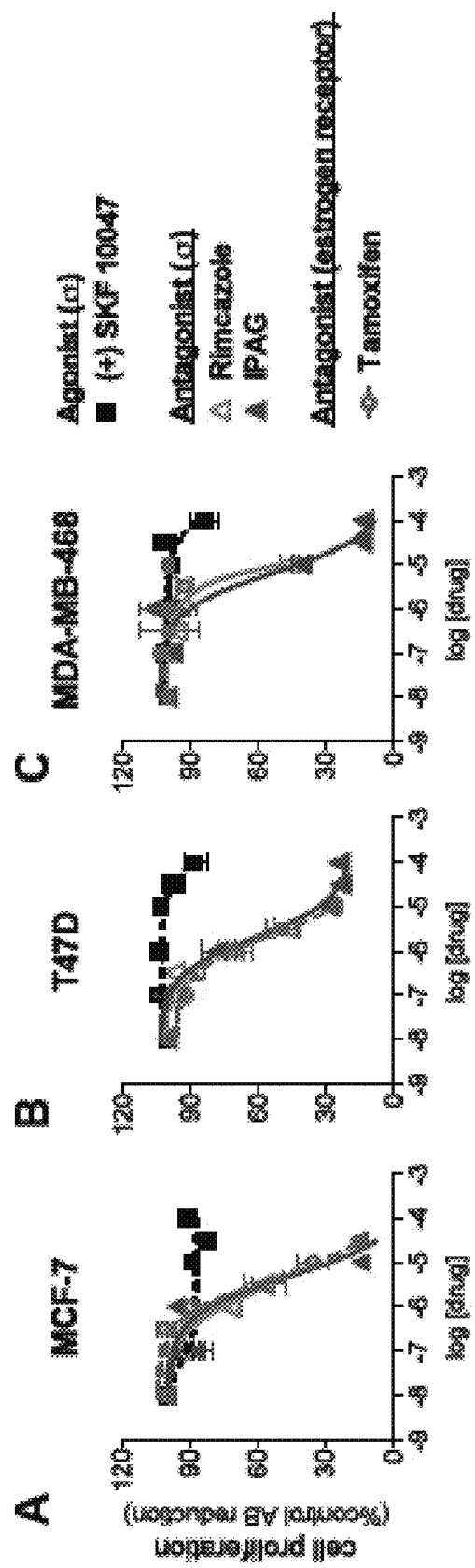
FIG. 27, comprising
Figure 28:
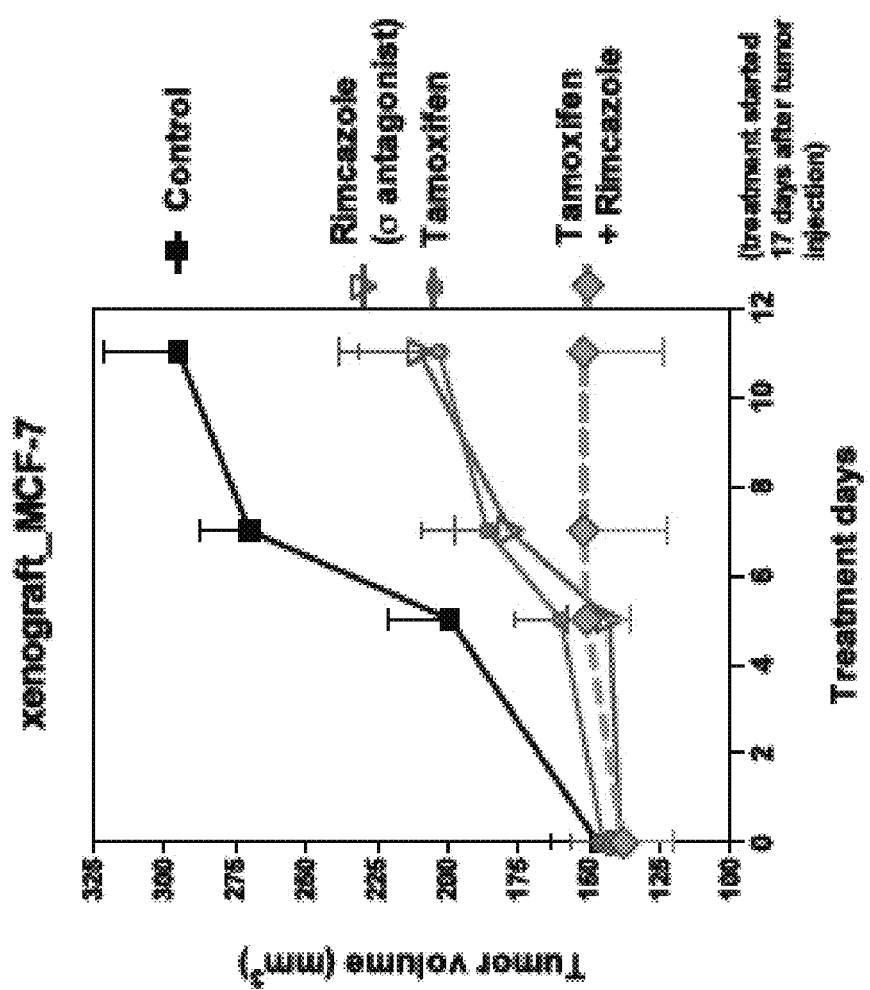
FIG. 28 is a graph illustrating the finding that a Sigma receptor antagonist potentiates tumor growth inhibition by anti-estrogen therapy. Tamoxifen potentiation by rimcazole was evaluated in vivo. Preliminary tumor xenograft experiments were performed according to MSKCC Tumor Assessment Core facility protocol. Briefly, β-estradiol treated athymic mice were injected with MCF7 cells, and drug treatment was initiated when mean tumor volume reached approximately 140 mm$^3$, which occurred 17 days following MCF-7 injection. Daily i.p. drug injections were performed for up to 11 days, and tumor volume was quantified by the formula: tumor volume=L×W$^2$×π/6. In this pilot experiment, 3-5 mice were tested per group. After 11 days of drug treatment, tamoxifen (1 mg/kg) and Rimcazole (10 mg/kg) had each inhibited tumor growth by approximately 50%. During the 11 day time course, tumor growth was completely inhibited when tamoxifen (1 mg/kg) and Rimcazole (10 mg/kg) were combined. An extended time course, with more mice per group and multiple drug doses, may be performed to determine whether the tumor growth inhibitory effect of combined drug treatment is additive or synergistic.
Figure 29:
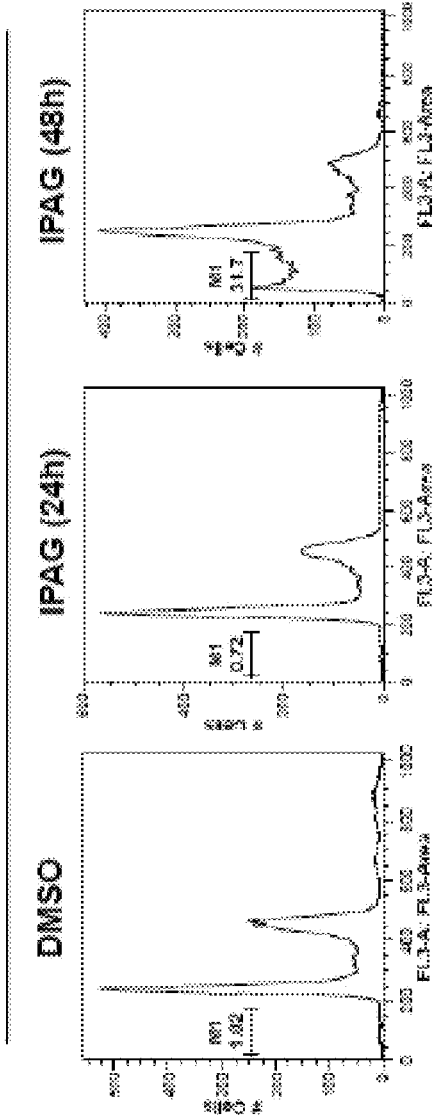
FIG. 29 illustrates the time-course of a Sigma1 antagonist inducing apoptotic cell death of breast adenocarcinoma cells. Treatment with Sigma1 antagonist, IPAG, induces apoptotic cell death of MDA-MB-468 cells, as indicated by the percentage of subG1 phase cells. MDA-MB-468 cell treated for 24 and 48 hours with 10 μM IPAG (Sigma1 ligand, putative antagonist) showed a significant increase in the number of subG1 (dead, apoptotic) cells after 48 h of treatment, 31.7% (indicated by M1 cell population). The far left panel represents cells treated or 24 hours with DMSO (vehicle control).
Figure 30:
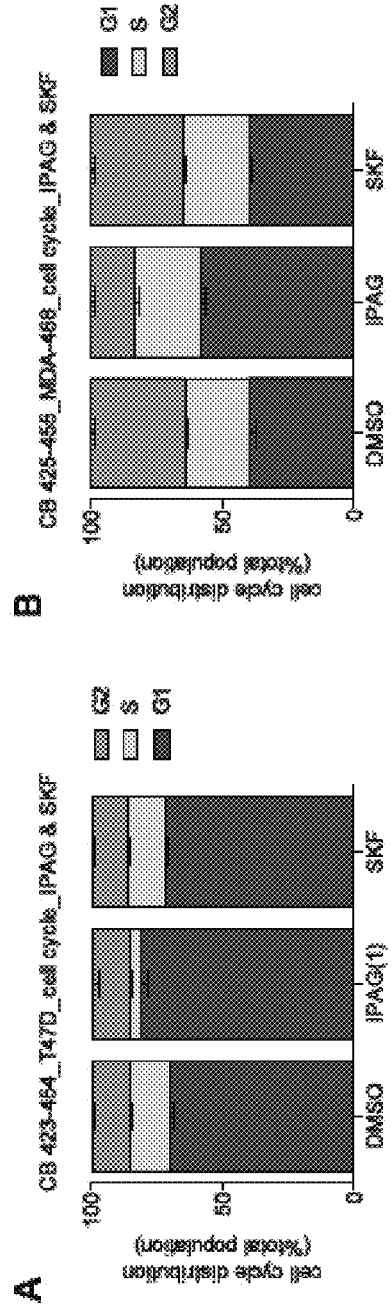
FIG. 30, comprising
Figure 31:
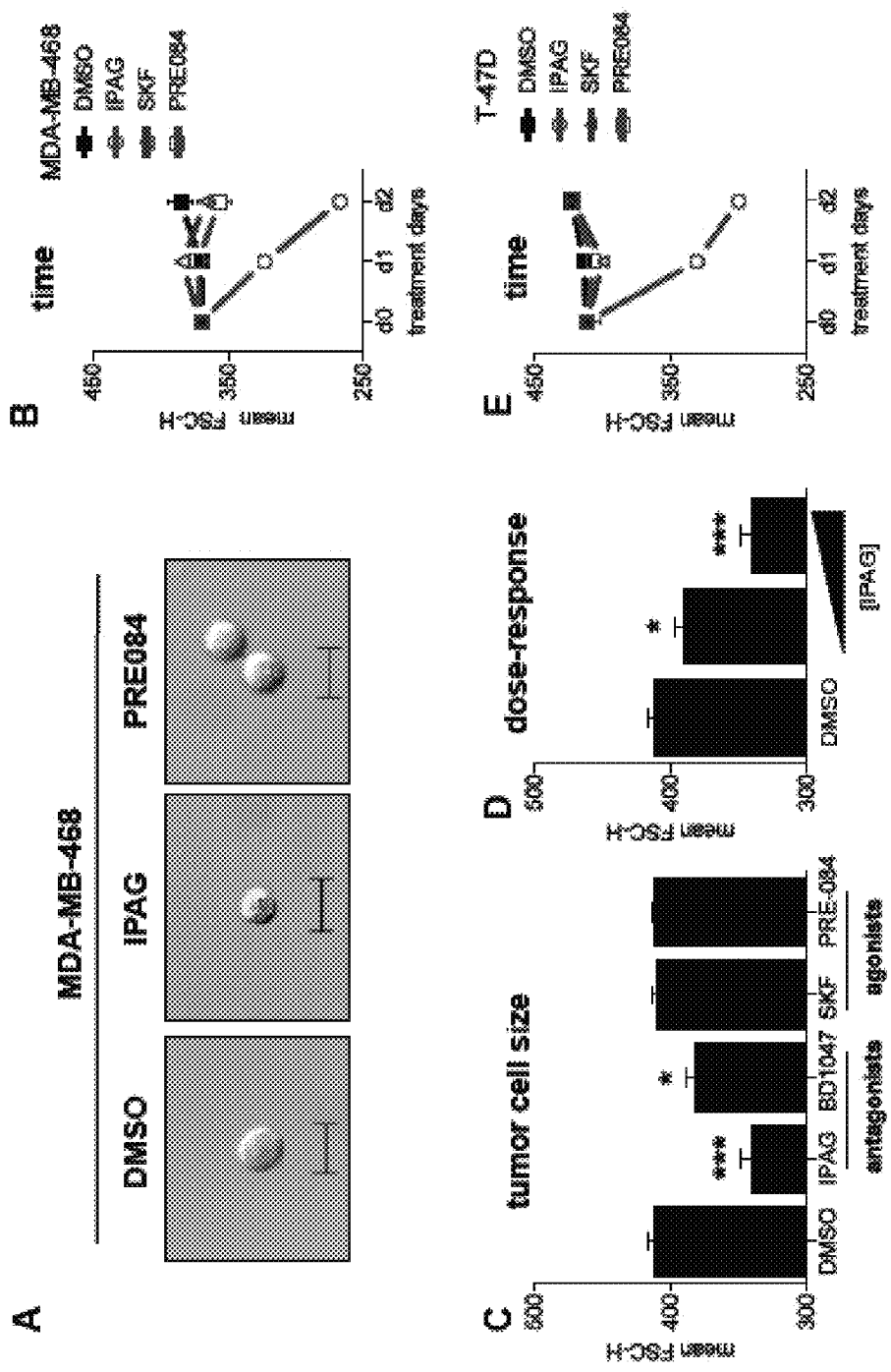
FIG. 31, comprising
Figure 32:
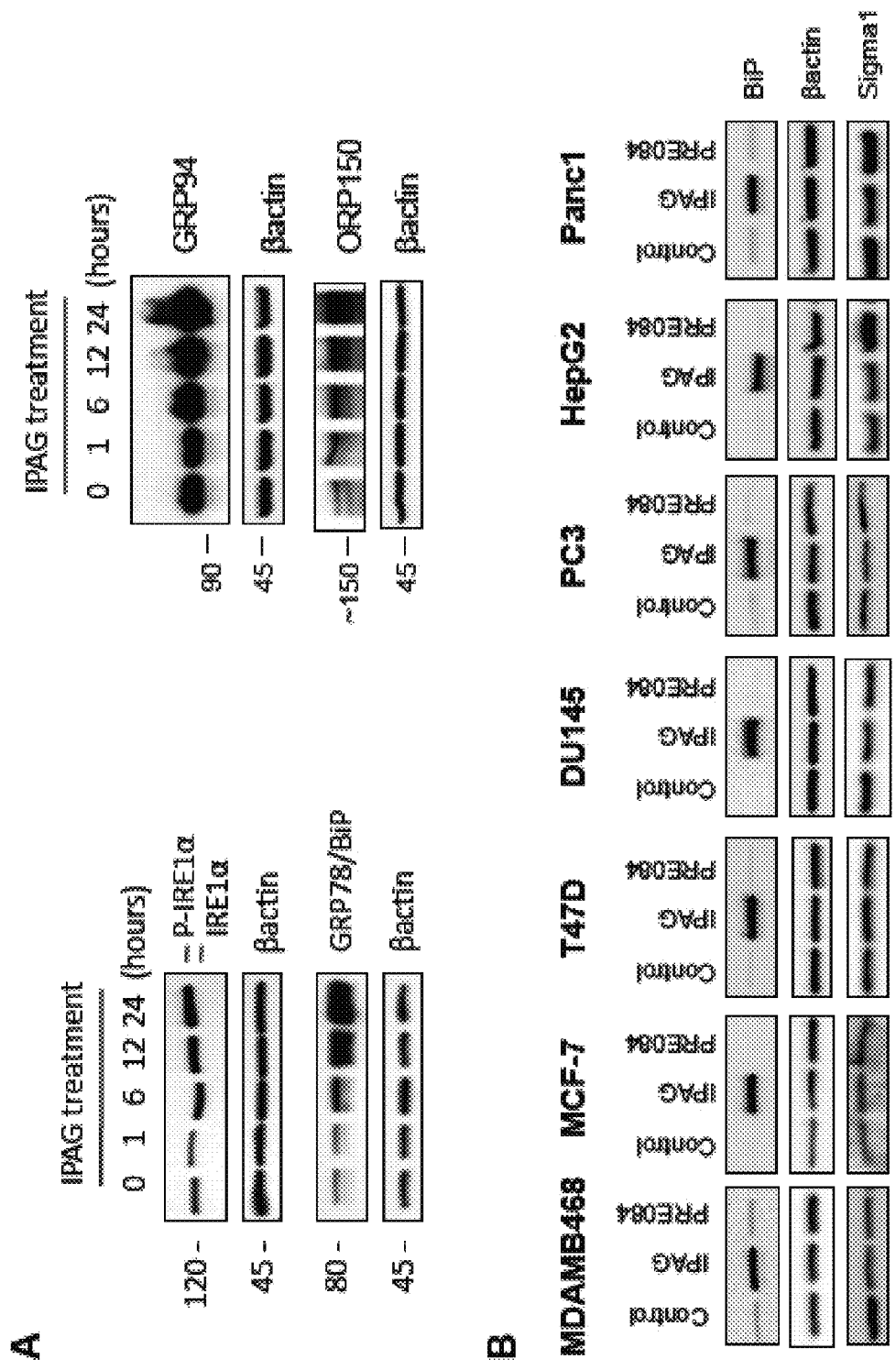
FIG. 32, comprising
Figure 33:
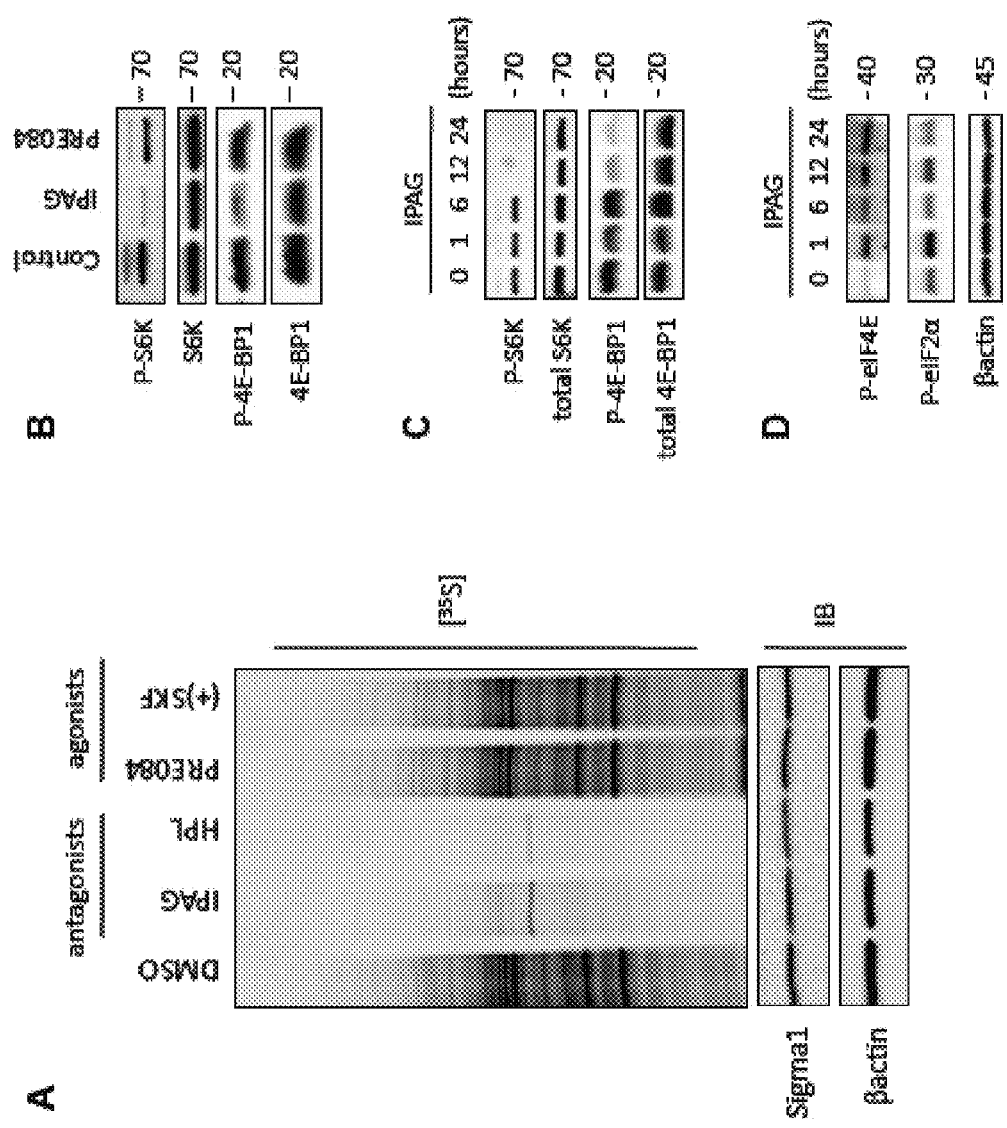
FIG. 33, comprising
Figure 34:
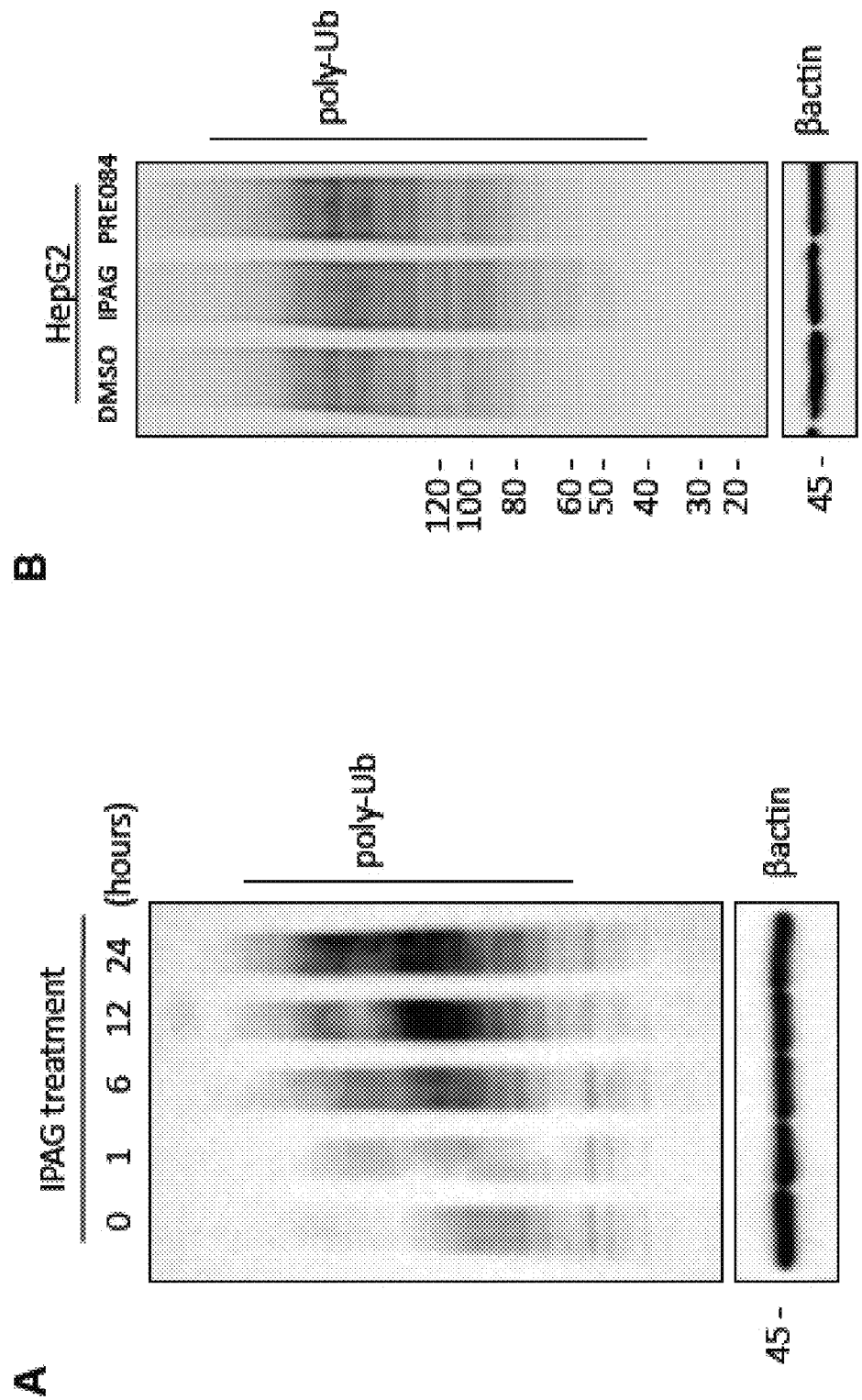
FIG. 34, comprising
Figures 35A, 35B, 35C:
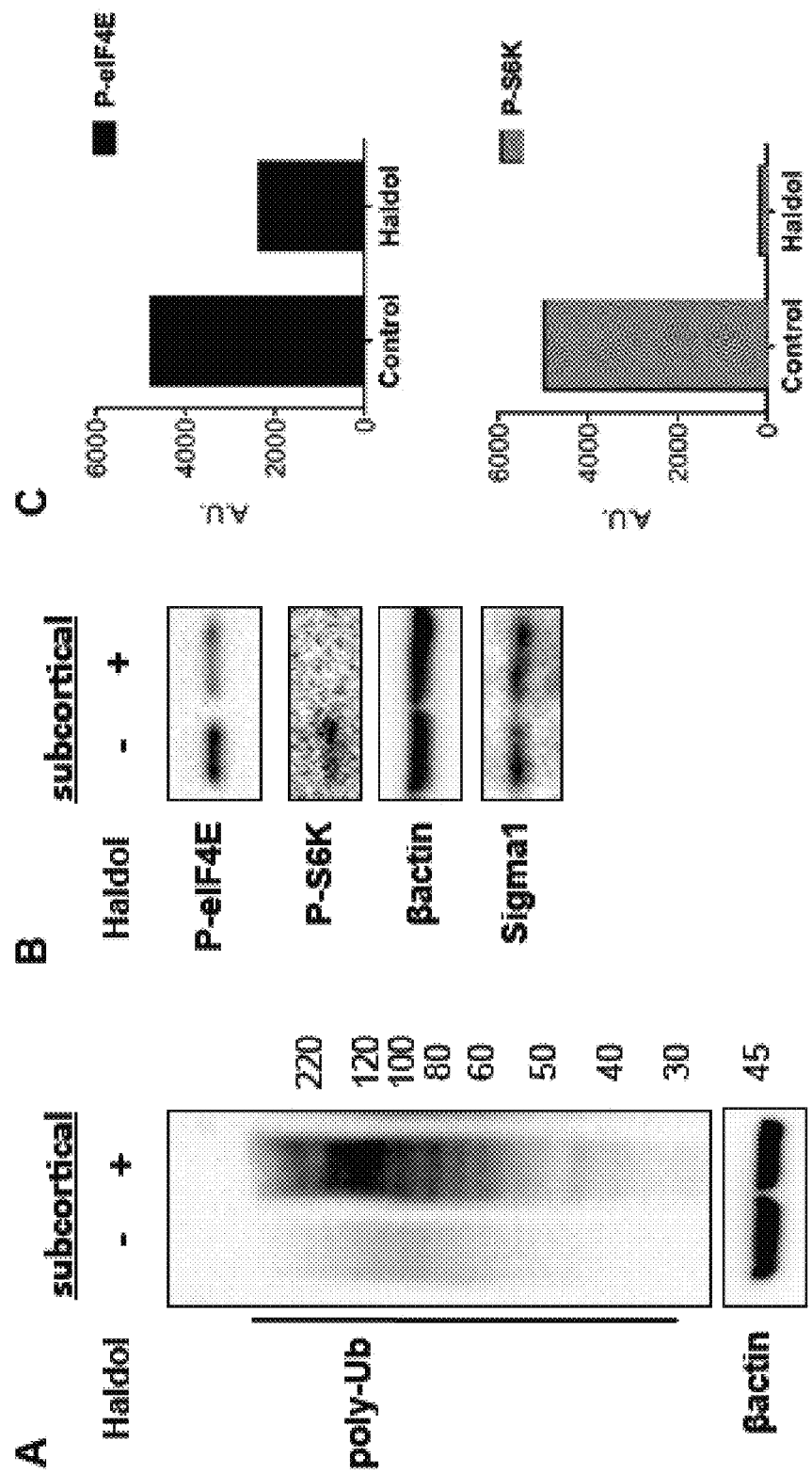
FIGS. 35A-35C, illustrates the finding that treatment with haloperidol resulted in elevated levels of poly-ubiquitylated proteins and translation arrest in subcortical structures. Subcortical region (subcortical) of Balb-c mouse brain dissected following 24 hour treatment with 10 mg/kg haloperidol (Haldol), injected intraperitoneally.
Figure 36:
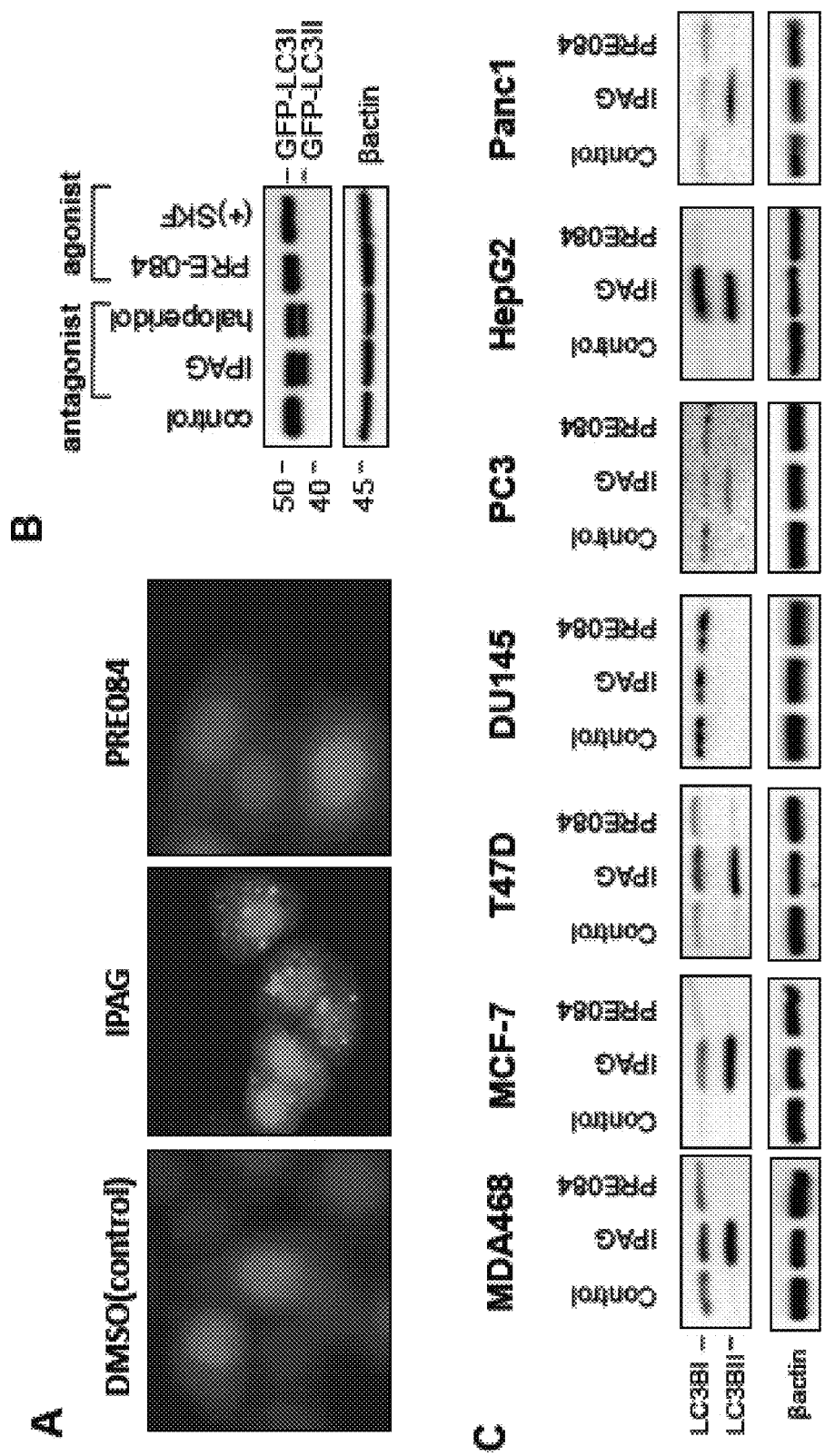
FIG. 36, comprising

Sigma antagonists may induce ER stress, which in turn, leads to autophagy through a series of steps comprising the progressive stages of UPR. The apoptosis observed with Sigma antagonist treatment is likely due to ER stress. It is believed that autophagy functions to restore the stressed cell to homeostasis by degrading toxic proteins and damaged organelles. However, as the cytoprotective capacity of autophagy is exceeded, the Sigma antagonist treated cell may proceed to apoptosis. However, recent work with breast adenocarcinoma supports the hypothesis that autophagy functions as a survival response, as blockade of autophagy markedly increases Sigma antagonist-induced apoptotic death. This multi-tiered survival response might be best described by the schematic in FIG. 27. This may apply to prostate cancer cell lines as well; preliminary data suggest that at least some prostate cancer cells may respond in a similar manner to Sigma antagonist treatment.

Example 10

Sigma1 Receptors Associate with Proteins Involved in ER Protein Processing, Cell Growth, and Survival Little is known regarding the cellular role of Sigma1, its relevance to ER function and thus induction of ER stress response by Sigma antagonists. A better understanding of its mechanisms may be achieved by identifying the proteins with which it associates. To address this question, liquid chromatography-tandem mass spectrometry (LC-MS/MS) techniques and co-immunoprecipitation experiments are performed to identify and confirm Sigma1 associated cellular factors. A plasmid construct is generated containing a dual carboxy-terminal affinity-tagged Sigma1 with tandem hemagglutinin (HA) epitope and six-histidine (His6) tag, Sigma1-HA-His6. This dual-tagged Sigma1 construct permits successive highly selective protein purification procedures.

Using this approach, a Sigma1-HA-His6 receptor complexes is isolated from a range of tumor cell lines, including prostate adenocarcinoma (PC3, DU145), breast adenocarcinoma (MDA-MB-468, MCF-7), neuroblastoma (BE(2)-C). Silver staining reveals a number of proteins that co-purified with Sigma1 (FIG. 13). LC-MS/MS analysis of the complex identifies approximately 80 Sigma1-associated proteins. Preliminary data reveal that ~85% of Sigma1-associated proteins are directly associated with ER homeostasis and stress response. Among these associated proteins are GRP78/BiP and GRP94, and at least 12 heat shock family chaperones.

Example 11

Sigma Receptor Antagonist Treatment Induces ER Stress and Activation of the Unfolded Protein Response As Sigma1 is highly enriched in the endoplasmic reticulum, and in light of LC-MS/MS results, whether Sigma antagonist treatment could induce ER stress response is examined. Consistent with Sigma1 association with ER homeostatic factors, preliminary data with three prostate cancer cell lines (PC3, DU145, LaPC4) reveals an increased level of ubiquitinated proteins with Sigma antagonist treatment, reminiscent of ERAD mediated increase in ubiquitylation (data for haloperidol treatment of PC3 shown in FIG. 14). Whether this is due to an accumulation of ubiquitylated proteins or due to an increase in ubiquitin ligase activity can be determined.

Progression of the ER stress response can be monitored by a set of markers, many of which have been directly linked to the UPR. The UPR comprises several signaling pathways that increase the protein folding and processing capacity of the ER in response to ER stress. The most extensively investigated sensors that initiate the UPR, IRE1α, PERK, and ATF6 transduce signals to a cascade of effectors (Marciniak et al. 2006, Cell 134:769-781; Ron et al. 2007, Nat. Rev. Mol. Cell Biol. 8:519-529; Xu et al., 2005, J. Clin. Invest 115:2656-2664; Schroder et al., 2005, Annu. Rev. Biochem. 74:739-789). Many of these UPR effectors function as transcription factors that induce the synthesis of ER chaperones, such as GRP78/BiP and GRP94, involved in maintaining protein homeostasis (Marciniak et al. 2006, Cell 134:769-781; Ron et al. 2007, Nat. Rev. Mol. Cell Biol. 8:519-529; Xu et al., 2005, J. Clin. Invest 115:2656-2664; Schroder et al., 2005, Annu. Rev. Biochem. 74:739-789). Preliminary experiments found that treatment of PC3 and DU145 PCa cells with Sigma1 antagonists, IPAG and haloperidol, resulted in salient induction of IRE1α and BiP levels (data shown for haloperidol in FIG. 15).

Example 12

Prostate Cancer Cell Lines

Figure 1:
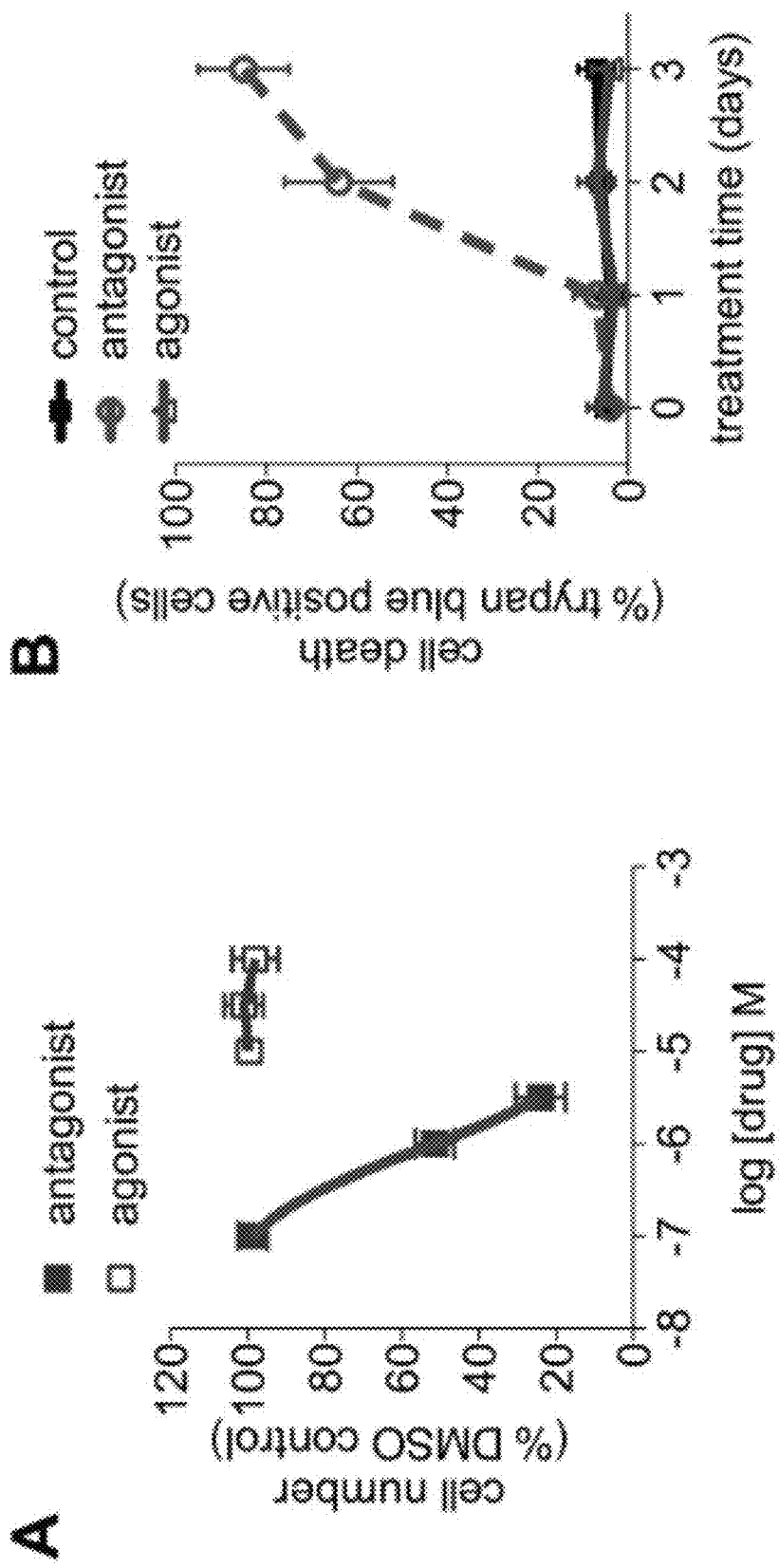
FIG. 1, comprising
Figure 2:
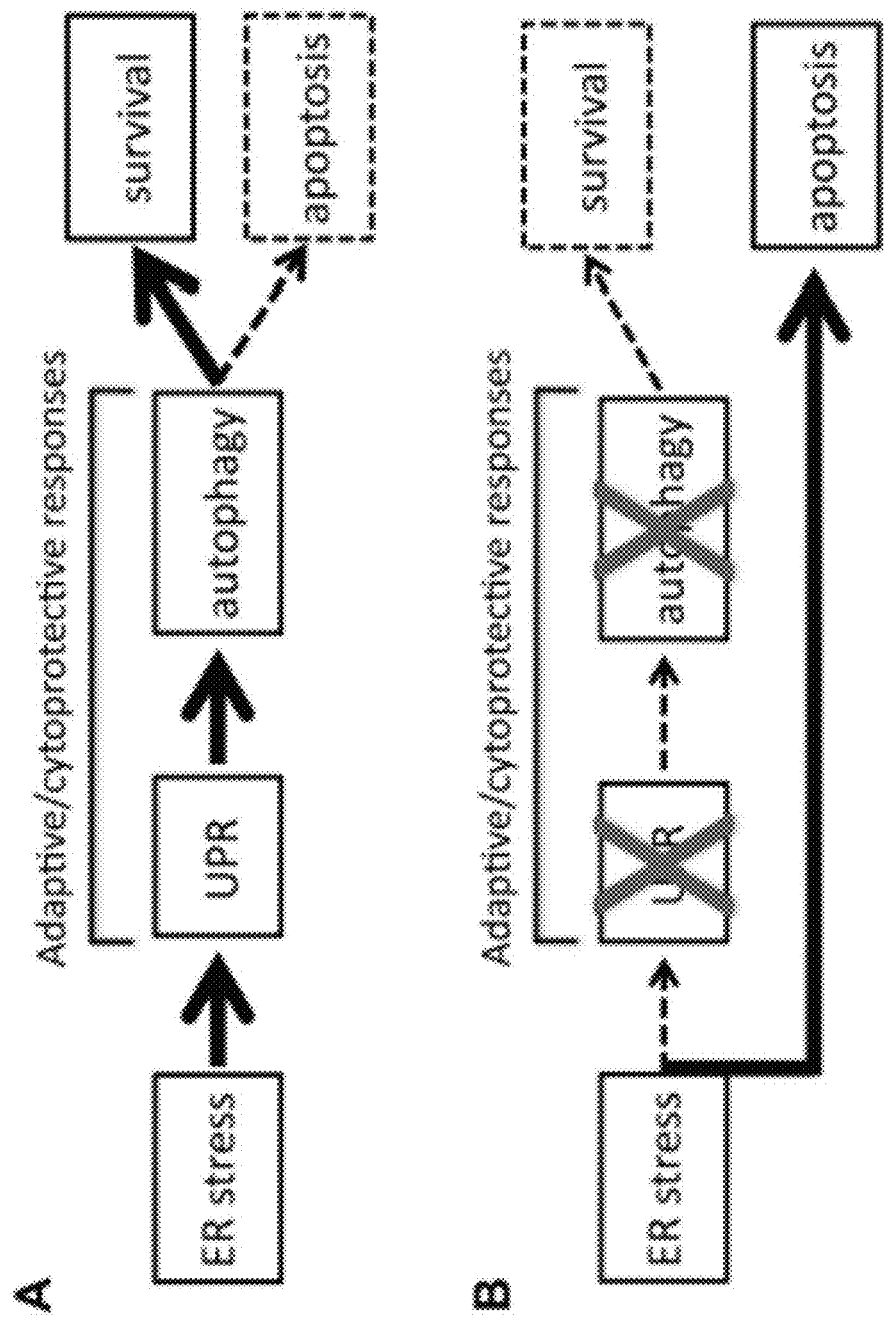
FIG. 2, comprising
Figure 3:
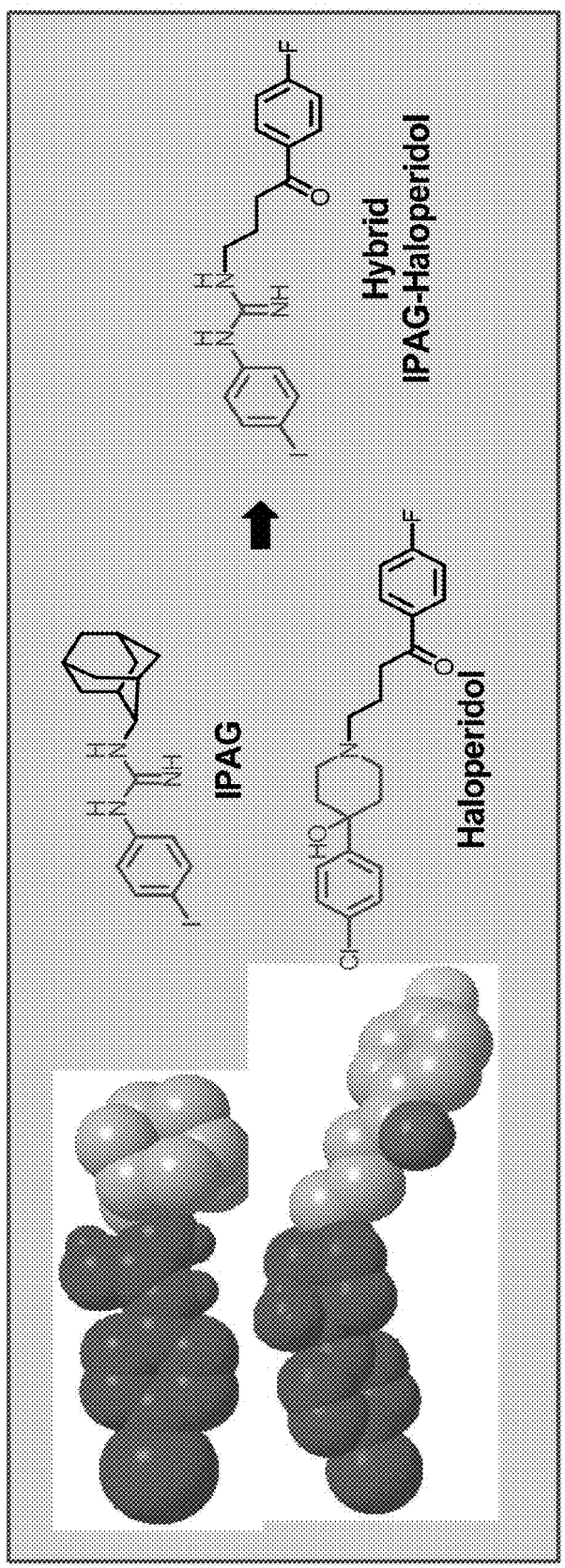
FIG. 3 is a scheme illustrating a size and volume comparison of the aryl guanidine of IPAG to the 4-phenylpiperidine moiety of haloperidol.

By identifying the cytoprotective signaling pathways mounted in response to Sigma antagonist treatment, more effective Sigma antagonist based combinations that induce ER stress and selectively block the survival response are designed (FIG. 2). This hypothesis is tested using a mixed set of widely studied androgensensitive and -insensitive prostate cancer cell lines, including DU145, PC3, LaPC4, LNCaP, MDA-PCa-2a and -2b, and cell lines from the CWR22 series. Preliminary results with DU145 and PC3 in addition to published results with other Sigma receptor ligand treatment of LNCaP cell lines are sensitive to Sigma antagonist-mediated proliferation arrest and cell death (Berthois, et al., 2003, Br. J. Cancer 88:438-446; Spruce et al., 2004, Cancer Res. 64:4875-4886, FIG. 1). MDA-PCa-2a and -2b, and selected CWR22 lines are tested; these cell lines can express readily detectable levels of prostate specific antigen and may be particularly useful in evaluating androgen-sensitive tumor growth and Sigma ligand response in xenograft experiments. This mixed set of cell lines provides clues to whether androgen-sensitive and -insensitive prostate cancer lines respond similarly to Sigma antagonist-treatment.

DU145, PC3, and LNCaP cell lines have been described to express the Sigma1 (Berthois, et al., 2003, Br. J. Cancer 88:438-446; Spruce et al., 2004, Cancer Res. 64:4875-4886). Sigma1 expression in MDA-PCa-2a, -2b, and CWR22 cell lines is unknown. However, Sigma1 has been detected in a broad range of tumor cell lines. In most of these lines, the number of Sigma1 binding sites has not been quantitated. Furthermore, the correlation between levels of Sigma1 binding sites and sensitivity to and kinetics of Sigma antagonist induced prostate cancer cell death is unclear. Therefore, Sigma1 binding sites in prostate cancer cells is first quantitated by radio-ligand binding assay using [$^3$H]-(+)-pentazocine and [$^3$H]-haloperidol. These are reference ligands for pharmacological characterization of Sigma binding sites, and they are commercially available. The binding affinity ($K_d$) and the number of binding sites per milligram of prostate cancer cell membrane ($B_{max}$) are determined using a standard Sigma1 binding assay protocol described elsewhere (Ryan-Moro et al., 1996, Neurochem. Res. 21:1309-1314).

Example 13

Sigma Receptor Ligands

Initially, the cell stress inducing properties of prototypic Sigma ligands that have been confirmed to inhibit proliferation and induce cell death of breast adenocarcinoma, neuroblastoma, leukemia, and three of the prostate cancer cell lines described above are characterized. This set of ligands includes: haloperidol, IPAG, rimcazole, and PB28 (Spruce et al., 2004, Cancer Res. 64:4875-4886; Hayashi et al., 2008, Expert Opin. Ther. Targets 12:45-58). These compounds are found to elicit ER stress response and autophagy in breast adenocarcinoma cell lines. These four Sigma receptor antagonists elicit autophagy at different rates and with different potencies. They also have different selectivity for Sigma1 versus Sigma2 subtypes (Hayashi et al., 2008, Expert Opin. Ther. Targets 12:45-58; Berardi et al., 1996, J. Med. Chem. 39:4255-4260; Ferris et al., 1986, Life Sci. 38:2329-2337). Interestingly, the Sigma1 selective compounds (haloperidol and IPAG) are more potent inducers of ER stress response and autophagy than the Sigma2 selective compounds (rimcazole and PB28). This is consistent with a recent report describing the potency of novel highly Sigma1 selective ligands derived from spipethiane, supports Sigma1 selectivity of anti-tumor Sigma ligands (Piergentili et al., J. Med. Chem. 53:1261-1269). Subsequently, a broader panel of commercially available prototypic Sigma receptor antagonists and agonists are evaluated.

Preliminary experiments with DU-145 and PC3 cells reveal activation of UPR and autophagy following a single time-point, 24 hour treatment, with a single dose of one Sigma ligand, 10 µM haloperidol (antagonist). Therefore, the dose-responsive induction of ER stress response (including ubiquitylation, UPR, and autophagy) and cell death is evaluated. Sigma ligand potency ($EC_{50}$) and efficacy, in terms of the maximal induction ($E_{max}$) of ER stress response and cell death, is established. Subsequently, the time-action of $EC_{20}$, $EC_{50}$, and $EC_{80}$ doses of a selected set of effective Sigma ligands is evaluated. Time-action experiments help to determine if treated cells can respond to and adapt to Sigma drug induced stress at low doses. $EC_{50}$ and $E_{max}$ values established here are used in experiments to evaluate drug combination synergy.

Example 14

Sigma Receptor Antagonist Treatment-Associated Increase in Ubiquitinated Protein Levels Immunoblot assays are performed to evaluate the time and dose-responsive increase of ubiquitinated protein levels in the absence and presence of the small synthetic peptide proteasome inhibitor MG-132 as described elsewhere (Korolchuk et al., 2009, Mol. Cell 33:517-527). Initial immunoblot experiments are performed with a widely used, commercially available anti-ubiquitin antibody (clone P4D1). Further experiments are performed to compare the rate of ubiquitylation versus UPS mediated degradation using a green fluorescent protein-tagged ubiquitin, Ub-GFP, and comparing it to a degradation resistant mutant ubiquitin, UbG76V-GFP, using an established [$^{35}$S]-label pulse-chase experimental procedure described elsewhere (Korolchuk et al., 2009, Mol. Cell 33:517-527).

These experiments clarify the dose-response and kinetics of UPS induction as well as clarify whether Sigma antagonist treatment increases ubiquitylation or inhibits degradation of ubiquitylated proteins. For the goals of this proposal, these assays are used to evaluate changes in UPS mediated degradation in response to Sigma antagonist treatment and to gauge and control for the activity of proteasome inhibitors when used in combination with Sigma antagonists. Established ubiquitin ligase assay protocols are used in the context of ER stress and autophagy (Korolchuk et al., 2009, Mol. Cell 33:517-527; Korolchuk et al., FEBS Lett. 584:1393-1398; Gao et al., Autophagy 6:126-137).

Example 15

Sigma Receptor Antagonist Treatment Associated ER Stress and Activation of the Unfolded Protein Response Induction of these stress response markers is evaluated by immunoblot. Commercial antibodies are available for most of them. Components of the IRE1α-JNK1/2 and eIF2α-ATF4 branches of the UPR, as well as the UPR-associated ER chaperones, GRP78/BiP (FIG. 15), GRP94, and ORP150 are assayed for as indicators of activated UPR (Marciniak et al., 2006, Physiol. Rev. 86:1133-1149; Ron et al., 2007, Nat. Rev. Mol. Cell. Biol. 8:519-529; Ni et al., 2007, FEBS Lett. 581: 3641-3651).

Translational arrest is another indicator of stress response to unfolded protein accumulation in the ER. To evaluate this response immunoblot assays are performed. Phosphorylation of 4E-BP1 and eIF4E reflect translational arrest. The utility is confirmed in breast adenocarcinoma, wherein a time-dependent induction of markers for ER stress, IRE1α and GRP78/BiP, is observed during treatment with the Sigma antagonist IPAG 35. This is accompanied by a progressive suppression of translation. Protein translational arrest is also evaluated by [$^{35}$S]-protein label pulse-chase experiments. This approach quantifies protein degradation as well as quantify translation arrest in response to Sigma drug treatment.

In one embodiment, not all cell lines express detectable levels of all UPR and stress markers (as has been experienced with breast cancer cell lines). For example, PERK phosphorylation, a hallmark of UPR induction, is undetectable in many cell lines in which several other UPR markers are clearly present by other markers. Various Sigma ligands may elicit UPR by distinct mechanisms. Furthermore, different cell lines may respond by activating distinct branches of the UPR or distinct stress response pathways. Therefore, a broad panel of markers are assessed and cell lines are used in which multiple markers of UPR induction are detectable. siRNA studies are performed to validate and confirm Sigma1-mediated activities.

Example 16

Autophagosome Formation and Autophagic Degradation Associated with Sigma Antagonist Treatment Sigma antagonist-induced ER stress leads to the activation of autophagy in several tumor cell lines, including PC3 and DU145 prostate cancer cells (FIG. 16). The established and widely used immunoblot and microscopy based assays described elsewhere herein are performed to characterize and quantify prostate cancer cell autophagic response to Sigma antagonist treatment (Klionsky et al., 2008, Autophagy 4:151-175). Differences in Sigma antagonist-induced autophagosome formation are analyzed qualitatively and quantitatively. Stable GFP-LC3 transfectants from the prostate cell lines described above are generated, as described previously. To confirm that Sigma antagonist-induced punctae are indeed autophagosomes, and not spurious aggregates or vesicles, control experiments with siRNA mediated knockdown of essential autophagy proteins such as ATG5 and Beclin1 are performed (Klionsky et al., 2008, Autophagy 4:151-175; Kuma et al., 2007, Autophagy 3:323-328). Whether Sigma antagonists induce autolysosomal degradation of cargo proteins is determined by using two immunoblot-based assays to detect and quantify LC3 degradation, as described herein and in the literature (Ron et al., 2007, Nat. Rev. Mol. Cell. Biol. 8:519-529).

Example 17

Autophagy Inhibitors and Sigma Receptor Antagonists

Sigma antagonists activate autophagy in PC3 and DU145 prostate cancer cells (shown for PC3 in FIG. 16). Inhibition of autophagosome formation or autophagic degradation by RNAi mediated knockdown of essential autophagy components or small molecule inhibition of autophagy using 3-methyladenine results in a salient acceleration and potentiation of Sigma antagonist-mediated apoptosis. Although useful as an experimental tool, the clinical utility of 3-methyladenine is questionable as it does not have good drug-like properties (Huyer et al., 2004, J. Biol. Chem. 279:38369-38378).

In addition to established autophagy inhibitors such as HCQ, combinations of Sigma antagonists with paclitaxel and vincristine, two widely used chemotherapeutics that have been recently shown to inhibit autophagy (Groth-Pedersen et al., 2007, Cancer Res. 67:2217-2225), are examined. Docetaxel/Sigma antagonist combinations are also examined. In vitro assays are performed including these autophagy inhibitors with the set of prostate tumor cell lines described above. Cell proliferation and death are evaluated as described below. In vivo, tumor xenograft experiments are performed according to the protocol described below, with docetaxel, paclitaxel and vincristine and hydroxychloroquine doses described elsewhere (Amaravadi et al., 2007, J. Clin. Invest. 117:326-336; Amaravadi et al., 2007, Clin. Cancer Res. 13:7271-7279; Groth-Pedersen et al., 2007, Cancer Res. 67:2217-2225; Canfield et al., 2006, Mol. Cancer Ther. 5:2043-2050; Kim et al., 2009, Autophagy 5:567-568).

Example 18

Proteasome Inhibitors and Sigma Receptor Antagonists

Figure 14:
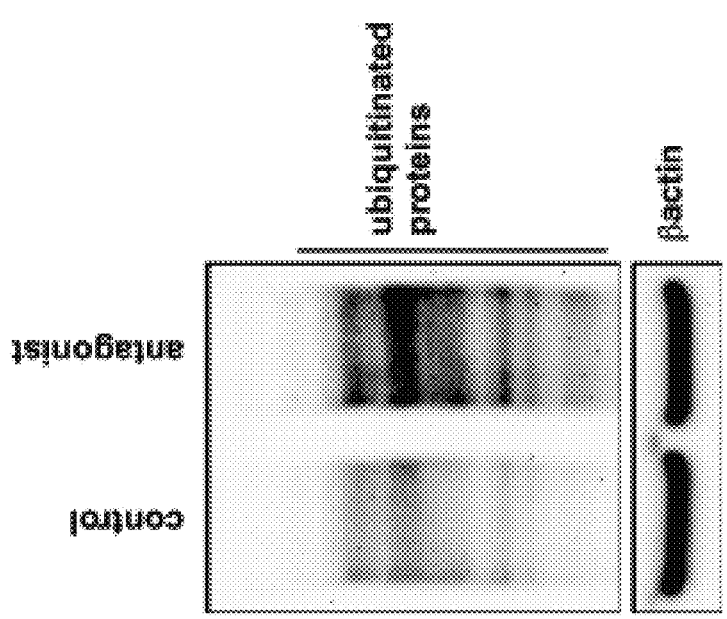
FIG. 14 is an image of an immunoblot illustrating the increased level of ubiquinated proteins associated with Sigma antagonist treatment. PC3 prostate adenocarcinoma cells treated with 10 µM haloperidol (antagonist) or DMSO (control). Total cell lysates were resolved by SDS-PAGE and immunoblotted with ubiquitin antibody (P4D1). Similar results were obtained with DU145 prostate cancer cells.

Sigma antagonist-treated cells present increased levels of ubiquitinated proteins (FIG. 14). This effect is likely due to either an increase in ubiquitin ligase activity or to inhibition of proteasomal degradation (see above). Studies demonstrating the efficacy of ER stress inducing agents combined with proteasome inhibitors such as bortezomib suggest potential for Sigma antagonist drug combinations. Sigma receptor antagonists are evaluated in combination with bortezomib and MG-132 (26S proteasome inhibitor and calpain inhibitor) in vitro. This is extended to prostate tumor xenograft experiments (described below).

Example 19

Molecular Chaperone Inhibitors and Sigma Receptor Antagonists

Preliminary data reveal that Sigma1 receptors bind to other molecular chaperones (FIG. 13). If Sigma1 functions in a molecular chaperone capacity, it is likely that Sigma1 antagonists induce ER stress by altering its physical association with partner proteins.

Antagonist-induced stress activates protein degradation pathways in prostate adenocarcinoma cell lines (FIG. 14). Furthermore, preliminary results reveal a direct physical association between Sigma1 and HSP90 family proteins, including GRP94. There is no reported evidence of Sigma ligand interaction with androgen receptor (AR) or AR associated signaling pathways. In light of preliminary data revealing Sigma1 binding to HSP family chaperones and other AR associated proteins, whether Sigma antagonists can modulate AR signaling by modulating AR protein levels, possibly by altering AR association with its cognate molecular chaperones, is also evaluated.

Example 20

Cell Death Assays

Several monolayer culture cell death assays are performed according to the availability of resources and need for experimental precision regarding type and magnitude of cell death. Colorimetric Alamar Blue or MTT (yellow tetrazolium salt) assays in a 96-well format are used for initial screens of drug combinations for their ability to decrease cell numbers. These assays are widely used, commercially available kits. However, these assays do not directly address whether decreased cell numbers are due to cell death or proliferation arrest or a combination of both. Therefore, selected drug treatments are followed up with trypan blue exclusion assays to confirm that decreased cell numbers in the Alamar Blue or MTT assay are indeed due to cell death. When quantitation of both cell cycle arrest and cell death is required, flow-cytometry-based propidium iodide staining assays are performed. Whether cell death is apoptotic is determined by evaluating Caspase 3 (Asp175) and PARP (Asp 214) cleavage by immunoblot, flow cytometry, or microscopy. These are also widely used assays to determine and quantify apoptosis.

Whenever possible, in parallel to these cell death assays, ER stress response and autophagy markers are evaluated. A portion of cells for trypan blue exclusion or propidium iodide staining assays and a portion for protein extraction for further biochemical analysis are used. Cell death, ER stress, and autophagy from the same treatment sample are directly compared.

Prior to prostate cancer cell inoculation into mice, soft agar tumor growth assays are performed. This is an important transitional experiment, as anchorage-independent, three-dimensional growth of aggregated prostate cancer cells growing in soft agar may react differently to ER stress inducing agents than in attached monolayer cell culture. The most promising drug combinations assays are evaluated in subsequent prostate tumor xenografts. In all of these in vitro assays, drug synergy is confirmed by isobolographic analyses (Zhao et al., 2004, Clin. Cancer Res. 10:7994-8004) (described elsewhere under *Statistical analysis of drug interactions*).

Example 21

Mouse Tumor Xenograft Models

The in vivo component comprises two major experimental groups: In Group 1 pharmacological characterization of Sigma ligands as single agent chemotherapeutics is performed; Group 2 evaluates the anti-tumor efficacy of Sigma ligands in combination with ubiquitin proteasome and autophagy inhibiting agents.

Both normal and castrated male mice are used to compare androgen sensitive versus insensitive growth of the androgen dependent and independent prostate cell lines described above. In initial experiments, subcutaneous injection of prostate tumors are performed as described (Spruce et al., 2004, Cancer Res. 64:4875-4886; Sirotnak et al., 2002, Clin. Cancer Res. 8:3870-3876). However, as subcutaneous inoculations would not evaluate the influence of the prostate tumor microenvironment, intraprostatic injection of prostate cancer cells is also performed (Spruce et al., 2004, Cancer Res. 64:4875-4886; Sato et al., 1997, Cancer Res. 57:1584-1589; Moussavi et al., Cancer Res. 70:1367-1376). In these experiments, tumor growth is tracked by measuring prostate specific antigen levels, in the case of MDAPCa-2a, -2b, LNCaP, and selected CWR22 cell lines (Navone, et al. 2000, Clin. Cancer Res. 6:1190-1197; Navone, et al. 1997, Clin. Cancer Res. 3:2493-2500; Fox et al., 2002, Clin. Cancer Res. 8:3226-3231; Agus et al., 1999, Cancer Res. 59:4761-4764; Denmeade et al., 2003, Prostate 54:249-257).

Group 1:

The pharmacological characterization of Sigma antagonists as single agent anti-tumor chemotherapeutics require a number of standardized approaches, described below. The studies primarily evaluate tumor regression or inhibition of growth in response to treatment with Sigma receptor drugs. The drugs are administered via intraperitoneal or intravenous injection.

Drug Potency and Efficacy

Potency is defined by the dose needed to produce half the maximal response ($ED_{50}$) while efficacy is defined functionally within an assay as the maximal effect ($E_{max}$) achieved. These are determined by examining increasing doses of drug and measuring dose-dependent tumor regression or inhibition of tumor growth as the experimental end-points. Groups of 3-5 mice and traditional dose-responses to determine the $ED_{50}$ and $E_{max}$ are used. Due to the variability associated with the inoculation of cancer cells and subsequent treatment, it is essential to have sufficient numbers of animals per set for proper statistical evaluation. Furthermore, dose-response curves require sufficient numbers of animals per drug concentration for the assessment of the response as well as adequate numbers of drug concentrations to define the curves and generate accurate $ED_{50}$ values and confidence limits. A typical experiment contains 4 drug concentrations and based upon prior utilization at least 3 experiments are anticipated to ensure reproducibility and to achieve statistically significant $ED_{50}$ values with narrow confidence limits. At least 4 of the Sigma antagonists to be evaluated are confirmed to be effective inhibitors of tumor growth in xenograft models.

Statistical Analysis of Single Agent Treatment

The statistical analyses used depend upon the type of measurement being made. Single comparisons are performed using either Student's t-Test, the Fisher Exact Test, or the Mann-Whitney U Test, depending on the data. Multiple comparisons require analysis of variance (ANOVA), followed by the appropriate post-hoc analysis.

Drug Reversibility

In order to ultimately design and develop a clinical treatment protocol, it is important to determine whether the pharmacological effects of Sigma antagonists are reversible or irreversible. The reversibility of potential side-effects is a particularly important consideration. Therefore, a set of experiments are also performed in which drug treatment is ceased when tumor growth is stabilized, and tumor growth in these mice is evaluated in the same manner as in mice undergoing continuous drug treatment.

Group 2:

In this group Sigma antagonists in combination with ubiquitin proteasome and autophagy inhibiting small molecule compounds are evaluated.

Selection of Drug Combinations for Prostate Tumor Xenograft Experiments

In vitro results guide the selection of drug combinations to be tested in vivo. In initial experiments, combinations that include Sigma antagonists with HCQ (autophagy inhibitor) or bortezomib (proteasome inhibitor) are used. Bortezomib and HCQ doses and treatment intervals are guided by published protocols (Williams et al., 2003, Mol. Cancer. Ther. 2:835-843: Williams et al., 2003, Cancer Res. 63:7338-7344; Amaravadi et al., 2007, J. Clin. Invest. 117:326-336; Amaravadi et al., 2011, Clin. Cancer Res. 17:654-666). Sigma antagonist doses are based on the dose-response studies performed above. Interactions among drugs and targets within tumors offer opportunities to optimize efficacy without increasing side-effects. Thus, although efficacy in tumor growth inhibition or regression is the primary read-out, potential side-effects of Sigma antagonists alone and in drug combinations are monitored.

Statistical Analysis of Drug Interactions

Drug interactions are evaluated using isobolographic analysis. The primary goal in these types of studies is to determine whether or not the drug interactions/combinations demonstrate synergy or simple additive effects. In this approach, the $ED_{50}$ for each drug or each site is determined and their ratio established. Dose-response curves for the interactions using this ratio are performed and the $ED_{50}$ for the combination is determined. The results are then plotted. The $ED_{50}$ value for each individual drug is plotted on either the X- or Y-axis. The $ED_{50}$ for the combination is added to the plot. If it lies on a line connecting the two individual determinations, the result is additive. If it falls below the line, the interactions are synergistic. If it falls above the line, they are antagonistic. The dose-response curves are performed as described above.

Biochemical Analysis of Xenografted Prostate Tumors

At the end of each treatment course, tumors and organs are resected, including liver and whole brain, postmortem. Tumors are analyzed for evidence of UPR, ER stress response, ubiquitylation, cell proliferation, autophagy, and apoptosis. Organs are obtained for biochemical studies in order to evaluate the effects of Sigma antagonist and drug combination treatment on other tissues, in order to help predict side-effects such as hepatotoxicity and potential neurotoxicity. The harvested prostate tumor is divided into three fragments for: (1) protein extraction and biochemical analysis (e.g., immunoblots to evaluate the markers and proteins described above); (2) mRNA extraction for RT-PCR experiments (e.g., when using XBP-1 splicing as a marker for UPR or when changes in transcription or mRNA stability or turnover of selected are suspected); (3) formalin fixed for immunohistochemistry (IHC) experiments. IHC procedures are used to evaluate Sigma1 (rabbit polyclonal and monoclonal Abs, mouse and hamster monoclonals generated in our lab), UPR markers (GRP78/BiP), autophagy (LC3II), apoptosis (cleaved Caspase 3), As demonstrated herein, Sigma1 antagonists, but not agonists, induced endoplasmic reticulum (ER) stress and subsequent unfolded protein response (UPR) (FIG. 4-8). Severe or prolonged Sigma1 antagonist-induced ER stress appeared to overwhelm the cytoprotective, adaptive capacity of the UPR and autophagy was engaged as a secondary response. Treatment with four Sigma1 antagonists (IPAG, haloperidol, rimcazole, PB28) resulted in autophagosome formation and flux. However, all three agonist did not induce UPR or autophagy. In addition to affinity to Sigma receptors, these compounds also bind to other receptor systems. For example, rimcazole binds to the DAT dopamine transporter with higher affinity than the Sigma receptor system. Haloperidol binds to D2 dopamine receptors and Sigma receptors with similar affinity. The Sigma ligands used in this study also have been described to have varying affinity and selectivity for Sigma receptor subtypes. For example, IPAG ($K_i$ 5±2 nM) has significantly higher affinity for the Sigma1 than does rimcazole ($K_i$ 80±22 nM). Interestingly, the two antagonists with greater Sigma1 binding affinity, haloperidol and IPAG, were significantly more potent inducers of autophagy (FIG. 4). The results of RNAi assays are consistent with Sigma1 as the principal mediator of this effect (FIG. 5).

Without wishing to be limited by theory, a possible explanation for the absence of agonist effect may be the predominance of receptors in a constitutive agonist conformation. Alternatively, because IPAG and haloperidol associated autophagosome formation is not blocked by PRE084 and (+)-SKF10047, it is possible that antagonists and agonists bind distinct regions of the receptor and thereby elicit different effects.

What is claimed is:

1. A compound selected from the group consisting of:
   1-(3-(4-fluorophenoxy)propyl)-3-(4-iodophenyl)guanidine (Compound A);
   1-(3-(4-fluorophenoxy)propyl)-3-(4-methoxyphenyl)guanidine (Compound B);
   1-(3-(4-fluorophenoxy)propyl)-3-(4-trifluoromethylphenyl)guanidine (Compound F);
   1-(3-(4-fluorophenoxy)propyl)-3-(4-chlorophenyl)guanidine (Compound G); or
   a salt, solvate or N-oxide thereof, and any combinations thereof.

2. A pharmaceutical composition comprising at least one compound of claim 1, or a pharmaceutically acceptable salt, solvate, or N-oxide thereof, and any combinations thereof.

3. A method of treating breast cancer or prostate cancer in a subject, the method comprising administering to the subject a therapeutically effective amount of a compound selected from the group consisting of:
   1-(3-(4-fluorophenoxy)propyl)-3-(4-iodophenyl)guanidine (Compound A);
   1-(3-(4-fluorophenoxy)propyl)-3-(4-methoxyphenyl)guanidine (Compound B);
   1-(3-(4-fluorophenoxy)propyl)-3-(4-trifluoromethylphenyl)guanidine (Compound F); and
   1-(3-(4-fluorophenoxy)propyl)-3-(4-chlorophenyl)guanidine (Compound G);
   or a pharmaceutically acceptable salt, solvate or N-oxide thereof, and any combinations thereof.

4. The method of claim 3, wherein the subject has breast cancer.

5. The method of claim 3, wherein the subject has prostate cancer.

6. The method of claim 5, wherein the prostate cancer comprises castrate-sensitive or castrate-insensitive prostate cancer.

7. The method of claim 3, wherein the subject is human.

8. A method of modulating a Sigma receptor in a subject, wherein the method comprises administering to the subject an effective amount of a compound selected from the group consisting of:
   1-(3-(4-fluorophenoxy)propyl)-3-(4-iodophenyl)guanidine (Compound A);
   1-(3-(4-fluorophenoxy)propyl)-3-(4-methoxyphenyl)guanidine (Compound B);
   1-(3-(4-fluorophenoxy)propyl)-3-(4-trifluoromethylphenyl)guanidine (Compound F); and
   1-(3-(4-fluorophenoxy)propyl)-3-(4-chlorophenyl)guanidine (Compound G);
   or
   a pharmaceutically acceptable salt, solvate or N-oxide thereof, and any combinations thereof.

9. The pharmaceutical composition of claim 2, further comprising at least one additional therapeutic agent that inhibits the ubiquitin proteasome system (UPS) or autophagic survival pathway.

10. The pharmaceutical composition of claim 9, wherein the therapeutic agent is selected from the group consisting of growth factor receptor inhibitors, monoclonal antibodies against growth factor receptors, hormone receptor antagonists, autophagy modulators, ER stress response inhibitors, proteasome inhibitors, p97/VCP inhibitors and any combinations thereof.

11. The compound of claim 1, wherein the compound is 1-(3-(4-fluorophenoxy)propyl)-3-(4-iodophenyl)guanidine (Compound A), or a salt, solvate or N-oxide thereof, and any combinations thereof.

12. The compound of claim 1, wherein the compound is 1-(3-(4-fluorophenoxy)propyl)-3-(4-methoxyphenyl)guanidine (Compound B), or a salt, solvate or N-oxide thereof, and any combinations thereof.

13. The compound of claim 1, wherein the compound is 1-(3-(4-fluorophenoxy)propyl)-3-(4-trifluoromethylphenyl)guanidine (Compound F), or a salt, solvate or N-oxide thereof, and any combinations thereof.

14. The compound of claim 1, wherein the compound is 1-(3-(4-fluorophenoxy)propyl)-3-(4-chlorophenyl)guanidine (Compound G), or a salt, solvate or N-oxide thereof, and any combinations thereof.

15. The pharmaceutical composition of claim 2, wherein the compound is 1-(3-(4-fluorophenoxy)propyl)-3-(4-iodophenyl)guanidine (Compound A), or a pharmaceutically acceptable salt, solvate or N-oxide thereof, and any combinations thereof.

16. The pharmaceutical composition of claim 2, wherein the compound is 1-(3-(4-fluorophenoxy)propyl)-3-(4-methoxyphenyl)guanidine (Compound B), or a pharmaceutically acceptable salt, solvate or N-oxide thereof, and any combinations thereof.

17. The pharmaceutical composition of claim 2, wherein the compound is 1-(3-(4-fluorophenoxy)propyl)-3-(4-trifluoromethylphenyl)guanidine (Compound F), or a pharmaceutically acceptable salt, solvate or N-oxide thereof, and any combinations thereof.

18. The pharmaceutical composition of claim 2, wherein the compound is 1-(3-(4-fluorophenoxy)propyl)-3-(4-chlorophenyl)guanidine (Compound G), or a pharmaceutically acceptable salt, solvate or N-oxide thereof, and any combinations thereof.

19. The method of claim 3, wherein the compound is 1-(3-(4-fluorophenoxy)propyl)-3-(4-iodophenyl)guanidine (Compound A), or a pharmaceutically acceptable salt, solvate or N-oxide thereof, and any combinations thereof.

20. The method of claim 3, wherein the compound is 1-(3-(4-fluorophenoxy)propyl)-3-(4-methoxyphenyl)guanidine (Compound B), or a pharmaceutically acceptable salt, solvate or N-oxide thereof, and any combinations thereof.

21. The method of claim 3, wherein the compound is 1-(3-(4-fluorophenoxy)propyl)-3-(4-trifluoromethylphenyl)guanidine (Compound F), or pharmaceutically acceptable salt, solvate or N-oxide thereof, and any combinations thereof.

22. The method of claim 3, wherein the compound is 1-(3-(4-fluorophenoxy)propyl)-3-(4-chlorophenyl)guanidine (Compound G), or a pharmaceutically acceptable salt, solvate or N-oxide thereof, and any combinations thereof.

23. The method of claim 3, wherein the subject is a subject in need thereof.

24. The method of claim 19, wherein the subject is a subject in need thereof.

25. The method of claim 20, wherein the subject is a subject in need thereof.

26. The method of claim 21, wherein the subject is a subject in need thereof.

27. The method of claim 22, wherein the subject is a subject in need thereof.

28. The method of claim 8, wherein the compound is 1-(3-(4-fluorophenoxy)propyl)-3-(4-iodophenyl)guanidine (Compound A), or a pharmaceutically acceptable salt, solvate or N-oxide thereof, and any combinations thereof.

29. The method of claim 8, wherein the compound is 1-(3-(4-fluorophenoxy)propyl)-3-(4-methoxyphenyl)guanidine (Compound B), or a pharmaceutically acceptable salt, solvate or N-oxide thereof, and any combinations thereof.

30. The method of claim 8, wherein the compound is 1-(3-(4-fluorophenoxy)propyl)-3-(4-trifluoromethylphenyl)guanidine (Compound F), or pharmaceutically acceptable salt, solvate or N-oxide thereof, and any combinations thereof.

31. The method of claim 8, wherein the compound is 1-(3-(4-fluorophenoxy)propyl)-3-(4-chlorophenyl)guanidine (Compound G), or a pharmaceutically acceptable salt, solvate or N-oxide thereof, and any combinations thereof.

* * * * *